US005651047A

United States Patent [19]

Moorman et al.

[11] Patent Number: 5,651,047
[45] Date of Patent: Jul. 22, 1997

[54] MANEUVERABLE AND LOCATEABLE CATHETERS

[75] Inventors: Jack W. Moorman, Los Gatos; John W. Wilent, deceased, late of Aptos, both of Calif., by Virginia B. Wilent, executor

[73] Assignee: Cardiac Mariners, Incorporated, Los Gatos, Calif.

[21] Appl. No.: 386,861

[22] Filed: Feb. 10, 1995

Related U.S. Application Data

[63] Continuation-in-part of Ser. No. 375,501, Jan. 17, 1995, abandoned, and Ser. No. 342,641, Nov. 21, 1994, abandoned, which is a continuation of Ser. No. 8,455, Jan. 25, 1993, abandoned and a continuation-in-part of PCT/US94/03737, Apr. 5, 1994, said Ser. No. 375,501, is a continuation of Ser. No. 42,742, Apr. 5, 1993, abandoned.

[51] Int. Cl.$^6$ ............................................. H05G 1/64
[52] U.S. Cl. ...................... 378/988; 378/19; 128/653.1
[58] Field of Search .................... 378/19, 98.3, 98.8; 250/368; 128/653.1, 659

[56] References Cited

U.S. PATENT DOCUMENTS

| | | | |
|---|---|---|---|
| 2,638,554 | 5/1953 | Bartow et al. | 250/99 |
| 2,667,585 | 1/1954 | Gradstein | 250/61.5 |
| 2,730,566 | 1/1956 | Bartow et al. | 378/146 |
| 2,825,817 | 3/1958 | North | 250/105 |
| 2,837,657 | 6/1958 | Craig et al. | 250/65 |
| 3,106,640 | 10/1963 | Oldendorf | 250/52 |
| 3,114,832 | 12/1963 | Alvarez . | |
| 3,499,146 | 3/1970 | Richards | 250/61.5 |
| 3,591,806 | 7/1971 | Brill et al. | 250/71.5 |
| 3,593,243 | 7/1971 | Trump et al. | 336/70 |
| 3,605,750 | 9/1971 | Sheridan et al. | 128/658 |
| 3,611,032 | 10/1971 | Skillicorn | 317/14 |
| 3,617,740 | 11/1971 | Skillicorn | 250/49.5 |
| 3,684,991 | 8/1972 | Trump et al. | 336/70 |
| 3,742,236 | 6/1973 | Richards | 250/321 |

(List continued on next page.)

OTHER PUBLICATIONS

Howard H. Pattee, Jr., "The Scanning X–ray Microscope", *Journal Opt. Soc. Amer.*, vol. 43, Jan., 1953, pp. 61–62.

Lewis Etter, *The Science of Ionizing Radiation*, at least by Dec., 1965, pp. 546–548.

Russell H. Morgan et al., "Clinical Potentialities of Screen Intensifying Systems", *American Journal of Roentgenology*, vol. 62, No. 5, Nov., 1949, pp. 635–644.

Robert J. Moon, "Amplifying and Intensifying the Fluoroscopic Image by Means of a Scanning X–Ray Tube", vol. 112, *Science*, Oct. 6, 1950, pp. 389–395.

Howard H. Pattee, Jr., "Possibilities of the Scanning X–Ray Microscope", at least by Dec., 1957, *X–ray Microscopy and Microradiography*, pp. 367–375.

Philips Photonics, "xP1700 Multichannel Photomultipliers", *xP1700 Family of Multi–channel Photomultipliers—Philips Photonic Handbook*, at least by Dec., 1993, pp. 1–15.

Digiray, "Digiray's Reverse Geometry X–ray System", *Digiray Marketing Brochure*, at least by Dec., 1992, pp. 1–2.

Albert G. Richards, "Variable Depth Laminagraphy", *ISA–Biomedical Sciences Instrumentation*, vol. 6, Imagery in Medicine, 7th Proc., May 1969, pp. 194–199.

(List continued on next page.)

*Primary Examiner*—Don Wong
*Attorney, Agent, or Firm*—Lyon & Lyon

[57] ABSTRACT

An x-ray imaging system according to the present invention comprising a stepped scanning-beam x-ray source and a multi-detector array. The output of the multi-detector array is input to an image reconstruction engine which combines the outputs of the multiple detectors over selected steps of the x-ray beam to generate an x-ray image of the object. A collimating element, preferably in the form of a perforated grid containing an array of apertures, interposed between the x-ray source and an object to be x-rayed. A maneuverable positioner incorporating an x-ray sensitive marker allowing the determination of the precise position coordinates of the maneuverable positioner.

19 Claims, 87 Drawing Sheets

U.S. PATENT DOCUMENTS

| | | | |
|---|---|---|---|
| 3,746,872 | 7/1973 | Ashe et al. | 250/313 |
| 3,778,614 | 12/1973 | Hounsfield | 250/362 |
| 3,780,291 | 12/1973 | Stein et al. | 250/363 |
| 3,809,886 | 5/1974 | Cochran et al. | 250/323 |
| 3,818,220 | 6/1974 | Richards | 250/61.5 |
| 3,830,128 | 8/1974 | Cochran et al. | 83/451 |
| 3,855,471 | 12/1974 | Ikegami | 250/320 |
| 3,873,834 | 3/1975 | Dammann et al. | 250/323 |
| 3,890,521 | 6/1975 | Shroff | 313/55 |
| 3,919,556 | 11/1975 | Berninger | 250/366 |
| 3,922,552 | 11/1975 | Ledley | 250/369 |
| 3,924,129 | 12/1975 | LeMay | 250/336 |
| 3,925,660 | 12/1975 | Albert | 250/272 |
| 3,936,639 | 2/1976 | Barrett | 250/369 |
| 3,944,833 | 3/1976 | Hounsfield | 250/367 |
| 3,946,234 | 3/1976 | Hounsfield | 250/363 |
| 3,949,229 | 4/1976 | Albert | 250/401 |
| 3,973,128 | 8/1976 | LeMay | 250/445 |
| 3,979,594 | 9/1976 | Anger | 250/369 |
| 3,983,397 | 9/1976 | Albert | 250/406 |
| 3,992,631 | 11/1976 | Harte | 250/302 |
| 4,002,917 | 1/1977 | Mayo | 250/445 |
| 4,005,311 | 1/1977 | Ledley | 250/445 |
| 4,007,375 | 2/1977 | Albert | 250/404 |
| 4,010,370 | 3/1977 | LeMay | 250/366 |
| 4,017,730 | 4/1977 | Barrett | 250/363 |
| 4,029,948 | 6/1977 | Hounsfield | 235/151.3 |
| 4,031,395 | 6/1977 | LeMay | 250/360 |
| 4,032,787 | 6/1977 | Albert | 250/402 |
| 4,048,496 | 9/1977 | Albert | 250/272 |
| 4,052,619 | 10/1977 | Hounsfield | 250/363 |
| 4,057,745 | 11/1977 | Albert | 313/55 |
| 4,066,902 | 1/1978 | LeMay | 250/363 |
| 4,078,177 | 3/1978 | Tiemens | 250/323 |
| 4,086,492 | 4/1978 | Lodge et al. | 250/416 |
| 4,104,526 | 8/1978 | Albert | 250/403 |
| 4,144,457 | 3/1979 | Albert | 250/445 T |
| 4,149,076 | 4/1979 | Albert | 250/402 |
| 4,167,672 | 9/1979 | Richards | 250/445 |
| 4,188,640 | 2/1980 | Dittrich et al. | 358/111 |
| 4,196,351 | 4/1980 | Albert | 250/416 TV |
| 4,204,226 | 5/1980 | Mistretta et al. | 358/111 |
| 4,216,526 | 8/1980 | Karwowski | 364/414 |
| 4,234,794 | 11/1980 | Voinea et al. | 378/146 |
| 4,259,582 | 3/1981 | Albert | 250/402 |
| 4,259,583 | 3/1981 | Albert | 250/416 TV |
| 4,260,885 | 4/1981 | Albert | 250/277 |
| 4,263,916 | 4/1981 | Brooks et al. | 128/654 |
| 4,288,697 | 9/1981 | Albert | 250/505 |
| 4,321,473 | 3/1982 | Albert | 250/505 |
| 4,322,808 | 3/1982 | Weiss | 364/515 |
| 4,323,779 | 4/1982 | Albert | 250/401 |
| 4,383,327 | 5/1983 | Kruger | 378/146 |
| 4,465,540 | 8/1984 | Albert | 156/252 |
| 4,519,092 | 5/1985 | Albert | 378/45 |
| 4,573,183 | 2/1986 | Relihan | 378/108 |
| 4,577,637 | 3/1986 | Mueller, Jr. | 128/658 |
| 4,595,014 | 6/1986 | Barrett et al. | 128/654 |
| 4,598,369 | 7/1986 | Wang et al. | 364/414 |
| 4,630,296 | 12/1986 | Haaker et al. | 378/2 |
| 4,646,338 | 2/1987 | Skillicorn | 378/110 |
| 4,694,480 | 9/1987 | Skillicorn | 378/119 |
| 4,730,350 | 3/1988 | Albert | 378/10 |
| 4,796,937 | 1/1989 | Mascuch et al. | 128/658 |
| 4,853,540 | 8/1989 | Nakajima | 250/327.2 |
| 4,873,708 | 10/1989 | Cusano et al. | 378/62 |
| 4,903,204 | 2/1990 | Dobbin, III | 364/413.24 |
| 4,945,894 | 8/1990 | Kawashima | 128/658 |
| 4,967,121 | 10/1990 | Nero | 315/411 |
| 4,974,929 | 12/1990 | Curry | 128/658 |
| 5,022,066 | 6/1991 | Haaker et al. | 378/2 |
| 5,029,338 | 7/1991 | Aichinger et al. | 378/108 |
| 5,132,539 | 7/1992 | Kwasnick et al. | 250/361 |
| 5,140,162 | 8/1992 | Stettner | 250/370.09 |
| 5,153,438 | 10/1992 | Kingsley et al. | 250/370 |
| 5,171,232 | 12/1992 | Castillo et al. | 128/658 |
| 5,185,773 | 2/1993 | Blossfeld et al. | 378/53 |
| 5,187,369 | 2/1993 | Kingsley et al. | 250/370 |
| 5,198,673 | 3/1993 | Rougeot et al. | 250/370 |
| 5,203,777 | 4/1993 | Le | 128/658 |
| 5,231,654 | 7/1993 | Kwasnick et al. | 378/147 |
| 5,231,655 | 7/1993 | Wei et al. | 378/154 |
| 5,237,598 | 8/1993 | Albert | 378/146 |
| 5,259,012 | 11/1993 | Baker et al. | 378/21 |
| 5,267,296 | 11/1993 | Albert | 378/113 |
| 5,276,604 | 1/1994 | Messman | 363/65 |
| 5,293,417 | 3/1994 | Wei et al. | 378/147 |
| 5,303,282 | 4/1994 | Kwasnick et al. | 378/147 |
| 5,304,898 | 4/1994 | Kataoka et al. | 315/411 |
| 5,319,749 | 6/1994 | Haaker et al. | 395/166 |
| 5,325,855 | 7/1994 | Daghighian et al. | 250/368 |
| 5,331,961 | 7/1994 | Inaba et al. | 250/368 |
| 5,424,546 | 6/1995 | Okada et al. | 250/368 |

OTHER PUBLICATIONS

Barrett et al., "The Theory of Image Formation, Detection, and Processing", vol. 2, *Radiological Imaging*, published at least by Dec., 1981, pp. 368–371.

Sashin et al., "Computer Electronic Radiography For Early Detection of Vascular Disease", vol. 173, SPIE, *Application of Optical Instrumentation in Medicine VII*, Mar., 1979, pp. 88–97.

Maravilla et al., "Digital Tomosynthesis: Technique for Electronic Reconstructive Tomography", vol. 4, *American Journal of Neuroradiology*, Jul./Aug., 1983, pp. 883–888.

Capp et al., "Photoelectronic Radiology Department", vol. 314, SPIE, *Digital Radiography*, Sep., 1981, pp. 2–8.

Gerald D. Pond, "Dynamic Linear Tomography and Routine Linear Tomography: a Clinical Comparison", vol. 233 SPIE *Application of Optical Instrumentation in Medicine VIII*, Apr., 1980, pp. 75–82.

ECRI, "Radiographic/Fluoroscopic Units, Mobile", *Healthcare Products Comparison System*, Sep. 1993, pp. 1–25.

OEC–DIASONICS, Salt Lake City, OEC, "Series 9600 Mobile Digital Imaging System", *OEC–DIASONICS Marketing Brochure*, published at least by Nov., 1994, pp. 1–3.

Thomas S. Curry, III, et al., "Christensen's Physics of Diagnostics Radiology," pp. 1–522, Fourth Ed., Lea & Febiger, 1990.

Swinth et al., "Biomedical Probe Using a Fiber–optic Coupled Scintillator", *Medical Physics*, vol.3, 1976, pp. 109–112.

W.C. Nixon, "High–resolution X–ray Projection Microscopy", vol. 232, *Proceedings of the Royal Society of London*, Nov., 1955, pp. 475–484.

George L. Clark, "The Encyclopedia of X–rays and Gamma Rays", 1963, pp. 608–610, 617.

V.E. Cosslett et al., "X–ray Microscopy", 1960, pp. 216–219, 296–303, 350–355, 368–369.

B. Skillicorn, "Insulators and X–Ray Tube Longevity: Some Theory and a Few Practical Hints", 1983, pp. 2–6.

R.M. Dolby et al., "A Spectrometer System for Long Wavelength X–ray Emisson Microanalysis", *X–ray Microscopy and X–ray Microanalysis*, 1960, pp. 351–357.

Center for Devices and Radiological Health, Radiological Health Bulletin, "FDA Draws Attention to Concerns about Radiation Risk from Fluoroscopy", Aug., 1992, pp. 1–3, 5.

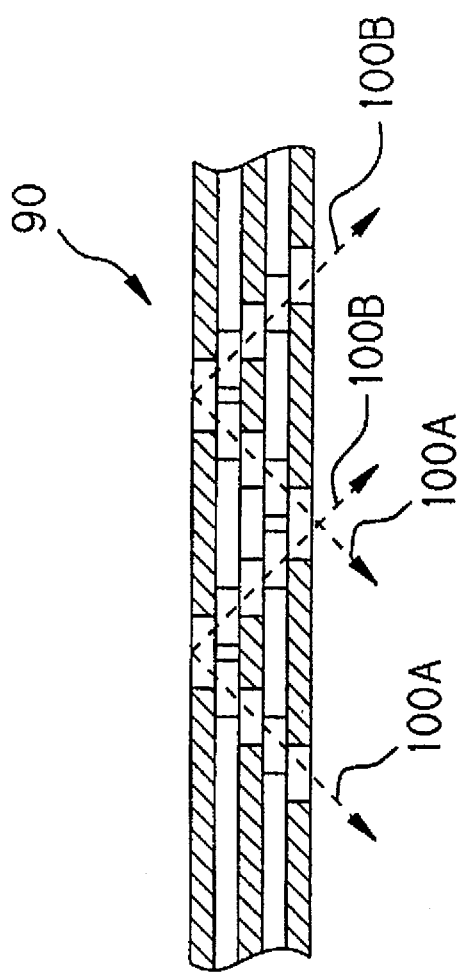

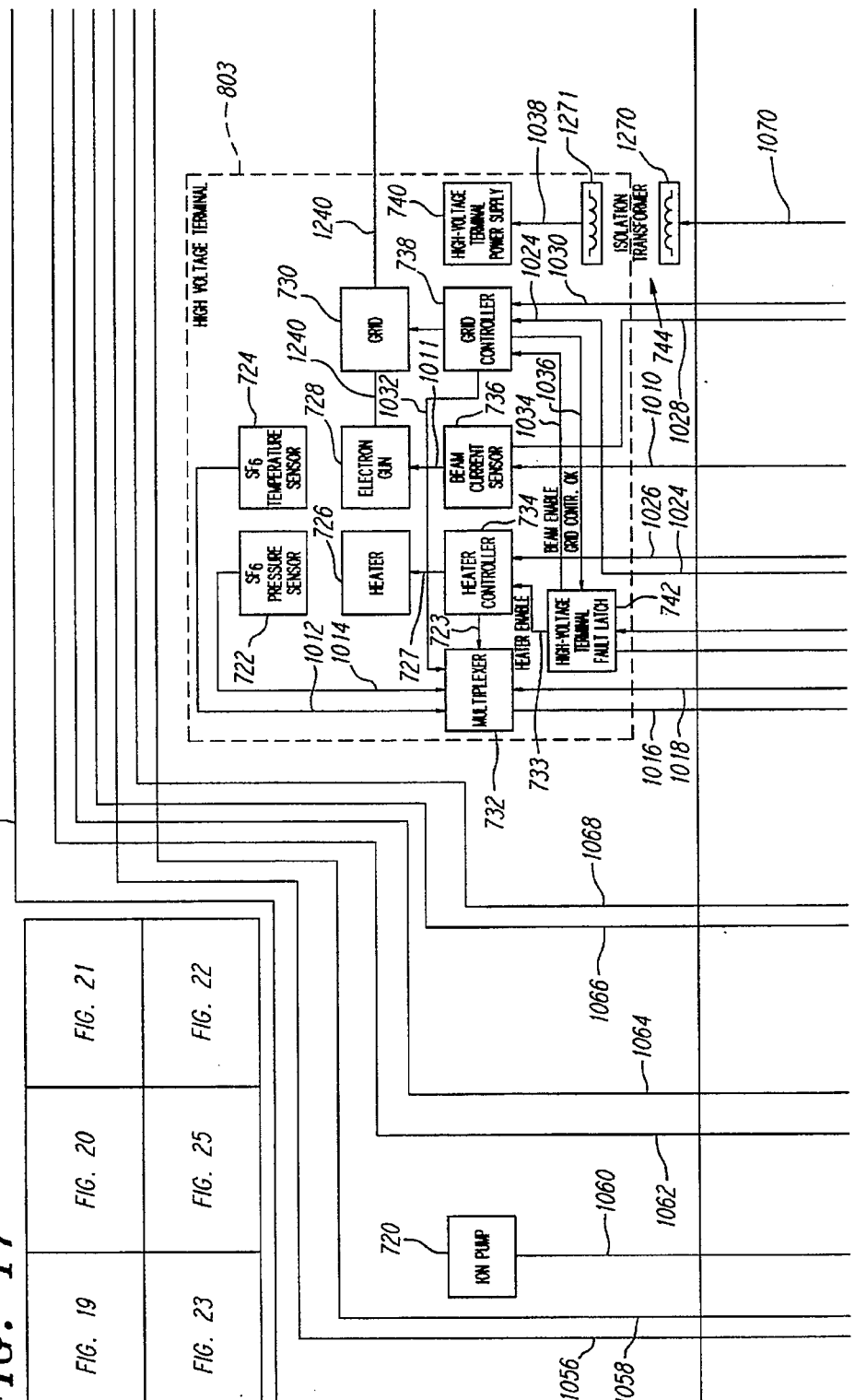

|   | A | B | C | D | E | F | G | H | J | K | L | M |   |
|---|---|---|---|---|---|---|---|---|---|---|---|---|---|
| 1 | 3 | 2 | 1 | 3 | 2 | 1 | 3 | 2 | 1 | 3 | 2 | 1 | 1 |
| 2 | 6 | 5 | 4 | 6 | 5 | 4 | 6 | 5 | 4 | 6 | 5 | 4 | 2 |
| 3 | 9 | 8 | 7 | 9 | 8 | 7 | 9 | 8 | 7 | 9 | 8 | 7 | 3 |
| 4 | 3 | 2 | 1 | 3 | 2 | 1 | 3 | 2 | 1 | 3 | 2 | 1 | 4 |
| 5 | 6 | 5 | 4 | 6 | 5 | 4 | 6 | 5 | 4 | 6 | 5 | 4 | 5 |
| 6 | 9 | 8 | 7 | 9 | 8 | 7 | 9 | 8 | 7 | 9 | 8 | 7 | 6 |
| 7 | 3 | 2 | 1 | 3 | 2 | 1 | 3 | 2 | 1 | 3 | 2 | 1 | 7 |
| 8 | 6 | 5 | 4 | 6 | 5 | 4 | 6 | 5 | 4 | 6 | 5 | 4 | 8 |
| 9 | 9 | 8 | 7 | 9 | 8 | 7 | 9 | 8 | 7 | 9 | 8 | 7 | 9 |
| 10 | 3 | 2 | 1 | 3 | 2 | 1 | 3 | 2 | 1 | 3 | 2 | 1 | 10 |
| 11 | 6 | 5 | 4 | 6 | 5 | 4 | 6 | 5 | 4 | 6 | 5 | 4 | 11 |
| 12 | 9 | 8 | 7 | 9 | 8 | 7 | 9 | 8 | 7 | 9 | 8 | 7 | 12 |
|   | A | B | C | D | E | F | G | H | J | K | L | M |   |

FIG. 36

|   | M | L | K | J | H | G | F | E | D | C | B | A |   |
|---|---|---|---|---|---|---|---|---|---|---|---|---|---|
| 1 |   |   |   |   |   | TLO | TRO |   |   |   |   |   | 1 |
| 2 |   |   |   | TLO | TLO | TLO | TRO | TRO | TRO |   |   |   | 2 |
| 3 |   |   | TLO | TLO | TLI | TLI | TRI | TRI | TRO | TRO |   |   | 3 |
| 4 |   | TLO | TLO | TLO | TLI | TLI | TRI | TRI | TRO | TRO | TRO |   | 4 |
| 5 |   | TLO | TLI | TLI | TLI | TLI | TRI | TRI | TRI | TRI | TRO |   | 5 |
| 6 | TLO | TLO | TLI | TLI | TLI | TLI | TRI | TRI | TRI | TRI | TRO | TRO | 6 |
| 7 | BLO | BLO | BLI | BLI | BLI | BLI | BRI | BRI | BRI | BRI | BRO | BRO | 7 |
| 8 |   | BLO | BLI | BLI | BLI | BLI | BRI | BRI | BRI | BRI | BRO |   | 8 |
| 9 |   | BLO | BLO | BLO | BLI | BLI | BRI | BRI | BRO | BRO | BRO |   | 9 |
| 10 |   |   | BLO | BLO | BLI | BLI | BRI | BRI | BRO | BRO |   |   | 10 |
| 11 |   |   |   | BLO | BLO | BLO | BRO | BRO | BRO |   |   |   | 11 |
| 12 |   |   |   |   |   | BLO | BRO |   |   |   |   |   | 12 |
|   | M | L | K | J | H | G | F | E | D | C | B | A |   |

*FIG. 38*

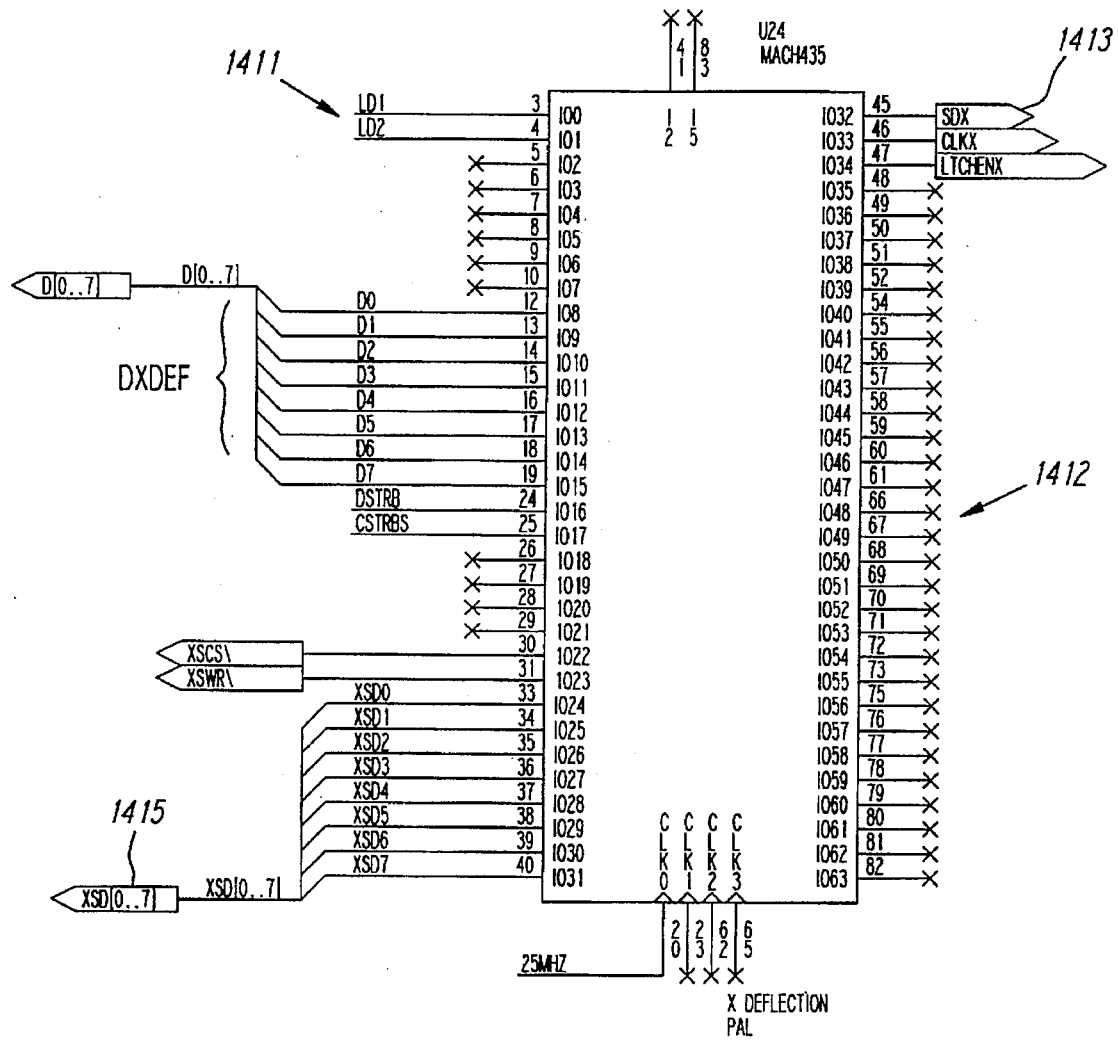
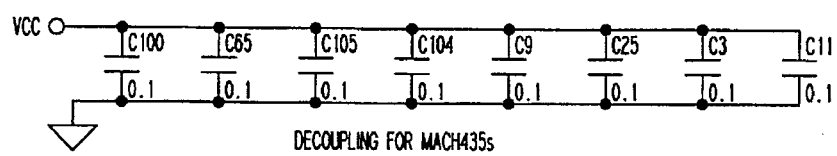
FIG. 55B

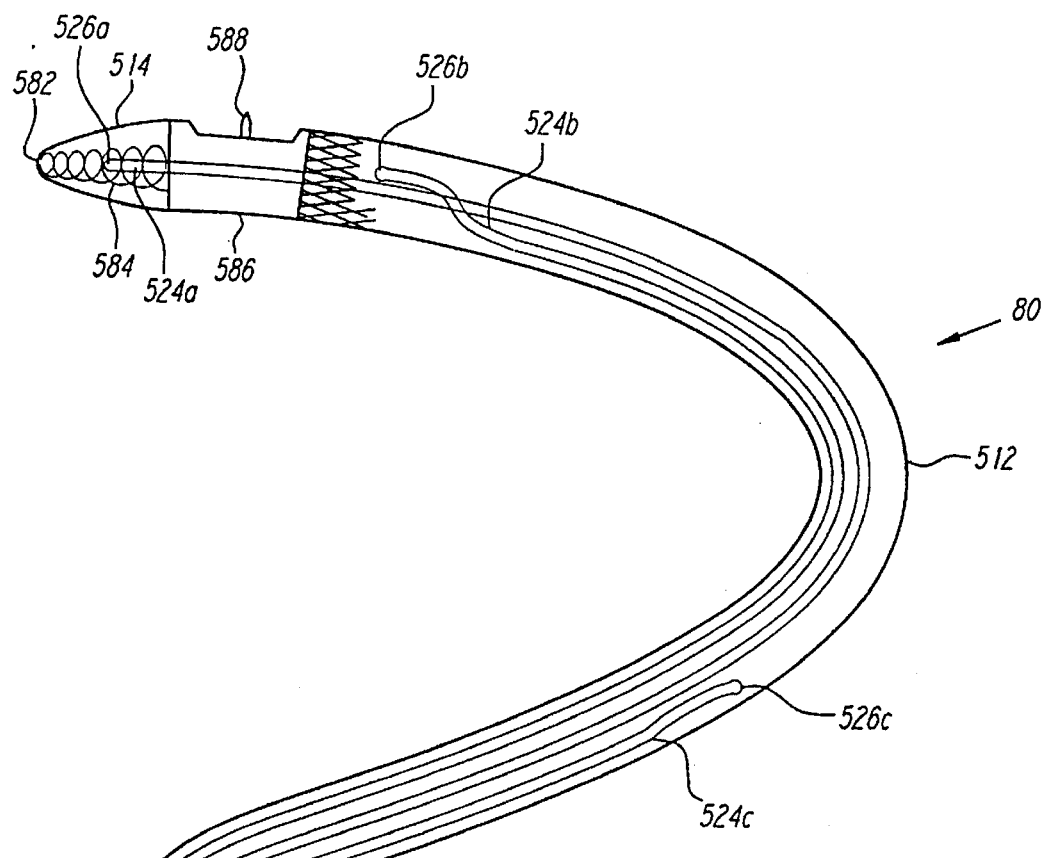
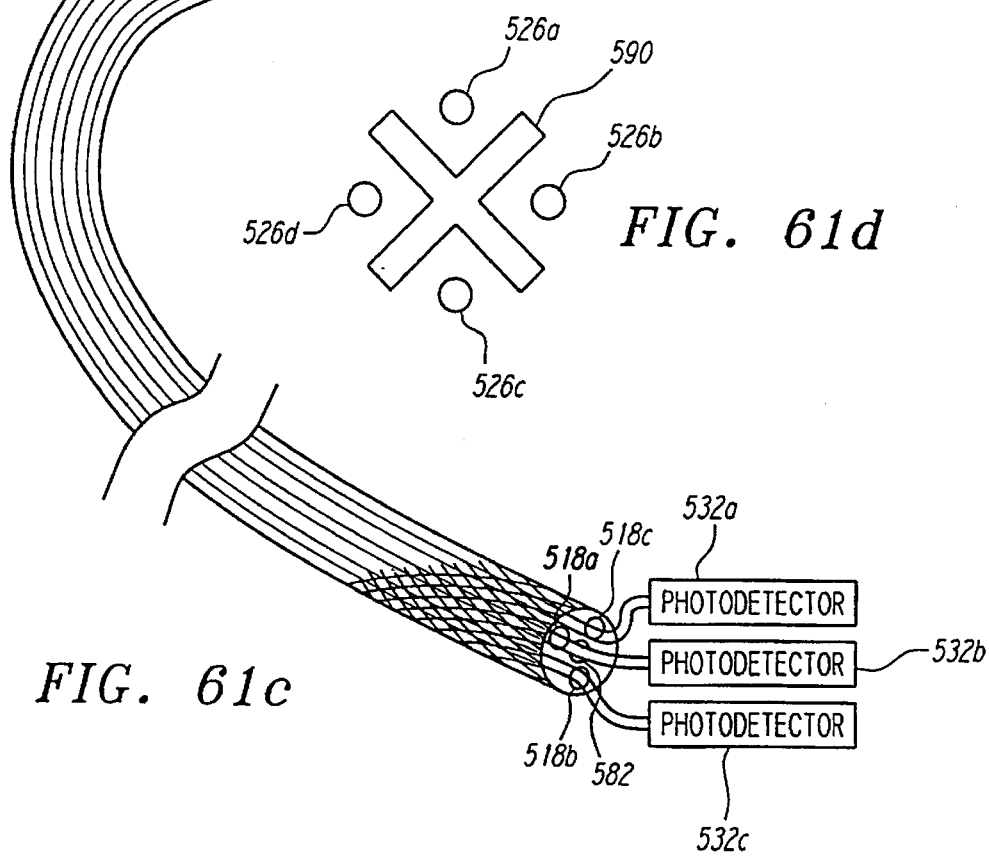
FIG. 61d
FIG. 61c

MANEUVERABLE AND LOCATEABLE CATHETERS

CROSS-REFERENCE TO RELATED APPLICATIONS

This application is a continuation-in-part of three prior applications: (1) U.S. patent application Ser. No. 08/375,501, filed Jan. 17, 1995, now abandoned which is a continuation of U.S. patent application Ser. No. 08/042,742, filed Apr. 5, 1993, now abandoned; (2) of U.S. patent application Ser. No. 08/342,641, filed Nov. 21, 1994, which is a continuation of U.S. patent application Ser. No. 08/008,455, filed Jan. 25, 1993, now abandoned; (3) and, of International Patent Application Ser. No. PCT/US94/03737, filed Apr. 5, 1994, which designated the United States from which priority is claimed under the provisions of 35 U.S.C. §§120 and 365, all of which are incorporated herein by reference in their entirety. The reader is referred to copending U.S. patent application Ser. Nos. 08/387,292, and 08/386,884 both filed Feb. 10, 1995 concurrently with this application, the disclosures of which are incorporated herein by reference in their entirety.

APPENDIX

Attached hereto is APPENDIX A, which contains the program listings for the preferred software modules for the programmable logic devices employed in an embodiment of the present invention. The contents of APPENDIX A are hereby incorporated by reference in its entirety.

BACKGROUND OF THE INVENTION

1. Field of the Invention

The field of the present invention pertains to diagnostic x-ray imaging equipment. More particularly, the present invention pertains to real-time scanning-beam x-ray imaging systems and to devices incorporating a marker, such as a medical catheter incorporating an x-ray sensor, which allows the determination of the device's precise position within another object.

2. Description of Related Art

Real-time x-ray imaging is increasingly being required by medical procedures as therapeutic technologies advance. For example, many electro-physiologic cardiac procedures, peripheral vascular procedures, PTCA procedures (percutaneous transluminal catheter angioplasty), urological procedures, and orthopedic procedures rely on real-time x-ray imaging. In addition, modern medical procedures often require the use of instruments, such as catheters, that are inserted into the human body. These medical procedures often require the ability to discern the exact location of instruments that are inserted within the human body, often in conjunction with an accurate image of the surrounding body through the use of x-ray imaging.

Current clinical real-time x-ray equipment produces high levels of x-ray exposure to both patients and attending staff. The United States Food and Drug Administration (F.D.A.) has reported anecdotal evidence of acute radiation sickness in patients, and concern among physicians of excessive occupational exposure. (Radiological Health Bulletin, Vol. XXVI, No. 8, August 1992).

A number of real-time x-ray imaging systems are known. These include fluoroscope-based systems where x-rays are projected into an object to be x-rayed and shadows caused by relatively x-ray opaque matter within the object are displayed on the fluoroscope located on the opposite side of the object from the x-ray source. Scanning x-ray tubes have been known in conjunction with the fluoroscopy art since at least the early 1950s. Moon, *Amplifying and Intensifying the Fluoroscopic Image by Means of a Scanning X-ray Tube*, Science, Oct. 6, 1950, pp. 389–395.

Reverse-geometry scanning-beam x-ray imaging systems are also known. In such systems, an x-ray tube is employed to generate x-ray radiation. Within the x-ray tube, an electron beam is generated and focussed upon a small spot on the relatively large anode (transmission target) of the tube, inducing x-ray radiation emission from that spot. The electron beam is deflected (electromagnetically or electrostatically) in a raster scan pattern over the anode target. A small x-ray detector is placed at a distance from the anode target of the x-ray tube. The detector typically converts x-rays which strike it into an electrical signal in proportion to the detected x-ray flux. When an object is placed between the x-ray tube and the detector, x-rays are attenuated and scattered by the object in proportion to the x-ray density of the object. While the x-ray tube is in the scanning mode, the signal from the detector is inversely proportional to the x-ray density of the object.

Examples of known reverse-geometry scanning-beam x-ray systems include those described in U.S. Pat. No. 3,949,229 to Albert; U.S. Pat. No. 4,032,787 to Albert; U.S. Pat. No. 4,057,745 to Albert; U.S. Pat. No. 4,144,457 to Albert; U.S. Pat. No. 4,149,076 to Albert; U.S. Pat. No. 4,196,351 to Albert; U.S. Pat. No. 4,259,582 to Albert; U.S. Pat. No. 4,259,583 to Albert; U.S. Pat. No. 4,288,697 to Albert; U.S. Pat. No. 4,321,473 to Albert; U.S. Pat. No. 4,323,779 to Albert; U.S. Pat. No. 4,465,540 to Albert; U.S. Pat. No. 4,519,092 to Albert; and U.S. Pat. No. 4,730,350 to Albert.

In a typical known embodiment of a reverse-geometry scanning-beam system, an output signal from the detector is applied to the z-axis (luminance) input of a video monitor. This signal modulates the brightness of the viewing screen. The x and y inputs to the video monitor are typically derived from the signal that effects deflection of the electron beam of the x-ray tube. Therefore, the luminance of a point on the viewing screen is inversely proportional to the absorption of x-rays passing from the source, through the object, to the detector.

Medical x-ray systems are usually operated at the lowest possible x-ray exposure level at the entrance of the patient that is consistent with the image quality requirements (particularly contrast resolution and spatial resolution requirements) for the procedure and the system. Typical patient entrance exposure in conventional 9" field of view image intensifier systems used in cardiac procedures, in the AP (anterior posterior) view with a standard adult chest, is approximately 2.0 to 2.8 R/min. The term "low dosage" used herein refers to a factor of 2 to 20 less than this.

Time and area distributions of x-ray flux follow a Poisson distribution and have an associated randomness which is unavoidable. The randomness is typically expressed as the standard deviation of the mean flux, and equals its square root. The signal-to-noise ratio of an x-ray image under these conditions is equal to the mean flux divided by the square root of the mean flux. i.e., for a mean flux of 100 photons, the noise is +/− 10 photons, and the signal-to-noise ratio is 10.

Accordingly, the spatial resolution and the signal-to-noise ratio of x-ray images formed by known reverse-geometry scanning x-ray imaging systems are dependent, to a large extent, upon the size of the sensitive area of the detector. If the detector aperture is increased in area, more of the diverging rays are detected, effectively increasing sensitivity and improving the signal-to-noise ratio. At the same time, however, the larger detector aperture reduces attainable spatial resolution as the "pixel" size (measured at the plane of the object to be imaged) becomes larger. This is necessarily so because most objects to be imaged in medical applications (e.g., structures internal to the human body) are some distance from the x-ray source. In the known systems, therefore, the detector aperture size has been selected so as to effect a compromise between resolution and sensitivity, it not being previously possible to maximize both resolution and sensitivity simultaneously.

In the medical field, several conflicting factors, among them patient dosage, frame rate (the number of times per second that the object is scanned and the image refreshed), and resolution of the image of the object, often work to limit the usefulness of an x-ray imaging system. For example, a high x-ray flux may easily yield high resolution and a high frame rate, yet result in an unacceptably high x-ray dosage to the patient and attending staff.

Similarly, lower dosages may be achieved from the known systems at the cost of a low resolution image or an inadequate refresh rate. A preferred medical imaging system should provide low patient dosage, high resolution and an adequate refresh rate of up to at least about 15 images per second—all at the same time. Therefore, systems such as the known reverse-geometry scanning-beam x-ray imaging systems described above are not acceptable for diagnostic medical procedures where exposure times are relatively long and where, as is always the case with live patients, the x-ray dose received by the patient should be kept to a minimum.

Minimally invasive procedures in medicine are typically characterized by access to areas inside the body using existing orifices such as the ureter or by percutaneous entry such as a puncture of the femoral vein. In such procedures, various tools and catheters may then be progressed into the body and maneuvered using a real-time x-ray imaging system for guidance. An estimated 3,000,000 medical procedures of this type were performed in 1993 under x-ray fluoroscopy guidance. Many of these procedures involve the introduction of a catheter into the coronary arteries and the heart, and the evaluation of cardiac function by inspection of images taken when contrast media is introduced via a lumen in the catheter. Some of the tools that may be inserted in this manner include lasers where the laser device is located outside the body and the laser light delivered to the site of interest with a fiber-optic wave guide disposed in a catheter, drug delivery systems adapted to deliver precisely measured quantities of a specific drug or radiological material to the site of interest, ultrasound systems in which a transducer on the tip is used to view a site of interest by delivering the image over to a video system which can then display and record images of the site of interest, and other tools known to the art. It is also possible to adapt such procedures to non-medical applications where access is difficult and the value of the procedure high, e.g., engine diagnosis and repair.

As used herein, the term "maneuverable positioner" is meant to collectively include and refer to, for example, catheters, probes, endoscopes, and other maneuverable positioners and tools.

The known medical x-ray imaging devices do not provide a highly-accurate determination of location for maneuverable positioners with a precise image of the patient's internal structure. Generally, the physician using known systems can roughly ascertain the position of maneuverable positioners relative to body features within the patient, but precision and repeatability, the ability to return to the exact same place, especially in the axis parallel to the x-ray beam, is lacking. Thus the distance between the x-ray emitting source and the maneuverable positioner within the body may not be readily or accurately determined with the precision useful in today's advanced medical procedures, which may require, among other things, the ability to determine a position with the maneuverable positioner, move the maneuverable positioner, and return the maneuverable positioner to the exact same place.

For example, since 1982 there has been increasing use of catheter ablation to cure certain types of arrhythmia. In these types of arrhythmia, such as Wolff-Parkinson-White syndrome, the conductive congenital muscle fibers can be made nonconductive by heating them locally to a sufficient temperature to cause scar tissue to form. Most of these ablations are done with radio-frequency energy but the emitting electrode must be placed within one to three millimeters of the muscle fiber location and it must stay in intimate contact with it for a number of heartbeats and respiratory cycles.

Although the treatment of arrhythmia through catheter ablation has some advantages, there are also some problems. The advantages of the procedure are that it has a very high success rate, it is minimally invasive, it can be performed in a few hours in a procedure room, and it is considerably less expensive than open chest surgery or a lifetime of drug therapy. The major disadvantage is that the length of the procedure is uncertain and typically long. This leads to difficulty in scheduling physicians and facilities, fatigue for both patient and staff, and high-radiation dosages for patient and physician.

Attempts to solve these problems have focused mainly on providing more steerable catheters to reduce the time to find the precise location of the ablation site and to position the catheter for remaining in contact with the substrate during the ablation time, which is typically five to ninety seconds. Having more steerable catheters has not yet reduced the time or uncertainty of time because the location of the catheter is generally determined by looking at an x-ray image projected on a monitor and by analyzing the electrocardiogram. Both of these actions must be done in real time in order to know whether to move the catheter and in which direction to move it. The actual direction of movement may be uncertain due to the nature of an x-ray image of soft tissue and blood, the poor control and feedback of the catheter, the movement of the heart, and the difficulty of determining direction from the electrocardiogram analysis.

In the U.S., there are currently 300,000 to 500,000 people who die each year due to arrhythmia that is a result of a myocardial infarction. However, it is believed that if the slow-conduction zone around the infarct could be electrically mapped and selectively ablated, that a cure could be obtained. Tests on animals and some humans have demonstrated the possibility of such a procedure but the success rate has been low. The reason for the low success is thought to be the need to map the entire area of the infarct and slow conduction zone and then to be able to ablate multiple sites without depending on acquiring a characteristic electrogram once the ablation has begun. Current investigations attempting to solve the problem utilizing a catheter network array of nodes suffers from the problem of extracting the catheter network array from inside the heart without damaging the internal structure of the heart.

For various reasons, the imaging modalities of MRI, CT, and ultrasound are not normally suitable when anatomical markers are needed during cardiac diagnostic and treatment procedures. In addition, the use of known methods employing x-ray fluoroscopes for imaging typically has the serious disadvantage of not being able to distinguish anatomical detail inside the heart. The physician relies on the shadows generated, his or her intimate knowledge of the anatomy, the characteristic movement of the image and catheters caused by the cardiac cycle and the respiratory cycle, and for fine positioning, the electrocardiogram.

Accordingly, there is a need for devices and methods to provide a precise determination of the coordinates of a maneuverable positioner within a human patient during a medical procedure. The same techniques and apparatus can also be used to advantage in any x-ray procedure which requires accurate determination of the X, Y and Z coordinates of the position of a maneuverable positioner which may be adapted to sense x-rays.

SUMMARY OF THE INVENTION

An x-ray imaging system according to the present invention comprises a scanning-beam x-ray source and a multi-detector array. The output of the multi-detector array is input to an image reconstruction engine which combines the outputs of the multiple detectors over selected positions of the x-ray beam to generate a real-time x-ray image of the object.

An embodiment of an aspect of the invention includes an x-ray tube including a charged particle beam source and an anode target. Beam control circuitry focusses the charged particle beam and directs or scans the beam across the anode target in a predetermined pattern. For example, the predetermined pattern may be a raster scan pattern, a serpentine or "S" shaped pattern, a spiral pattern, a random pattern, a gaussian distribution pattern centered on a predetermined point of the anode, or such other pattern as may be useful to the task at hand.

A collimating element, preferably in the form of a grid, may be interposed between the x-ray tube and an object to be x-rayed. In one preferred embodiment, the collimating element is composed of a round metal plate having a diameter of about 25.4 cm (10 in) and includes a staggered array of apertures numbering 500 by 500 at the center row and column of the collimating element. The collimating element is preferably placed immediately in front of the emitting face of the x-ray tube. Other collimating element configurations may also be used. In one preferred embodiment, each of the apertures in the collimating element is constructed so that each of the axes of each of the apertures is directed toward (or points at) a detection point, e.g., the center of a multi-detector array, located a selected distance from the collimating element. That distance is selected to allow placement of the object to be x-rayed between the collimating element and the multi-detector array. In the preferred embodiment, the function of the collimating element is to form thin pencil beams of x-rays, all directed from a focal spot on the anode target of the x-ray tube toward the multi-detector array.

A multi-detector array,. preferably containing an array of detector elements (preferably an area array such as a $DET_x$ by $DET_y$ rectangle or square, or, more preferably, a pseudo-round array), is centered at the detection point. The multi-detector array preferably comprises a plurality of densely packed x-ray detectors. The multi-detector array is designed, positioned and applied, according to the present invention, in a manner that yields high sensitivity without loss of resolution. This results in an x-ray system having a resolution comparable to or better than that of known conventional x-ray systems at an exposure at least an order of magnitude less than that of the known x-ray systems. This aspect of the present invention provides important benefits in medical and other applications. X-ray dosage to patients and attending medical staff is reduced when using this aspect to perform current medical procedures. Procedures now believed to have too high a radiation exposure risk may become acceptable.

The output of the multi-detector array is preferably an intensity value for each detector of the multi-detector array for each x-ray beam emitted through an aperture in the collimating element. Because each aperture is located at a different point in space relative to the multi-detector array and the object under investigation, different outputs will be available from each detector of the multi-detector array for each aperture that the x-ray beam travels through. The multi-detector array output may be converted into an image in a number of ways.

The imaging system of the present invention is also capable of use in stereo imaging. In one embodiment, the collimation element contains two groups of apertures. For stereo imaging, the axes of one group of apertures is constructed to point to a first detection point on a first multi-detector array and the axes of a second group of apertures is constructed to point to a second detection point on a second multi-detector array. By constructing two images from the outputs of the multi-detector array and using conventional stereoscopic display methods, a stereo image may be produced.

An imaging system of the present invention is also capable of highlighted imaging of materials which exhibit different x-ray transmissivities at different x-ray photon energies. Accordingly, for example, microcalcification, which is associated with approximately 60% of the breast cancer diagnosed, may be imaged. Calcium is also typically associated with heart disease when found in the coronary arteries. In one embodiment, by constructing the collimation element and/or anode target to sequentially emit two or more groups of x-rays beams each having different x-ray energy spectra, and directing each group to the multi-detector array (more than one multi-detector arrays could also be used), the difference of transmissivities of the object under investigation at the various x-ray photon energies can be used to create an image, thus highlighting only those materials within the object under investigation which exhibit differential x-ray transmissivity. Optimized for the detection of calcium, for example, such an imaging system is a powerful tool for use in the early detection of breast cancer and other anomalies.

Utilizing a multi-detector array which intercepts the entire x-ray beam emitted from each aperture of the collimator element and image processing the array output is the preferred embodiment of the detector. It provides a maximum sensitivity without sacrificing the resolution provided by using a single small area detector. While a single detector of the same area as the multi-detector array would provide the same sensitivity, it would do so at the cost of a loss of resolution.

Additionally, sampling techniques utilizing information from less than a 1:1 image pixel to aperture ratio may be used for generating data from the multi-detector array which can reduce the complexity of the system, required processing speed, and energy consumption while providing virtually the same image quality.

An aspect of the present invention can also be used to identify the unique location of a marker transported within another object by a maneuverable positioner. In its most general sense, this would be accomplished by an x-ray sensitive marker disposed in a body and includes the transmission of an indication of the presence of x-ray radiation outside of the body in which it is disposed.

According to one embodiment of this aspect of the invention useful in medical applications, a catheter comprises an elongated body having a distal end adapted to be inserted into a body cavity, blood vessel, digestive tract, or the like and a proximal end available to a person performing a medical procedure. The catheter includes at least one lumen running therethrough. An optical fiber is disposed in the lumen and extends from the distal end to the proximal thereof. A miniaturized ("mini") x-ray sensor comprised of an x-ray sensitive material is disposed at the end of the optical fiber positioned at the distal end of the catheter. The end of the optical fiber at the proximal end of the catheter is coupled to a photodetector. The reaction of the sensor material of the mini x-ray sensor to an x-ray beam sequentially transmitted through a collimator, coupled with the transmission of that reaction to the photodetector, allows the determination of the precise position of the sensor material. Embodiments of the techniques to determine this precise position from the mini x-ray sensor reaction is discussed in detail below.

Another aspect of the present invention is the ability to determine the distance of a maneuverable positioner containing a mini x-ray sensor from a known reference plane. Each x-ray beam emitted through a collimation grid aperture of the present invention is shaped like a diverging cone with its apex at the anode target and its divergence angle determined by electron beam spot size on the anode target and the geometry of the collimation grid apertures with respect to the anode target. The divergent beams are designed to overlap more and more the farther you get from the x-ray source. The mini x-ray sensor in this aspect is preferably disposed in a maneuverable positioner and may have (but is not required to have) a size smaller than the spacing between the apertures of the collimation grid. When such a sensor is disposed in the x-ray field it will detect, during a complete scan cycle, x-rays from only a certain number of apertures, the number depending upon the mini x-ray sensor's distance from the output face of the collimation grid. When the mini x-ray sensor is located close to the output face of the collimation grid, it will react to x-ray pulses from a first number of apertures per scan cycle. At a greater distance from the output face, it will react to x-ray pulses from a second number of apertures greater than the first number. When the mini x-ray sensor is near the x-ray multi-detector array, it will react to x-ray pulses from an even greater number of apertures per scan cycle. By calibrating the number of apertures per scan cycle to which the mini x-ray sensors reacts with the mini x-ray sensor's distance from a known reference, the distance of the mini x-ray sensor from the reference may be determined by consulting a look-up table and/or by interpolation.

When used as described herein, the above-described embodiment of the present invention answers the long felt need for anatomical markers during cardiac diagnostic and treatment procedures. Since typical reference positions for electrocardiograms are the high right atrium, the bundle of HIS, the apex of the right ventricle, and the coronary sinus, there is an opportunity to have at least three points located in the x-ray image during the cardiac cycle. These three points can precisely locate the coordinates of the ablation catheter. Knowing the coordinates of these points, the physician can then map an area with the catheter and correlate its position with the electrocardiograms. He can then return to the same spot after leaving it and can measure bounce or other movement, he can also measure internal dimensions of the heart mapping points, determine wall thicknesses, build 3D images from the data and overlay cardiac action potentials. In addition, in a subsequent procedure the same locations may be found from overlaying the maps of anatomy and cardiac potentials.

The initial work performed with this aspect of the invention was to analyze the images from a biplane x-ray system when it was gated to the cardiac cycle. In some cases this positioning using image analysis is adequate but the precision can be greatly improved if an x-ray marker is included in the catheter. With conventional image intensifier technology, such a point sensor would not be useful since the entire field of view is irradiated simultaneously. However, in a scanning-beam x-ray system, the beam irradiates only a small field of view at a given time and therefore the location of the sensor in each individual catheter can be uniquely identified. By utilizing a stereo or biplane scanning-beam system, the sensor can be located in three dimensions provided that the two beams are synchronized. The advantage of the above described medical catheter embodiment of the invention is that it permits existing catheters inside the patient to now also function as anatomical markers when a mini x-ray sensor is employed, significantly reducing the time to map and ablate. Additional advantages are more detailed mapping of the cardiac substrate, correlation of the intercardiac electrodes with anatomical location, display in three dimensions of the intercardiac electrodes on an image of the heart, and comparison of electrograms from studies done at different times by overlaying.

It is an object of one aspect of the present invention to provide a scanning-beam x-ray imaging system capable of use in medical diagnostic procedures undertaken on living human patients.

It is also an object of another aspect of the present invention to provide a scanning-beam x-ray imaging system which provides high resolution images at adequate frame rates while minimally exposing the object under investigation to x-ray radiation.

It is a further object of another aspect of the present invention to provide a scanning-beam x-ray imaging system having improved resolution at a distance from the plane of the source of the x-rays while maintaining decreased x-ray flux levels.

It is also a further object of an aspect of the present invention to provide a method and apparatus for precisely determining the position of a maneuverable positioner within an object undergoing an x-ray procedure.

It is yet a further object of an aspect of the present invention to provide a method and apparatus for precisely and simultaneously determining and displaying information related to the X, Y and Z coordinates of a maneuverable positioner within an object undergoing an x-ray procedure.

It is also a further object of an aspect of the present invention to provide an electronic glove and other improvements in safety for medical applications by feedback of position from a mini x-ray sensor.

It is an object of another aspect of the present invention to provide for improved image quality by employing region of interest scanning.

It is a further object of an aspect of the present invention to provide a scanning beam x-ray imaging system for non-medical applications where scatter may degrade image quality, e.g., to image or inspect honeycomb airplane structures, corrosion, and printed circuit boards.

An advantage of an aspect of the present invention is that it can provide a method and apparatus for generating a "road map." For example, once a maneuverable positioner incorporating a mini x-ray sensor in accordance with the present invention has been threaded to a particular location of interest within the body or object, it can be removed and then re-threaded along the same path by generating waypoints, e.g., by determining X, Y and Z coordinates of various locations passed through during the first insertion. These waypoints may be obtained as frequently as desired along the first path taken to the location of interest to facilitate retracing the same path on subsequent occasions. This aspect of the present invention may have important application in intravascular and intracardiac ultra sound procedures.

Another advantage of an aspect of the present invention is that it can provide a method and apparatus to precisely locate and monitor the shape or position of stents. The precise location of the surface of a stent can be obtained through use of an x-ray sensing maneuverable positioner in accordance with the present invention by defining points along the surface of the stent, determining the X, Y and Z coordinates of those points and recording them. Subsequently, X, Y, and Z coordinates for those defined points can be redetermined and recorded over time and changes in shape or position of the stent can be observed and plotted.

Another advantage of an aspect of the present invention is that it can provide a method and apparatus for repeatable delivery of drugs, radiologic and similar materials to a specific site in the body.

These and many other objects and advantages of the present invention will become apparent to those of ordinary skill in the art from a consideration of the drawings and the description of the invention contained herein. The principles of the present invention may be employed in any application, medical or industrial. Principles or aspects of the present invention can be applied for example where location of internal features of an object is desired and insertion of an x-ray sensitive device is feasible. Industrial applications are variously called x-ray inspection, x-ray analysis, failure analysis, non-destructive testing, and in-situ testing.

BRIEF DESCRIPTION OF THE DRAWINGS

FIGS. 3A, 3B, 3C, and 3D are partial cross-section representations of collimation grids useful in the inventive device.

FIG. 17 is a layout arrangement plan for FIGS. 18–25.

FIGS. 18–25 provide a single functional block diagram of components of a preferred scanning-beam x-ray imaging system.

FIG. 18 and 19 are partial functional block diagrams comprising a preferred x-ray source for a scanning-beam imaging system.

FIG. 20 is a partial functional block diagram comprising a preferred dual multi-detector array for a scanning-beam imaging system.

FIGS. 21 and 22 are partial functional block diagrams comprising preferred monitor for a scanning-beam imaging system.

FIGS. 23 and 24 are partial functional block diagrams comprising a preferred scan generator for an scanning-beam imaging system.

FIG. 25 is a partial functional block diagram depicting the functional interconnection of the functional blocks of FIGS. 20, 22 and 23.

FIG. 36 diagrammatically depicts a preferred detector arrangement of 144 logical detector elements in the presently preferred image reconstruction engine.

FIG. 38 is a diagram showing the preferred beam alignment octant arrangement.

FIGS. 55A–E comprise schematics of the preferred beam controller interface.

FIG. 61d depicts an atherectomy catheter that incorporates an embodiment of in x-ray sensor locating device.

FIG. 61d is a diagram showing how the presently preferred x-ray markers may be used to determine the rotational orientation of the catheter in which they are employed

DESCRIPTION OF THE PREFERRED EMBODIMENTS

The following description of the aspects of the present invention is illustrative only and not to be construed as in any way limiting to the inventive concepts disclosed and claimed herein.

System Overview

Figure 1:
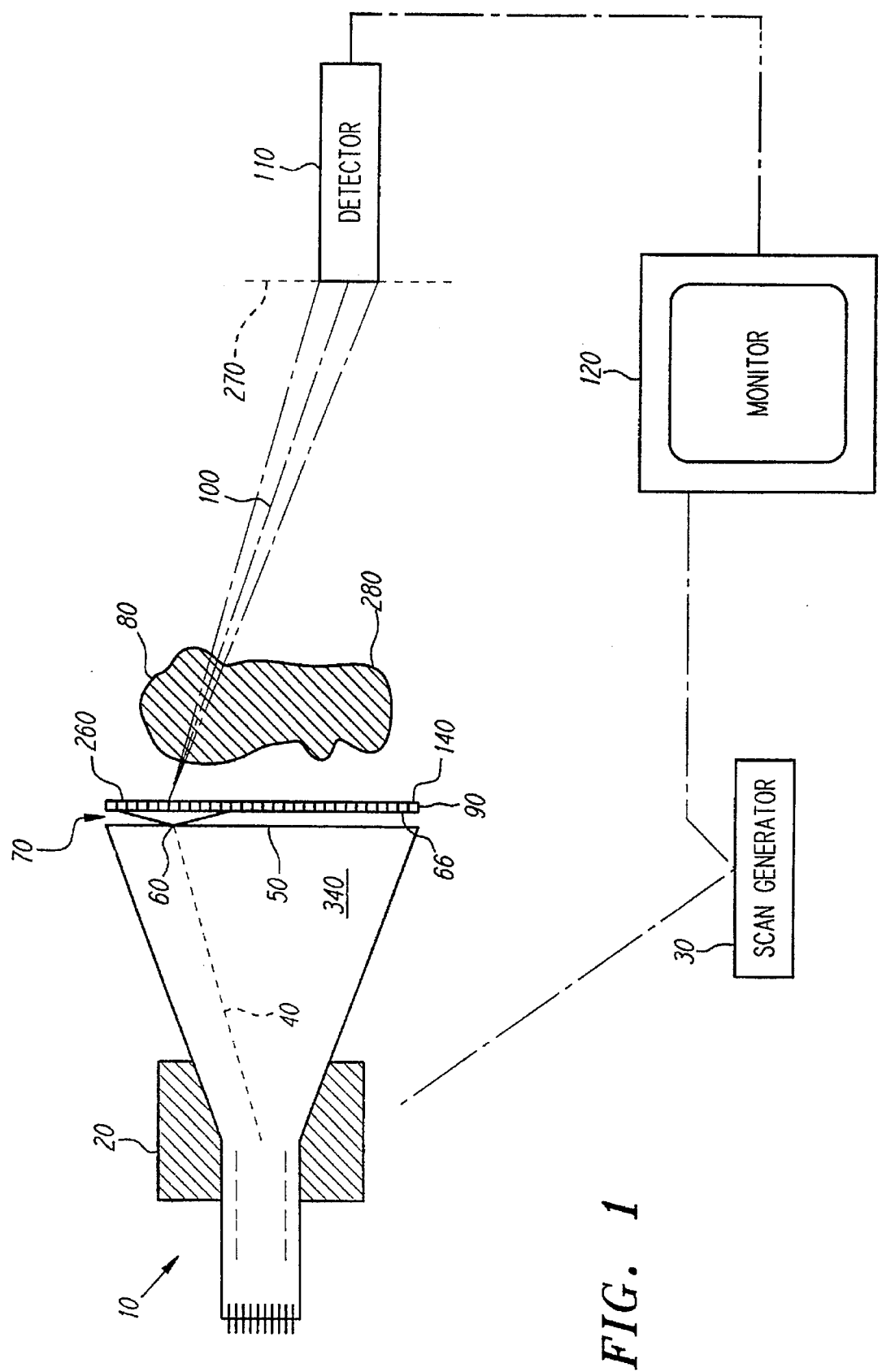
FIG. 1 is a diagram showing the basic components of a preferred low dosage scanning-beam x-ray imaging system.

Turning to FIG. 1, a scanning-beam x-ray imaging system according to a preferred embodiment of the present invention is diagrammed. The x-ray source is preferably a scanning x-ray source 10 preferably comprising a power supply capable of generating approximately −100 kV to −120 kV, which can operate x-ray tube 10 at about −70 kV to −100 kV. At this voltage level, x-ray source 10 produces a spectrum of x-rays ranging to 100 keV. As used herein, the term 100 keV x-rays refers to this spectrum. X-ray source 10 includes deflection yoke 20 under the control of scan generator 30. An electron beam 40 generated within x-ray source 10 is scanned across a grounded anode target 50 within x-ray source 10 in a predetermined pattern. Hereinafter, for simplicity, anode target 50 is referred to as target 50. For example, the predetermined pattern may be a raster scan pattern, a serpentine (or "S" shaped) pattern, a spiral pattern, a random pattern, a gaussian distribution pattern centered on a predetermined point of the target, or such other pattern as may be useful to the task at hand. Presently preferred is the serpentine (or "S" shaped) pattern which eliminates the need in a raster scan pattern for horizontal "fly back."

As electron beam 40 strikes target 50 at focal spot 60, a cascade of x-rays 70 is emitted and travel outside of x-ray source 10 toward the object 80 to be investigated. To optimize system performance of the presently preferred embodiment, a cone of x-ray photons should be generated that will diverge in a manner that will just cover the multi-detector array 110.

Figure 2:
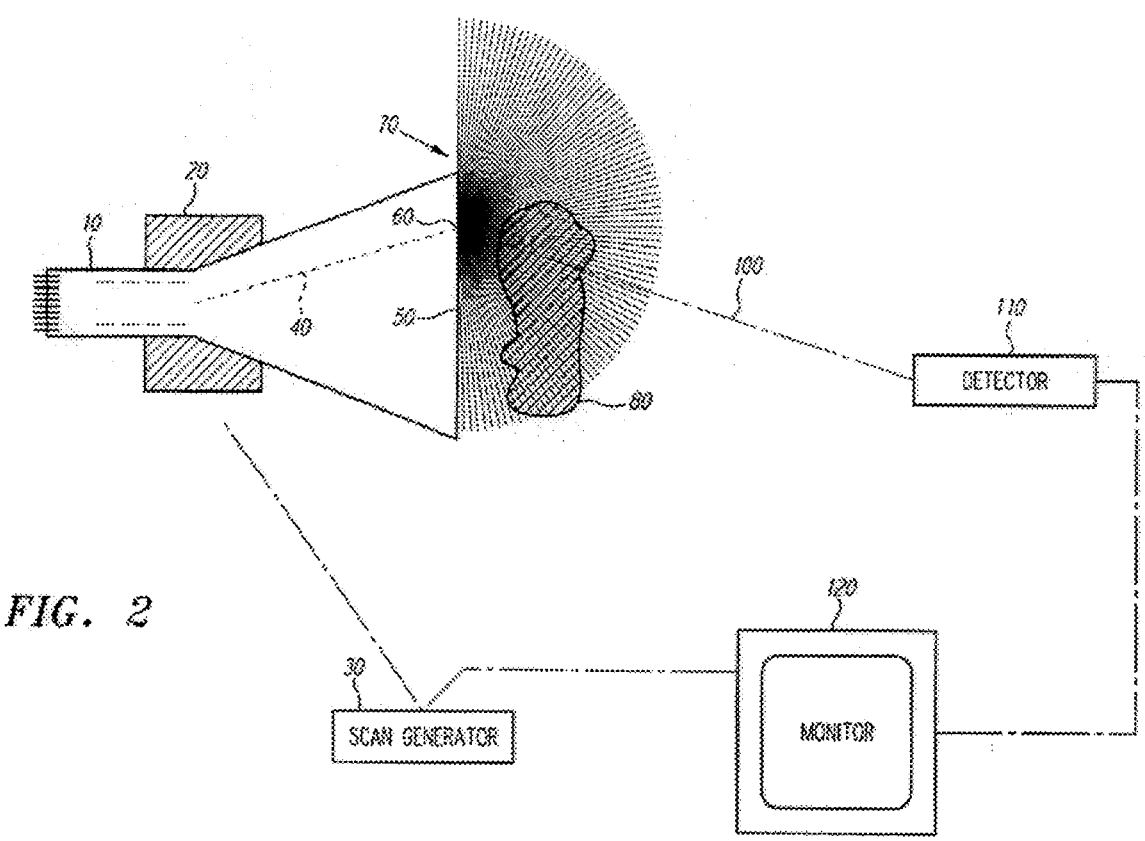
FIG. 2 is a diagram showing the distribution of x-rays in the forward direction from a scanning-beam x-ray imaging system in the absence of a collimation grid.

This is preferably accomplished by placing a collimating assembly between the target 50 of the scanning x-ray source 10 and the multi-detector array 110, and more preferably between the target 50 and the object to be imaged. The presently preferred collimating assembly is a collimation grid 90, containing a grid of x-ray transmissive apertures 140. Collimation grid 90 is designed to permit passage of only those x-ray pencil beams 100 whose axes lie in a path that directly intercepts multi-detector array 110. Collimation grid 90 does not move with respect to multi-detector array 110 while the system is in operation. Thus, as electron beam 40 is scanned across target 50, at any given moment there is only a single x-ray pencil beam 100 which passes through object 80 to multi-detector array 110. This preferred result is in contrast to the result in FIG. 2, which depicts the distribution of x-rays 70 from a scanning-beam x-ray source in the absence of a collimator assembly. For purpose of illustration only, the scatter from x-rays 70 which strike multi-detector array 110 is not shown in FIG. 2.

The output of multi-detector array 110 is processed and displayed on monitor 120 as luminance values. Image processing techniques can be used to produce a computer driven image on an appropriate display or photographic or other medium.

The embodiment of the inventive system disclosed herein is a low exposure system in that it typically exposes the cardiology patient at a rate of about 0.09 to 0.33 R/min with a 30 frame/sec refresh rate measured at the entrance to the patient, which in conventional systems under the same conditions would typically be between 2.0 to 2.8 R/min. Whole body exposure with a 30 frame/sec refresh rate with the present inventive system will be lower than that for conventional systems as well.

The X-Ray Tube

Figure 3:
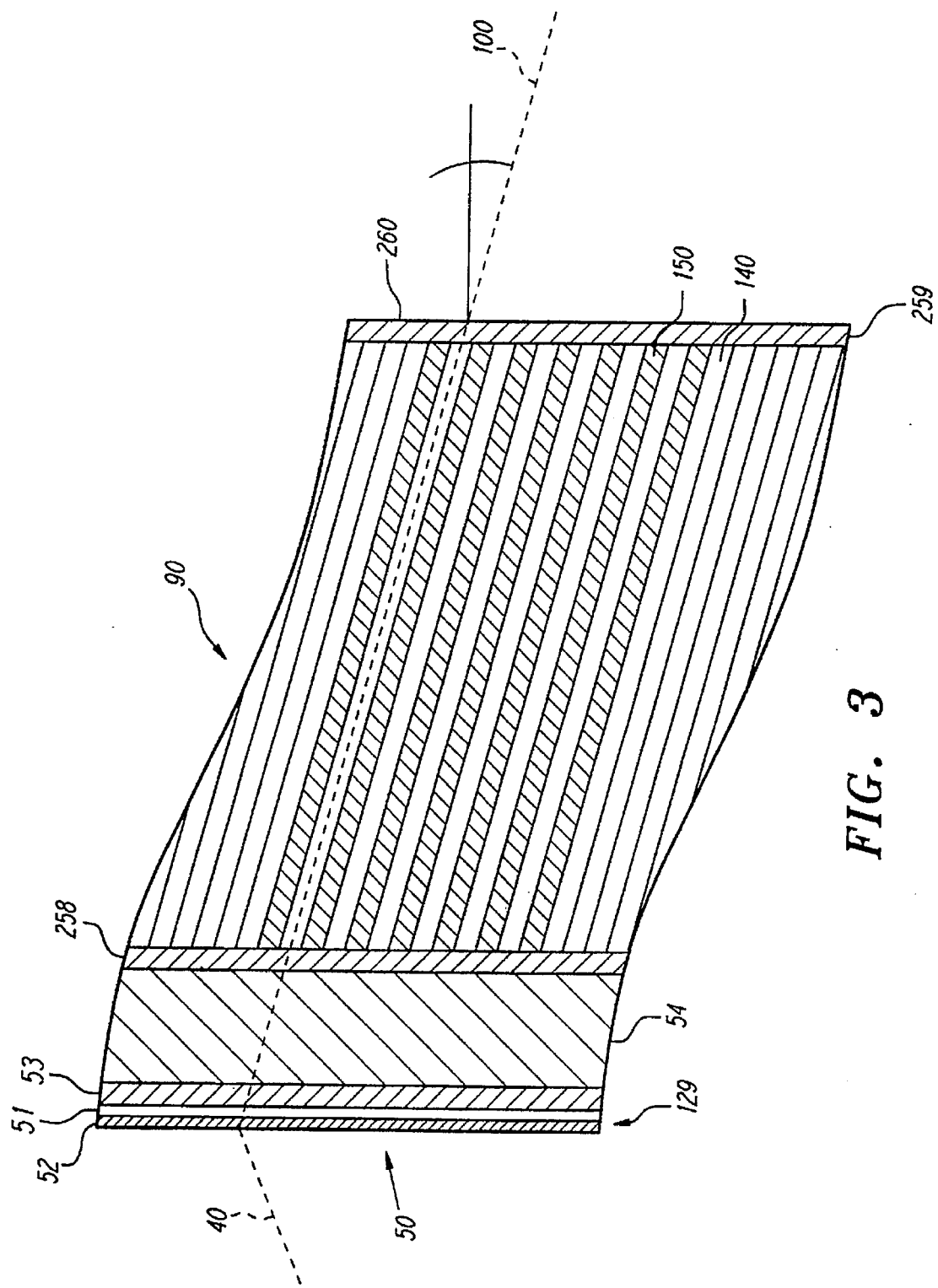
FIG. 3 is an enlarged cross sectional representation of a portion of a preferred collimation grid and target of an x-ray tube for use in a preferred low dosage scanning-beam x-ray imaging system.

FIG. 3 depicts a magnified diagrammatic view of a preferred collimation grid and target structure. Target 50 is preferably comprised of a target layer 129 of a material having good vacuum characteristics and the ability to withstand high heat and electron bombardment, which is then formed upon a beryllium target support 53. Aluminum or other relatively x-ray transparent materials can be used to fabricate the target support 53 as well. A preferred construction of the target layer 129 is a first layer of niobium 51 approximately 1 micron thick sputter-deposited upon the beryllium target support 53 to which is then sputter-deposited a second layer of tantalum 52 approximately 5 microns thick. This structure is presently preferred because niobium has a thermal coefficient of expansion intermediate to the coefficients of thermal expansion of tantalum and beryllium, thus reducing or preventing microcracking due to thermal cycling of the target as the electron beam 40 scans across the target. Another embodiment is a layer of tantalum approximately 5 microns thick sputter deposited directly on the beryllium target support 53. Yet another embodiment is a layer of tungsten-rhenium approximately 5 microns thick sputter-deposited on the beryllium target support 53. Still another embodiment is a layer of tungsten approximately 5 to 7 microns thick sputter deposited on the beryllium target support 53. Tantalum, tungsten and tungsten-rhenium are presently preferred for use in target layer 129 because they have relatively high atomic numbers and densities and readily emit x-rays when bombarded by an electron beam. Tungsten's high melting point of 3370° C. and good vacuum characteristics make it suitable for the high temperature and hard vacuum conditions within the x-ray source. Tantalum and tungsten-rhenium have similar characteristics as known to those of skill in the art. The thicknesses of the target layers are preferably selected so that they are approximately equivalent to the distance necessary to efficiently convert 100 keV electrons to x-rays.

Beryllium is presently preferred for target support 53 because it is strong and does not significantly attenuate or scatter the x-rays emitted from target layer 129. The thickness of beryllium target support 53 is preferably about 0.5 cm. In the presently preferred embodiment of the present invention, target support 53 should be constructed as thin as possible subject to the physical constraint that it must be strong enough to withstand the pressure gradient of one atmosphere across it.

A cooling chamber 54 is preferably located between the target support 53 and collimation grid 90.

Collimation grid 90 preferably consists of an array of apertures 140, the axes of each, according to one preferred embodiment of the present invention, are oriented or pointed toward multi-detector array 110. That is to say that the axes of apertures within the collimation grid 90 are not parallel to each other and form an acute to the line perpendicular to the output face 260 of the collimation grid 90. For example, a collimation grid for a chest x-ray application may comprise apertures forming an angle with a line perpendicular to the output face 260 of the collimation grid 90 of between 0° at the center of the collimation grid 90 to as much as 20° at the edge of the grid 90. A mammogram application on the other hand may have a collimation grid 90 comprising apertures forming an angle with a line perpendicular to the output face 260 ranging to 45° at the edge of the grid. Thus, a different collimation grid 90 may be selected and inserted for use in different medical applications.

The number of apertures 140 in collimation grid 90 may correspond to the number of image pixels to be generated on the monitor. For example, 500 by 500 to 1024 by 1024. Alternatively, the image pixel to aperture ratio may be increased, i.e., fewer apertures than image pixels may be used, in conjunction with the technique of "sub-sampling" discussed below. The system spatial resolution may be determined, in part, by the pitch of the apertures in collimation grid 90. The precise number of apertures suggested above is illustrative only, and is not intended in any way to be limiting.

Some of the factors preferably used to determine the thickness of collimation grid 90 and the diameter of apertures 140 are the distance of the multi-detector array 110 from target 50, which is presently preferably 94.5 cm (37.2 in), the desire to significantly attenuate all x-rays 70 not aimed at the multi-detector array 110, and the size of the multi-detector array 110 (not shown in this figure). Apertures 140, as viewed from output face 260, are preferably laid out in a rectangular row and column pattern containing a substantially circular boundary 25.4 cm (10 in) in diameter forming a circular active array. The aperture array may, however, be of any convenient layout to resolve the image of object 80. Further, the electron beam 40 may be scanned in a pattern which employs only a portion of the apertures 140. The circular active area according to one preferred embodiment of the present invention has a diameter of approximately 500 apertures.

The x-ray absorbent portion 150 of preferred collimation grid 90 is designed to absorb errant x-rays so that they do not illuminate object 80. This is accomplished by fabricating the preferred collimation grid 90 with sufficient thickness so that the x-ray radiation passing through an aperture 140 towards the multi-detector array 110 is substantially greater than the cumulative x-ray radiation passing through x-ray absorbent portion 150 in all directions other than toward multi-detector array 110. Such errant x-rays would provide the object 80 and attending staff with x-ray dosage but contribute no meaningful information to the image.

Figure 3A:
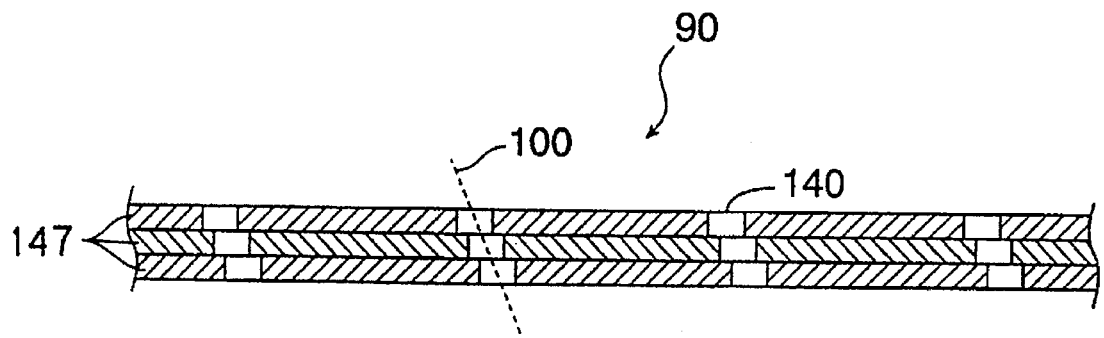

Collimation grid 90, as shown in FIG. 3A, is preferably fabricated from a number of sheets 147 of x-ray absorbing materials having apertures 140 therethrough to form an x-ray pencil beam 100 as the x-rays pass through the collimation grid to the multi-detector array 110. The material used for the sheets 147 can be formed from x-ray opaque materials such as molybdenum, brass, lead, copper, tungsten, tantalum, gold or any of these used in combination. The collimation grid 90 is preferably fabricated of 50 thin sheets of 0.0254 cm (0.010 in) thick molybdenum which are stacked and held together by end plates 258 and 259. Molybdenum is a preferred material for sheets 147 because it readily absorbs x-rays so that x-rays generated by x-ray source 10 which are not directed to multi-detector array 110 will be absorbed before they impinge upon object 80, which, of course, may be a human patient. The end plates 258 and 259 are constructed from an x-ray transmissive material, preferably aluminum. Aluminum is a preferred material for plate 259 to minimize x-ray generation in molybdenum collimation sheets 147.

Alternatively, collimation grid 90 can be formed of sheets 147 fabricated out of both high atomic number materials and low atomic number materials to minimize the amount of fluorescent K x-rays which emanate to the patient. Fluorescent K x-rays, which are generated by the interaction of the x-rays emanating from the target 50 with the materials of the collimator sheets 147, are typically undesirable because they increase patient exposure without contributing to the formation of an x-ray image. The K x-rays can be attenuated by plate 259, but plate 259 should also be transparent to pencil beam 100. This is preferably accomplished by using materials of low atomic number for sheets 137, preferably brass, since low atomic number materials produce low energy K x-rays which can be strongly attenuated by plate 259. For example, a sheet of aluminum 1 mm thick for plate 259 will typically reduce the K x-ray intensity of brass by approximately 99.9%, while being relatively transparent to the higher energy x-rays of pencil beam 100. Brass is therefore a superior material for sheets 137 from the point of view of stopping K x-rays but, by itself, provides inadequate attenuation for the x-rays emanating from target 50 which do not pass through collimator aperture 140. Therefore collimator sheets 137 preferably comprise a combination of materials, with higher atomic number materials such as tungsten, lead or molybdenum at the side of collimation grid 90 closest to the target 50 and low atomic number material such as brass on the side closest to the object 80 to be imaged. Presently preferred is a combination of molybdenum and brass, which provides for high collimation grid efficiency while producing low energy K x-rays which are strongly attenuated by plate 259.

The apertures 140 of collimation grid 90 are preferably either round or square in cross section. Other shapes could also be used, particularly hexagons, although the shape of the aperture holes should preferably match the shape of the multi-detector array, since the aperture shape affects the shape that x-ray beams will tend to diverge into. For example, the presently most preferred round aperture hole will tend to produce an x-ray beam that diverges into a circular shaped beam at the multi-detector array. Therefore, if round apertures are used, the multi-detector array is preferably circular to maximize its exposure and coverage to the circular x-ray beams.

If square apertures 140 are used they should preferably be 0.0381 cm (0.015 in) by 0.0381 cm in dimension while round apertures are preferably 0.015 in (0.038 cm) in diameter. Both square and round apertures yield a cross sectional area at multi-detector 110 that is about $\frac{1}{100}$ the cross sectional area of detectors of known x-ray fluoroscopes. The cross sectional area of the face of the multi-detector array 110 is much smaller than in known conventional systems. As a result, x-rays scattered at the object miss the multi-detector array and do not tend to fog the image as they do in conventional systems which typically utilize relatively large surface area detectors.

Figure 3B:
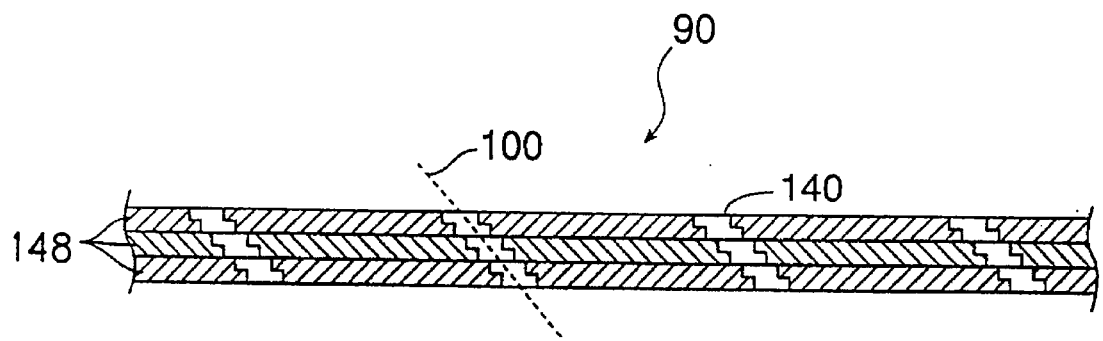

The presently preferred method for fabricating the collimation grid 90 is by photo-chemical milling or etching. Photo-chemical milling is presently preferred because it is cost effective and accurate. According to one embodiment of this method, a set of 50 photo masks is created to etch holes or interstices into 50 thin sheets of 0.0254 cm (0.010 in) thick material. In an alternate embodiment, a set of 100 photo masks is created to etch holes or interstices into each side of the 50 thin sheets of 0.0254 cm (0.010 in) thick material. The etched sheets are then preferably stacked, aligned and held together to form a grid assembly having a plurality of stepped apertures, each of a predetermined angular relationship with respect to the sheets. FIG. 3A shows an embodiment of the preferred collimation grid 90. This variation includes a number of x-ray absorbing sheets 147 having individual apertures with a constant cross-section (however, the cross-section need not be constant). The resulting aperture 140 has a stepped configuration, as shown, while allowing the x-ray pencil beam 100 to pass through to the multi-detector array 110. The variation shown in FIG. 3B is quite similar to that shown in FIG. 3A except that the individual apertures formed in x-ray absorbing sheets 146 are themselves stepped. These stepped apertures may be made by milling or chemical etching from each side of sheet 146 with a slight offset as described above so as to result in the configuration shown. The FIG. 3B configuration is highly desirable because less x-ray energy need be absorbed within the stepped apertures 140 of collimation grid 90 and consequently, the x-ray flux at the edge of the x-ray beam 100 is not attenuated as much as in the variation shown in FIG. 3A. X-rays are generally unaffected by the roughness of the channels due to the stepped surface, and even if they are scattered within the aperture, the scattering will not measurably affect the resultant beam. The stepped apertures shown in FIGS. 3A and 3B can also be beneficial in controlling the K x-ray intensity as discussed in U.S. Pat. No. 2,638,554, issued to Bartow et. al., entitled "Directivity Control of X-rays."

Figure 4:
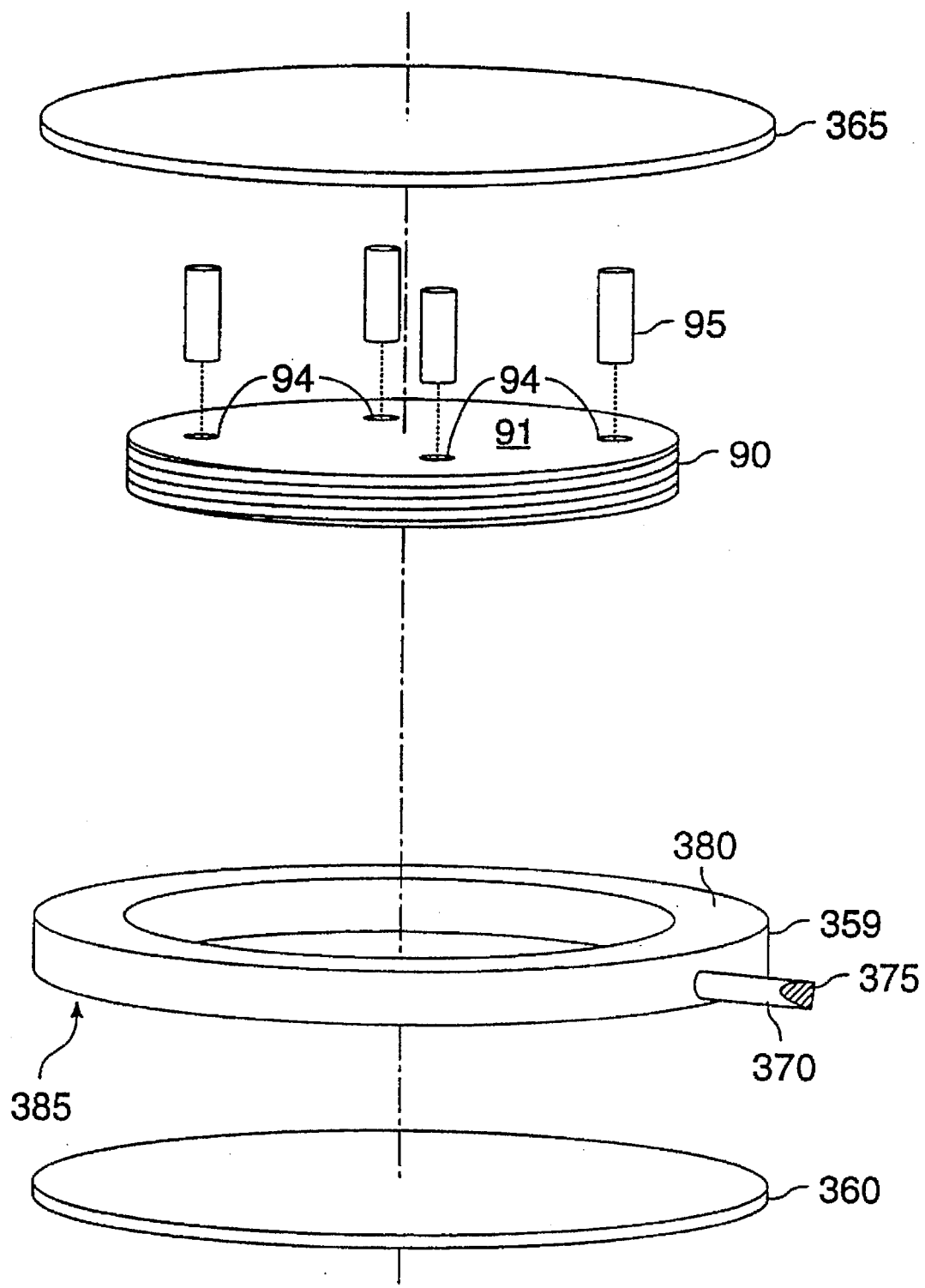
FIG. 4 is a perspective exploded diagram showing assembly for a preferred embodiment of a collimator grid.

FIG. 4 shows a preferred method for assembling the preferred collimation grid assembly 90 from etched sheets 91. Preferably 50 etched sheets 91 are each provided with alignment holes or alignment apertures 94. Alignment pegs 95 are placed in each alignment aperture 94 to align the etched sheets 91. The assembled sheets 91 and pegs 95 are placed in aluminum ring 359. Aluminum ring 359 is provided with a vacuum port 370 which may, after assembly, be sealed with pinch off 375. Aluminum sheet 365 which is preferably 0.1 cm in thickness is bonded and sealed with a vacuum adhesive to upper surface 380 of ring 359. Aluminum sheet 360 is similarly bonded to a lower surface 385 of ring 359. A partial vacuum is then pulled through port 370 and the port 370 is then sealed at pinch off 375. The partial vacuum causes relatively x-ray transparent aluminum sheets 360 and 365 to provide a clamping action tending to hold etched sheets 91 together and in alignment to form a collimation grid 90. The presently preferred tolerance for the aperture center-to-center distance is +/−0.00127 cm (0.0005 in) without cumulative error. The presently preferred tolerance on the aperture sizes is +/−0.00254 cm (0.001 in). For ease in assembly the diameters of apertures in every other sheet may be fabricated to be larger than the diameter at the output face of the collimator. Thus, only every other sheet need be carefully aligned. The material used for the sheets 91 as discussed above can be molybdenum, brass, lead, copper, tungsten, tantalum, gold or any of these used in combination. Molybdenum is a preferred material for use in the sheets 91, but more preferred at present is a combination of molybdenum and brass.

In an alternate method to fabricate collimator grid 90, the alignment holes 94 are etched along with the apertures 140. However, due to the differential between the sizes of the apertures 140 and the alignment holes 94, undercutting of the apertures 140 occurs because the time for etching is governed by the time it takes to etch the large holes. In a presently preferred alternative method, pilot alignment holes smaller than the final size of the alignment pegs are etched into the sheets 91. The etched sheets 91 then undergo an additional procedure such as reaming to enlarge the pilot alignment holes to the desired diameter. The finished sheets are aligned and clamped together as previously described.

Alternative methods for fabricating collimation grid 90 include electron beam machining, drilling, mini-machining, and laser drilling. Drilling and laser drilling are useful for generating round holes, but a drawback is the relative difficulty in generating square holes with either method. In addition, these non-etch methods typically require greater time and costs when compared to the above described etching methods.

Figure 5:
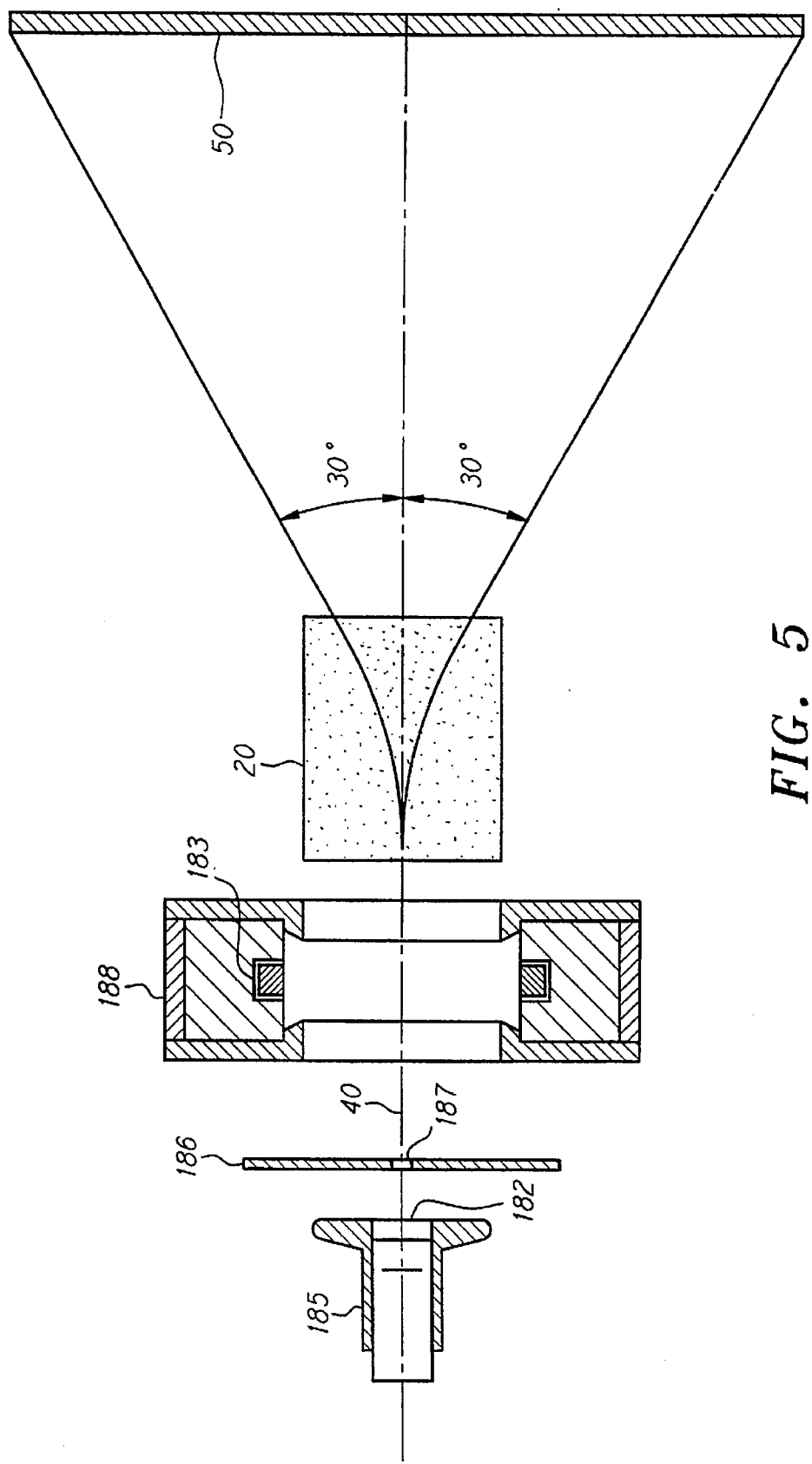
FIG. 5 is a functional representation of components of an x-ray tube for a scanning-beam x-ray imaging system.
Figure 6:
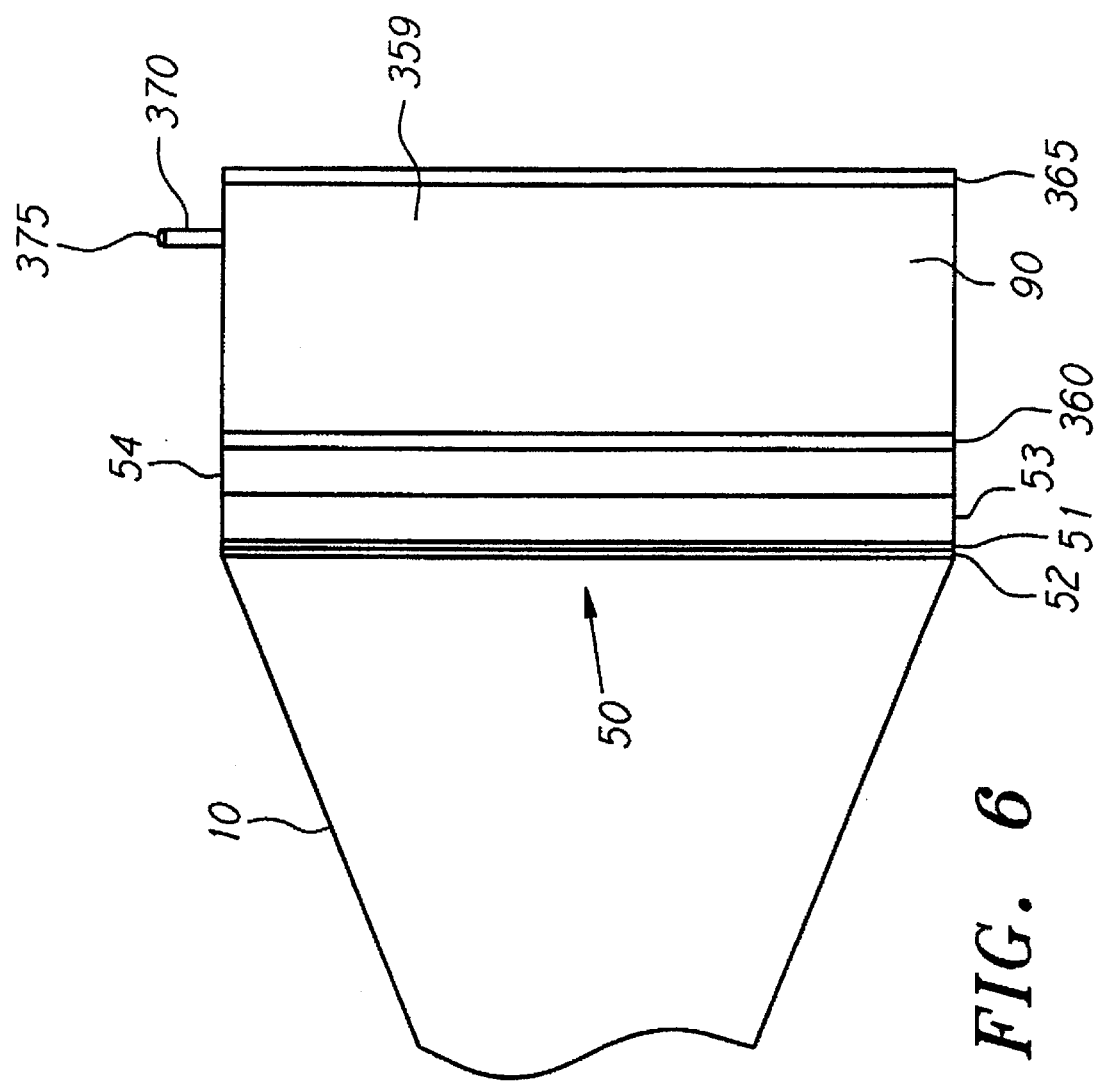
FIG. 6 is a diagram showing the target end of a preferred x-ray tube for a low dosage scanning-beam x-ray imaging system.

More details of the preferred scanning x-ray source 10 are shown in FIGS. 5 and 6. Grid controlled electron gun 185 is preferably located opposite the face of x-ray tube 10 and is operated at a potential between −70 kV to −120 kV. The electron beam 40 emanating from electron gun 185 can be controlled in amplitude and can be rapidly reduced to zero by the application of an appropriate voltage to a control grid 182. Grounded target 50 is preferably located at the face of the tube and electron beam 40 is preferably emitted from electron gun 185 towards target 50. A grounded anode 186 is preferably located near electron gun 185 and includes an aperture 187 at its center for electron beam 40 to accelerate the electrons as they pass through. Divergent electron beam 40 is accelerated towards anode 186 and passes through aperture 187. Magnetic focus lens 188, preferably of fixed power, causes the electron beam 40 to become convergent so that it strikes target 50 at focal spot 60. Focal spot 60 preferably has a diameter of 0.3 mm. Varying currents flowing in the coils of magnetic deflection yoke 20 preferably deflect the electron beam 40 so that focal spot 60 moves over the surface of target 50 in the previously mentioned preferred serpentine pattern. Dynamic focus coil 183 is energized by a current which varies in synchronism with the varying current in deflection yoke 20 to maintain the preferred 0.3 mm diameter for focal spot 60 as the electron beam 40 is scanned over the surface of target 50. The tube is preferably fabricated to have a 25.4 cm (10 in) diameter sweep area to correspond with the circular active area of the collimator grid 90. Electron beam 40 intersects target 50 at an angle of up to about 30° at the extremities of the circular active area. When the x-ray source 10 is in use, no more than one aperture 140 (possibly two for stereo) of collimation grid 90 will be passing an x-ray pencil beam 100 at any given instant. According to one preferred embodiment, the electron beam 40 may be shut off by application of a short rise voltage pulse to control grid 182 when focal spot 60 is not positioned directly in front of an aperture 140. Thus the x-ray tube may be operated effectively in a scanned-pulsed mode to reduce power consumption approximately 25% and heating of the target 50.

Turning to FIG. 6, a cross-sectional view of the front portion of the preferred x-ray source 10 is depicted. The interior of the x-ray source 10 is maintained at a vacuum. Target 50 as discussed above is comprised of a suitable target material deposited on beryllium target support 53 which is 0.5 cm thick. Forward of beryllium target support 53 is cooling jacket 54 which is preferably 0.2 cm thick and may be adapted to carry water, forced air or preferably Fluorinert". Aluminum grid supports 360 and 365 are each preferably 0.1 cm thick and help support collimation grid 90 which is preferably 1.27 cm (0.5 in) thick. Aluminum grid supports 360 and 365 together with the beryllium target support 53 and the coolant in cooling jacket 54 preferably form an x-ray filter which filters out low energy x-rays. The presently preferred x-ray source is described more fully in copending U.S. patent application Ser. No. 08/386,884 which has been incorporated herein by reference in its entirety.

Stereoscopic X-ray Imaging

Figure 7:
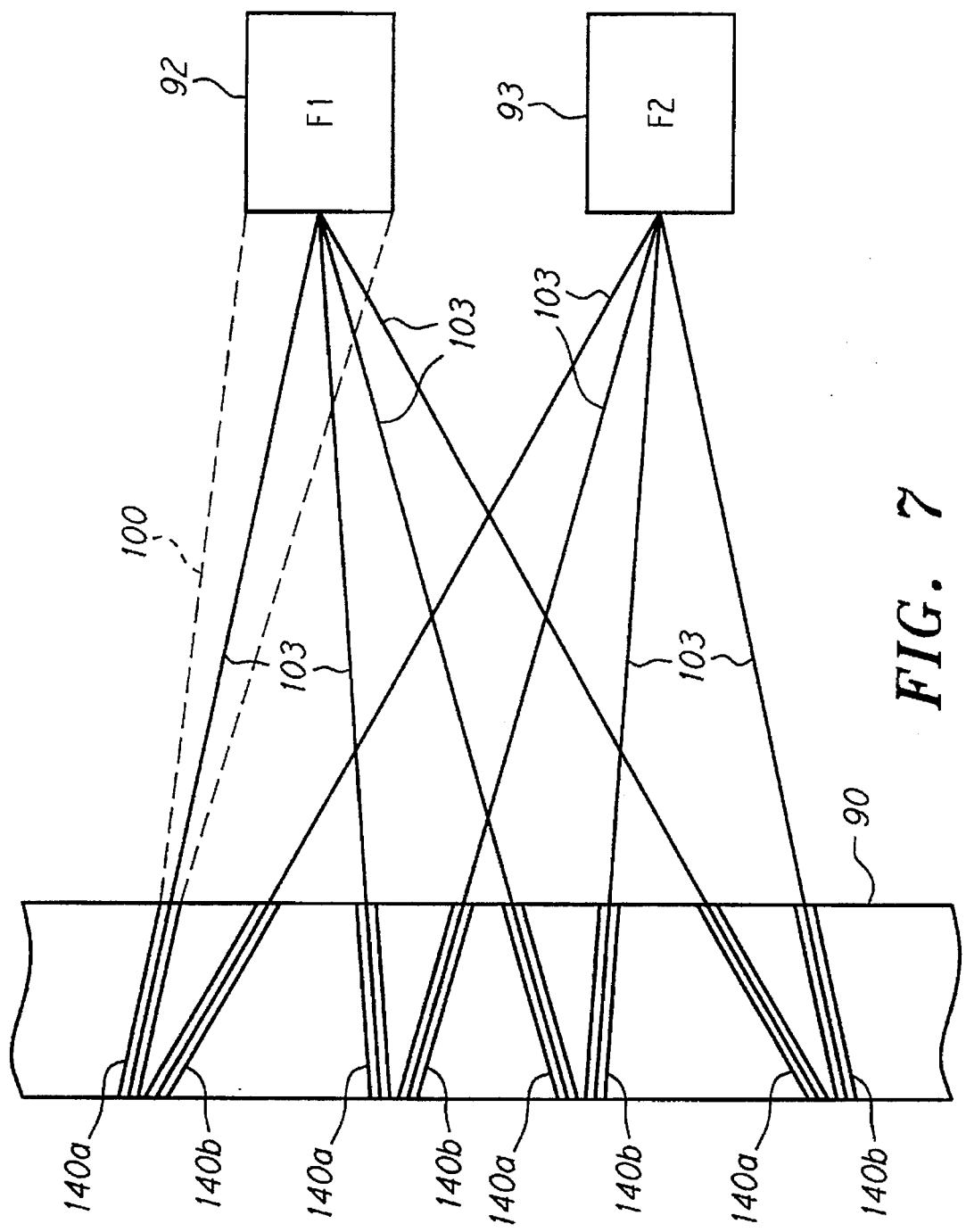
FIG. 7 is a diagram showing the axes of x-ray beams for a stereoscopic scanning-beam x-ray imaging system.

Turning now to FIG. 7, a collimation grid having more than one focal point may be provided so that stereoscopic x-ray images may be obtained. If, for example, the axes 101 of the x-ray pencil beams 100, corresponding to the aperture axes of every other row of apertures 140a in grid 90 are pointed at focal point F1 at the center of multi-detector array 92 and the aperture axes of the remaining apertures are pointed at focal point F2 at the center of multi-detector array 93, one can scan the apertures in a raster or serpentine pattern and create a "line" of data from the first multi-detector array, and a line of data from the second multi-detector array. Repeating this, it is possible to build up two complete images, as seen from two distinct angles and thereby display them with conventional stereoscopic imaging display systems to provide a stereoscopic x-ray image.

Figure 3C:
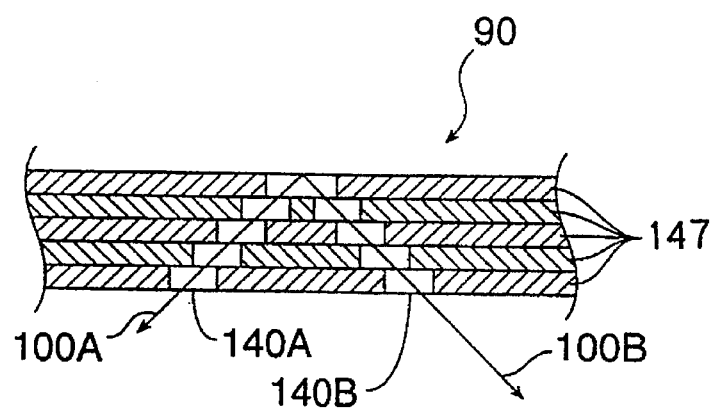

FIG. 3C depicts how one may construct such a stereoscopic collimation grid out of layers 147 of x-ray absorptive material. In this embodiment apertures 140A, 140B may diverge from a common first aperture 140 to form a "V" as shown providing separate paths along the "legs" of the "V" for x-ray pencil beams 100A, 100B. There is no requirement, however, that apertures 140A, 140B diverge from a common aperture as shown, but an advantage of the "V"-shaped aperture where the x-rays enter at the common aperture or apex of the "V' is that both multi-detector arrays 92 and 93 will be illuminated simultaneously, the "V" acting as an x-ray splitter with some of the x-rays going to multi-detector array 92 and some to multi-detector array 93. This decreases by 50% the power required for the beam current.

Additionally, the system may be designed to such that the common adjacent holes in the first sheet share common holes in the last sheet last two sheets as shown in FIG. 3D.

The Multi-Detector Array

To achieve resolutions of several line pairs per millimeter or more at the object plane, as are required in some medical applications, the spatial resolution limit in known reverse-geometry systems is in large part determined by the size of the single nonsegmented detector. Generally speaking, a small non-segmented detector can provide high spatial resolution while a large non-segmented detector provides high collection efficiency. It has in part been this trade-off that has been a problem in developing low dosage x-ray imaging systems. Other parts have been the inability to fabricate a suitable collimator and the lack of a high efficiency x-ray scintillator also having a fast decay time.

Figure 8A:
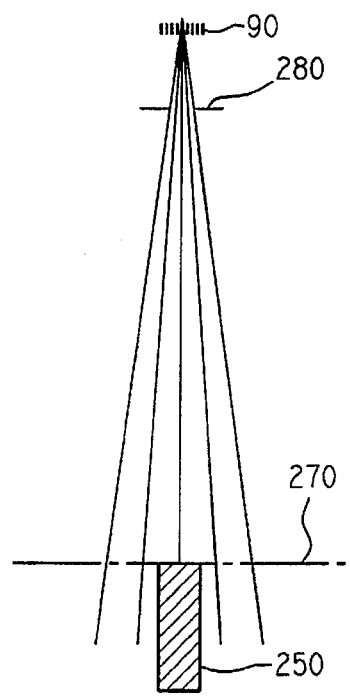
FIG. 8A depicts an x-ray beam from a single aperture of an apertured x-ray source interacting with a multi-detector array.
Figure 9:
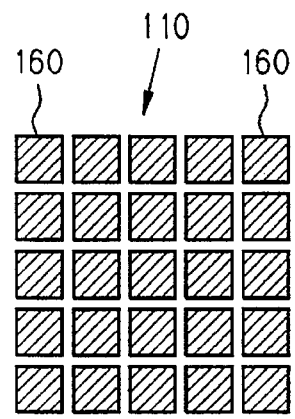
FIG. 9 is a front view of a 5×5 detector array.

When such a detector is small to increase resolution, a large proportion of the x-rays emitted by target 50 are unused by the single detector 250, as shown in FIG. 8A even when a collimator grid 90 is used. This is, in fact, how industrial reverse-geometry scanning-beam x-ray inspection systems are designed, where dose is usually not a consideration. Accordingly, while one can decrease the size of a detector by placing, for example, a lead washer in front of the single detector 250 and thereby increase spatial resolution, the x-ray intensity and/or exposure time would have to be increased to maintain contrast resolution By fabricating a multi-detector array having a large area subdivided into multiple smaller detector array elements (e.g., as shown by the front view of the multi-detector array 110 in FIG. 9) a large capture area is achieved, while simultaneously through image reconstruction techniques described herein retaining an image resolution that is comparable to the size of a single small detector element without increasing x-ray intensity an/or exposure time.

Figure 8B:
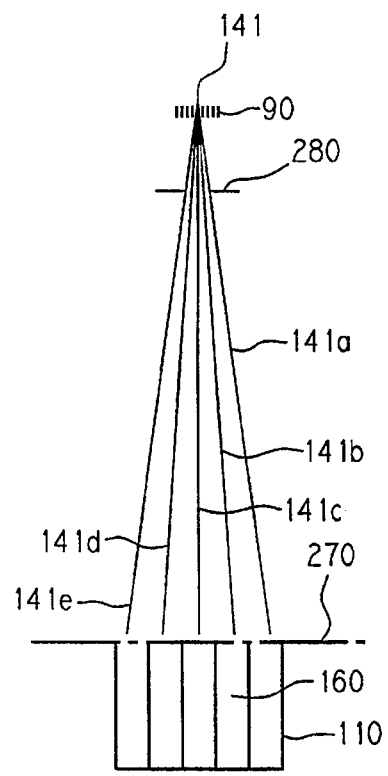
FIG. 8 depicts a single nonsegmented detector that is smaller in width than the x-ray beam emitted from an apertured x-ray source.
FIG. 8C depicts the axes for x-ray beams from a number of apertures of an apertured x-ray source passing through the same image pixel interacting with a segmented detector array.
FIG. 8D is a diagram of x-ray beams from two apertures of an x-ray collimation grid interacting with an object under investigation at various distances from the x-ray source.
Figure 8C:
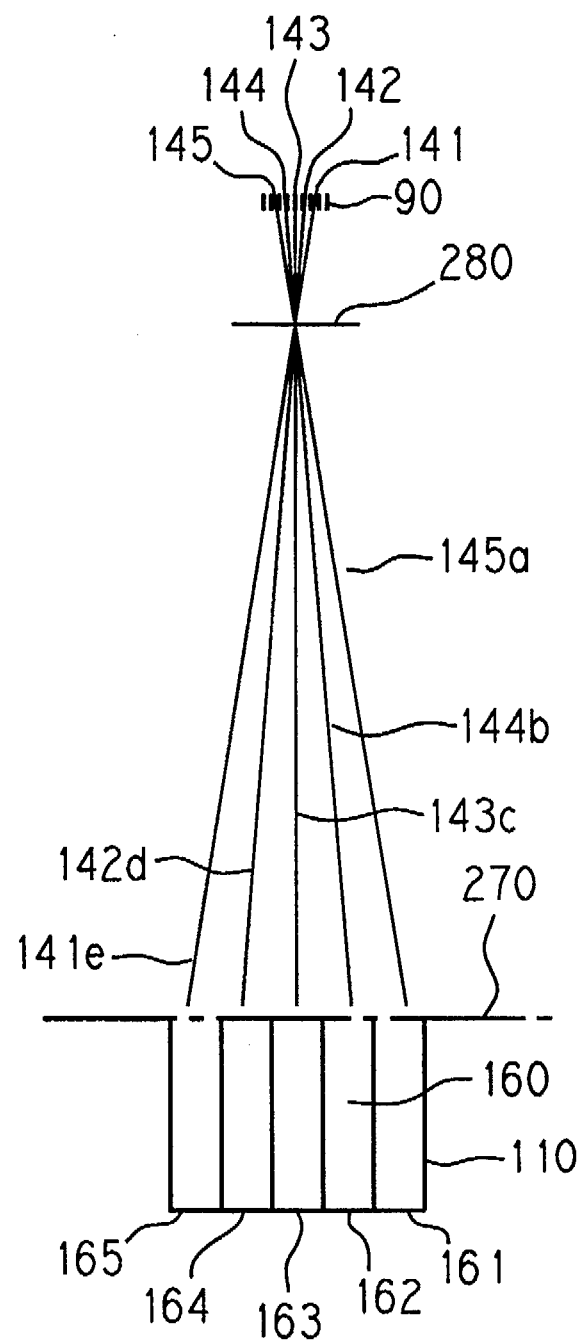

The resolution defined by the individual detector elements 160 is maintained by distributing and summing the outputs from the individual detector elements 160 into a memory buffer in which each address, i.e., image pixel, corresponds to a specific location in the object plane 280. As an electron beam 40 is moved discretely across the target 50, illuminating the area behind selected apertures 140 of the collimation grid 90, the address, to which the output of a given individual detector element 160 is added, changes. The imaging geometry is shown in FIG. 8B and 8C. In FIG. 8B a single x-ray beam 100 is shown along with how it generates information for 5 image pixels. Effectively, the single x-ray pencil beam 100 emanating from individual aperture 141 is divided into x-ray micro-beams, the number of x-ray micro-beams created corresponding to the number of individual detector elements 160 which comprise the multi-detector array 110. In the case shown in FIG. 8B. The axes of five x-ray micro-beams 141a, 141b, 141c, 141d and 141e are shown. In FIG. 8C the sequential positions of the axes of the x-ray micro-beams from x-ray pencil beams 100 emanating from five consecutive apertures 141 through 145 illuminating a single image pixel ("IP") are shown. The outputs from the five individual detector elements 161, 162, 163, 164 and 165 receiving the x-ray flux from the five x-ray micro-beams, 145a, 144b, 143c, 142d and 141e respectfully, are added together to provide the luminance for the single pixel IP.

Stated differently, the output for each of the individual detector elements 160 is stored for later summation in an image buffer, at a memory address that corresponds to a very small specific region in the object plane 280, e.g., a single image pixel.

Accordingly, in one embodiment the memory storage address for the output of each individual detector element 160 changes with the position of the scanning x-ray beam 40 in an ordered fashion such that each memory address contains the sum of the radiation passing through a specific image pixel or spot in the object plane 280. In this way the spatial resolution of the system is determined by the size of a single individual detector element 160, while the contrast resolution of the system is determined by the area of all of the individual detector elements comprising the multi-detector array 110.

Figure 8D:
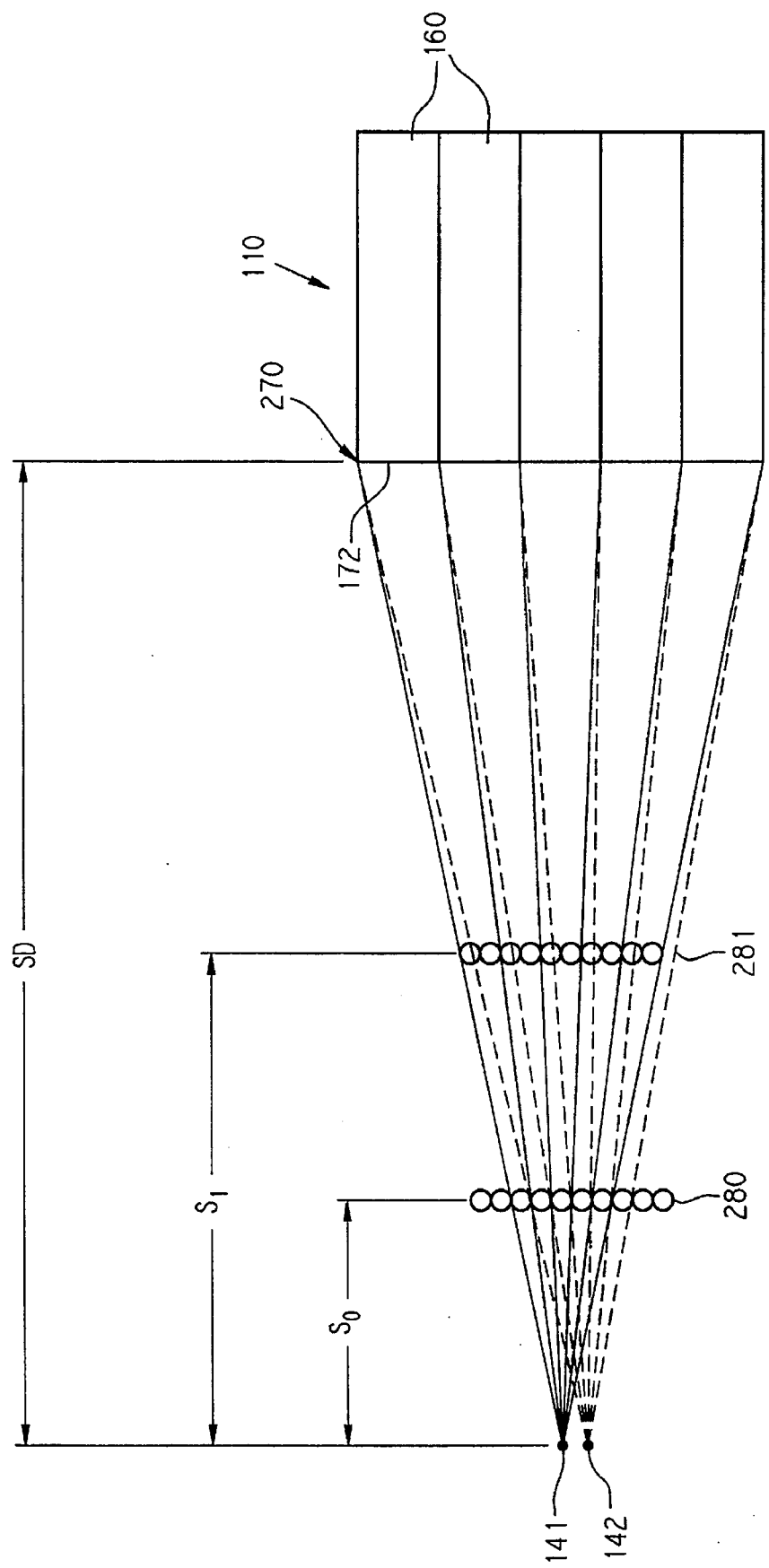

An additional benefit of this multi-detector array imaging geometry is that the depth of field of the object plane 280 is narrowly defined. Structures lying in front of or behind it will be blurred (out of focus). X-ray pencil beams from a first aperture 141 and a second aperture 142 are depicted in FIG. 8D passing through an object plane 280 a distance $S_0$ from apertures 141,142 and passing through a plane 281 a distance $S_1$ from apertures 141, 142 where $S_1 > S_0$. The bubbles represent image pixels $IP_1$ through $IP_{10}$. As can be readily seen, the resolution at $S_1$ is less than that available at $S_0$. This feature provides for improved localization and visualization of detailed structures in the plane of interest 280, while providing an adequate depth of field that may be modified by the system geometry.

The multi-detector array 110 of the presently preferred embodiment comprises 96 individual detector elements 160 arranged in a pseudo-round array of square scintillator elements 0.135 cm on a side disposed within a circle of diameter about 1.93 cm (0.72 in). This number of individual detector elements is merely illustrative. The preferred multi-detector array 110 is described more fully in co-pending patent application Ser. No. 08/387,292 which has been incorporated herein by reference in its entirety.

The Detector Elements

Conventional image intensifier technology typically has basic constraints that limit a system's sensitivity. One of the objects of the present invention is to provide a scanning-beam x-ray imaging system which will result in the subject under examination being exposed to the lowest possible level of x-rays commensurate with achieving image quality adequate to meet the requirements of the procedure being performed. This means that the system used to detect the x-ray photons emerging from the subject preferably has the highest possible detective quantum efficiency. To achieve this, the scintillating material used in the individual detector elements preferably has a length in the direction in which the x-ray photons travel that is sufficient to ensure that no x-ray photons emerge from the end opposite the incident x-rays, i.e., the x-ray photon energy should be adequately dissipated in the material to maximize the output of the detector.

There are several types of individual detector elements which can be used in the presently described scanning-beam x-ray imaging system. That which is currently preferred comprises a scintillator in which x-ray photon energy is converted to visible light energy and the light intensity is then converted to an electrical signal by means of a photomultiplier, photo diode, CCD or similar device. Because the information from each aperture must be obtained in a very short time period, the scintillating material should have a fast response and a minimum afterglow time. Afterglow is the phenomenon wherein the scintillator continues to emit light after the stimulating incident x-rays have ceased. Even faster response and shorter afterglow times are required if x-ray intensity measurements are obtained using the preferred x-ray photon counting technique.

Plastic scintillators, such as organic loaded polystyrene, are suitable from a standpoint of speed in that they have the required fast response and minimum afterglow characteristics. However, plastic scintillators have a relatively small x-ray photon interaction cross section so that their linear x-ray absorption coefficients are also small in value. The consequence is that a considerable thickness is required to absorb x-ray photons. For 100 kV x-rays, a typical plastic scintillator should be about 28 cm. (1.1 in.)-thick to capture 99% of the incident x-rays. More preferred materials at present (and in order of preference) are: (1) YSO (cerium doped yttrium oxy-orthosilicate) available from Airtron (Litton) of Charlotte, N.C.); (2) LSO (cerium doped lutetium oxyorthosilicate) available from Schlumberger, Inc.); and (3) BGO (bismuth germanate, available from Rexon Components, Inc. of Beachwood, Ohio). YSO and LSO are advantageous in that they may be used at room temperature. BGO must be heated to about 100° C. in order to achieve a suitable light output decay period of the order of 50 nanoseconds. These scintillating materials need not be as long as the plastic scintillator and are typically effective at a length of 0.10 cm, and preferably at a length of several millimeters.

According to one embodiment of the present invention, multi-detector array 110 comprises at its input face a pseudo-round array of 96 densely packed scintillators including two rows of 12 and two columns of 12 at its horizontal and vertical midplanes spaced a distance of preferably 91.4 cm (36 in), and more preferably 94.5 cm (37.2 in), from the x-ray source 50. (FIG. 15) A square 5 by 5 and a square 3 by 3 array are also contemplated as is a non-square array of scintillators square cross sections filling a circle about the center of the multi-detector array. If scintillators 170 have parallel sides, x-rays entering near the edges may strike the scintillator walls and pass through to a neighboring scintillator of an adjacent detector element causing the detected element to generate an output seemingly from the wrong spatial position in the subject with consequent degradation of the image quality. This problem is addressed by placing shielding material between the neighboring scintillators. While some x-ray photons are lost, in that they may not generate a light photon, due to the image reconstruction method employed, the resultant image is not affected to any substantial degree.

Figure 10:
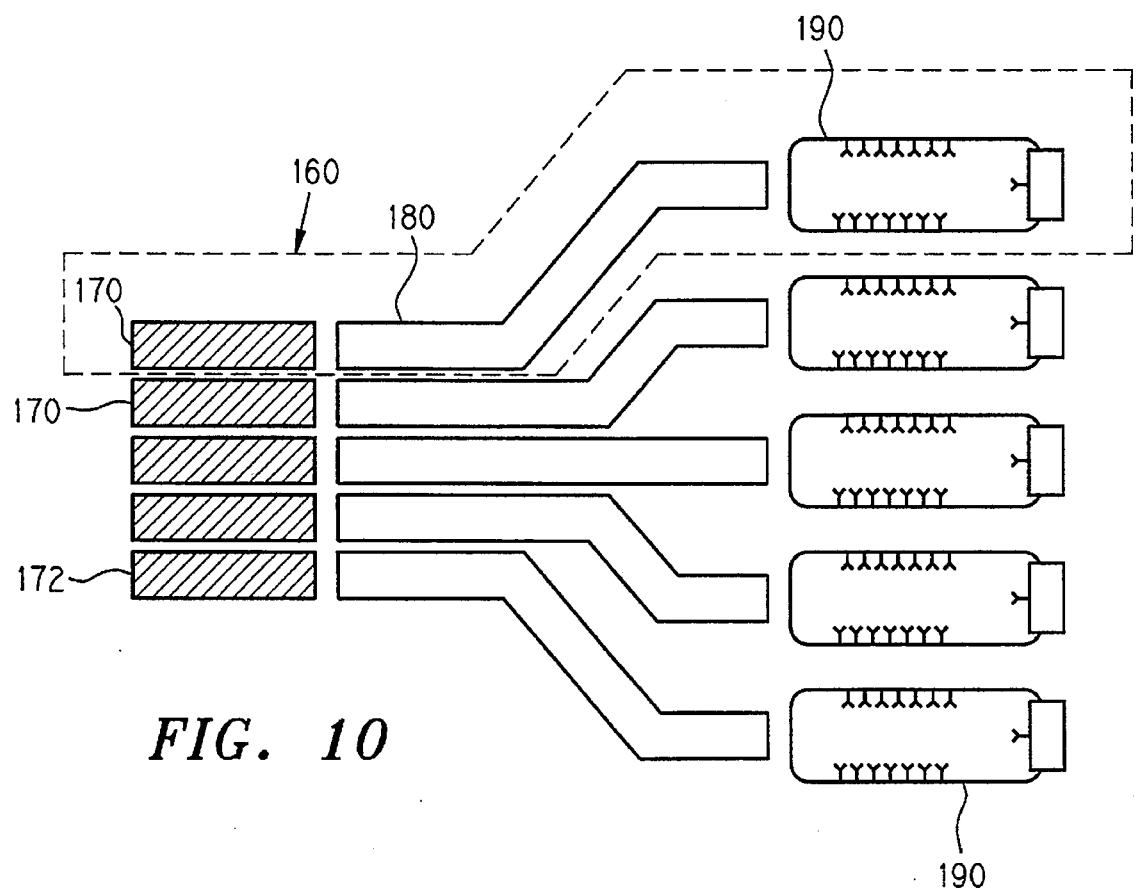
FIG. 10 is a functional representation of one row or column of detector elements for a 5×5 detector array for an embodiment of a low dosage scanning-beam x-ray imaging system.

Referring now to FIG. 10, according to one presently preferred embodiment of the detector element 160, each scintillator element 170 is preferably in contact with a light pipe or fiber-optic coupler 180 which optically couples each scintillator element 170 with a corresponding photomultiplier tube 190 or solid state detector. A coupling oil is preferably used between each end of the fiber optic coupler to ensure proper transmission at the interfaces. Alternatively, scintillators 170 may be located in close physical proximity to their corresponding photodetectors, eliminating the fiber optic coupler.

Figure 11:
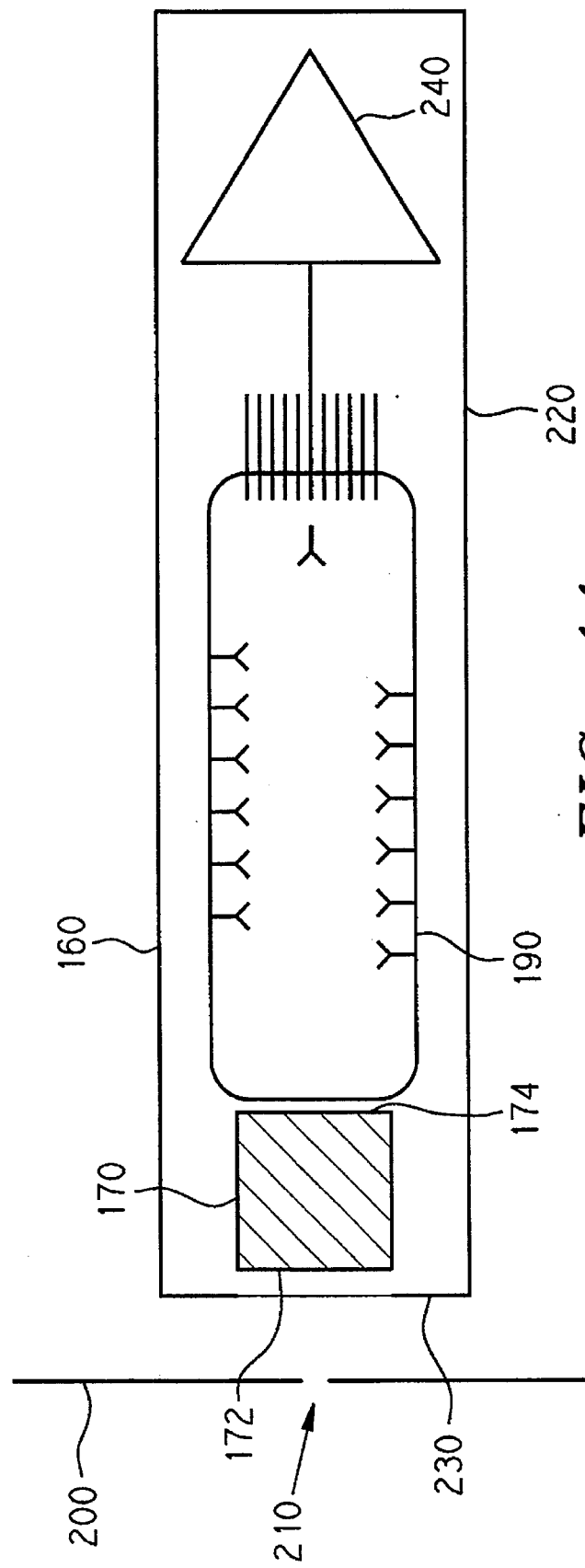
FIG. 11 depicts an embodiment of a detector element for a low dosage scanning-beam x-ray imaging system.

FIG. 11 shows an alternative configuration of a detector element 160 without the optical coupler. An x-ray opaque sheet 200 with apertures 210 corresponding to each detector element 160 is disposed in front of multi/detector array 110. Each detector element 160 is enclosed in a light tight enclosure 220 which may also be x-ray opaque. A light blocking window 230, preferably made of thin aluminum sheet is located at the front of light tight enclosure 220. Light blocking window 230 is x-ray transmissive. Within light tight enclosure 220 is a scintillator element 170 in close proximity to a photomultiplier tube 190 which is preferably electrically connected to a pre-amplifier 240.

Alternatively, scintillators could be placed in direct or close contact with an array of photo diodes, photo transistors or charge coupled devices (CCDs) to achieve a rugged and compact detector. Where solid state devices, particularly CCDs, are used, cooling, such as with a Peltier-type cooler, or the like, may be employed to increase the signal-to-noise ratio of the device. Alternatively, the scintillator array could be placed in direct or close contact with one or more position sensitive photomultiplier tubes which provide an output signal which identifies the position coordinates of the light source as well as its amplitude.

According to a presently preferred embodiment of the present invention, the scintillators are coated along their lengths and the input face with a material which reflects light, such as preferably titanium dioxide, to prevent light from escaping from or entering the scintillators and to aid in internal reflection within the scintillators.

Figure 12:
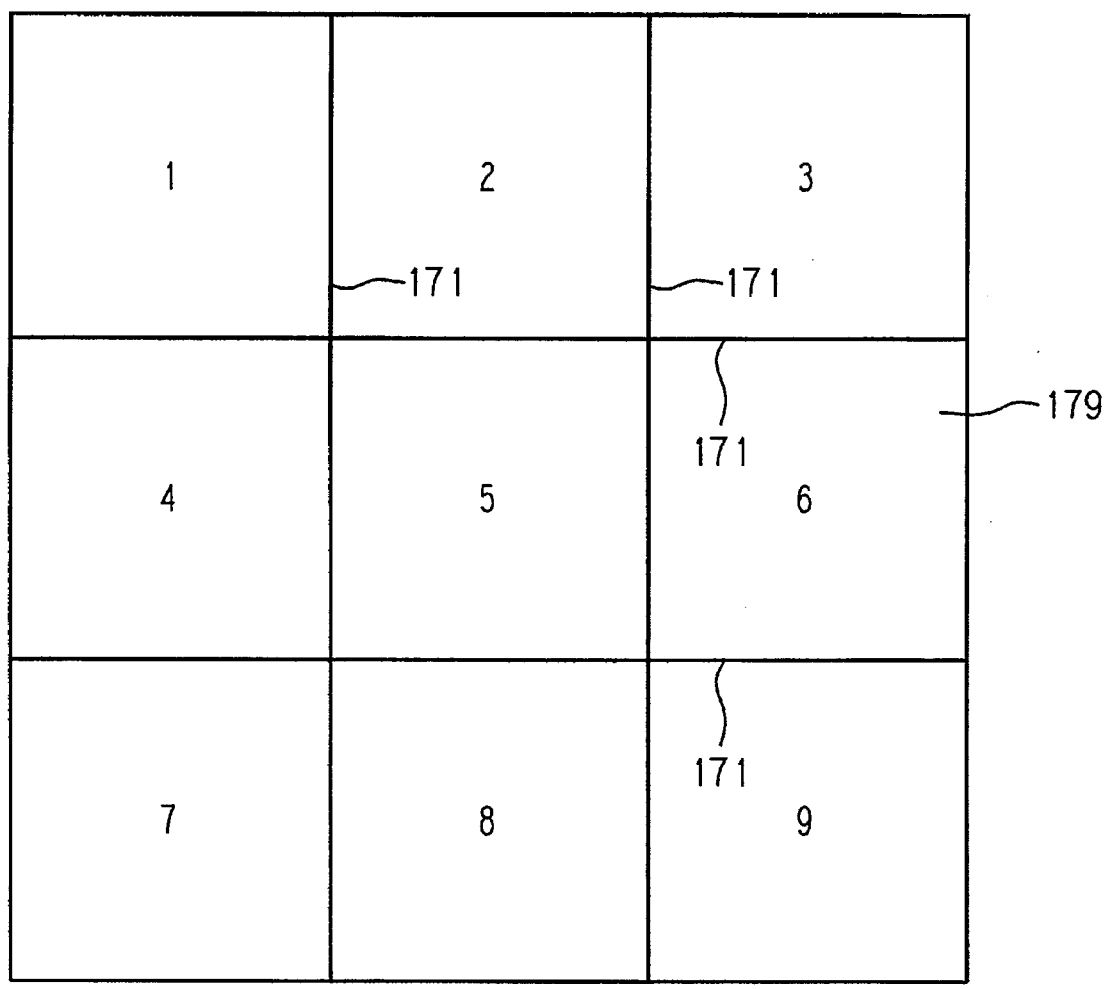
FIG. 12 is a diagram of a front view of a 3×3 multi-detector array for an embodiment of a low dosage scanning-beam x-ray imaging system.

According to a preferred embodiment of the present invention, each scintillator element 170 is isolated from its adjacent scintillator elements 170 by a thin sheet 171 of a highly x-ray opaque material such as, for example, gold or lead. Sheets 171 may be about 0.0102 cm (0.004 in) to 0.0127 cm (0.005 in) thick and is most preferably 0.0051 cm (0.002 in) to 0.0127 cm (0.005 in). An example of the position of sheets 171 between the scintillators 170 is shown in FIG. 12.

The area of the circular active area of collimation grid 90 is preferably larger than the area of multi-detector array 110. Thus the axes of the x-ray pencil beams 100 emitted from the respective apertures 140 of collimation grid 90 all converge toward the multi-detector array 110 while each individual x-ray pencil beam 100 diverges, or spreads, as would a flashlight beam to cover the face of the multi-detector array 110.

Image Reconstruction

An important advancement of the present invention concerns the application of an image reconstruction system to obtain high quality x-ray images. The output of the multi-detector array is preferably not applied directly to the luminance input of a video monitor. Instead, digitized intensity data for each image pixel are stored in a discrete address in a "frame store buffer". More than one such buffer may be used in certain applications. Pixel addresses within the buffer can be randomly accessed and the intensity value can be manipulated mathematically. This function has application in applying various image enhancement algorithms and it allows for pixel assignment of the data from discrete segments of the detector array.

Figure 13:
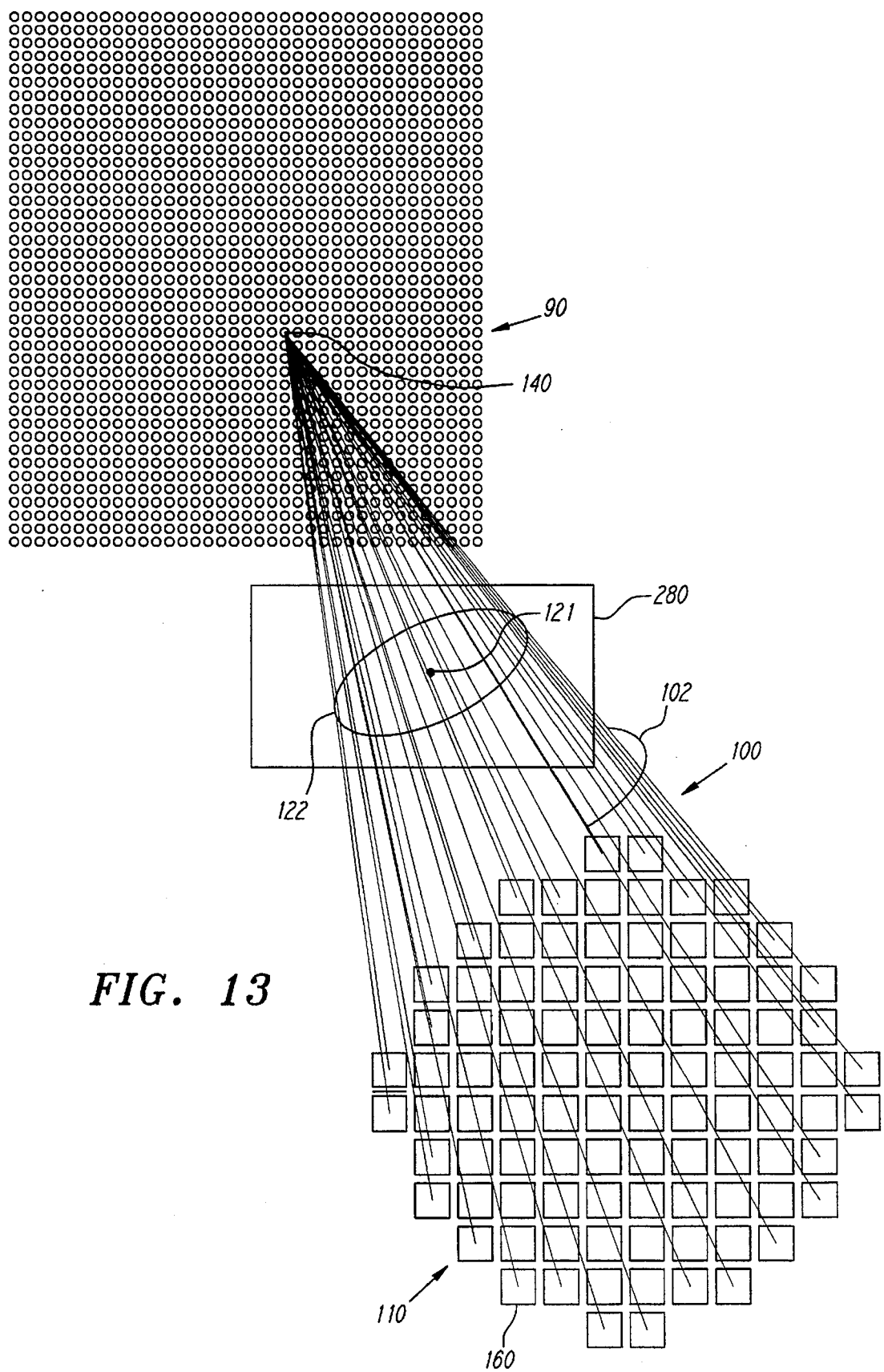
FIG. 13 depicts a x-ray paths of an x-ray beam emanating from a single collimator aperture passing through an object plane to a multi-detector array.

Referring to FIG. 13, this diagram illustrates the divergence of a single x-ray pencil beam 100 from aperture 140 to the multi-detector array and how it intersects an object 80 (not shown) at object plane 280. Image pixel 121 is just one of the image pixels comprising the x-ray pencil beam intersection area 122 of object plane 280. A representative sample of the axes 102 of the x-ray micro-beams created by having a segmented array are also shown. In FIG. 13, x-ray pencil beam 100 is shown emitted through a single aperture 140 of collimator grid 90. X-ray pencil beam 100 as it exits aperture 40 will diverge forming a cone having a cross section the size of the aperture as it exits the aperture to a cross section covering the scintillators of the detector elements of the multi-detector array by the time it reaches the 96 element multi-detector array 110. The 96 element multi-detector array 110 is preferably positioned and designed such that the area of the cone of the x-ray beam 100 just covers the surface area of the multi-detector array 160 when the x-ray pencil beam 100 intersects the face of the multi-detector array.

As x-ray pencil beam 100 passes through an object 80, information about object 80 will be detected by the multidetector array 110 as x-ray intensity values. Because multi-detector array 110 is composed of 96 separate detector elements, each detector element 160 will detect only the intensity value for the particular x-ray micro-beam 101 of a segment of x-ray pencil beam 100 that it intersects with. The cross sectional shape and area of the x-ray micro-beams will correspond to the cross sectional area and shape as the input face of the detector elements. For example, if the input faces are square, the x-ray micro-beam will have a square cross section. The x-ray pencil beam 100 emitted from each aperture 140 on collimator grid 90 will therefore generate one group of 96 separate or discrete pieces of information (the intensity value at each detector element) about 96 areas of object 80 in the x-ray pencil beam's 100 path 122. The intensity information from each of the x-ray micro-beams provide partial image pixel information which can be used to compile complete image pixel information for each image pixel in a desired plane of object 80.

Figure 14:
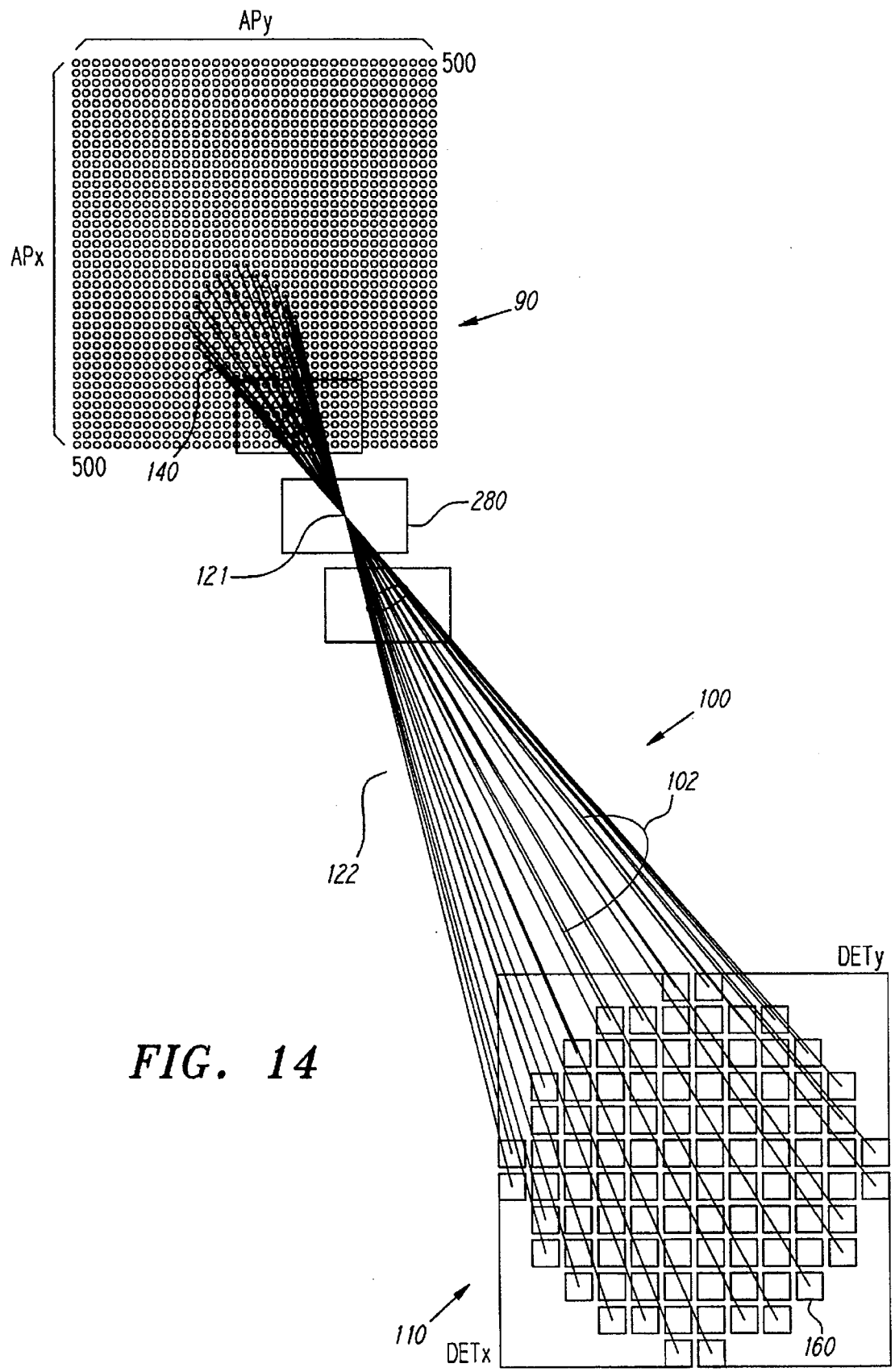
FIG. 14 depicts x-ray paths of multiple x-ray sub-beams emanating from multiple apertures passing through a single pixel to a multi-detector array.

FIG. 14 illustrates the axes 102 of all of the x-ray micro-beams from all of the apertures 140 that intersect a single image pixel 121 in object plane 280 as they travel to the multi-detector array 110. This image pixel group of x-ray micro-beams is ultimately processed to generate an image pixel on a video monitor. In a preferred embodiment of the scanning-beam x-ray system, the apertures 140 on collimator grid 90 will generate x-ray pencil beams 100 in a predetermined pattern. As x-ray pencil beams 100 pass through an object, x-ray micro-beams 101 from adjacent and nearby apertures will intersect at, for example, point 121 (e.g. an image pixel) in the object. The intensity of each of these x-ray micro-beams 101 from these x-ray pencil beams 100 after they pass through the object provide information about these intersecting points in the object. In this preferred embodiment, each intersecting point on the object can therefore be considered a single-image "pixel" 121. In accordance with the techniques explained in more detail herein, each image pixel 121 is preferably mathematically reconstructed from the intensity information of the separate x-ray micro-beams 101 that were generated by the detector elements 160 for each of the emitted x-ray pencil beams 100 from, for example, the image pixel group of apertures that generated x-ray micro-beams whose axes passed through the object at that point, image pixel 121.

According to a preferred embodiment of the present invention, the output image would preferably consist of up to about 250,000 pixels, arranged in 500 rows and 500 columns. For the purpose of the explanatory example below, it is assumed that the scanning x-ray source is momentarily centered upon the point, P, located at row 100 and column 100 of collimation grid 90. It is further assumed in regard to this embodiment that the detector array 110 consists of a square 3-by-3 multi-detector array 110 containing 9 detectors 179 (FIG. 12) and that each detector 179 is sized so as to intercept all of the x-ray emissions associated with a single image pixel. Other array configurations obviously may be used as are detailed herein.

The resulting intensity values, preferably digitized from the individual detectors of the multi-detector array 110, may be assigned to pixel buffer addresses as follows:

detector 1—row 99, column 99
detector 2—row 99, column 100
detector 3—row 99, column 101
detector 4—row 100, column 99
detector 5—row 100, column 100
detector 6—row 100, column 101
detector 7—row 101, column 99
detector 8—row 101, column 100
detector 9—row 101, column 101

In this example, a corresponding pattern of data assignment is repeated as the scanning x-ray beam passes behind all of the pixels.

In the displayed image, with a sub-sampling ratio of 1:1, the numerical value of each image pixel is equal to the sum of "n" parts where "n" is the number of detectors 179 in the multi-detector array 110 (in this example, n=9).

When constructed as shown in this example, the multi-detector array 110 together with the image reconstruction method selected, has the effect of fixing the working distance at which optimum focus is obtained and providing a plane of optimum focus not available in prior art non-segmented detector scanning-beam imaging systems.

The following parameters must be taken into consideration in design of the multi-detector array:

1. The size and shape of the collimated beam from the x-ray source (target 50);
2. The distance between the target 50 and the multi-detector array 110, "SD" (FIG. 8);
3. The distance between the source 50 and the center of the object of interest 280, "SO";
4. The desired resolution, or pixel size at the object of interest 80; and,
5. In medical applications, the total area of the multi-detector array 110 must be large enough to intercept all of the x-rays in x-ray pencil beam 100 emanating from the collimation grid 90, to avoid exposing the patient to x-ray radiation which does not contribute to the image.

In a preferred embodiment of the invention, the distance between the target 50 and the exit side 260 of collimation grid 90 is about 2.271 cm (0.894 in), and more preferably 2.54 cm (1.00 in) (see FIGS. 3 and 6). Apertures 140 are preferably round with a diameter of 0.0381 cm (0.015 in). If the apertures are square they are preferably 0.0381 cm on a side. The spot size of electron beam 40 on target 50 is preferably about 0.0254 cm (0.010 in) in diameter. The multi-detector array 110 is preferably about 91.4 cm (36 in), and more preferably about 94.5 cm (37.2 in), from target 50. The preferred beam divergence angle of x-ray pencil beam 100 is calculated by 2*ARCTAN((spot diameter/2)/( (aperture width/2)+(spot diameter/2))* (spot diameter). The projected x-ray pencil beam 100 diameter is SD * TAN (divergence angle). It has been determined that the preferred size of the multi-detector array 110 should be about 2.54 cm (1 in) in diameter for the more preferred embodiment.

For example, with a multi-detector array size of 2.54 cm (1 in) square, if the object plane to be imaged is 22.86 cm (9 in) from target 50 and the desired image pixel size is 0.0508 cm (0.020 in) at the object plane, and the distance from the target 50 to the multi-detector array is 91.4 cm (36 in), the projected size of image pixels at the detector plane 270 is (SD/SO)*pixel size at object, or 0.2032 cm (0.080 in). The desired resolution may be obtained by dividing 2.54 cm (1 in) by 0.2032 cm (0.080 in) yielding a square multi-detector array having 12 to 13 detector elements on a side. Other configurations are possible depending upon the circumstances in which the invention is to be used.

Outside of the plane of optimum spatial resolution, SO (280 in FIG. 8D and FIG. 14), spatial resolution will degrade. In some applications, such as imaging of the human heart, degraded spatial resolution outside of the depth of field of the system may be seen as being advantageous because blurring of detail outside of the area of interest may tend to increase the perception of details within the area of interest.

A number of methods can be used to obtain a useable image from the data obtained as described above. As described above, a simple convolution method may be used. Two additional methods are presently preferred for obtaining maximal resolution and sensitivity from the captured data. These are called the multi-image convolution method and the multi-output convolution method. For both cases, the following is assumed:

Assume there are $AP_x$ rows of apertures and $AP_y$ columns of apertures in collimation grid 90 (FIG. 14). Each intersection of a column and row is an "aperture point." Those aperture points outside of the circular active area of collimation grid 90 are treated as if they contribute no measured intensity to the image, i.e., they are treated as if they are "dark". Aperture points not illuminated by electron beam 40 during a scan are similarly treated as if they contribute no measured intensity to the image, i.e., they are also treated as if they are "dark".

Figure 15:
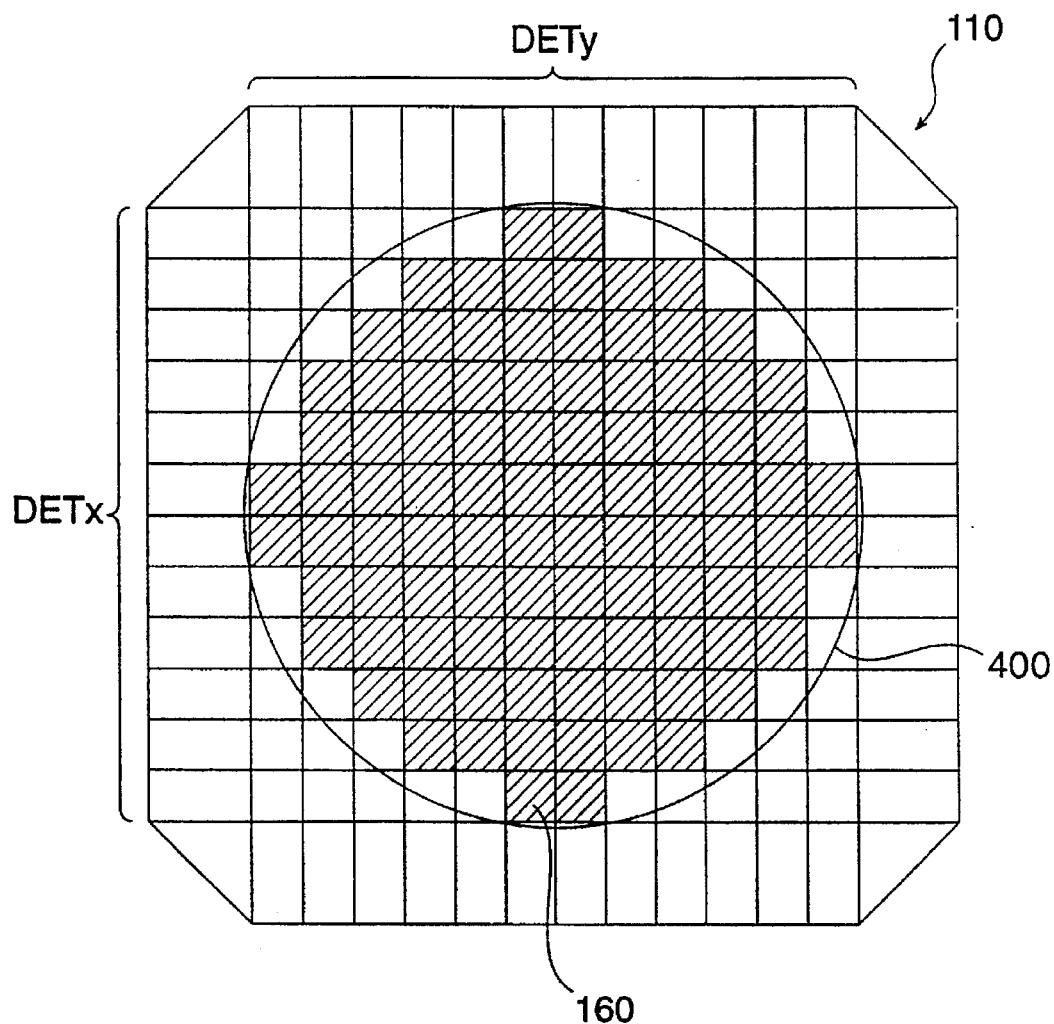
FIG. 15 is a front view of the presently preferred embodiment of a 96 element scintillator array.

Turning now to FIGS. 14 and 15, in multi-detector array 110 assume there are a maximum of $DET_x$ rows of detector elements 160 and a maximum of $DET_y$ columns of detector elements 160 in a pseudo-round arrangement.

ZRATIO is a real number between 0 and 1. If ZRATIO=1, the focus will be at the detector plane 270 and if ZRATIO=0, the focus will be at the target 50 plane. If ZRATIO=0.5, then the focus is half way between the target 50 and the detector plane 270, and so on. PIXELRATIO is the number of image pixels per physical distance between adjacent detectors in a column or row. For example, if the spacing between image pixel centers at object plane 280 is 0.01 cm, and the spacing between the centers of the detector elements at detector plane 270 is 0.1 cm, then PIXELRATIO=10. FOCUS= ZRATIO*PIXELRATIO. Focus is typically in the range of 0.5 to 2.0 and is usually 1.0.

IMAGE is a data array of size $DET_x$ by $DET_y$ containing the intensity information for a particular scan and corresponding to a particular aperture point. PIXEL is a 4-dimensional array of size $DET_x \times DET_y \times AP_x \times AP_y$ which contains the IMAGE data arrays obtained by scanning all (or part of) the apertures. PIXEL is refreshed after each scan according to one preferred embodiment of the present invention.

As the electron beam 40 is scanned across the target 50 surface, it is, in effect, positioned at the center of selected apertures 140, "fired," and then repositioned. Thus for each firing or pulse an IMAGE array of data will be acquired. While these arrays of data could be constructed into a displayable image having some use directly, more resolution and sensitivity at lower dosage is obtained by combining them.

The first preferred method for combining the images is called the multi-image convolution method. In the multi-image convolution method, an OUTIMAGE array of intensities of size $AP_x \times AP_y$, which can be displayed on a CRT or like display means, is formed by assigning to OUTIMAGE (y,x) the value of:

$$\frac{\sum_{j=1}^{j=DET_y} \sum_{i=1}^{i=DET_x} PIXEL(j,i,y+j*FOCUS,x+i*FOCUS)}{DET_x * DET_y} \qquad \text{(EQ. 1)}$$

The second presently preferred method for combining the $AP_x \times AP_y$ number of IMAGE data arrays into a useful picture is called the multi-output convolution method. In this case, with a sensor array of $DET_x \times DET_y$ sensors there will be $DET_x \times DET_y$ digitizers (or their equivalents, multiplexed) and the same number of pixel summing circuits. The digitized values from each sensor are called SENSOR(j,i). The final OUTIMAGE array is computed as follows—for each pixel in the output image array OUTIMAGE(y,x) [for y=1 to $AP_y$ and x=1 to $AP_x$] one pixel from each of the $DET_x \times DET_y$ source images SENSOR(j,i) is summed [for j=1 to $DET_y$ and ii to $DET_x$] into destination image pixel OUTIMAGE(y-j*FOCUS,x-i*FOCUS). Normalization is then carried out over the OUTIMAGE array by dividing each element thereof by $DET_x * DET_y$.

A further improvement upon these techniques may be obtained by performing linear interpolation based upon the fractional part of the FOCUS factor.

An advantage of the multi-image convolution method over the multi-output convolution method is that the former allows the plane of optimum focus to be selected in software after the data is captured while the latter does not. The latter method, however, may be performed quicker where timing is a limitation.

Three Dimensional Image Reconstruction

The scanning-beam imaging system described herein may be used to generate a set of sequential planar images which can then be used to form a tomograph or a three dimensional display of the object 80. An image set can be analyzed to produce a 3D image consisting of a series of images at various depths by re-analyzing the data set with various values of FOCUS. The natural FOCUS values to use are $n/DET_x$ or $n/DET_y$ where n is an integer from 0 to $DET_x$ or $DET_y$, respectively. Normally, only the focus values corresponding to planes of interest in the object 80 would be analyzed. For example, in the scanning-beam imaging system described in TABLE I (below), the planes of focus would be spaced at approximately 2.54 cm (1 in) intervals around the normal object plane of 22.86 cm (9 in) (plane of optimum focus).

The following preferred formula shows where the sequential planar images are located in terms of distance from the target 50.

$$F_t(FOCUS) = \frac{F_d * \lambda_s * FOCUS}{\lambda_d} \qquad \text{EQ. 6}$$

Where $F_t(FOCUS)$=Distance from the target to the particular focal plane of interest $F_d$=Distance from the detector to focal plane (distance from the target to the detector less $F_1$)

$\lambda_s$=Center-to-center spacing between adjacent collimation grid apertures $\lambda_d$=Spacing between centers of adjacent detectors 160 within detector array 110.

When using the sub-sampling method, the basic method of computation does not change—only the data from the collimation grid apertures which are not "skipped" need be processed. Note that $\lambda_s$ remains the same even if intervening collimation grid holes are skipped.

Negative Feedback X-Ray Flux Control

Figure 16:
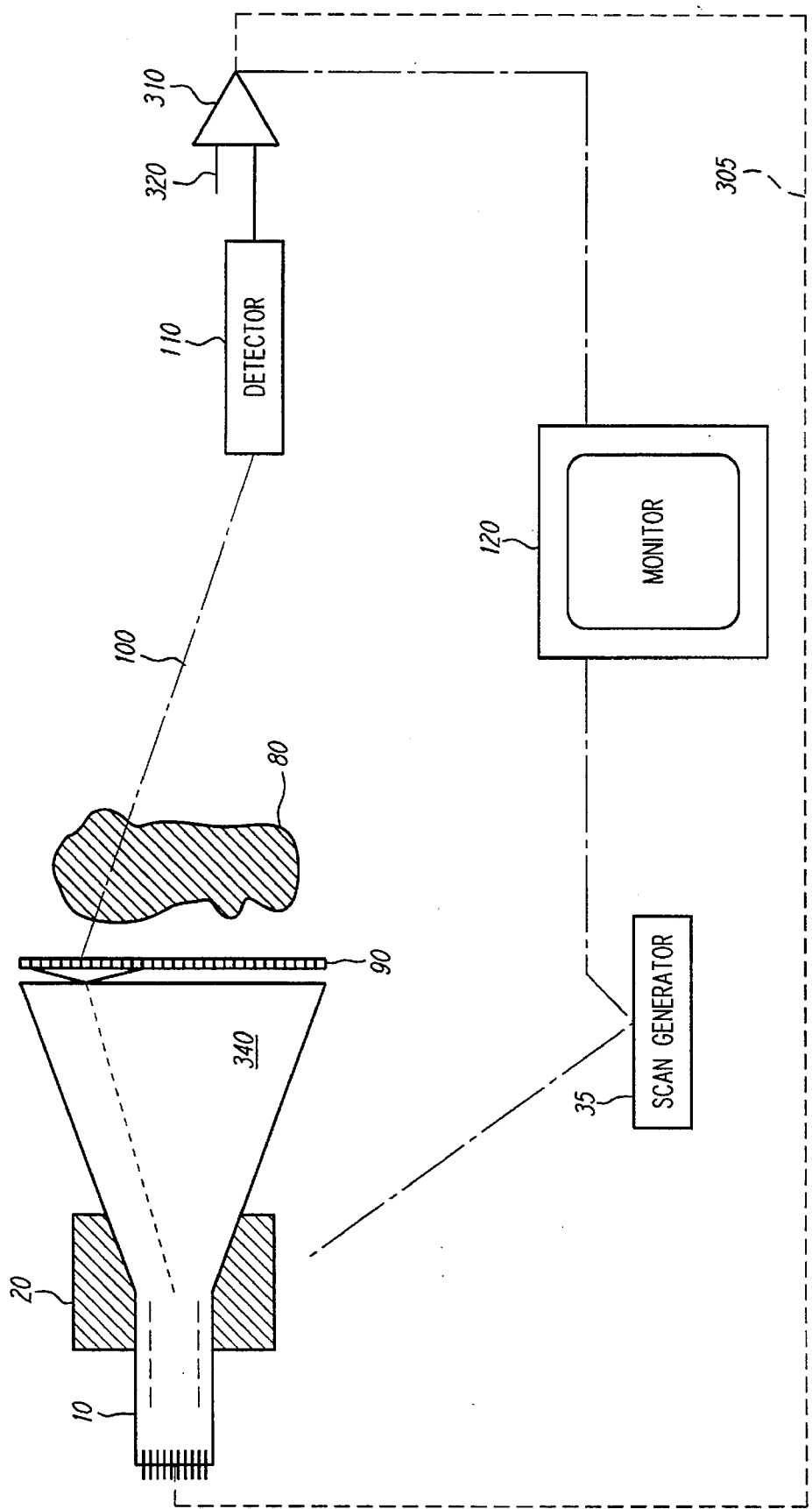
FIG. 16 is a diagram showing a preferred low dosage scanning-beam x-ray imaging system utilizing negative feedback to control x-ray flux.

Turning now to FIG. 16 an embodiment of the preferred scanning-beam imaging system employing a negative feedback path 305 to control the x-ray flux of x-ray pencil beams 100 is depicted. Negative feedback from the multi-detector array 110 can be utilized to control x-ray flux so that the multi-detector array 110 always sees approximately the same flux level. In this way when soft tissue (which is relatively transparent to x-rays) is being scanned, the x-ray flux can be lowered, without degrading the image reducing the overall dosage to the patient (or object). Improved contrast and dynamic range are provided by using negative feedback flux control. According to this embodiment, differential amplifier 310 has an adjustable reference level 320 which may be set by the user. Negative feedback loop 305 feeds back to x-ray tube 10 to control the x-ray flux.

Time Domain Scanning Mode

A time domain x-ray imaging system may also be implemented using the principles disclosed herein. In such a system, the time to reach a predetermined measured x-ray flux from the various pixels could be computed and mapped. Negative feedback control could then be employed to turn off or reduce x-ray flux from apertures corresponding to pixels which had reached the predetermined flux level for the scan period in question. In this case, the information gathered would be time to flux level and the mapped or imaged information would correspond to time rather than intensity. Such a system has the potential to provide much higher signal-to-noise ratios, improved contrast, drastically reduced x-ray dosage to the object under investigation, and improved dynamic range.

Multiple Energy X-ray Imaging Mode

According to one preferred embodiment of the present invention, two or more groups of x-ray pencil beams 100 are directed toward one or more detector arrays through two or more groups of aperture 40. A first group of x-ray pencil beams 100 has a first characteristic x-ray energy spectrum. A second group of x-ray pencil beams 100 has a different second characteristic x-ray energy spectrum. By comparing the measured transmissivities of the first and second group of x-ray pencil beams 100, the presence of certain materials in the object under investigation may be detected. The basic concept of use of differential x-ray imaging in known imaging systems is disclosed, for example, in U.S. Pat. No. 5,185,773 entitled "Method and Apparatus for Nondestructive Selective Determination of a Metal" which is hereby incorporated herein by reference.

The two groups of x-rays may be generated in a number of ways. One such way is by fabrication of a special target 50 having a first material or first thickness of a material adjacent to the apertures of the first group of apertures and a second material or second thickness of material adjacent to the apertures of the second group of apertures. In this manner, the apertures associated with the first group will preferably emit x-rays having a first characteristic energy spectrum and the apertures associated with the second group will preferably emit x-rays having a second characteristic energy spectrum.

Alternatively, K-filtering (or K-edge filtering) can be used by placing filter material (such as, for example, molybdenum) within a portion of the apertures 140 to produce a similar effect. In this case, a first group of apertures would comprise a first filter inserted therein and a second group of apertures would comprise a second filter inserted therein. The second filter could be no filter at all. As in the previous case, two groups of x-rays having different characteristic energy spectra would be associated with the two groups of apertures.

Once at least two groups of apertures are associated with different characteristic x-ray spectra, it is now easier to detect micro-calcification (associated with breast cancer and coronary artery diseases) and other abnormalities not normally visible with broadband x-rays. For example, by performing a scan of the first group of apertures to form a first image, then performing a scan of the second group of apertures to form a second image, and dividing the images to highlight their ratios, it is easier to detect microcalcification and other such abnormalities with a low dosage scanning-beam x-ray imaging system—in real time. Similarly, a multiple detector array arrangement could be used with group 1 apertures directed toward a first detector array and group 2 apertures directed toward a second detector array, etc.

Another embodiment of multiple energy imaging uses an x-ray photon counting detector system in which the amplitude of the electrical pulse from a detected x-ray photon is proportional to the energy (keV) of the photon and the pulses coming from photons in two or more energy bands are counted separately. The pulses are separated by amplitude (i.e., x-ray photon energy) and then counted and processed separately, forming two or more separate images. Those images can be displayed as ratios. It is also possible to rapidly change the selected energy levels to distinguish different density regions in the object. The advantage of this embodiment is that it is more flexible than those described above, and does not require special collimation grids, target materials or dual detectors.

While a number of preferred embodiments have been discussed above for various configurations of the present invention, the following specifications are illustrative of a presently preferred scanning-beam imaging system according to the present invention:

TABLE I

| | |
|---|---|
| Grid | |
| Shape: | round |
| Diameter: | 25.4 cm (10 in) |
| Aperture Pitch: | 0.0508 cm (0.020 in), 0.152 cm (0.060 in for sub-sampling) |
| Max. No. of Apertures in a row or col: | 500 (166 for sub-sampling) |
| Cir. Active Area of grid: | 506.45 sq. cm (78.5 sq. in) |
| Number of apertures: | 196,350 approx. (approx. 21,630 for sub-sampling) |
| Aperture cross-section: | round |
| Aperture Diameter: | 0.0381 cm (0.015 in) |
| Space between apertures: | 0.0127 cm (0.005 in) (0.045 in for sub-sampling) |
| Grid Output Face to target surface Dist: | 2.54 cm (1.0 in) |
| General System Config. | |
| Source-Detector Distance: | 94.5 cm (37.2 in) |
| Location of Object Plane: | 23.6 cm (9.3 in) from Source |
| Scan Frequency: | Adjustable to 30 Hz (Unless region of interest scanned) |
| Operating voltage on x-ray tube: | 70–120 kV |
| Detector Array | |
| Overall shape: | pseudo-round (per FIG. 15) |
| Shape of input face of detector elements: | square |
| Size of input face of detector elements: | 0.142 cm × 0.142 cm |
| Number of detector elements: | 96 |
| Array diameter: | 1.83 cm (0.72 in) |
| Field of view at Plane of Optimum Focus: | 19.05 cm (7.5 in) |
| Pixel size at Plane of Optimum Focus: | 0.038 cm |
| Detector spacing: | 0.152 cm |
| Resolution: | approximately 20 line pairs/cm |

Accordingly, one embodiment of the scanning-beam imaging system utilizing a multi-detector array has been shown and described which simultaneously provides high resolution, high sensitivity, and low x-ray dosage to the object under investigation. The system also permits the plane of optimum focus to be varied between the target 50 and the multi-detector array 110, and provides an effective working depth of field.

Sub-sampling Technique

The following relates to a particular preferred embodiment of the present invention which uses the technique of sub-sampling which reduces the computer processing overhead, and power consumption of the scanning-beam x-ray system.

Standard video quality images typically use 640×480 pixels and are updated at 30 Hz. This usually requires a pixel sample rate of about 12 Mhz. Positioning the high voltage electron beam of the x-ray tube accurately behind 250,000 different apertures at that rate typically requires high precision and relatively high power consumption. Digitization of signals from a large array of x-ray detectors at a 12 Mhz rate is similarly expensive and power intensive. Thus reduction of the pixel sample rate below 12 Mhz without significant reduction of the spatial or time resolution of a scanning-beam imaging system is useful in reducing initial unit costs, operating costs due to electronic power consumption, and cooling requirements for the waste heat developed by the x-ray tube.

Accordingly, a method for reducing the pixel sample rate while providing virtually the same spatial and time resolution has been developed. This method is referred to herein as "sub-sampling" and is best implemented with the embodiment of the scanning-beam imaging system described herein, although it could be adapted to be used with other configurations. Advantages of this embodiment include reduced power consumption and simpler circuitry for electron beam deflection within the x-ray tube 10, reduced cost of fabrication of the collimation grid 90, reduced complexity of the calculations needed to resolve an image of the object 80 and other advantages as would be obvious to those of skill in the art.

Pursuant to this embodiment a collimation grid 90 is fabricated having a number of apertures less than the number of desired image pixels. In other words, in sub-sampling the ratio of the number of apertures ("AP") to the number of Image Pixels ("IP") is less than one (Total AP/Total IP<1). Preferably, $AP_x=AP_y=166$ rather than 500, although other numbers are within the scope of the invention. The advantage of this reduction from a computational point of view will become apparent below. From a manufacturing point of view, it is a much simpler structure with approximately one-ninth the number of apertures which need to be fabricated. Because this sub-sampled system requires fewer apertures than a fully sampled system, it is easier to fabricate grids with higher deflection angles (i.e., the angle that the aperture makes with respect to the front face 260 of the collimation grid) without running into problems of having apertures 90 interfere with adjacent apertures. This is particularly useful when stereo grids are to be manufactured, since adjacent apertures in a stereo grid are directed to different detector arrays and hence may require more physical separation than non-stereo grids to avoid aperture interference.

In the presently preferred embodiment the apertures 140 of the collimator grid 90 preferably have a circular arrangement of maximum dimension $AP_x$ rows by $AP_y$ columns. For computational purposes in the presently preferred embodiment this arrangement is treated as a rectangle of dimension $AP_x$ rows by $AP_y$ columns with the apertures outside of the circular boundary contributing no information, i.e., never being used to pass x-ray pencil beams 100.

The input face of the detector elements 160 of the multi-detector array 110 are also preferably arranged in a circular array of maximum dimension $DET_x$ rows by $DET_y$ columns as shown in FIG. 15. For computational purposes, in the presently preferred embodiment this arrangement is treated as a rectangle of detector elements 160 of dimension $DET_x$ rows by $DET_y$ columns with the detectors outside of the circular boundary contributing no information, i.e., always being "dark", or non-illuminated by x-rays.

The pixel sample rate is reduced by illuminating less than all of the apertures 140 of the collimation grid, if the total number of apertures is equal to the number of image pixels, i.e., by sub-sampling. Preferably a collimation grid without the not-to-be-illuminated apertures is used, e.g. the collimation grid includes the number of apertures corresponding to the desired aperture to image pixel ratio. In a collimator grid 90 having more apertures than is necessary to achieve the desired aperture to image pixel ratio, an image is formed using the multi-detector array 110, by illuminating only the collimator holes in each row and only the collimator holes in each column that needs to be illuminated to achieve the desired aperture to image pixel ratio. Thus the image may be built up out of image tiles of pixels corresponding to the number of detector elements in a row in the multi-detector array 110 that provides information for a single image pixel ($VDET_x$) and the number of detector elements in a column of the multi-detector array 100 that provides information for that same image pixel ($VDET_y$) as the electron beam 40 is scanned across the target 50. This corresponds to a sub-sampling ratio of $(DET_x \times DET_y / VDET_x \times VDET_y):1$ which, for no sub-sampling, reduces to a sub-sampling ratio of 1:1. The sub-sampling ratio may thus be adjusted by changing the number of virtual detector elements from $DET_x$ to $VDET_x$ in the X-direction (rows) and from $DET_y$ to $VDET_y$ in the Y-direction (columns). In accordance with a preferred embodiment, $VDET_x=VDET_y=4$ as shown in FIG. 36, yielding an image to aperture pixel ratio of (12×12/4×4):1, i.e., 9:1.

Where a 12×12 detector is used and the sub-sampling ratio is 144:1, the image is fabricated from a plurality of non-overlapping images which are in effect "pasted" together—much like a photomosaic. Because real world scintillators and detectors are usually not all perfectly and identically responsive, the x-ray pencil beam 100 is usually not perfectly uniform, the collimation grid apertures are usually not all exactly identical with identical areas, and because a circular, rather than a square detector is used in the preferred embodiment, some degree of overlap is highly desirable in order to permit averaging out detector nonlinearities and noise.

If the sub-sampling ratio is less than the detector size in image pixels (that is, less than 144:1 in this embodiment), the image will be built up from overlapping "tiles", which are summed or averaged. If the sub-sampling ratios are not "even" multiples of the detector size (in image pixels) or if the multi-detector array 110 is not rectangular as in the preferred embodiment there will be different numbers of samples added to each image pixel. To obtain a more uniform picture the values from each of the virtual detectors is normalized using different divisors to average the resultant values to generate each image pixel.

In the calculations that follow, $VDET_x$ represents the sub-sampling value in the X direction (rows), and $VDET_y$ represents the sub-sampling value in the Y direction (columns). For example, if $VDET_x=VDET_y=12$, there is no sub-sampling. Similarly, if $VDET_x=VDET_y=1$, in this embodiment, the pixels are tiled. If every third aperture of the collimator grid 90 which has an array of apertures 500×500 is illuminated, then 166×166 apertures will be scanned, i.e., one-third in X and one-third in Y, reducing the data obtained by a factor of 9 with the 12×12 detector this will provide a sub-sampling ratio of (12×12/4×4):1 or 9:1. Note that if one is only going to use 166×166 apertures all of the time, there is no need for 500×500 apertures and only 166×166 need be included in the collimation grid.

In accordance with one embodiment, only ⅑ of the apertures in the collimation grid (500×500 apertures) are used or illuminated by the electron beam 40 to generate an image. If the frame rate is kept constant, e.g., 30 Hz, then the number of electron beam steps is reduced by 9, as is the frequency response of the circuit that drives the electron beam. The number of scan lines is reduced by ⅓, so that the average horizontal beam velocity across the target is reduced by ⅓. The image reconstruction pixel rate is the same as the collimation grid aperture rate (rate at which apertures are scanned or illuminated), and is also reduced by ⅑.

In accordance with this embodiment in which the collimator grid 90 includes a 500×500 array of apertures, and the multi-detector array 110 includes a 12×12 array of detector elements 160, arranged such that when each aperture is illuminated an image pixel to aperture ratio of 1:1 is achieved, the number of detector element outputs averaged into each image pixel is $VDET_x * VDET_y$. When using the sub-sampling ratio of 144:1 where $VDET_x$ and $VDET_y=1$, only one digitizer sample is used for each image pixel. The normalizing of the detector element outputs smooths out non-uniformities in the beam, the scintillators, the detectors, and the amplifiers. The sub-sampling ratio should be set to an appropriate level for the conditions presented in order to assure acceptable image quality. This may be adjusted in accordance with the user's preference for image quality and the conditions presented by a particular set of circumstances.

M,N Image Reconstruction

Figure 67:
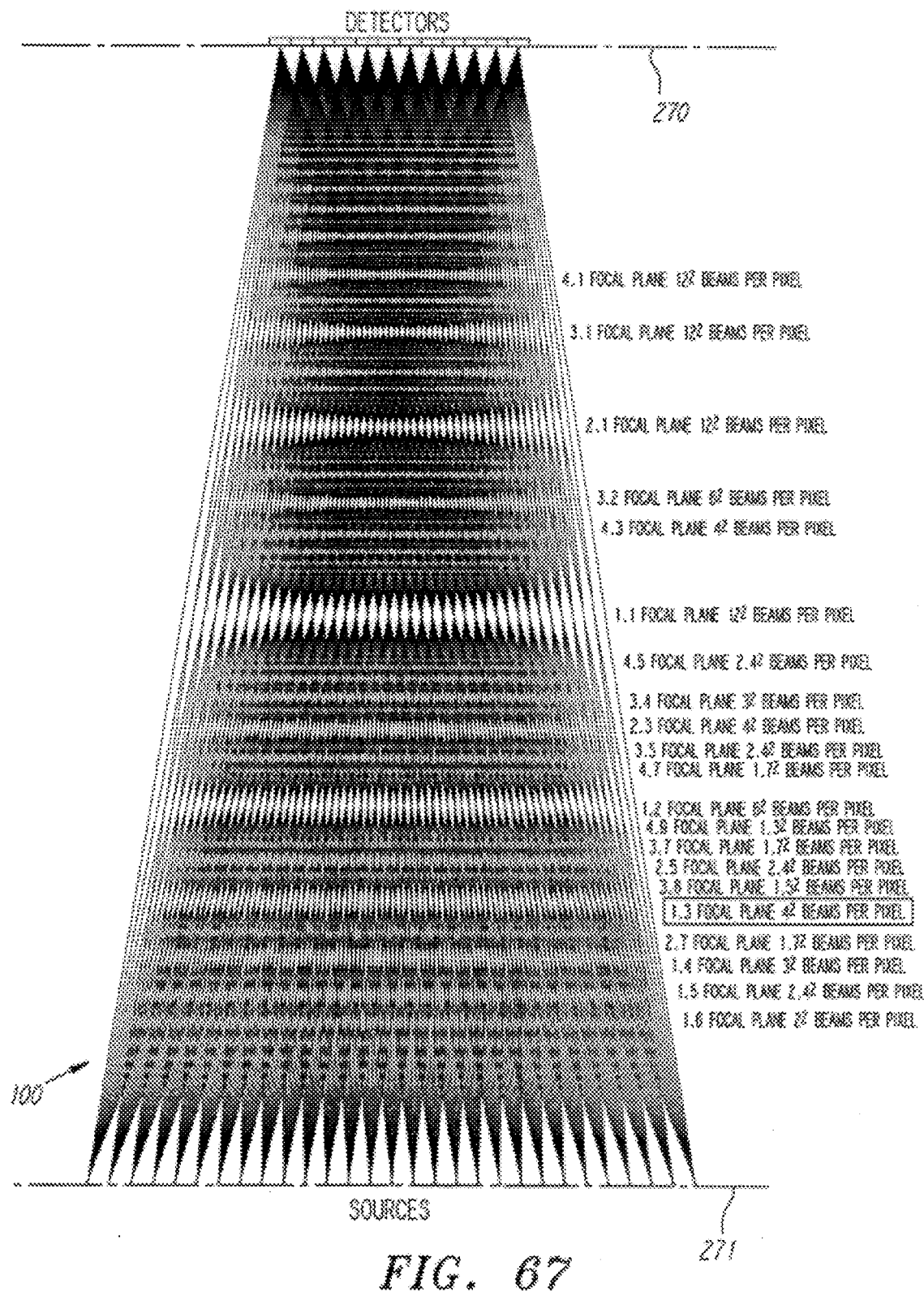
FIG. 67 is a cross-sectional view through a two-dimensional of regularly-spaced x-ray sources and a two-dimensional array of regularly-spaced detectors.

An alternatively preferred image reconstruction method can be employed to reconstruct images along multiple focal planes. This preferred image reconstruction method is referred to as m,n image reconstruction. FIG. 67 shows a cross-sectional view through a two-dimensional array of regularly-spaced x-ray sources and a two-dimensional array of regularly-spaced detectors. It will be noted that there are numerous planes parallel to the source plane 271 and detector plane 270 where multiple beams pass through regularly-spaced points in the plane. These planes are referred to as focal planes or image planes. The regularly-spaced points are referred to as image pixels. Each focal or image plane comprise characteristics which differ from other focal planes, including distance from the source, spacing of image pixels, and size of the image plane. In accordance with the present invention, a method is provided to reconstruct any of these image planes.

To illustrate an embodiment of this method, an array of sources, preferably a rectangular array of $SOURCE_x$ by $SOURCE_y$ sources on a pitch $\lambda_s$ in both the x- and y-directions, is employed with an array of detectors, preferably a rectangular array of $DET_x$ by $DET_y$ detectors on a pitch $\lambda_d$ in both the x- and y-directions. Each source produces a pencil beam of x-rays 100 which illuminates all the detectors in the array. Each x-ray pencil beam 100 is therefore segmented into an array of x-ray microbeams with one x-ray microbeam per detector. In this example, there are $DET_x * DET_y$ microbeams per pencil beam and $SOURCE_x * SOURCE_y$ pencil beams for a total of $DET_x * DET_y * SOURCE_x * SOURCE_y$ microbeams.

INTENSITY(i,j,k,l) is the intensity of the x-ray illumination detected at detector DET(i,j) when source SOURCE(k, l) is illuminated. For this example, i=[1,$DET_x$], j=[1,$DET_y$], k=[1,$SOURCE_x$], and l=[1,$SOURCE_y$].

Figure 68:
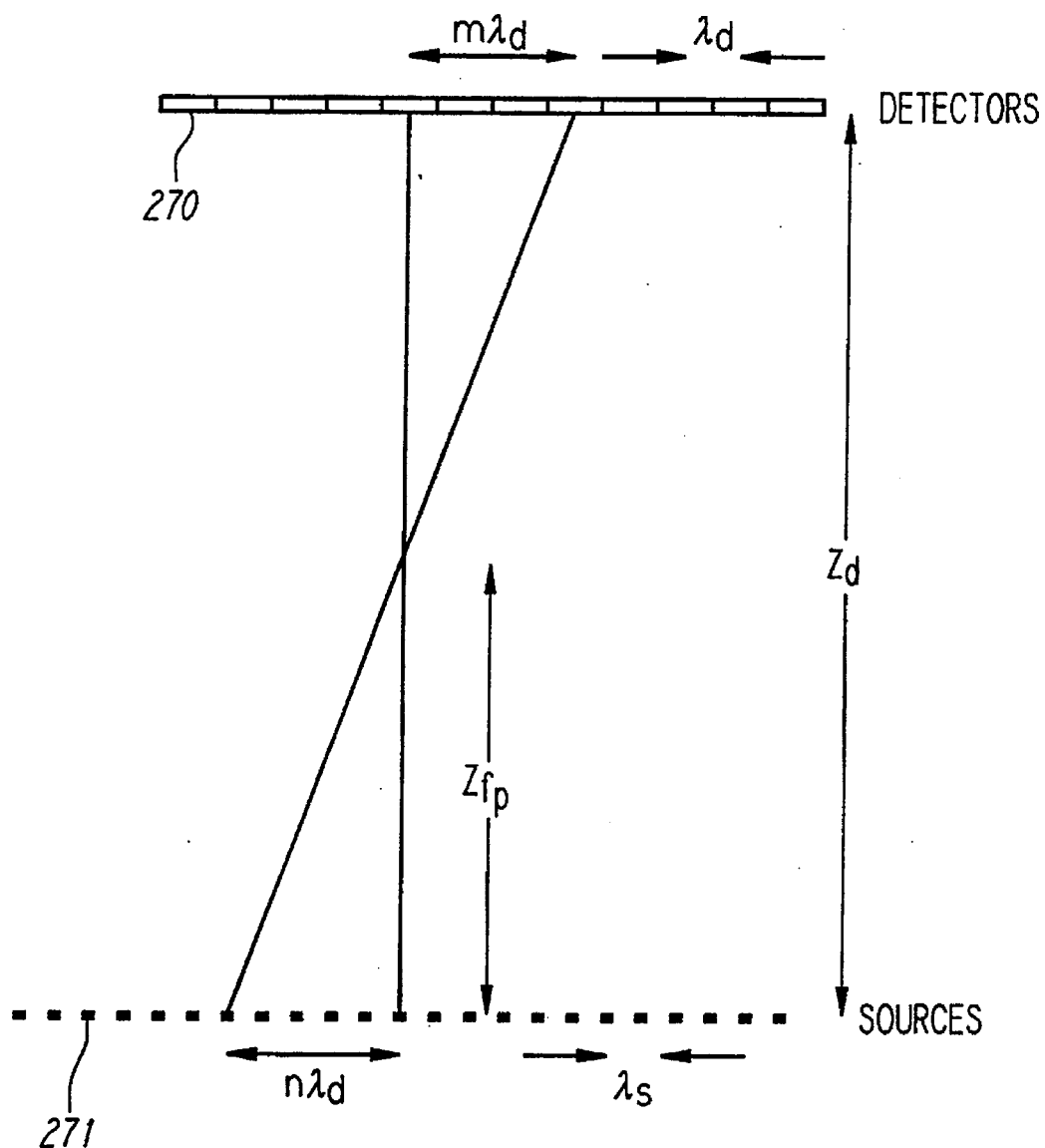
FIG. 68 is a diagram showing focal plane location for one embodiment of scanning beam x-ray imaging system.

Each focal plane can be described by a pair of natural numbers (integers≧1) m and n, where $m*\lambda_d$ and $n*\lambda_s$ are the baseline lengths of the similar triangles, shown in FIG. 68, which determine the location of the focal plane. For this example, $Z_d$ equals the distance from source to detector while $Z_{fp}$ equals the distance from source to focal plane. Therefore, the distance $Z_{fp}$, from the source plane 271 to a particular focal or image plane which is described by the values of m,n can be expressed as:

$$Z_{fp}(m,n) = Z_d \frac{n*\lambda_s}{n*\lambda_s + m*\lambda_d} \quad \text{EQ. 2}$$

According to this method, reconstruction of an image at a particular focal plane m,n can be performed by creating the two-dimensional array $IMAGE_{m,n}$ by summing each value of INTENSITY(i,j,k,l) into image pixel $IMAGE_{m,n}(i*n+k*m, j*n+l*m)$ respectively.

The maximum x- and y-indices of array $IMAGE_{m,n}$ can be expressed as: $DET_x*n+SOURCE_x*m$ and $DET_y*n+SOURCE_y*m$.

For the particular parameters of this embodiment, not all values of the natural numbers m and n are appropriate. For example, if m and n have a common factor (e.g. m=6, n=2) then the array $IMAGE_{m,n}$ will be sparsely filled. The image reconstructed using m=6, n=2 is equivalent to the image reconstructed using m=3, n=1. Although the array $IMAGE_{6,2}$ will have four times as many elements as $IMAGE_{3,1}$ only one-fourth of the elements in $IMAGE_{6,2}$ will be non-zero. Removing the all-zero rows and columns in $IMAGE_{6,2}$ yields $IMAGE_{3,1}$.

Referring to FIG. 68, in this example it will also be noted that, e.g., doubling or tripling both baselines of the similar triangles does not change the location of the resulting focal plane.

The pitch of the image pixels at the focal plane $\lambda_{fp}$ can be expressed as follows:

$$\lambda_{fp}(m,n) = \frac{\lambda_d}{n} * \frac{Z_{fp}(m,n)}{Z_d} \quad \text{EQ. 3(a)}$$

$$= \frac{\lambda_d}{n*} \frac{n*\lambda_s}{n*\lambda_s + m*\lambda_d} \quad \text{EQ. 3(b)}$$

$$= \frac{\lambda_d*\lambda_s}{n*\lambda_s + m*\lambda_d} \quad \text{EQ. 3(c)}$$

Referring to FIG. 68, it will be noted that every mth detector in the x- and y-directions is used to reconstruct any particular image pixel. Therefore, there are, on average, $DET_x*DET_y/m^2$ microbeams per image pixel. Since the total number of microbeams in this example is $DET_x*DET_y*SOURCE_x*SOURCE_y$, the number of image pixels can be expressed as:

$$\frac{DET_x*DET_y*SOURCE_x*SOURCE_Y}{DET_x*DET_y/m^2} = SOURCE_x*SOURCE_Y*m^2 \quad \text{EQ. 4}$$

Due to partial image reconstruction around the perimeter of the image, the number of fully reconstructed image pixels is slightly lower than the above number and the total number of fully and partially reconstructed image pixels is slightly higher than the above number.

In this example, when the size of the source array is $SOURCE_x*\lambda_s$ by $SOURCE_y*\lambda_s$, the size of the field of view (at the focal plane) can be expressed as:

$$SOURCE_x*\lambda_s*\left(1-\frac{Z_{fp}}{Z_d}\right) \text{ by } SOURCE_y*\lambda_s*\left(1-\frac{Z_{fp}}{Z_d}\right) \quad \text{EQ. 5}$$

The m,n image reconstruction method is more flexible than the previously described reconstruction methods. As FIG. 67 shows, m,n image reconstruction can generate a wide variety of focal planes at numerous positions between the source and detector planes. Many of the focal planes have a small pitch between image pixels which can be used to produce images with high spatial resolution.

The ability to reconstruct a wide variety of focal planes can be used to move the focal plane with respect to the source and detector by simply selecting a suitable image plane near the region of interest of the object to be imaged.

The m,n image reconstruction method can also be used to increase the effective depth of field of an image by simultaneously reconstructing multiple focal planes around a region of interest. The reconstructed planes can be combined to produce a single image with high spatial resolution over a larger range of distances from the x-ray source plane. The multiple reconstructed planes can be combined, for example, by adding together only the high spatial frequency components from each reconstructed plane.

System Description

FIGS. 18–25 are functional block diagrams of a preferred stereoscopic scanning-beam x-ray imaging system according to the present invention. FIG. 17 depicts the manner in which FIGS. 18–25 can be arranged to create a single block diagram of this presently preferred system. For medical applications the x-ray source and the multi-detector arrays are preferably mounted on a movable C-arm with the x-ray source mounted above an adjustable patient table and the multi-detector arrays located below the table.

FIG. 18 includes a representative block diagram of high-voltage terminal 803, which is part of x-ray source 798. High-voltage terminal 803, which is preferably contained in a housing (not shown) includes electrical components for producing and controlling the electron beam 1240. The high voltage necessary to power the x-ray source is supplied to the high voltage terminal from an external adjustable high-voltage power supply 790 by a single cable 1010. All of the electronic components in the high voltage terminal 803 preferably float at the output potential of the high-voltage power supply. The unique construction of the high voltage terminal results in only this single electrical connection to the high voltage terminal. All other data and power transmission to and from the high voltage terminal is preferably accomplished via fiber optic links and via an isolation transformer. A more detailed description of the structure and operation of the presently preferred high voltage terminal is provided in copending U.S. patent application Ser. No. 08/386,884, which has been incorporated herein by reference in its entirety.

Because of the high operating voltages with respect to ground in the high-voltage terminal 803 (−100 kV to −120 kV), the housing is preferably filled with an electrically insulating medium, preferably pressurized $SF_6$ (sulphur hexafluoride) gas, to electrically isolate the high voltage terminal 803 from its surroundings.

High voltage isolation transformer 744 supplies power for the circuitry in the high-voltage terminal 803. The secondary winding 1271 of isolation transformer 744 is part of the high-voltage terminal 803, while the primary winding 1270 is separated from the terminal by a gap filled with the pressurized $SF_6$ gas. The primary winding 1270 preferably forms a part of the high voltage terminal housing and is supplied with power from the high voltage terminal power supply driver 772 located in the C-arm cart. The preferred construction of the isolation transformer is described more fully in copending U.S. patent application Ser. No. 08/386,884 which has been incorporated herein by reference in its entirety.

In addition to the components necessary for generating and controlling an electron beam, the high voltage terminal preferably includes components for monitoring certain parameters located within the high voltage terminal. The monitored information is preferably communicated outside the housing via fiber optic cables. The circuitry for converting the electrical signals to light signals and the light signals to electrical signals is described more fully in connection with the detailed description of FIGS. 40 and 41, and is enclosed within the high voltage terminal housing.

A pressure sensor 722 preferably monitors the pressure of the $SF_6$ gas in the housing to ensure adequate electrical isolation. Additionally, the temperature of the pressurized $SF_6$ gas is preferably monitored by temperature sensor 724. This information is transmitted via multiplexer 732 and I/O controller 762 to control computer 890. If the pressure drops below a predetermined threshold or the temperature increases above a predetermined threshold, the control computer will shut the system down.

The electric current from the high voltage power supply is preferably sensed by passing the current through a beam current sensor 736 which provides information to a current sense monitor 788 which is preferably located in the C-arm cart.

In addition the heater controller 734, which controls the heater 726 located in the electron gun 728, provides information concerning heater current and voltage to multiplexer 732 for transmission to the control computer 890.

The voltage of the electron grid 730, located in front of the emitting face of electron gun 728, is controlled by grid controller 738. The voltage level of electron grid 730 can preferably be varied between zero and −2000V with respect to the cathode to adjust the current of the electron beam 1240, thereby controlling the x-ray flux emitted by target 1250. When the electron grid is at a potential of approximately −2000V, the electron beam is effectively shut off. The beam-on control signal 1024 instructs the grid controller 738 to apply either −2000V to the grid to turn the electron beam off, or to apply the beam-on grid voltage set via fiber optic link 1030 to the grid to turn the electron beam on to a preset current. The grid controller 738 also relays the beam-on and beam-off grid voltages to the multiplexer 732. Fault conditions in the grid controller will trip the high voltage terminal fault latch 742 which will shut the electron beam off by turning off heater 726 via heater controller 734 and setting the voltage of electron grid assembly 730 to −2000V via grid controller 738. The entire x-ray source will also be shut down via fiber-optic cable 1020 and fail safe controller 760.

The status information from various components within high voltage terminal 803, which are input to multiplexer 732, are transmitted to I/O controller 762. Multiplexer 732 includes a voltage to frequency converter which drives an LED for conversion of the electrical status signals from a selected component into light pulses and transmits these signals to I/O controller 762 via fiber-optic cable 1016. I/O controller 762 controls the sequence of transmission of each component's status information sent via multiplexer 732 by sending a channel select signal to multiplexer 732 via fiber-optic cable 1018.

Ion pump 720 maintains the vacuum within the x-ray source 798. Ion pump 720 is powered by ion pump power supply 758, which in the preferred embodiment is located within C-arm cart 811. Ion pump power supply 758 also has an output which indicates the vacuum pressure to control computer 890 via I/O controller 762.

Figure 19:
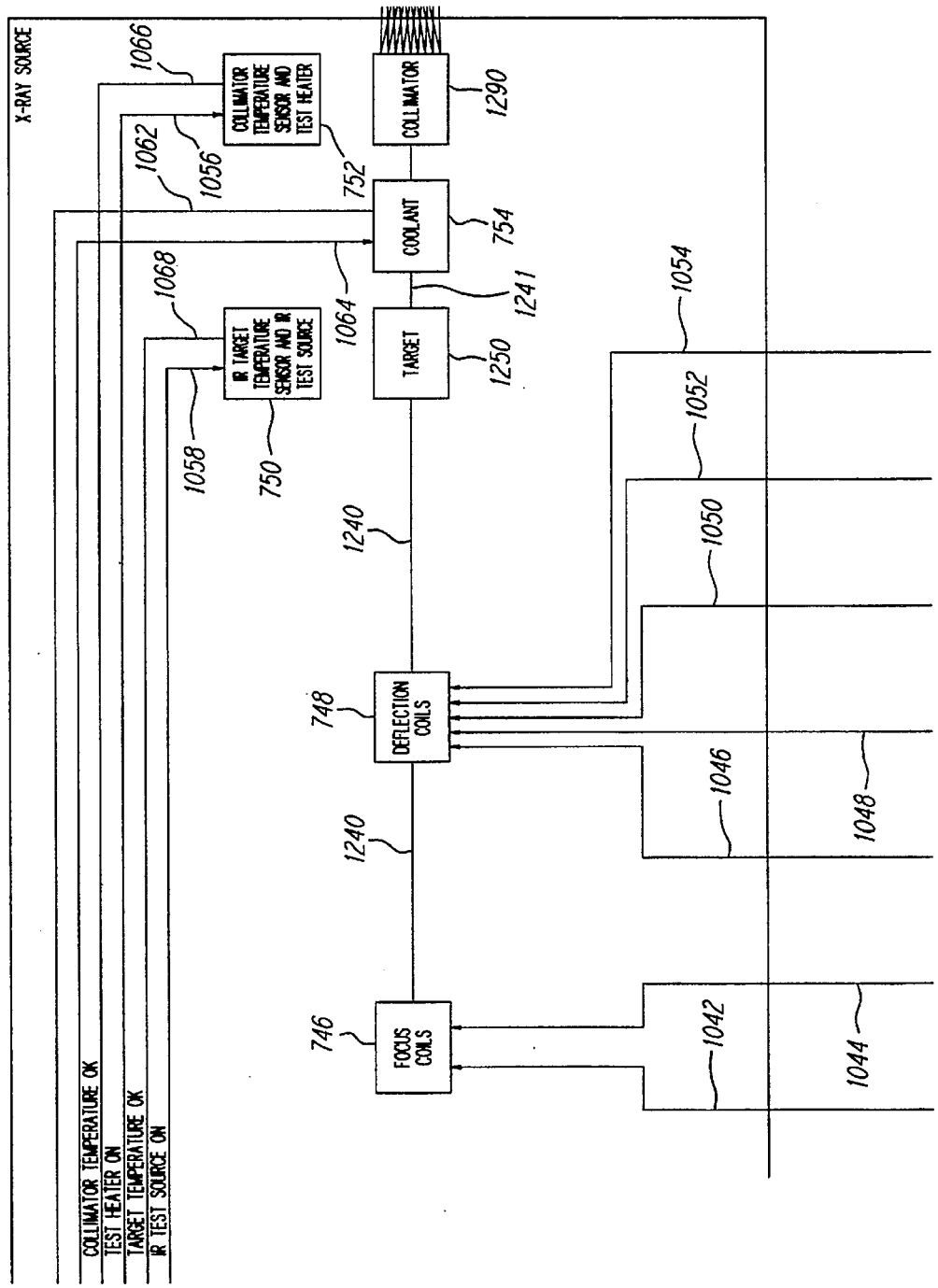

Referring now to FIG. 19, electron gun 728 emits a beam of electrons 1240 toward grounded target 1250 which preferably passes through focus coils 746 and deflection coils 748 to focus and position electron beam 1240 at a desired location on target 1250. The deflection coils 748 aim electron beam 1240 at a specific location on the surface of target 1250. Target 1250 emits x-rays 1241 at the spot illuminated by electron beam 1240. Infra-red temperature sensor 750 constantly monitors the temperature of target 1250 for abnormal increases in temperature caused by malfunctioning of the beam scanning. If infra-red temperature sensor 750 detects an over-temperature condition, it trips the fail-safe controller 760 to shut down the x-ray source. To verify proper operation of the temperature sensor, an infra-red test source is provided which can be activated by the control computer to simulate an over-temperature condition to verify that the infra-red temperature sensor will detect a fault and shutdown the x-ray source.

A cooling chamber 754 for cooling the target 1250 is preferably located between the target 1250 and the collimator 1290. The coolant from cooling chamber 754 is preferably circulated through a heat exchanger 756 (FIG. 24) preferably housed within the C-arm. Since the collimator 1290 may come in contact with the patient during imaging procedures, the collimator 1290 is preferably monitored for excessive temperatures by collimator temperature sensor 752. In this preferred embodiment, collimator temperature sensor 752 checks for temperatures in excess of 40° C. If the temperature exceeds this threshold, the fault is communicated to the fail-safe controller 760, which shuts down the x-ray source. To verify proper operation of the temperature sensor, a test heater is provided which can be activated by the control computer to simulate an over-temperature condition to verify that the temperature sensor will detect a fault and shutdown the x-ray source.

Figure 23:
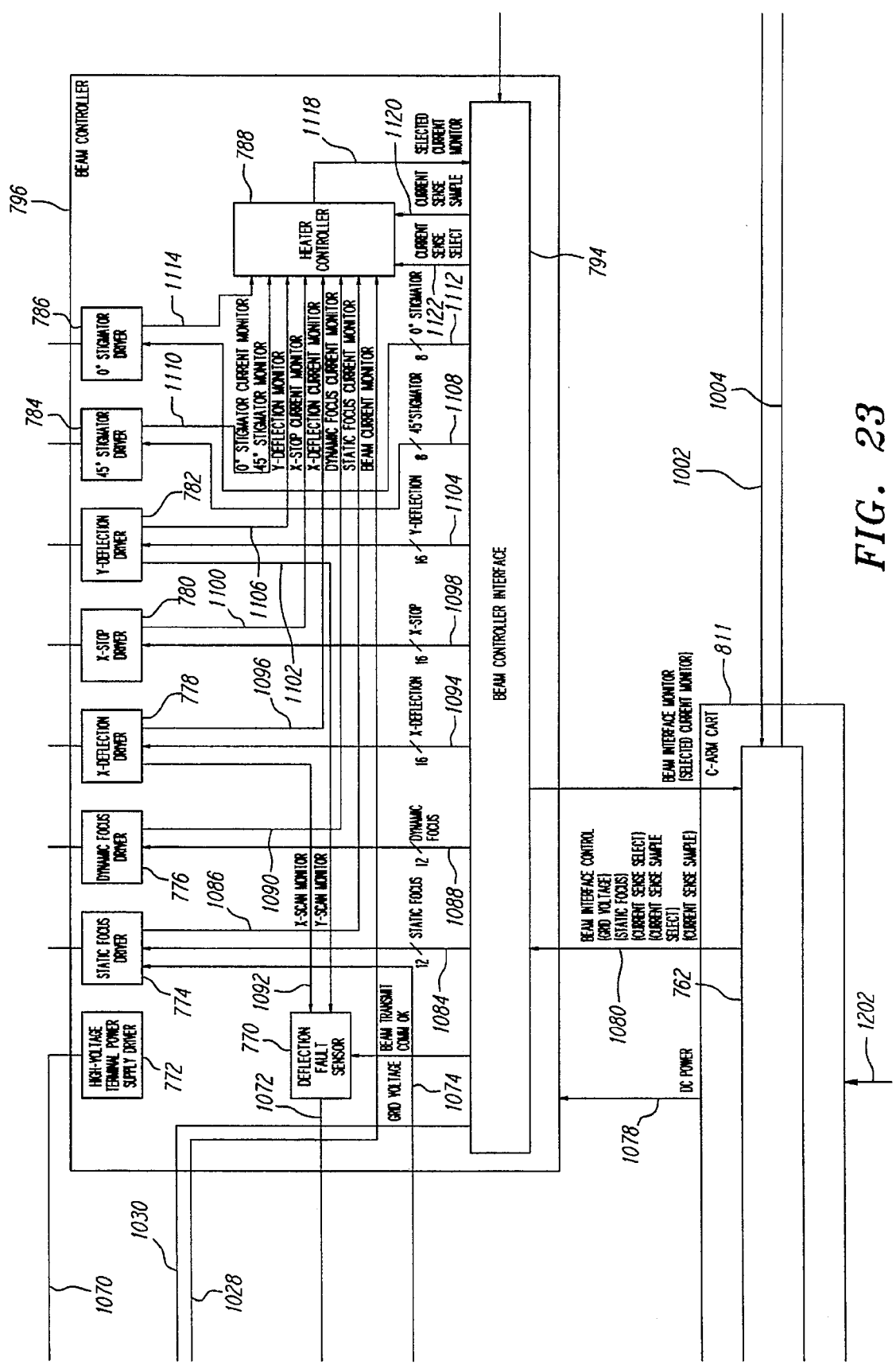

FIG. 23 is a block diagram comprising beam controller 796 and a portion of the C-arm cart. The beam controller interface 794 receives data from the tube controller via a high speed fiber optic link 1000. Consequently, beam controller interface 794 includes the light signal to electrical signal conversion circuitry described more fully in conjunction with FIGS. 40 and 41.

Beam controller 796 preferably controls the focus coils 746 through two separate drivers, a static focus driver 774 and a dynamic focus driver 776. Static focus driver 774 is preferably set only once for a given operating voltage of the high voltage power supply. The dynamic focus driver 776 adjusts the precise focussing of the electron beam 1240 as it scans across target 1250.

Beam controller 796 preferably controls the deflection coils 748 through five separate drivers: x-deflection driver 778, x-step driver 780, y-deflection driver 782, 45° stigmator driver 784, and 0° stignator driver 786.

The x-deflection driver 778 communicates a conventional linear input pattern to the deflection coils via wires 1046 to drive the electron beam horizontally across the target whereas the x-step driver 780 communicates a novel sawtooth input signal to the deflection coils 748 via wires 1048. The net effect is a stepped movement of the electron beam across the target. The y-deflection driver 782 communicates a conventional y-deflection pattern to the deflection coils 748 via wires 1050 to drive the electron beam 1240 vertically across the face of the anode. The 45° stigmator driver 784 and the 0° stigmator driver 786 and their respective coils correct for aberrations in the electron beam spot to maintain a circular spot on the target. More detailed information about these circuits can be found in copending U.S. patent application Ser. No. 08/386,884 which has been incorporated herein by reference.

Current sense monitor 788 is preferably used to monitor the output of any of the beam controller drivers to verify their correct operation as well as to measure the electron beam current as previously discussed.

A failure in the deflection system could result in the electron beam not scanning across the target in the x direction or the y direction. This could result in thermal damage to the target. Deflection fault sensor 770 preferably receives x-scan and y-scan monitoring information from x-deflection driver 778 and y-deflection driver 782. Deflection fault sensor 770 preferably transmits a fault status signal to fail-safe controller 760 via fiber-optic cable 1072. If a deflection fault condition occurs, fail-safe controller 760 will shutdown the x-ray source.

Figure 24:
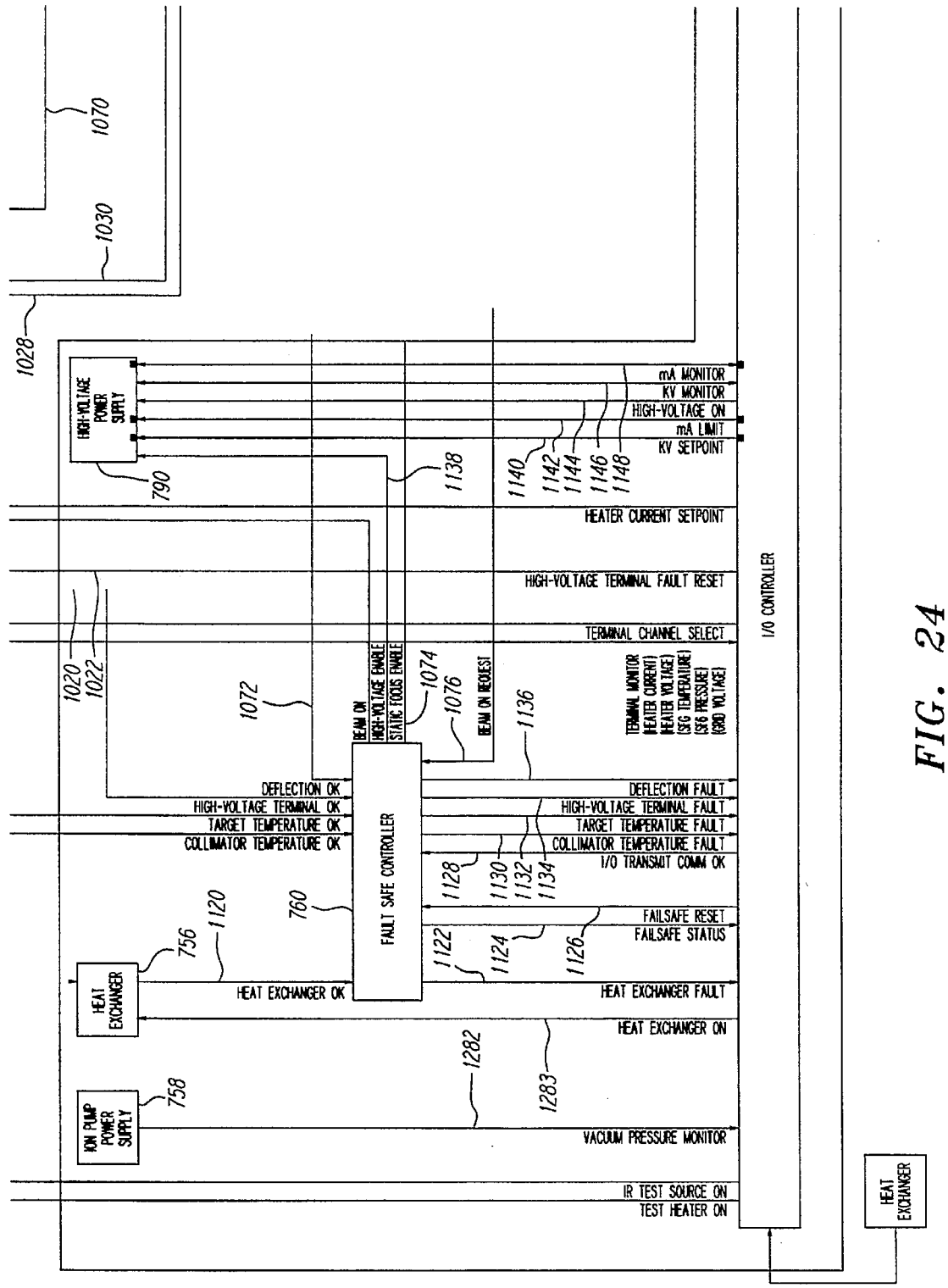

FIGS. 23 and 24 include a functional block diagram of the components preferably housed in the C-arm cart 811. Power is preferably supplied to the C-arm cart 811 from a 208 volt 3-phase AC power supply via cable 763. DC power is fed from the c-arm cart to the beam controller 796 via cable 1078.

Figure 40:
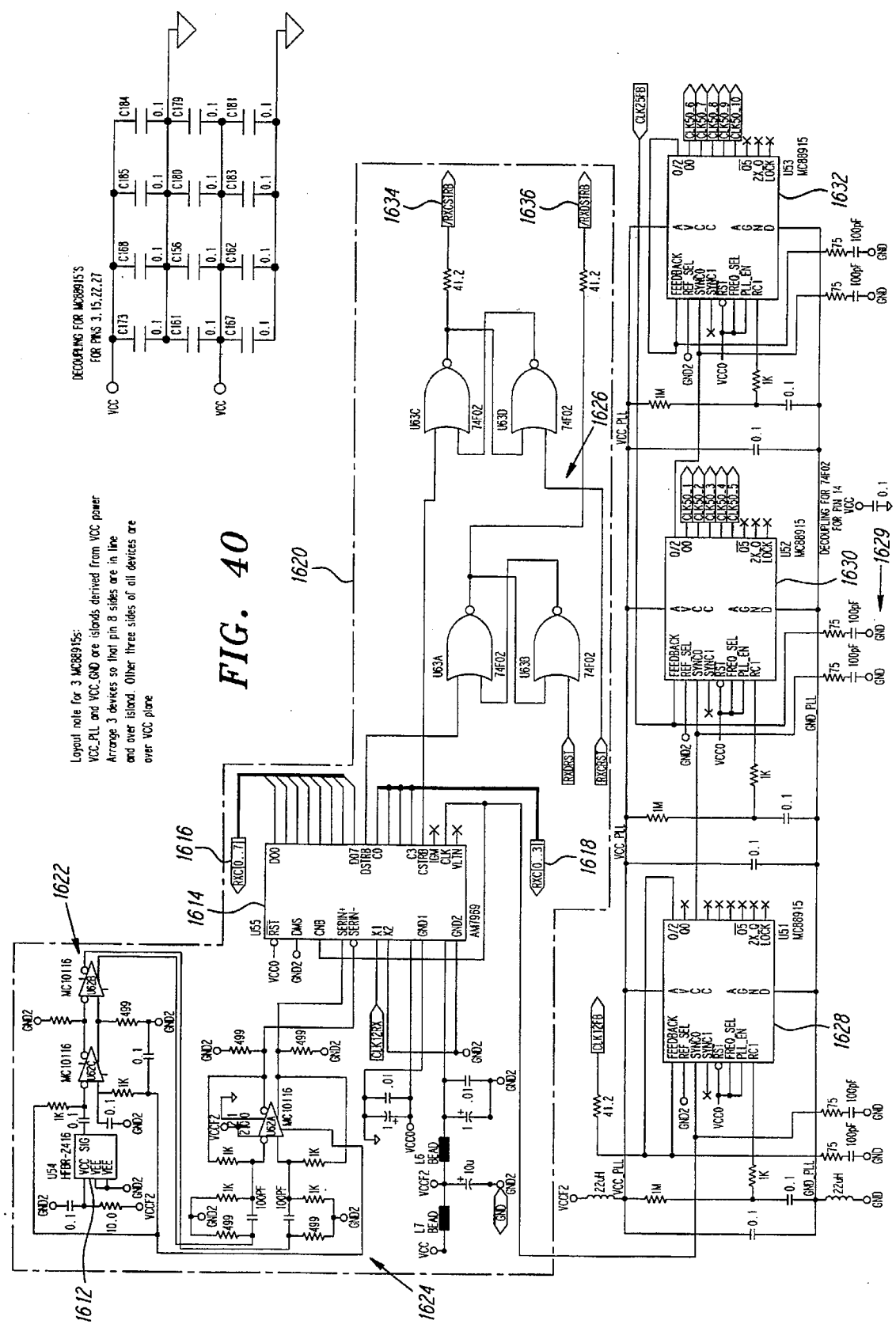
FIG. 40 and 41 comprise schematics of the preferred real time eye optical to electrical and electrical to optical conversion circuitry.
Figure 41:
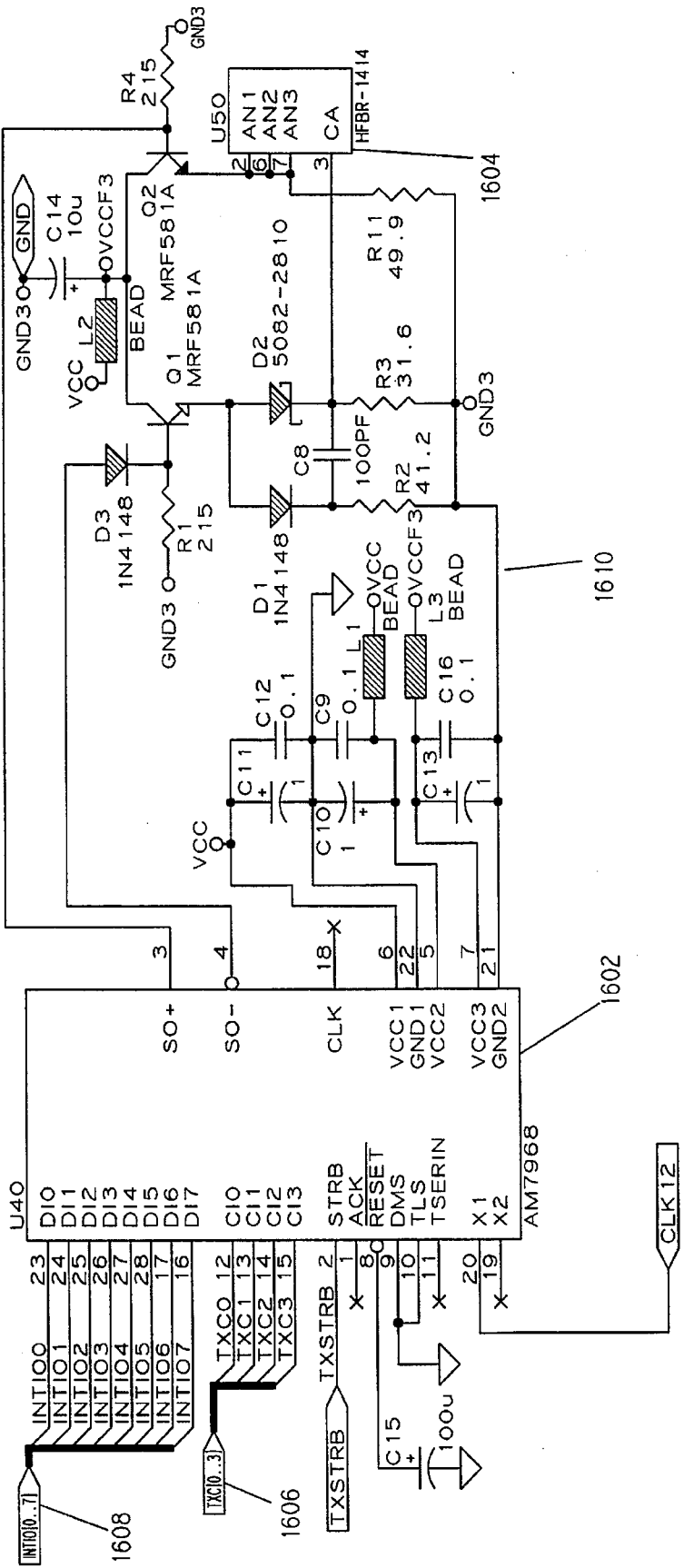

I/O controller 762 (FIGS. 23 and 24) preferably communicates with the control computer 890 via high speed fiber-optic cables 1002 and 1004 and includes the electrical to light and light signal to electrical signal conversion circuitry described more fully in conjunction with FIGS. 40 and 41. Beam controller interface information including grid voltage, static focus current, current sense select, current sense sample select information and current sense sample information, is transmitted to beam controller interface 794 from I/O controller 762 via cable 1080.

As discussed, fail-safe controller 760 preferably receives and monitors status information from various components of the system and is designed to disable the system upon detection of a potential safety problem. If the fail-safe controller 760 detects such a potential problem, it will preferably: (1) signal the grid controller 738 to disable (turn off) the electron beam; (2) shut down the high-voltage power supply 790; and (3) shut down the static focus driver 774 to defocus the electron beam.

In the preferred embodiment, fail-safe controller 760 receives fault status signals from: heat exchanger 756 via wire 1120; collimator temperature sensor 752 via wire 1066; IR target temperature sensor via wire 1068; high-voltage terminal fault latch 742 via fiber-optic cable 1020; and deflection fault sensor 770 via fiber-optic cable 1072. Fail-safe controller 760 also relays the fault status signals to the control computer via I/O controller 762 so that fault conditions may be displayed and logged by the control computer.

High-voltage power supply 790 is preferably located on C-arm cart 811. The signal to turn on the high-voltage power supply 790 is sent from the I/O controller 762 to the high voltage supply 790 via wire 1144. Voltage setpoint is sent to high-voltage power supply 790 via wire 1140, and current limit is sent via wire 1142. Voltage monitoring signal is sent to the I/O controller from the high voltage supply via wire 1146 and current monitoring signal is sent via wire 1148.

Figure 20:
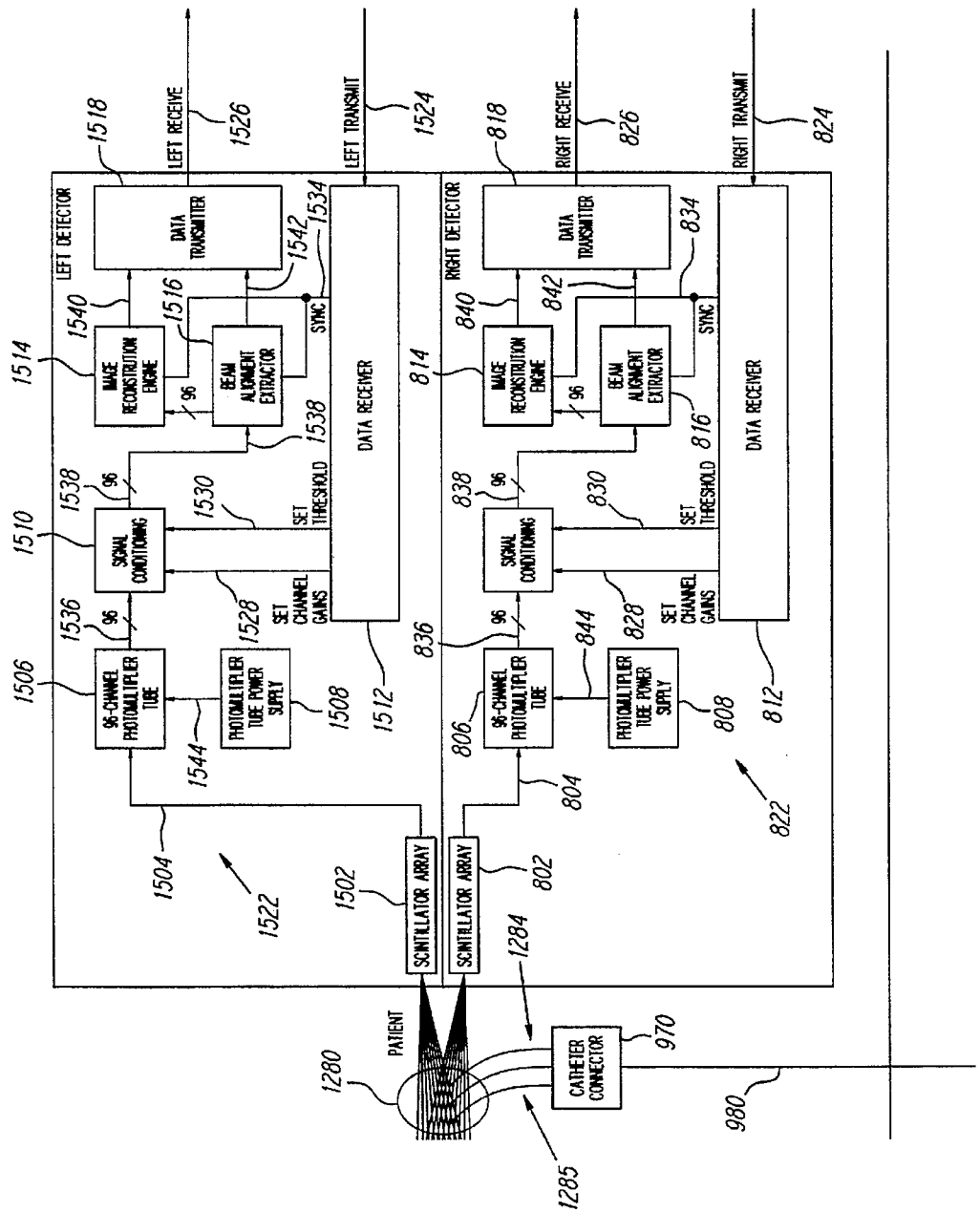
Figure 21:
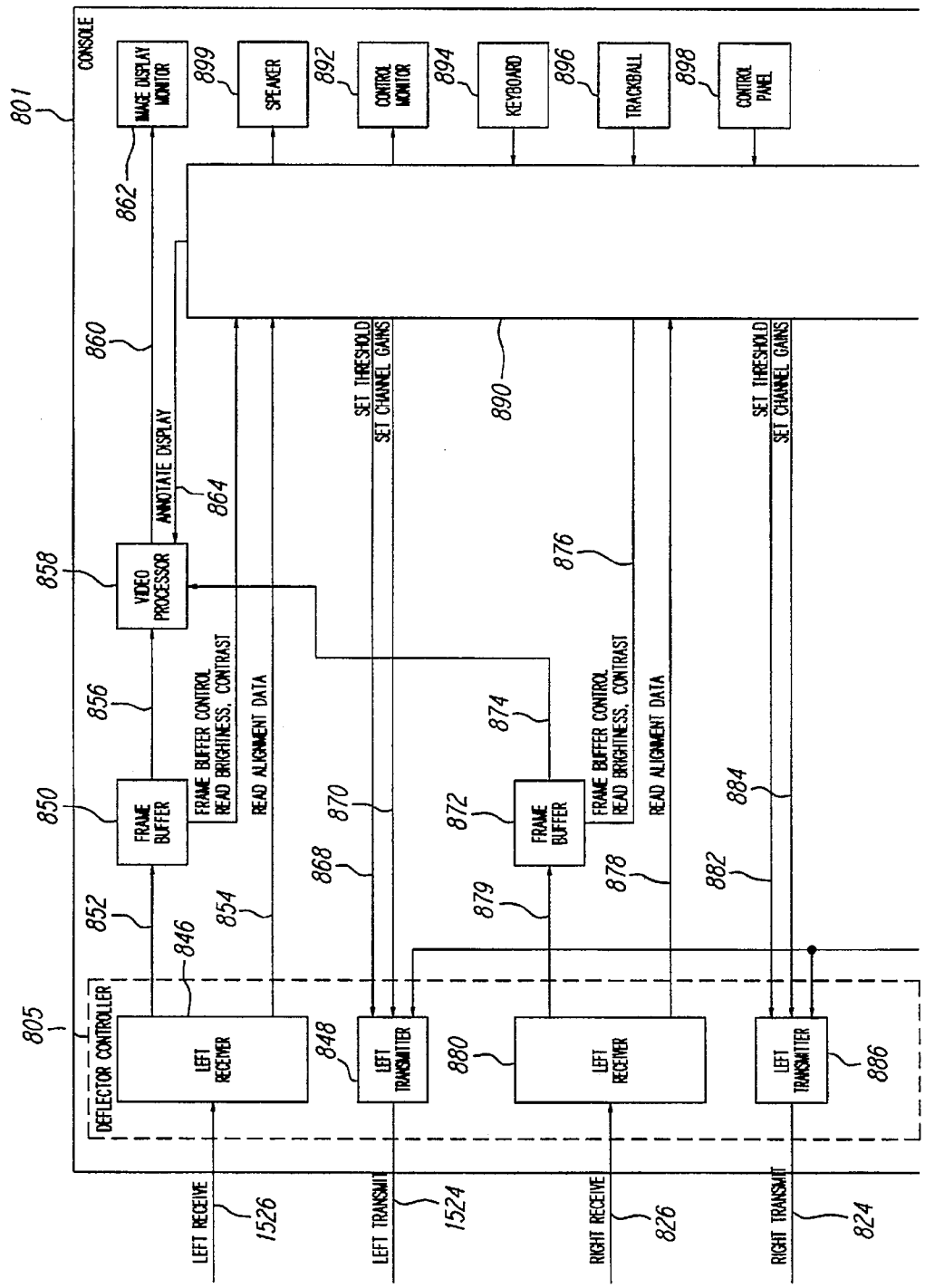

In FIG. 20, maneuverable and locatable catheters 1285 are shown inserted into patient 1280. The proximal end 1284 of catheters 1285 are preferably connected to catheter connector 970. Catheter connection 970 is preferably connected to a multi-channel photomultiplier tube 900 (FIG. 22) through fiber-optic cable 980.

FIG. 20 also functionally diagrams preferred right 822 and left 1522 detectors of the present invention. Since both detectors in FIG. 20 function in a similar fashion, only the right detector 822 will be discussed in detail. The components bearing a number having the same last two digits perform the same function.

Scintillator array 802 preferably comprises ninety-six elements and in response to x-ray photons generates visible light energy which is transmitted to photomultiplier tube 806 comprising ninety-six channels via a tapered fiber-optic bundle 804. The photomultiplier tube 806 converts the received light energy into electrical signals which are sent to signal conditioner 810 via 96 separate electrical connections 836. These signals are referred to herein as raw partial image pixel information. The multi-detector array preferably comprises a scintillator array 802, fiber-optic taper 804 and photomultiplier tube 806. It should be noted that while the preferred embodiment includes 96 channels, more or less than that number are within the spirit and scope of the present invention. Photomultiplier tube 806 is powered by photomultiplier tube power supply 808.

Signal conditioner 810 is preferably comprised of 48 circuit boards 1343. Each circuit board 1343 comprises two sets of signal conditioning amplifier circuits 1830, with each signal conditioning amplifier circuit 1830 feeding its output to a corresponding discriminator 1832. Thus 96 sets of signal conditioning amplifier circuits 1830 and discriminators 1832 are employed, with each set paired to a corresponding photomultiplier tube channel. The signal conditioner 810 outputs ninety-six separate signals for every step of the electron beam. This information is referred to as the partial image pixel information.

The outputs of the signal conditioners are preferably input into the beam alignment extractor 816. Beam alignment extractor 816 processes the information from each position of the electron beam on the target and sends processed alignment data to data transmitter 818. Clock signals are sent to the beam alignment extractor from data receiver 812.

Beam alignment extractor 816 sends the partial image pixel information from signal conditioner 810 to image reconstruction engine 814. For diagnostic purposes, the partial image pixel information sent from signal conditioner 810 may be modified by the beam alignment extractor 816 before it is sent to the image reconstruction engine 814. Image reconstruction engine 814 processes the partial image pixel information and sends image pixel data to data transmitter 818. The image reconstruction engine 814 receives clock signals from data receiver 812 via electrical connection 834.

The detector controller 805 (FIG. 21) for the detectors 822 and 1522 preferably transmits and receives optical signals to and from the detectors. Right receiver 880 receives image pixel data and beam alignment data from the right detector 822 through high-speed fiber-optic cable 826. Right detector 822 transmits this data through a data transmitter 818 (FIG. 20), which preferably includes circuitry for conversion of the signals from image reconstruction engine 814 and beam alignment extractor 816 into a serial signal. This serial signal is converted into light pulses using an LED. Right receiver 880 also comprises a light detector and related circuitry for receiving and decoding the light pulse from a serial signal into parallel signals. The beam alignment data is transmitted to control computer 890. The image pixel data is preferably transmitted to frame buffer 872. The left receiver 846 operates in a similar fashion to receive image pixel data and beam alignment data from the left detector 1522.

Figure 25:
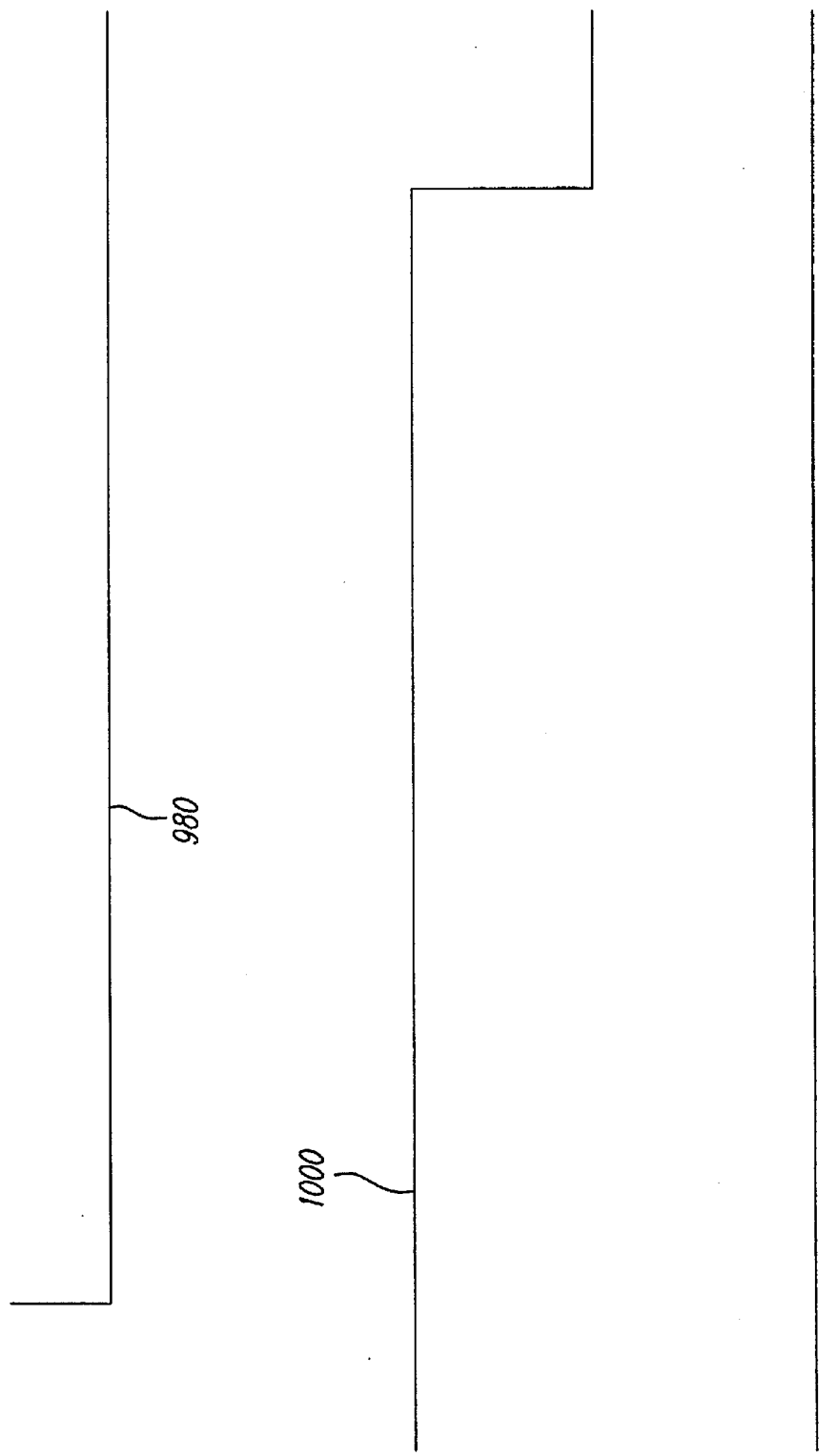

Right transmitter 886 comprises circuitry for converting parallel signals into serial signals. Right transmitter 886 receives, among other signals, signals to set channel gains and threshold levels from control computer 890. Right transmitter 886 also receives clock signals from beam deflection lookup table 918 (FIG. 25). These signals are converted into serial signals which are then transmitted as light pulses to the right detector 822 through high-speed fiber-optic cable 824. Right data receiver 812, which contains a light detector and circuitry to convert light pulses into parallel signals receives these signals. The signal to set channel gain is transmitted to the signal conditioner 810 through wire 828. The left transmitter 848 operates in a similar manner to communicate control signals to the left detector 1522.

Image pixel data transmitted to right frame buffer 872 is subsequently transmitted to video processor 858 where in a stereoscopic system, it is preferably combined with image pixel data from left frame buffer 850. Brightness and contrast information are transmitted from the right frame buffer 872 and from the left frame buffer 850 to control computer 890. This information is used to set the output of the x-ray source for optimal image quality and x-ray exposure control. Control computer 890 transmits information to the video processor 858 for annotation of the image display. The output of video processor 858 is preferably sent to image display monitor 862 where the image is displayed.

Control computer 890 preferably controls the operation of the system via detector controller 805, tube controller 807, and beam controller 796. Control computer 890 may receive operator instructions from input sources such as keyboard 894, trackball 896, and control panel 898. The operator receives system information from the control computer through control monitor 892 and speaker 899.

Figure 22:
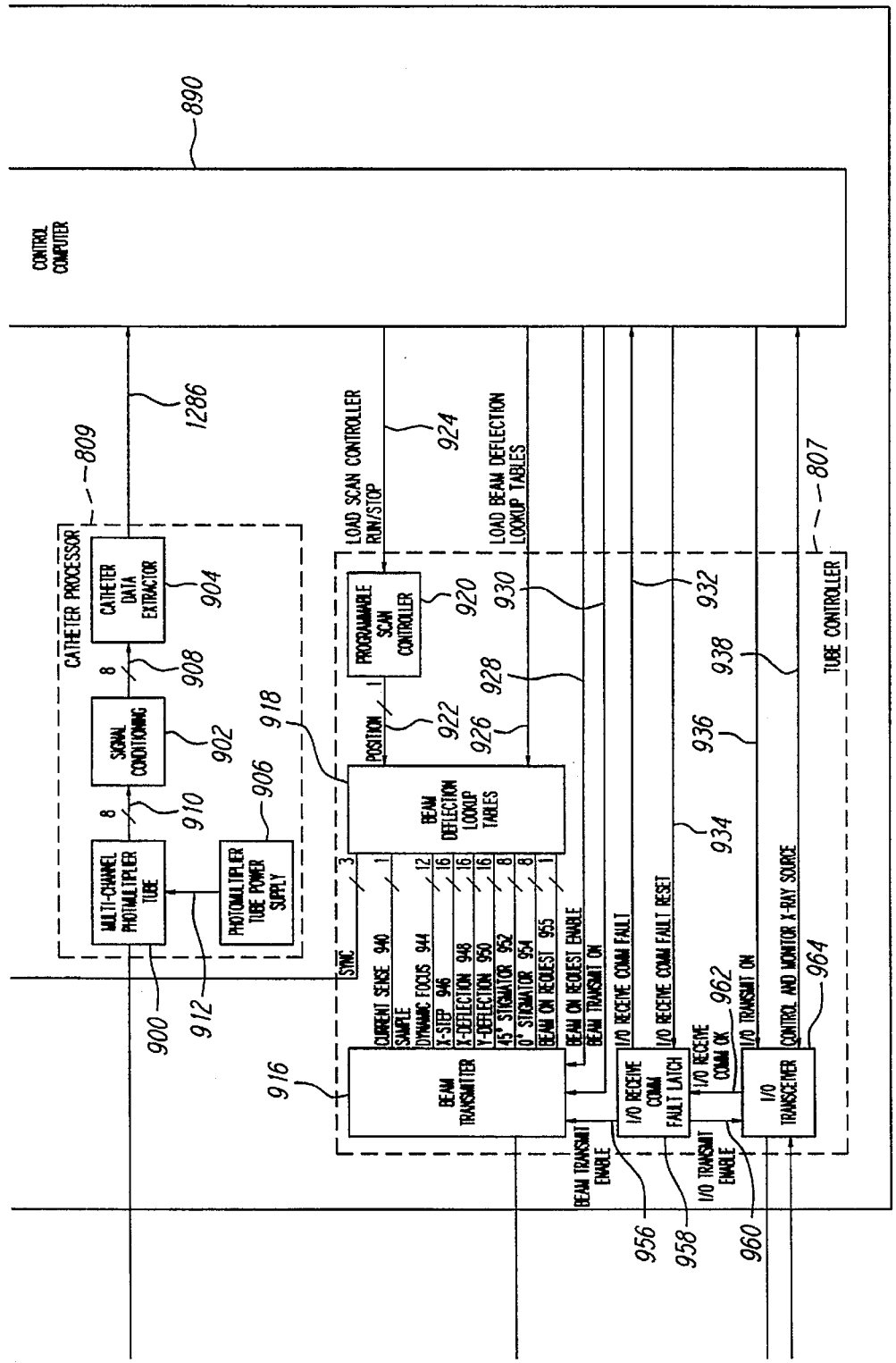

Referring to FIG. 22, catheter processor 809 preferably receives information from up to eight catheters 1285 via fiber-optic cables 980. The light pulses received through fiber-optic cables 980 are preferably detected by the catheter multi-channel photomultiplier tube 900. The catheter multi-channel photomultiplier tube 900 is powered by power supply 906. The information received by the catheter multi-channel photomultiplier tube 900 is preferably sent to catheter signal conditioning circuit 902 via electrical connection 910. The catheter signal conditioning circuit 902 outputs data to the catheter data extractor 904 via electrical connection 908. The catheter information from catheter data extractor 904 is transmitted to the control computer 890.

Tube controller 807 transmits data to and from the I/O controller 762 and the beam controller 796 to control the operation of x-ray source 798. Tube controller 807 preferably comprises beam deflection lookup table 918, programmable scan controller 920, beam transmitter 916, I/O transceiver 964, and I/O fault latch 958.

Programmable scan controller 920 is preferably set by control computer 890 to produce a particular scan. These setting may include, for example, scan rate, serpentine or raster scan, and round or square scan. Programmable scan controller 920 transmits a sequence of desired beam positions to beam deflection lookup table 918. For each desired location of the electron beam, the beam deflection lookup table preferably contains values for deflection and focus necessary to produce a well focused spot at the correct location on the target. The data in the beam deflection lookup table 918 is preferably programmed by control computer 890.

Data from the beam deflection lookup table 918 is preferably sent to beam controller interface 794 via beam transmitter 916 and high-speed fiber-optic link 1000. This data includes: (1) current sense sample signals; (2) dynamic focus; (3) x-step; (4) x-deflection; (5) y-deflection; (6) 45° stigmator; (7) 0° stigmator; and (8) "beam on request" signals. Preferably, approximately every 1.28 microseconds, a new set of data is sent from the beam deflection lookup table 918 to the beam controller interface 794.

I/O transceiver 964 provides the communications link between the control computer 890 and the I/O controller 762. Control computer 890 sends data and control signals to I/O controller 762. Information from the x-ray source 798 is sent to the control computer 890 via I/O transceiver 964.

If a fault condition occurs during the transmission of information from beam transmitter 916 to beam controller interface 794, deflection fault sensor will detect the fault and shut the x-ray source down via fail safe controller 760. If a fault condition occurs during the transmission of information from I/O transceiver 964 to I/O controller 762, the I/O controller will detect the fault and shut the x-ray source down via fail safe controller 760. If a fault condition occurs during the transmission of information from I/O controller 762 to I/O transceiver 964, I/O transceiver 964 will set the I/O fault latch 958 which will disable communications via fiber-optic cables 1000 and 1002. This will be detected as faults by the deflection fault sensor and by the I/O controller which will shut the x-ray source down as described above.

Real-Time Eye

Figure 26:
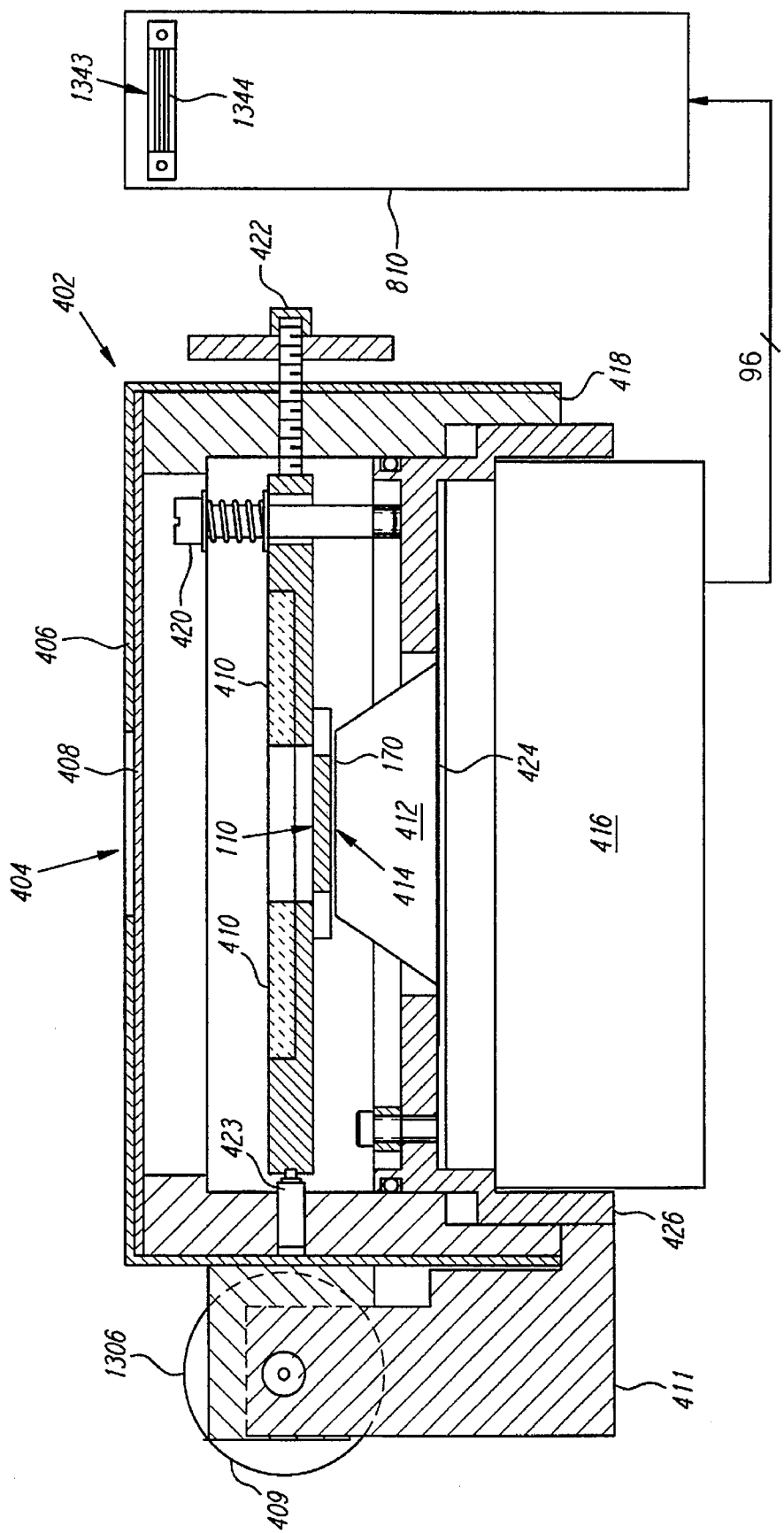
FIG. 26 is a partial cross-sectional representation of a preferred real-time eye assembly.

FIG. 26 depicts "real-time eye" assembly 402 which comprises the multi-detector array according to a presently preferred embodiment of the present invention. X-rays enter through x-ray window 404 in lead shield 406. X-ray window 404 is preferably circular and about 1.91 cm (0.75 in) in diameter to permit x-rays coming from the apertures 140 of the collimation grid 90 to strike the multi-detector array 110 while attenuating scattered x-rays. A light shield 408 is preferably provided to shield the eye from ambient light. The light shield 408 may be made of a thin sheet of aluminum or beryllium chosen to attenuate light without substantially attenuating the x-rays, and is preferably 0.0125 cm thick. The multi-detector array assembly 402 is preferably enclosed in a light-tight outer detector housing 418 to minimize stray light from generating noise. Three centering screws 422 are provided for planar and linear alignment. Rotational alignment in one embodiment is achieved by rotating outer detector housing 418 with respect to PMT mount 426.

Scintillator array 112 is preferably mounted beneath the x-ray window 404. Scintillator array 112 is preferably comprised of 96 scintillator elements 170 arranged in a pseudo-circle, with each scintillator element 170 preferably cut to a square horizontal cross-section. The length of the individual scintillator elements 170 are preferably about 0.50 cm and the front input faces are preferably 0.135 cm×0.135 cm. The scintillator elements 170 are preferably YSO, LSO or BGO but other scintillating materials may also be used.

For a suitably reduced decay time for its light output in this application (to about 50 nsec), BGO needs to be heated to approximately 100° C. When using BGO, the scintillator array is located near heating element 410 for use with a BGO scintillator. If a BGO scintillator is used heating element 410 may be a resistive heating element designed to keep the BGO scintillator crystal array 112 at an operating temperature of about 100° C. Accordingly a resistive heating element may be provided, as shown in FIG. 26. YSO is preferably used as the scintillator material, thereby avoiding the need for a heater.

A fiber-optic imaging taper 412 of the preferred multidetector array 110 directs light photons emerging out of the bottom 414 of the scintillator crystal array 112 to a 96 channel photomultiplier tube (PMT) 416. A presently preferred fiber-optic imaging taper 412 is available from Collimated Holes of Campbell, Calif. and has a circular input aperture of diameter 2.03 cm (0.8 in) and a circular output aperture of diameter 3.38 cm (1.33 in). Taper 412 matches each scintillator crystal pitch dimension (0.06") to that of the PMT 416 (0.10"), i.e., it has a magnification of 1.667 times.

High viscosity optical coupling fluid available from Dow Corning (Type 200) with a refractive index approximately matching that of the glass may be used at the two faces of the taper as an optical coupling medium to maximize the light transfer efficiency from the scintillator crystals 170 to the taper 412 and from the taper 412 to the PMT input face 424.

Photomultiplier tube 416 is preferably a 96 channel tube (one channel corresponding to each scintillator crystal 170) model number XP 1724A available from the Philips Corporation. Photomultiplier tube 416 preferably has a fiber-optic face plate so that the spatial arrangement of the scintillator crystal array 112 is accurately carried through to the PMT photocathode located in the PMT on the other face of the faceplate. An x-ray photon striking one of the scintillators 170 produces many light photons which are coupled to the PMT photocathode. This produces a corresponding electron pulse at the photocathode and the pulse is amplified in one channel of the PMT dynode structure up to 1,000,000 times.

Figure 27:
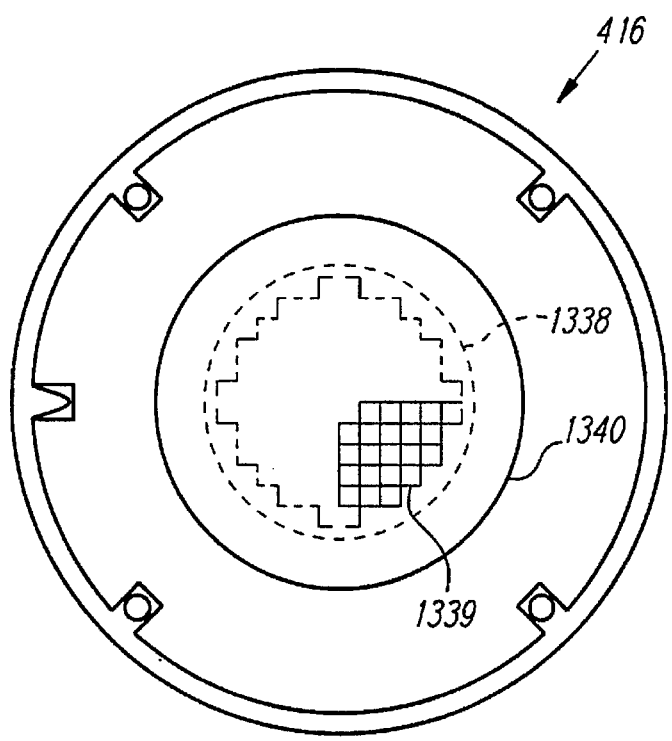
FIG. 27 is a diagram of a top view of a preferred 96-channel photomultiplier tube.
Figure 28:
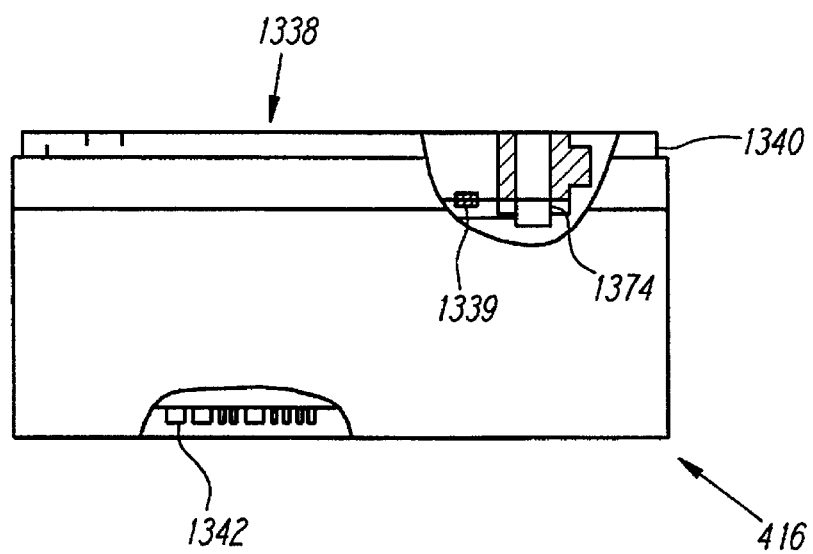
FIG. 28 is a partial cross-sectional side view of the photomultiplier tube of FIG. 27.

Referring to FIGS. 27 and 28, the front face of PMT 416 includes a glass window 1340 which extends beyond the PMT encapsulation by 0.1 mm. 96 photo-cathode elements 1339 are arranged in a pseudo-circular array in the center of the front face of PMT 416. Each photo-cathode element is square in shape with dimensions of 2.54 mm×2.54 mm. PMT 416 is attached to the PMT mount by means of attachment bolts set into PMT 416 at bolt holes 1374.

This pseudo-circular array of 96 photo-cathode elements creates a light-sensitive circular area 1338 on the PMT 416 with a diameter of 30.5 mm. It is this light sensitive area 1338 that interfaces with the tapered fiber-optic bundle 412. Each PMT photocathode element 1339 has a corresponding electrical output connector 1342. When light photons reach the PMT 416, the photocathode elements 1339 generates raw partial image pixel signals which is output at PMT connector 1342. The raw partial image pixel signals are transmitted via PMT connector 1342 to signal conditioner 810. Further details of a presently preferred real time eye assembly can be found in co-pending U.S. patent application Ser. No. 08/387,292, which has been incorporated herein by reference in its entirety.

Signal Conditioner

Signal conditioner 810 preferably converts the 96 outputs of PMT 416 into 96 pulse trains with each pulse in the pulse train corresponding to a single x-ray photon arriving at the corresponding scintillator element 170. Signal conditioner 810 is preferably comprised of 48 circuit boards 1343. Each circuit board 1343 comprises two sets of signal conditioning amplifier circuits 1830, with each signal conditioning amplifier circuit 1830 feeding its output to a corresponding discriminator 1832. Thus 96 sets of signal conditioning amplifier circuits 1830 and discriminators 1832 are employed, with each set paired to a corresponding photomultiplier tube channel. The signal conditioner 810 outputs ninety-six separate pulse trains for every step of the electron beam. This information is referred to as the partial image pixel information.

The signal conditioning amplifiers 1344 shape and amplify the raw partial image pixel signals from the photomultiplier tube, and output a pulse train of partial image pixel signals to the beam alignment and image reconstruction boards. To even out any performance variations between the individual photomultiplier tube channels, a separate gain signal is sent to each of the signal conditioning amplifier circuits 1830. However, the same threshold signal is sent to each discriminator 1832.

Figure 29:
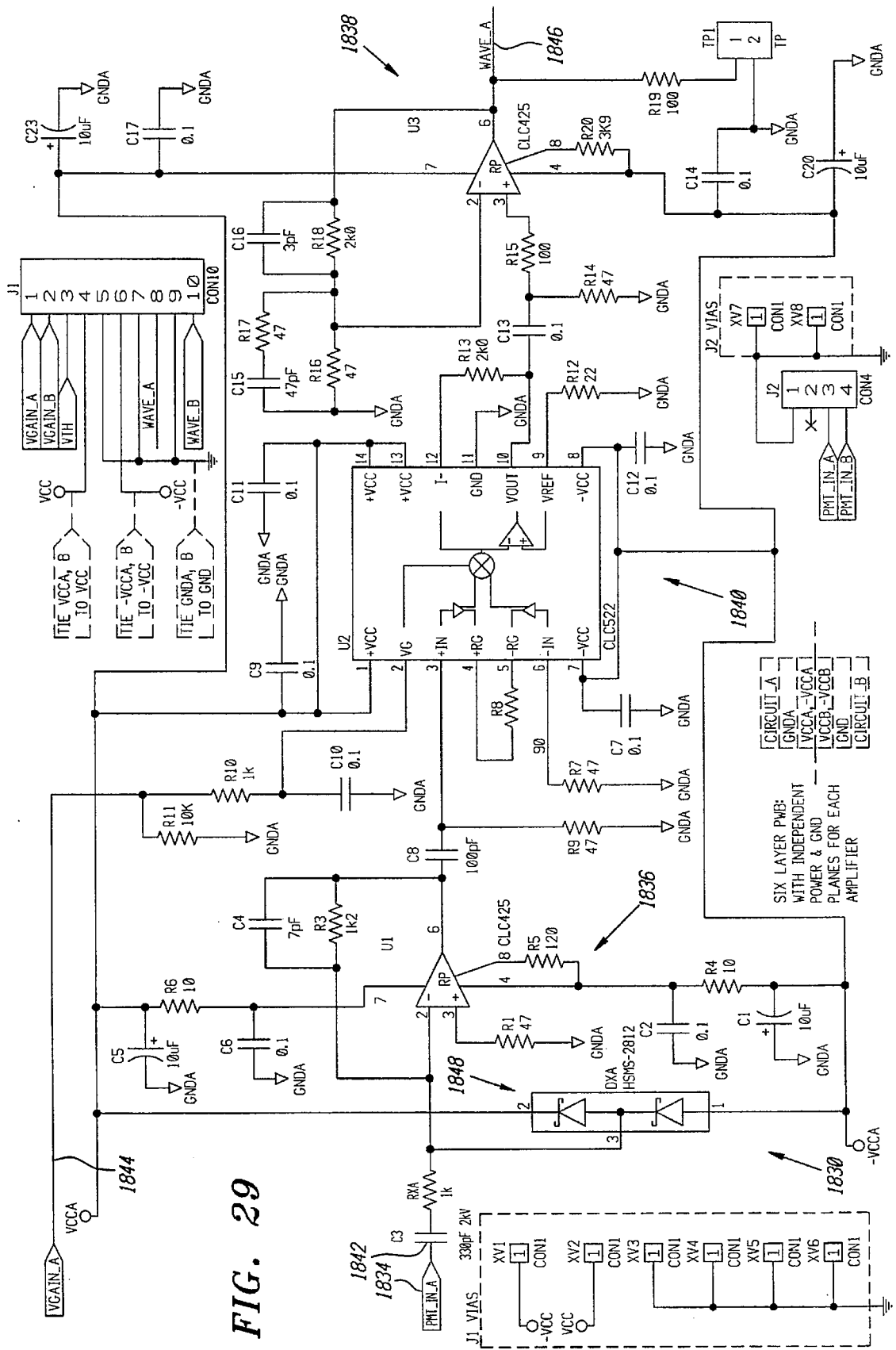
FIG. 29 is a schematic of a preferred signal conditioning amplifier.

FIG. 29 is a circuit diagram of a preferred signal conditioning amplifier circuit 1830. Raw partial image pixel signals from a single photomultiplier tube channel are input to the signal conditioning amplifier circuit 1830 via input line 1834. Signal conditioning amplifier circuit 1830 is preferably AC coupled to eliminate offset drift problems. The AC coupling low frequency cut-off is high, e.g., 30 Mhz, so that the pulse is differentiated. This eliminates the need for a DC restorer circuit to keep the baseline reference voltage constant as the pulse rate varies. Clamping diodes 1848 provide voltage protection for the amplifiers within the signal conditioning amplifier circuit 1830.

Signal conditioning amplifier circuit 1830 preferably comprises three stages of current amplification. The input partial image pixel signals are coupled through a coupling capacitor 1842 to a fixed gain first stage amplifier 1836. The output of the first stage amplifier is fed to a variable gain second stage amplifier 1840, which receives gain control signals applied over input line 1844. The output from the variable gain second stage amplifier 1840 is fed to a fixed gain third stage amplifier 1838, which sends an amplified partial image pixel waveform to the discriminator via line 1846. Supply voltages of +5 V and −5 V are applied to the each amplifier stage within the signal conditioning amplifier circuit 1830. Each of the 96 signal conditioning amplifier circuits 1830 function similarly to process raw partial image pixel signals from its corresponding photomultiplier tube channel.

Figure 30:
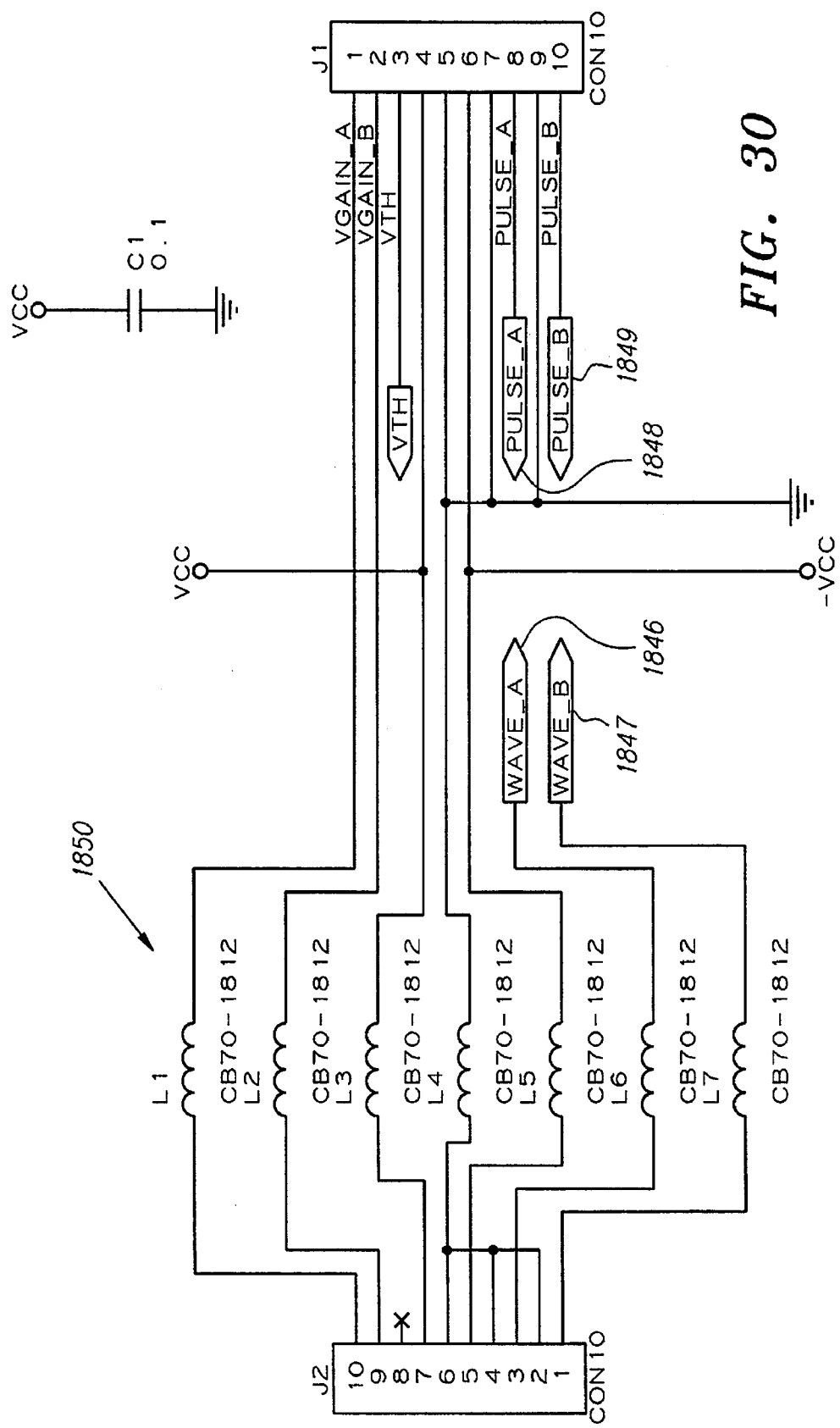
FIG. 30 is circuit diagram of the input and output connectors for a preferred discriminator.

Referring to FIG. 30, the discriminator 1832 essentially digitizes the partial pixel information by comparing the amplified partial image pixel waveform from a signal conditioning amplifier circuit 1830 with a threshold value and producing a high or low value depending on whether the threshold value is crossed. This high or low value corresponds to whether an x-ray photon was detected or not. FIG. 30 diagrams the preferred input and output connectors for each pair of discriminators 1832 located on a single circuit board 1343. The amplified partial image pixel waveforms from two sets of signal conditioning amplifier circuits 1830 are coupled to the discriminators 1832 via input lines 1846 and 1847. Surface mount ferrite bead inductor 1850 are preferably employed to filter noise from the input waveforms. Digitized output pulses from the discriminators 1832 are output via output lines 1848 and 1849.

Figure 31:
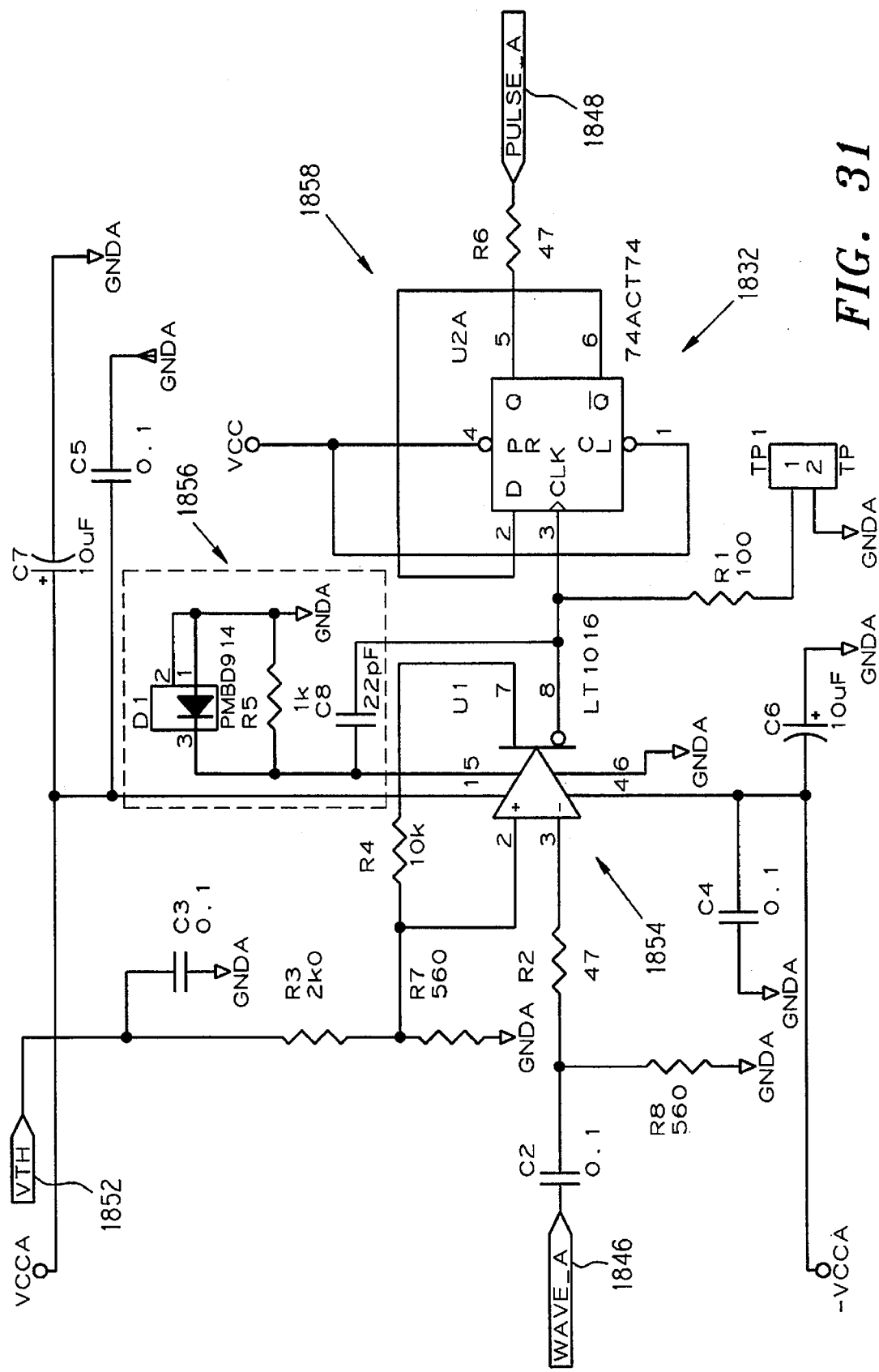
FIG. 31 is a schematic of a preferred discriminator.

FIG. 31 is a circuit diagram of a preferred discriminator 1832. The amplified partial image pixel waveforms from the signal conditioning amplifier circuit 1830 are input, via input line 1846, to a comparator 1854 which provides a constant amplitude output pulse regardless of the amplitude of its input. The threshold reference signal, applied to comparator 1854 via input line 1852, is preferably set to a value which is slightly higher than the amplifier noise output level so that it will not trigger on the noise level. The supply voltage inputs for the comparator 1854 are preferably set at +5 V and −5 V.

The preferred comparator 1854, a standard LT1016 comparator available from Linear Technology, functions as both a comparator and a register. Comparator 1854 generates a latched output which is preferably coupled to a pulse stretching circuit 1856, which is comprised of a circuitry diode, grounded resistor and a capacitor. The pulse stretching circuit 1856 allows the comparator 1854 to generate output pulses approximately 29 nanoseconds wide. The output pulse from the comparator is preferably fed to a divide-by-two counter 1858, to reduce the frequency of the output pulses. No information is lost since subsequent circuits count the edges of this pulsed output. The pulsed output, containing digitized partial image pixel signals, are output from the divide-by-two counter 1858 to the next processing stage via output line 1848. Each of the 96 discriminators 1832 function in a similar manner to process partial image pixel waveforms from its corresponding signal conditioning amplifier circuits 1830.

Figure 32:
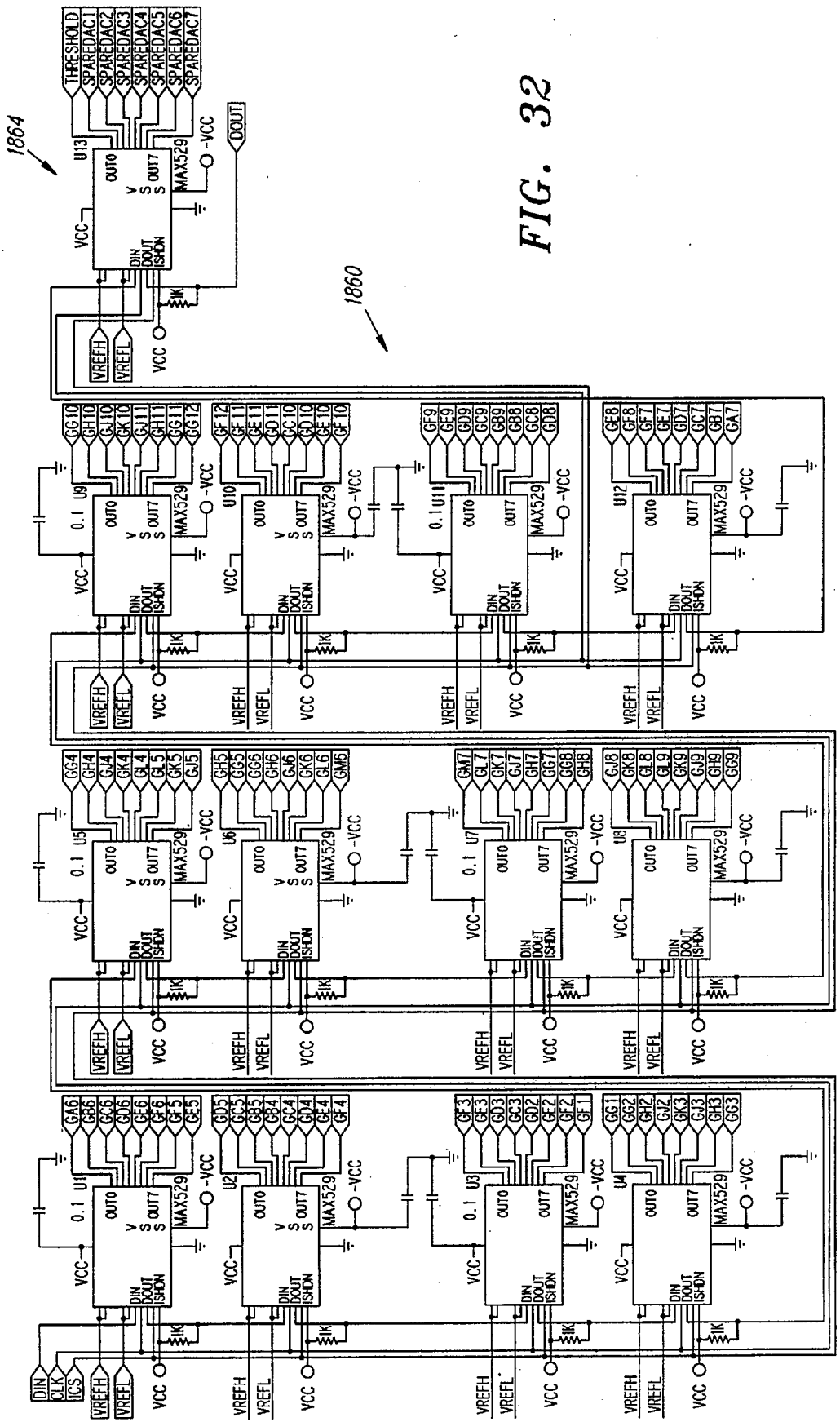
FIG. 32 is a schematic of preferred digital-to-analog converters provide gain and threshold control signals to the signal conditioner.
Figure 33:
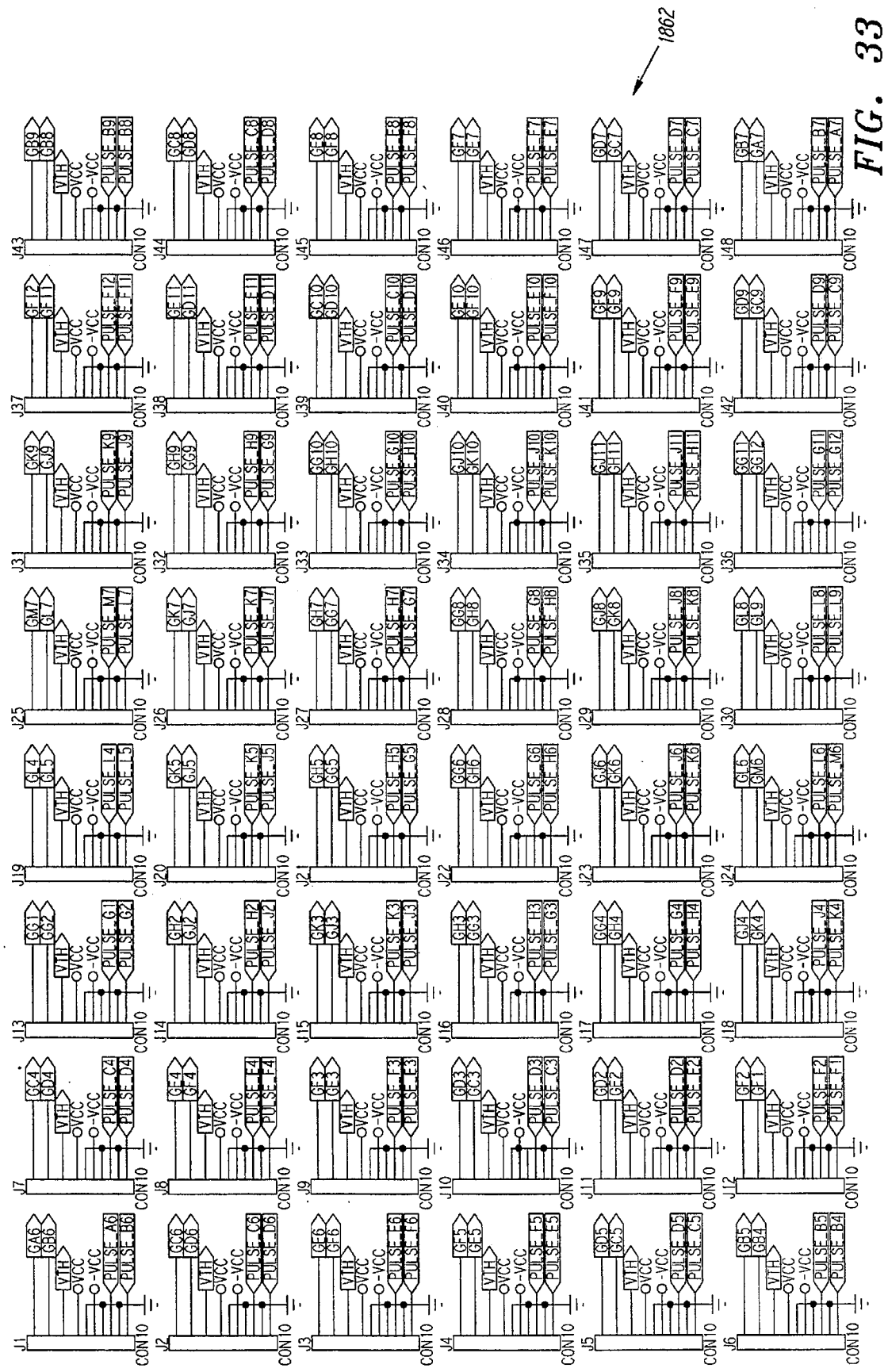
FIG. 33 is a circuit diagram of the preferred interface connectors between the DACs of FIG. 32 and the signal conditioning amplifier circuit of FIG. 29.
Figure 34:
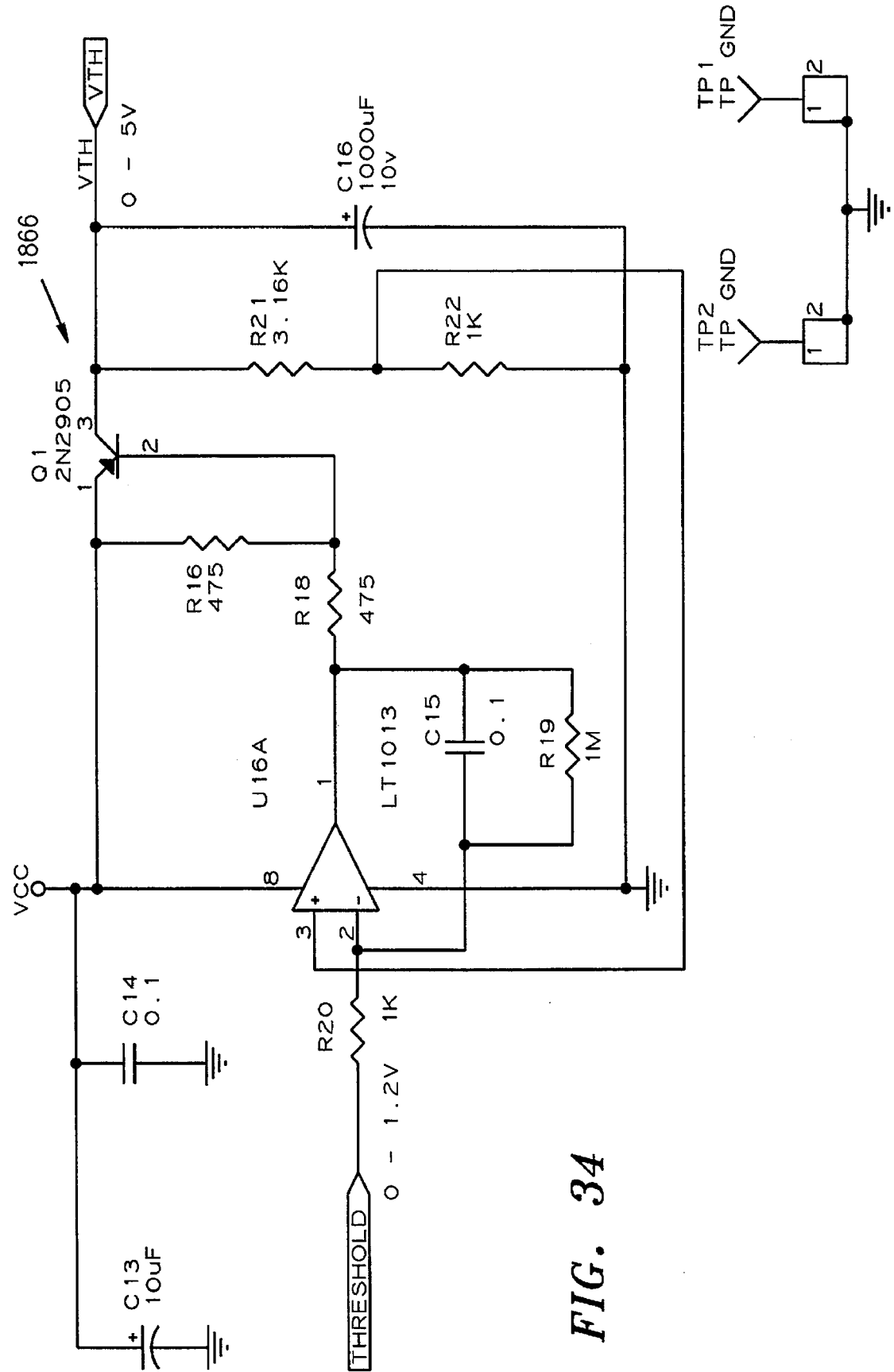
FIG. 34 is a circuit diagram of a preferred buffer amplifier for threshold control signals.

FIG. 32 diagrams the DACs (digital-analog converters) which preferably provide the gain and threshold control signals for the signal conditioner 810. The 12 gain control DACs 1860 each receive serial control data from the control computer, and output a total of 96 parallel analog gain control signals through 48 interface connectors 1862 (FIG. 33) to corresponding signal conditioning amplifier circuits 1830. A threshold control DAC 1864 receives digital control data from the control computer, and outputs a single threshold reference signal which is sent to all 96 discriminators 1832. Threshold control DAC 1864 feeds its output threshold reference signal to a buffer amplifier 1866 (FIG. 34), which provides the power to drive all 96 threshold reference inputs to the individual discriminators 1832.

Figure 35:
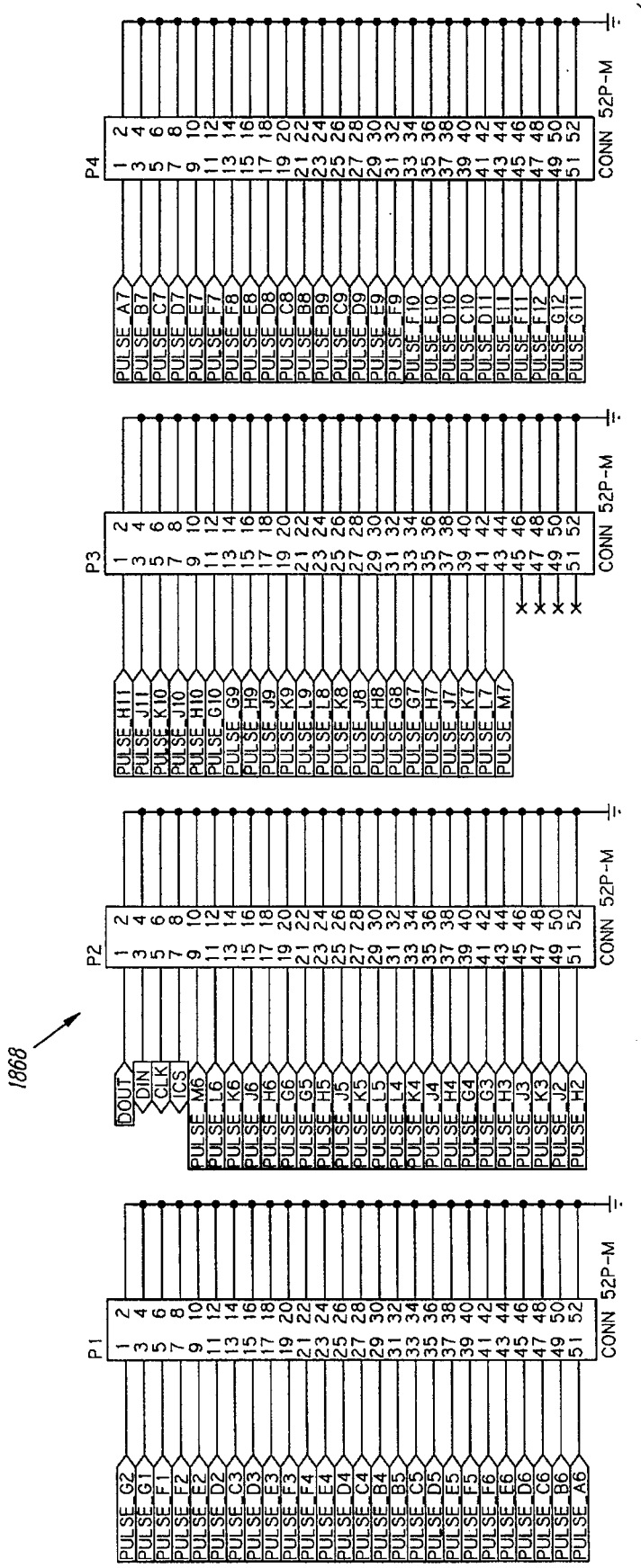
FIG. 35 is a circuit diagram of the preferred connectors between the discriminator of FIG. 31 and the preferred image reconstruction board.

FIG. 35 diagrams the connectors 1868 between the output of the discriminators 1832 and the image reconstruction and beam alignment circuit boards.

Image Reconstruction with Sub-sampling

The presently preferred image reconstruction method utilizes the sub-sampling method to process the detected information. Preferably the sub-sampling method is employed in a reverse geometry scanning beam x-ray system utilizing a sub-sampling ratio of 9:1 with a multi-detector array 822 including ninety-six detector elements arranged in a pseudo-circle.

FIG. 36 is a diagram of a 12 by 12 logical array 823 of detector elements. The logical array includes both active detector spaces 642 and inactive detector spaces 640. In the presently preferred image reconstruction method the 96 active detector element spaces each include a detector element and form an active logical array 822 which occupy the center spaces of a 12 by 12 logical array arranged in a symmetrical pattern about the horizontal midline and the vertical midline. The remaining 48 logical detector spaces of the array are inactive detectors and preferably do not include a detector element. In the preferred embodiment the inactive detector spaces do not output real information about the object.

To generate an image pixel, the processed x-ray intensity values detected by the multi-detector array 110 for each x-ray micro-beam passing through that image pixel IP are summed and output to a video monitor. For image reconstruction using a sub-sampling ratio of 1:1 each logical detector element of the logical array is capable of providing information about each image pixel in the object. For image reconstruction with a sub-sampling ratio of x:1, where x is a number greater than 1, less than all of the logical detector elements are capable of contributing information about a particular image pixel. The actual number capable of contributing information will depend on the particular sub-sampling ratio selected. With a presently preferred sub-sampling ratio of 9:1 in the presently preferred embodiment, only 16 logical detector elements of the 144 logical detector element logical array 823 will provide information about any particular image pixel.

In the sub-sampling method with a sub-sampling ratio of 9:1 the logical array 823 includes sixteen virtual detectors, e.g., 644, 646, 648 and 649. In this embodiment the virtual detectors each include 9 logical detectors arranged in a 3 by 3 array. Alternatively, if a sub-sampling ratio of 4:1 were used, there would be 36 virtual detectors, each including 4 logical detector elements. Using a sub-sampling ratio of 1:1 there would be 144 virtual detectors each including 1 logical detector element.

Each of the 16 logical detector elements used to reconstruct a single image pixel using a sub-sampling ratio of 9:1 are preferably situated in different virtual detectors. In this embodiment, each virtual detector contributes partial image pixel information for nine different image pixels. Complete image pixel information is obtained by combining the information from the logical detectors in the same virtual array location from all 16 virtual detectors.

The presently preferred image reconstruction method utilizes a novel string method. In the string method there is one string for each logical detector in a virtual detector. For example, using the preferred sub-sampling ratio of 9:1 there are nine strings. Referring to FIG. 36, each of the virtual array locations of the virtual detectors have been assigned numbers 1 through 9. String 1 includes all of the logical detectors assigned the number 1. String 2 includes all of the logical detectors assigned the number 2. And so on. Each row of the logical array 823 is assigned a number, 1 through 12, going from top to bottom. Each column of the logical array is assigned an alpha character, A through M, going from left to right. Naturally the use of right, left, top and down is relative and the particular orientation selected is merely to more easily explain the method of image reconstruction.

Figure 37:
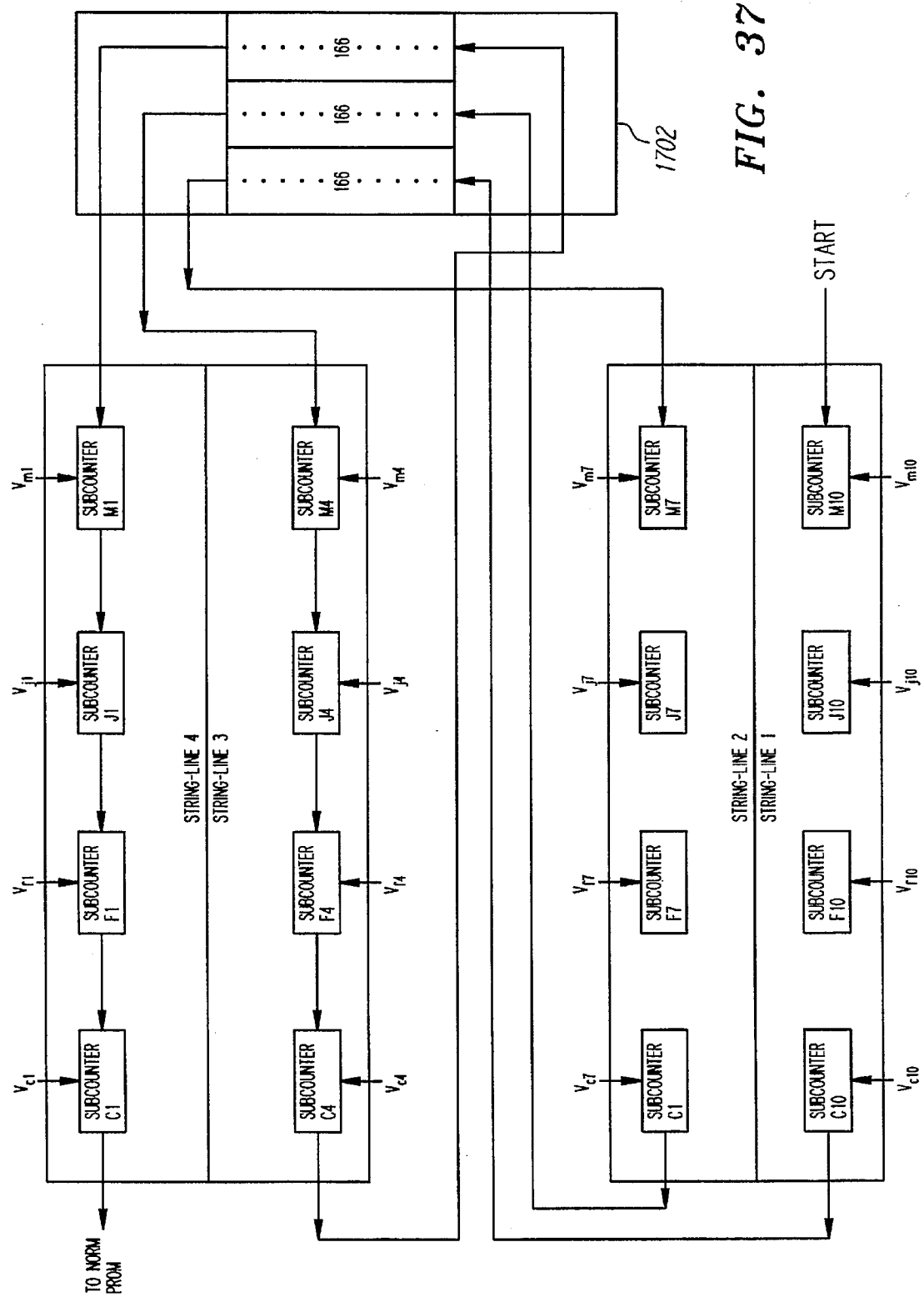
FIG. 37 comprises a partial functional diagram of a string counter in a preferred image reconstruction engine.

FIG. 37 is a diagram of the process flow used in the string method. Since the string method is the same for all strings, the method will be described in detail with regard to only string 1.

String 1 is comprised of the following logical detectors, M1, J1, F1, C1, M4, J4, F4, C4, M7, J7, F7, C7, M10, J10, F10 and C10. Assuming the electron beam moves from left to right for each row and top to bottom, and the sub-sampling ratio is 9:1, using the preferred multi-detector array 110, the first logical detector element that is capable of receiving information for a particular image pixel is M10 (FIG. 36). When the electron beam is positioned behind the next aperture (one hole to the right from the view of the output face of the collimator), the second logical detector capable of receiving information about that same image pixel is J10. And so on.

Referring back to FIG. 37, the partial pixel information for each image pixel is preferably processed for each string in accordance with the following method. The method will first be described in accordance with the embodiment in which each of the logical detectors are active and a sub-sampling ratio of 9:1 is selected resulting in a collimator including 167 rows and 167 columns. The description begins when the electron beam is positioned behind aperture $AP_{50,50}$. For purposes of this description image pixel $IP_1$ is located along the axes of the x-ray micro-beam detected by logical detector M10. Further, when the electron beam is described as being located behind a particle aperture, it means that the electron beam is aimed at the intersection of target layer and the axis of the x-ray pencil beam (which is aimed at the center of the multi-detector array) formed by that aperture.

As the electron beam is being positioned behind $AP_{50,50}$, subcounter M10 is reset to zero. While the electron beam is positioned behind $AP_{50,50}$ the partial image pixel information detected by logical detector M10 is input to subcounter M10. As the electron beam is positioned behind the next aperture in the same collimator row $AP_{50,51}$, the information contained in subcounter M10 is moved to subcounter J10. While the electron beam is positioned behind the next selected aperture $AP_{50,51}$ an x-ray micro-beam will pass through $IP_1$ and strike logical detector J10. The partial image pixel information detected by logical detector J10 will be input to and added to the contents of subcounter J10.

As the electron beam is positioned behind the next aperture in the same collimator row $AP_{50,52}$, the information contained in subcounter J10 is moved to subcounter F10. While the electron beam is positioned behind the next selected aperture $AP_{50,52}$, an x-ray micro-beam will pass through $IP_1$ and strike logical detector F10. The partial image pixel information detected by logical detector F10 will be input to and added to the contents of subcounter F10.

As the electron beam is positioned behind the next aperture in the same collimator row $AP_{50,53}$, the information contained in subcounter F10 is moved to subcounter C10. While the electron beam is positioned behind the next selected aperture $AP_{50,53}$, an x-ray micro-beam will pass through $IP_1$ and strike logical detector C10. The partial image pixel information detected by logical detector C10 will be input to and added to the contents of subcounter C10.

As the electron beam is positioned behind the next aperture in the same collimator row $AP_{50,54}$, the information contained in subcounter C10 is moved to a FIFO register. The reason for this is that because of the geometry of the preferred system, when the electron beam is positioned behind the next selected aperture $AP_{50,54}$, no x-ray micro-beam will pass through $IP_1$ and strike any logical detector in the array until the electron beam is moved to the next row. In accordance with this embodiment, no x-ray micro-beam will pass through $IP_1$ and strike any logical detector until the electron beam is positioned behind $AP_{51,50}$.

As the electron beam is being positioned behind $AP_{51,50}$, subcounter M7 is loaded with the partial image pixel information stored in the FIFO corresponding to the partial pixel information output from C10. While the electron beam is positioned behind $AP_{51,50}$ the partial image pixel information detected by logical detector M7 is added to the contents of subcounter M7.

As the electron beam is positioned behind the next aperture in the same collimator row $AP_{51,51}$, the information contained in subcounter M7 is moved to subcounter J7. While the electron beam is positioned behind the next selected aperture $AP_{51,51}$ an x-ray micro-beam will pass through $IP_1$ and strike logical detector J7. The partial image pixel information detected by logical detector J7 will be input to and added to the contents of subcounter J7.

As the electron beam is positioned behind the next aperture in the same collimator row $AP_{51,52}$, the information contained in subcounter J7 is moved to subcounter F7. While the electron beam is positioned behind the next selected aperture $AP_{51,52}$, an x-ray micro-beam will pass through $IP_1$ and strike logical detector F7. The partial image pixel information detected by logical detector F7 will be input to and added to the contents of subcounter F7.

As the electron beam is positioned behind the next aperture in the same collimator row $AP_{51,53}$, the information contained in subcounter F7 is moved to subcounter C7. While the electron beam is positioned behind the next selected aperture $AP_{51,53}$, an x-ray micro-beam will pass through $IP_1$ and strike logical detector C7. The partial image pixel information detected by logical detector C7 will be input to and added to the contents of subcounter C7.

As the electron beam is positioned behind the next aperture in the same collimator row $AP_{51,54}$, the information contained in subcounter C7 is moved to a FIFO register. Again, the reason for this is that because of the geometry of the preferred system, when the electron beam is positioned behind the next selected aperture $AP_{51,54}$, no x-ray microbeam will pass through IP$_1$ and strike any logical detector in the array. In accordance with this embodiment, no x-ray micro-beam will pass through IP$_1$ and strike any logical detector until the electron beam is positioned behind AP$_{52,50}$.

As the electron beam is being positioned behind AP$_{52,50}$, subcounter M4 is loaded with the information stored in the FIFO corresponding to the partial pixel information output from subcounter C7. While the electron beam is positioned behind AP$_{52,50}$ the partial image pixel information detected by logical detector M4 is input to and added to the contents of subcounter M4.

As the electron beam is positioned behind the next aperture in the same collimator row AP$_{52,51}$, the information contained in subcounter M4 is input to subcounter J4. While the electron beam is positioned behind the next selected aperture AP$_{52,51}$ an x-ray micro-beam will pass through IP$_1$ and strike logical detector J4. The partial image pixel information detected by logical detector J4 will be input to and added to the contents of subcounter J4.

As the electron beam is positioned behind the next aperture in the same collimator row AP$_{52,52}$, the information contained in subcounter J4 is moved to subcounter F4. While the electron beam is positioned behind the next selected aperture AP$_{52,52}$, an x-ray micro-beam will pass through IP$_1$ and strike logical detector F4. The partial image pixel information detected by logical detector F4 will be input to and added to the contents of subcounter F4.

As the electron beam is positioned behind the next aperture in the same collimator row AP$_{52,53}$, the information contained in subcounter F4 is moved to subcounter C4. While the electron beam is positioned behind the next selected aperture AP$_{52,53}$, an x-ray micro-beam will pass through IP$_1$ and strike logical detector C4. The partial image pixel information detected by logical detector C4 will be input to and added to the contents of subcounter C4.

As the electron beam is positioned behind the next aperture in the same collimator row AP$_{52,54}$, the information contained in subcounter C4 is moved to a FIFO register. Again, the reason for this is that because of the geometry of the preferred system, when the electron beam is positioned behind the next selected aperture AP$_{52,54}$, no x-ray micro-beam will pass through IP$_1$ and strike any logical detector in the array. In accordance with this embodiment, no x-ray micro-beam will pass through IP$_1$ and strike any logical detector until the electron beam is positioned behind AP$_{53,50}$.

As the electron beam is being positioned behind AP$_{53,50}$, subcounter M1 is loaded with the information stored in the FIFO corresponding to the partial pixel information output from subcounter C4. While the electron beam is positioned behind AP$_{53,50}$ the partial image pixel information detected by logical detector M1 is input to and added to the contents of subcounter M1.

As the electron beam is positioned behind the next aperture in the same collimator row AP$_{53,51}$, the information contained in subcounter M1 is moved to subcounter J1. While the electron beam is positioned behind the next selected aperture AP$_{53,51}$ an x-ray micro-beam will pass through IP$_1$ and strike logical detector J1. The partial image pixel information detected by logical detector J1 will be input to and added to the contents of subcounter J1.

As the electron beam is positioned behind the next aperture in the same collimator row AP$_{53,52}$, the information contained in subcounter J1 is moved to subcounter F1. While the electron beam is positioned behind the next selected aperture AP$_{53,52}$, an x-ray micro-beam will pass through IP$_1$ and strike logical detector F1. The partial image pixel information detected by logical detector F1 will be input to and added to the contents of subcounter F1.

As the electron beam is positioned behind the next aperture in the same collimator row AP$_{53,53}$, the information contained in subcounter F1 is moved to subcounter C1. While the electron beam is positioned behind the next selected aperture AP$_{53,53}$, an x-ray micro-beam will pass through IP$_1$ and strike logical detector C1. The partial image pixel information detected by logical detector C1 will be input to and added to the contents of subcounter C1.

As the electron beam is positioned behind the next aperture in the same collimator row AP$_{53,54}$, the information contained in subcounter C1 is output to a monitor where the information can be processed for display. The output of C1 will contain complete image pixel information for pixel IP$_1$. The reason for this is that because of the geometry of the preferred system, no other apertures, other than those identified above will include an x-ray micro-beam that passes through IP$_1$.

In accordance with the string method, at the same time that information for IP$_1$ is being collected in string 1, information for IP$_2$ is being collected in string 2. The complete image pixel information for IP$_2$ is collected in accordance with the same method as with string 1 except that the logical detectors for string 2 (L10, H10, E10, B10, L7, H7, E7, B7, L4, H4, E4, B4, L1, H1, E1 and B1) collect the information and subcounters L10, H10, E10, B10, L7, H7, E7, B7, L4, M4, E4, B4, L1, H1, E1 and B1 combine the information as the electron beam is positioned behind AP$_{50,50}$, AP$_{50,51}$, etc. The same process is also used with the corresponding subcounters and logical detectors for strings 3, 4, 5, 6, 7, 8 and 9. Thus, after the electron beam has been positioned behind aperture AP$_{53,53}$ complete information for nine image pixels can be output to a video monitor for display. Also, a new string 1, string 2, . . . and string 9 are started every time the electron beam is positioned behind a new aperture. It should be noted that a FIFO may be replaced by any storage mechanism that can store the intermediate outputs of the strings until complete image pixel information has been collected.

As shown in FIG. 36, preferably only 96 of the 144 logical detectors are active. For example, string 1 is preferably mapped to 11 active (J10, F10, C10, M7, J7, F7, C7, J4, F4, C4 and F1) and 5 inactive detector elements (M10, M4, M1, J1 and C1). Since these inactive detector elements do not provide any information about the image pixel a zero value is input into the corresponding subcounters. Also, as noted, if it is determined that the inactive logical detectors will never be used to collect image pixel information, they need not have an actual detector associated with them. Similarly, for string 2, the inactive logical detectors (those outside the active detector array area 822) also input zero values to their corresponding subcounters, and so forth with the other strings.

When less than all of the logical detectors are active it is preferable to normalize the complete image pixel information to account for differences in the number of active detector elements for each string. As shown in Table II, the number of active detector elements providing input data vary between 10, 11 or 12 depending on the particular string. The complete image pixel information from each of the nine strings is preferably normalized by dividing the complete image pixel information by the number of active detectors in that string and then multiplying by 12.

TABLE II

| STRING | NUMBER OF ACTIVE ELEMENTS |
| --- | --- |
| 1 | 11 |
| 2 | 10 |
| 3 | 11 |
| 4 | 10 |
| 5 | 12 |
| 6 | 10 |
| 7 | 11 |
| 8 | 10 |
| 9 | 11 |

Alignment

The electron beam 40 in x-ray source 10 is preferably precisely aligned such that it will illuminate the area on the target layer at the exact point at which the axis of the collimator hole intersects the target layer. When no object is interposed between the target 50 and the multi-detector array 110, such a precisely aligned electron beam will result in a near symmetrical distribution of x-ray intensity across the face of detector elements 160 of the multi-detector array 110, within the pseudo-circle 400. An electron beam which is not so precisely aligned may create a non-symmetrical distribution of x-ray intensities across the face of the detector elements 160 of the multi-detector array 110.

Alignment of the electron beam behind the collimator holes is preferably accomplished with a 2-step process. An initial alignment procedure is preferably performed to approximate the correct positioning of the electron beam 40. The initial alignment procedure is preferably followed by a fine alignment procedure that optimizes the position of the center of the electron beam profile relative to the collimator holes.

The first step of the preferred initial alignment procedure is comprised of locating the electron beams using a-priori knowledge related to the physical, electrical and magnetic properties of the scanning system. The relative spacing of the electron beam positions may be reasonably correct at this point, but the absolute positions of the electron beams may not be because of the difficulty in indexing the electron beam position array to the collimator holes, and because of small cumulative errors. Therefore, a "dithering" process is preferably employed whereby several measurements are made by making small adjustments of the index position for a whole array of electron beam positions. Typically, 25 measurements are made where the index point is moved in a 5 by 5 x-y grid. The total size of the grid is approximately the spacing of one collimator hole. The data collected for each measurement consists of the total intensity measured by the multi-detector array for each of the collimator holes.

The collected data for a give collimator hole will preferably be an array of 25 values. Many of the values will indicate that little or no x-ray flux impinged upon the multidetector array, but several will indicate that at least part of the electron beam produced x-rays that impinge upon the multidetector array. An approximate optimum beam position location is determined by mathematically fitting a multi-dimensional surface to the illuminated data.

Thus, approximate optimum beam positions are determined by this procedure. These positions are refined using the fine alignment method described below.

To initiate the fine alignment procedure, initial x-deflection values and y-deflection values are preferably computed for each collimator aperture, employing the initial alignment procedure described above. Using these computed initial deflection values the electron beam is scanned across the target, momentarily stopping at each of the computed locations corresponding to the computed x and y deflection values. The partial image pixel information obtained from each detector element for each x-ray pencil beam generated by stopping at each computed location is analyzed for even distribution of the x-ray intensity over several frames. (A complete scan of the target is referred to as a frame.) If the analysis results in a determination that the distribution of x-ray intensity is not even, new x-deflection values and/or y-deflection values are calculated and the alignment procedure is repeated to ensure optimal distribution.

The preferred way of analyzing the distribution of x-ray flux across the face of the multi-detector array is to compare the average intensity of the x-ray rays detected by selected areas of the face of the multi-detector array. This is preferably accomplished by dividing the preferred ninety-six detector element multi-detector array into eight areas comprising substantially the same number of detector elements.

FIG. 38 is a representational diagram of the face of a multi-detector array divided into eight areas. Each of the eight areas is referred to as an "octant." The eight octants are identified as the top right outer octant ("TRO") 1345, top right inner octant ("TRI") 1346, top left outer octant ("TLO") 1349, top left inner octant ("TLI") 1350, bottom right inner octant ("BRI") 1347, bottom right outer octant ("BRO") 1348, bottom left outer octant ("BLO") 1351, and bottom left inner octant ("BLI") 1352.

In the preferred embodiment, the 96 detector elements 1339 are evenly divided among the eight octants. Therefore each octant contains 12 detector elements 1339. However, it is contemplated that other arrangements may be used in the present invention. For example, an alternative arrangement could consist of 13 detector elements 1339 associated with each inner octant, with 11 detector elements 1339 associated with each outer octant.

The beam alignment calculations are preferably determined separately for the x-axis 1662 and the y-axis 1660. The preferred sequence of steps to determine the proper beam alignment along the y-axis 1660 are as follows. The process begins when an x-ray pencil beam from a single collimator aperture strikes the scintillator elements of multi-detector array 110.

The total intensity values for each octant is summed by counting the number of x-ray photons which are received by each detector element 1339 associated with each octant. For example, arbitrarily selecting the variable V to refer to the sum of the photon counts in a particular area, $V_{TRO}$ is the sum of all the photon counts in the TRO octant 1345. Similarly, $V_{TRI}$ is the sum for the TRI octant 1346, $V_{TLO}$ for TLO octant 1349, $V_{TLI}$ for TLI octant 1350, $V_{BLO}$ for BLO octant 1351, $V_{BLI}$ for BLI octant 1352, $V_{BRI}$ for BRI octant 1347, and $V_{BLO}$ for BLO octant 1348. The intensity values for each octant, for each x-ray pencil beam from each collimator aperture for each of a predetermined number of succeeding frames, is accumulated. The presently preferred embodiment uses the octant values from 100–120 frames to perform the beam calculations. Thus, there are a total of eight octant values for each beam/aperture combination.

The accumulated values for the octants in the top and bottom halves of the PMT array are then separately summed. Thus the top octant accumulated value is $V_{top}=V_{TRO}+V_{TRI}+V_{TLI}+V_{TLO}$. The bottom octant accumulated is $V_{bottom}=V_{BRO}+V_{BRI}+V_{BLI}+V_{BLO}$.

Next the top octant accumulated value is compared to the bottom octant accumulated value. This comparison produces a y-axis alignment factor ($AF_{y\text{-}axis}$) which is a measure of the accuracy of the x-ray beam alignment with respect to a particular aperture along the y-axis. The formula to determine the $AF_{y-axis}$ is:

$$AF_{y-axis} = \frac{V_{top} - V_{bottom}}{V_{top} + V_{bottom}} \qquad \text{EQ. 7}$$

If the electron beam is properly aligned with the aperture under analysis along the y-axis, the accumulated intensity values for the top and the bottom octants should be the same. Thus when $V_{top}$ is equal to $V_{bottom}$, $AF_{y-axis}=0$ and the beam is properly aligned along the y-axis for the aperture under analysis.

If the electron beam was positioned to favor the top half of the multi-detector array, then $V_{top}$ will be greater than $V_{bottom}$. This results in $AF_{y-axis}>0$. If the electron beam is positioned to favor the bottom half of the multi-detector array, then $V_{top}$ will be less than $V_{bottom}$. This results in $AF_{y-axis}<0$. The value of $AF_{y-axis}$ generally indicates the amount the y-deflection value should change to optimize the alignment.

The method to determine the optimal electron beam alignment along the x-axis is similar. For this calculation, the accumulated values for the left and right octants are separately summed. Thus the right octant accumulated value is $V_{right}=V_{TRO}+V_{TRI}+V_{BRO}+V_{BRI}$. The left octant accumulated value is $V_{left}=V_{TLO}+V_{TLI}+V_{BLO}+V_{BLI}$. The formula to determine the x-axis alignment factor ($AF_{x-axis}$) is:

$$AF_{x-axis} = \frac{V_{right} - V_{left}}{V_{right} + V_{left}} \qquad \text{EQ. 8}$$

Calculations almost identical to those used for the y-axis alignment are used to determine the optimal alignment of the electron beam along the x-axis.

The x-axis and y-axis alignment factors are transmitted to the control computer 890. Control computer 890 processes these alignment factors to determine the amount of correction required at the x-ray source 798 to optimally align the x-ray pencil beam. The control computer 890 next updates the beam deflection lookup tables 918.

By adjusting the electron beam's positioning on the target 1250, x-rays are emitted from the target at a different position relative to the collimator grid aperture. The x-ray pencil beams passing through the collimator grid aperture would then illuminate the multi-detector array at a corrected optimally aligned position.

This alignment may be performed whenever the system is activated, at preset intervals or continuously.

While the previous discussion explores alignment calculations along the x and y axes, other octant calculation methods are also contemplated within the boundaries of this aspect of invention. For example, angular alignment calculations may be performed by comparing the accumulated value of the top right octants with the values of the bottom left octants and the top left octants with the bottom right octants.

Beam Alignment Extractor and Image Reconstruction Engine

Figure 39:
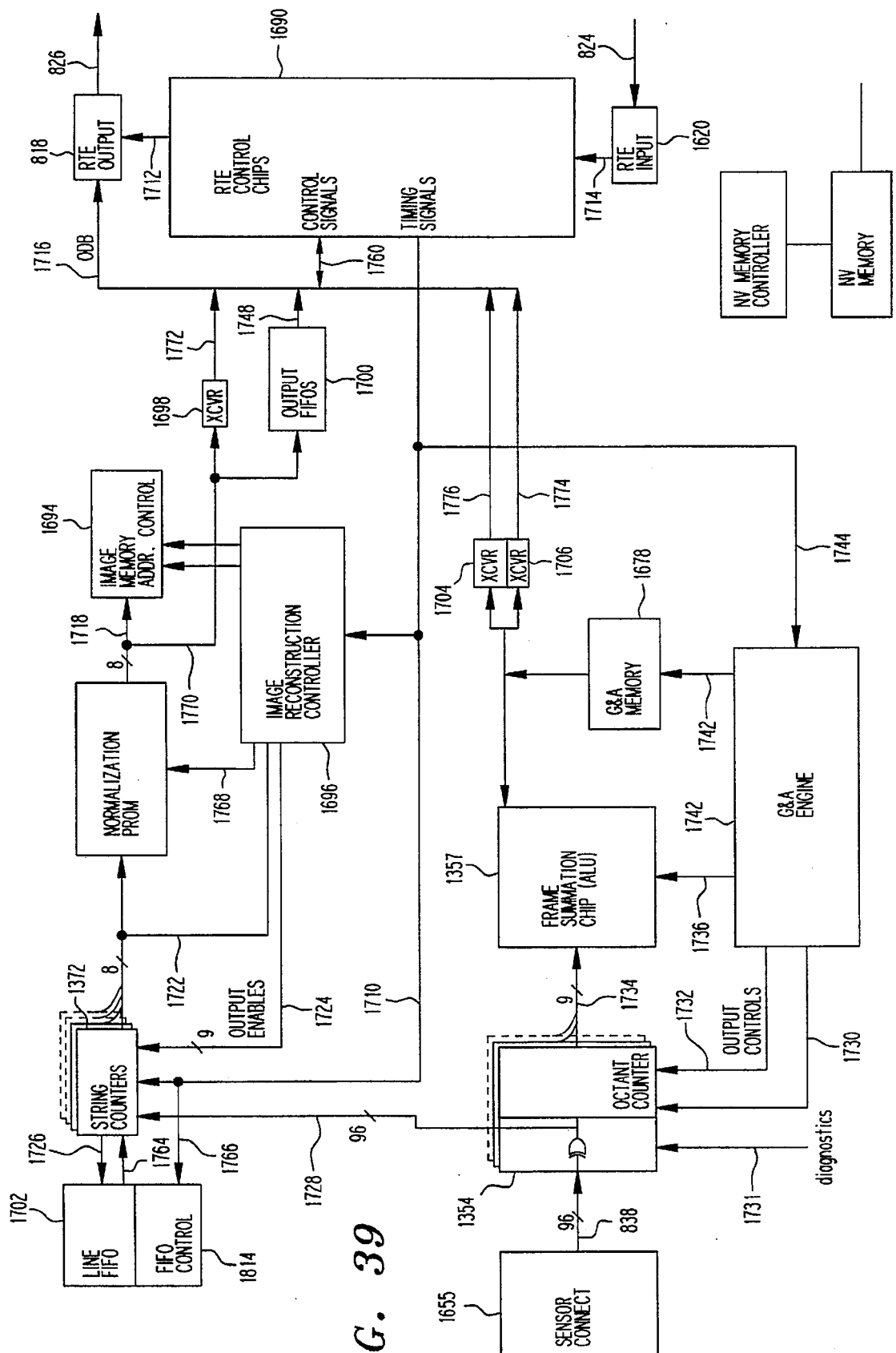
FIG. 39 comprises a partial functional block diagram of an image reconstruction engine.

FIG. 39 is a block diagram of the circuitry for the beam alignment extractor and image reconstruction engine. The output signals of the signal conditioner 810 are input, via connectors 1655, to the beam alignment extractor.

The conditioned partial image pixel signals from each detector element for each step of the electron beam are input to RTE octant counters 1354. There are preferably eight RTE octant counters. Each of the octant counters receives the conditioned partial image pixel signals from one of the eight octants. Each RTE octant counter 1354 splits the conditioned partial image pixel signals into two essentially identical signals. One set of the conditioned partial image pixel signals is used to analyze the optimal alignment of the electron beam. The other set is transmitted to the image reconstruction engine ultimately to be used to reconstruct the image of the object being investigated.

Each RTE octant counter 1354 then processes the input conditioned image pixel signals to obtain a total photon count for its corresponding octant. In sequential order, the RTE octant counters 1354 next transmit the total photon sum for each octant to the frame-summation chip 1357. This process is controlled and outputs to the frame summation chip are enabled by control signals communicated to the RTE octant counters 1354 from the gain & alignment engine 1674.

The frame-summation chip 1357 is an arithmetic logic unit ("ALU"). For each photon count input from a RTE octant counter 1354, the frame-summation chip 1357 also inputs an accumulated octant value from the gain & alignment memory 1678. This accumulated octant value corresponds to the sum of the photon counts from one or more previous frames for the same octant and for the same aperture on the collimator which was illuminated to produce the present photon count. The frame summation chip 1357 adds the photon count to the accumulated octant value to produce a new octant value, which is then stored at the gain & alignment memory 1678.

The gain & alignment engine 1674 controls the operation of the octant counters 1354, frame-summation chip 1357 and gain & alignment memory 1678. After approximately 100–120 frames of information have been collected at the gain & alignment memory 1678, the gain & alignment engine 1674 communicates instructions to the gain & alignment memory 1678 to output the beam alignment information, which is transmitted through transceivers 1704 and 1706 to the RTE output circuits 818.

The string counters 1372 input partial image pixel signals from the RTE octant counters 1354. The string counters 1372 process partial image pixel values to reconstruct data values for complete image pixels, as explained more fully in the detailed description of FIG. 37.

During the image reconstruction process, partially constructed image pixel values are stored by the string counters 1372 at the line FIFO ("first in first out") chips 1702. After 166 items of partial image pixel values are input into a line FIFO chip 1702, each successive item stored at that line FIFO chip 1702 will cause the line FIFO chip 1702 to transmit the then earliest stored string data value back to the string counters 1372. Line FIFO 1702 receives timing signals from the RTE control chips.

The string counters 1372 transmit data values for complete image pixels to the normalization PROM 1692. The normalization PROM adjusts this data value based upon the number of active detector elements which contribute partial image pixel information for that image pixel (this is explained in more detail in conjunction with the detailed discussion of FIG. 37). The normalization PROM 1692 receives control signals from the image reconstruction controller 1696 through electrical connection 1768.

Normalization PROM 1692 outputs normalized image pixel information to the output FIFOs 1700 through electrical connection 1746. Three lines of normalized image pixel information are stored at the output FIFOs 1700 before the normalized image pixel data is transmitted to the RTE output circuit.

The normalized image pixel information from the normalization PROM 1692 is also input to the image memory unit 1694. The normalized image pixel information for the entire image is stored and properly ordered at the image memory unit 1694. The control computer can access this image data through transceiver 1698.

The image reconstruction controller transmits the control signals which operate the components of the image reconstruction engine. Control and addressing signals are communicated to the image memory unit 1694 on electrical connections 1758 and 1756. Control signals are sent, via electrical connection 1768, to the normalization PROM. The image reconstruction controller 1696 communicates control signals, via electrical connection 1724, to the string counters 1372.

Control information from the control computer 890 are input to the real-time eye through RTE input circuit 1620, which receives light pulses from high-speed fiber-optic cable 824. The RTE input circuit 1620 comprises a light detector and circuitry which detects and demodulates the light pulses into electrical signals which contain the control information from the control computer 890. The control information is sent from RTE input circuit 1620 to the RTE control chips 1690 through electrical connection 1714.

The RTE control chips 1690 send timing signals to the RTE circuitry through electrical bus connection 1710. The RTE control chips 1690 send control signals to the RTE circuitry through electrical bus connection 1760.

RTE output circuit 818 sends image reconstruction and gain & alignment information to the control computer 890 through high-speed fiber-optic cable 826. RTE output circuit 818 comprises a high radiance LED and circuitry which converts electrical signals into light pulses.

Turning to FIG. 40, a detailed diagram is presented of the RTE input circuit 1620. RTE input circuit 1620 receives light pulses from right transmitter 880. Light pulses are detected and converted to an electrical signal by the fiber-optic receiver 1612. The electrical signal is filtered and shaped by circuits 1622 and 1624. The electrical signal is then input to the taxi chip 1614, a standard AM7969 chip available from AMD Corp, which functions as a serial to parallel converter. The electrical input signal was necessarily in a serial format because of its transmission through a fiber-optic cable. Four bits of control signals and eight bits of data signals are output from taxi chip 1614. While the present description of FIG. 40 is directed to the RTE input circuit 1620 of the data receiver 812, a similar circuit exists for other components of the present invention which receives light pulses through fiber-optic cables.

Phase locked loop (PLL) circuit 1629, located in data receiver 812, receives and locks onto a master 12.5 Mhz clock signal that is generated in the programmable scan controller 920 (FIG. 22). This master clock signal drives both the taxi chip 1614 in the data receiver 812 and the taxi chip 1602 in the data transmitter 818 to generate an output at a clock rate of 12.5 Mhz. MC88915 clock doublers 1628, 1630, and 1632 are used to quadruple the 12.5 Mhz clock signal to a 50 Mhz frequency. Timing circuit 1626 uses this 50 Mhz clock to synchronize taxi chip 1614 with the other components of the beam alignment extractor and image reconstruction circuitry. Timing circuit 1626 generates a data strobe signal which is transmitted via electrical connection 1636. Timing circuit 1626 generates a control strobe signal which is transmitted via electrical connection 1634.

FIG. 41 diagrams the RTE output circuit 818, which is also referred to as the right data transmitter. Taxi chip 1602 is another standard AM7968 chip available from AMD Corp. which also functions as a parallel to serial converter. Parallel data bits from the image reconstruction engine and the beam alignment extractor are input to the taxi chip 1602, which outputs a serial data signal. This serial data signal is then shaped by the conditioning circuitry 1610. The output signal from the conditioning circuit 1610 is sent to fiber-optic transmitter 1604, which transforms the serial data signal into light pulses through the use of a high-radiance LED. The light pulses are sent to a data receiver 880 through high-speed fiber-optic cable 826. While the present description of FIG. 41 is directed to the RTE output circuit 1620 of the real-time eye, a similar circuit exists for other components of the present invention which transmits light pulses through fiber-optic cables.

Figure 42:
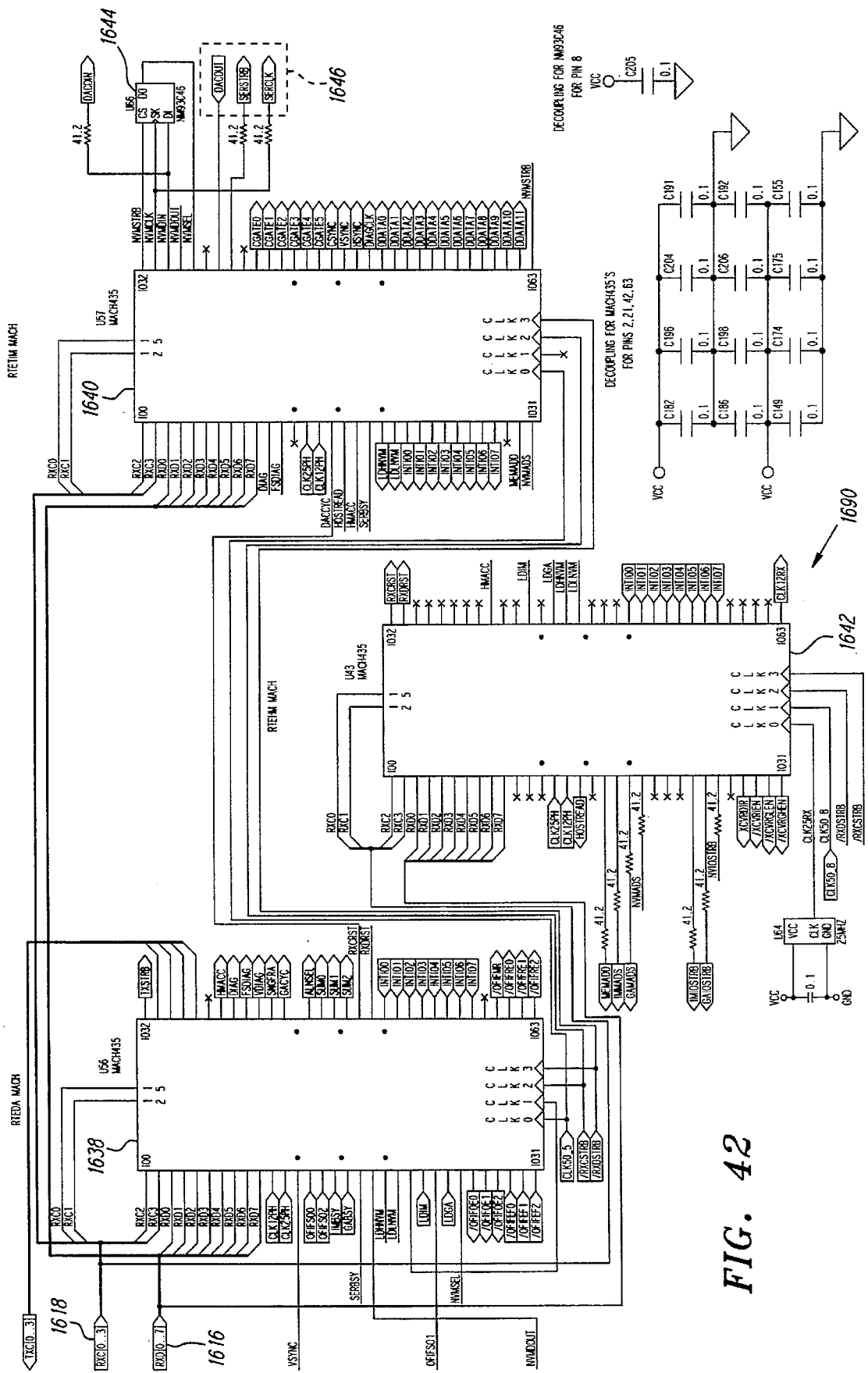
FIG. 42 is a schematic of the controller for the image reconstruction engine and gain & alignment circuitry.

FIG. 42 is a circuit diagram of the RTE control chips 1690 which are located in the data receiver 812. Information from the control computer 890 that is acquired through the RTE input circuit 1620 is distributed to the various components of the multi-detector array through the RTE control chips 1690, each of which is a MACH435 programmable IC chip available from AMD Corp. Data outputs from the RTE input taxi chip 1614 are input to the RTE control chips via 8 bit electrical connection 1616. Control information outputs from the RTE input taxi chip 1614 are input to the RTE control chips via 4 bit electrical connection 1616.

Data acquisition control chip 1638 distributes control information relating to the selection of data that is acquired and processed by the components of the multi-detector array 822. Host memory control chip 1642 communicates instructions to the image memory unit 1694 and the gain & alignment memory unit 1678. Timing control chip 1640 communicates timing and diagnostic signals to the circuitry of the beam alignment extractor and the image reconstruction engine. The timing control signals for the signal conditioner 1510 (FIG. 33) is output from the timing control chip 1640 through connection 1646. 1 Kbyte of nonvolatile memory 1644 stores calibration information for the circuitry of the beam alignment extractor and the image reconstruction engine. The preferred software modules for data acquisition control chip 1638, host memory control chip 1642, and timing control chip 1640 are included in Appendix A.

Figure 43:
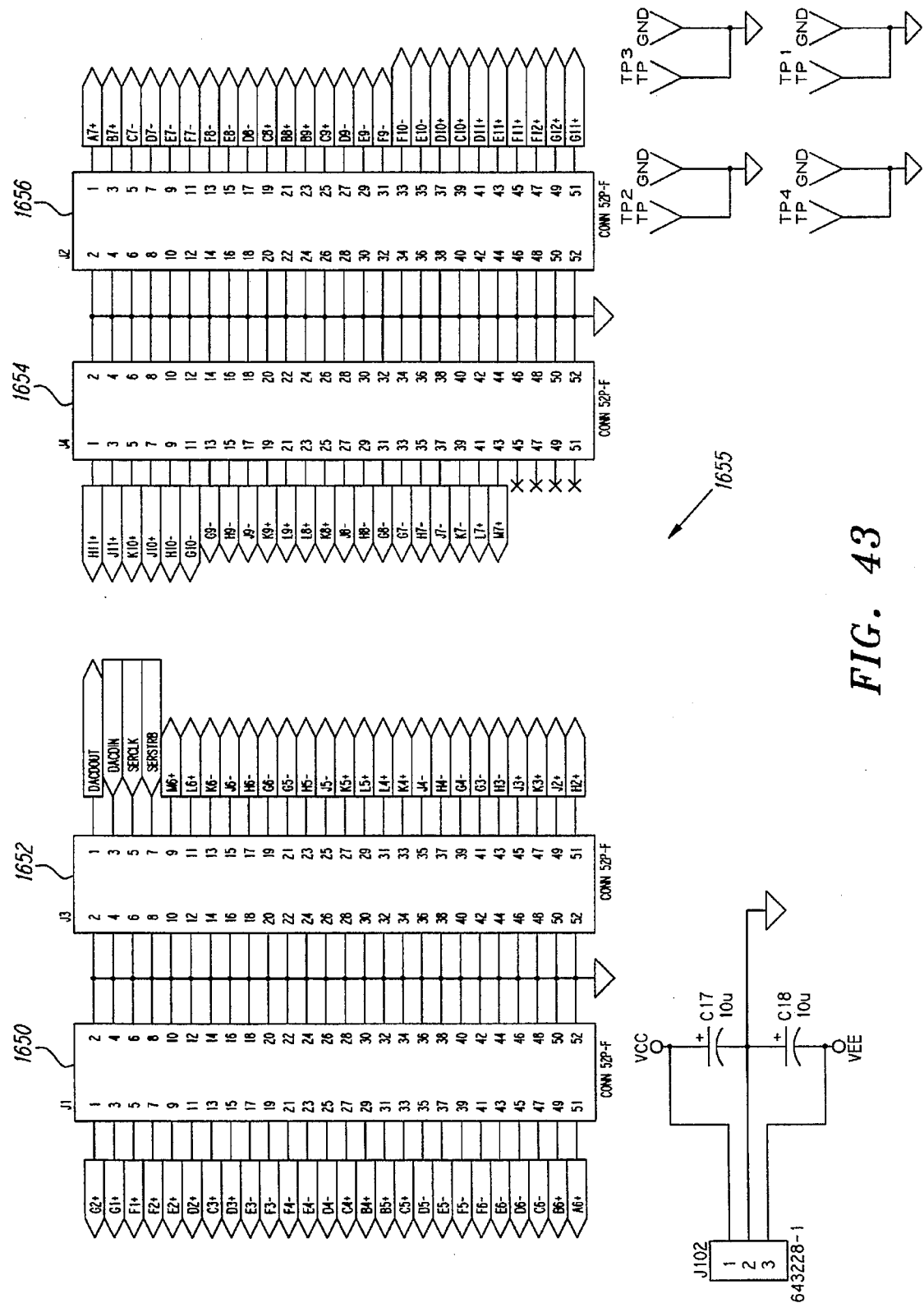
FIG. 43 is a diagram showing the preferred input sensor connectors between the photomultiplier tube and the signal conditioning circuits in the Real-time eye.

Referring to FIG. 43, four connectors 1650, 1652, 1654, and 1656 form the sensor connections 1655 between the signal conditioner 810 and the RTE octant counters 1354. After signal conditioning, signals from each of the 96 PMT detector elements 1339 connects the RTE octant counters 1354 through one of 96 electrical connections on the four connectors 1650, 1652, 1654, and 1656.

Figure 44A:
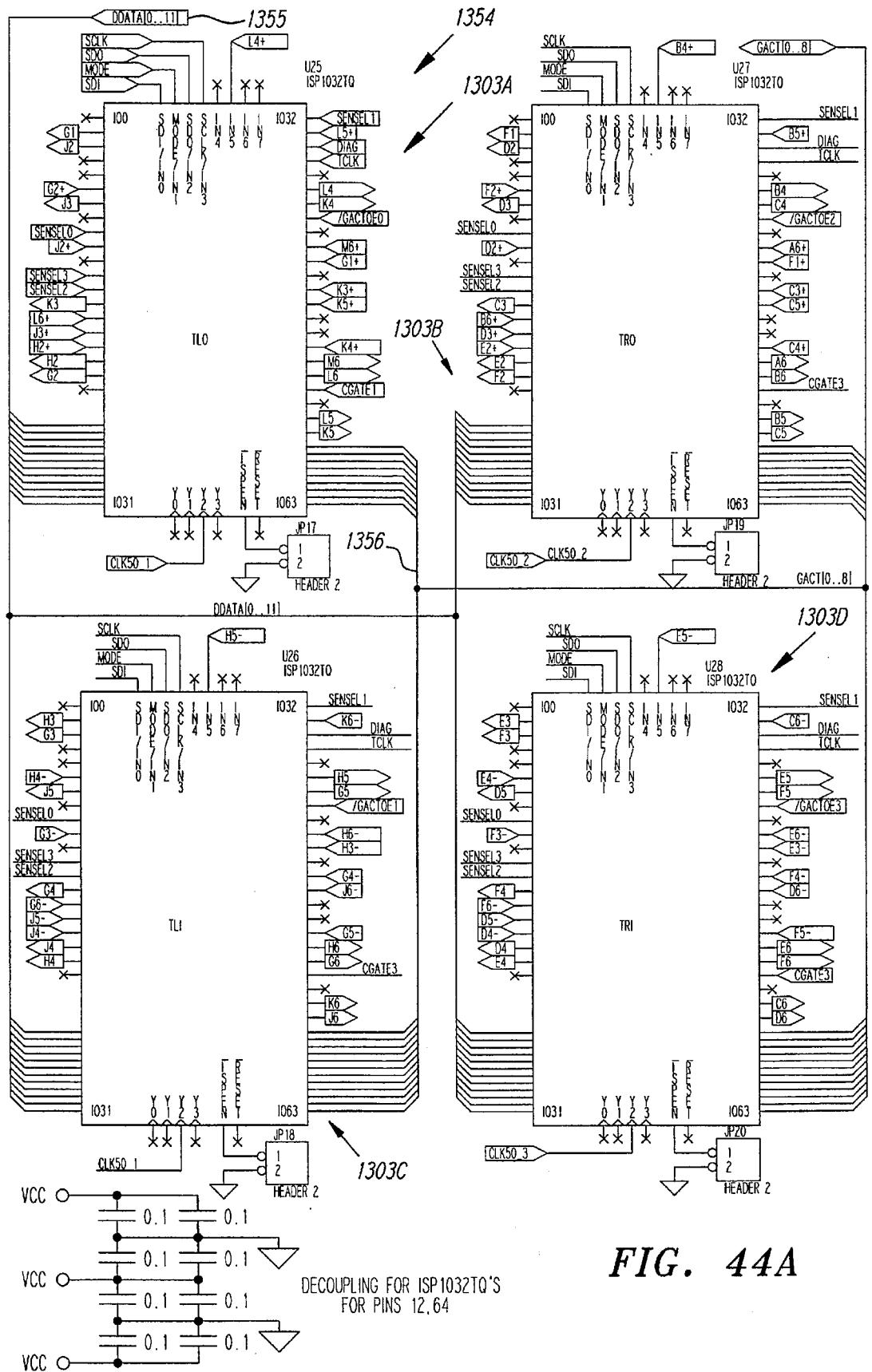
FIGS. 44A–B comprise schematics of the preferred octant counters.
Figure 44B:
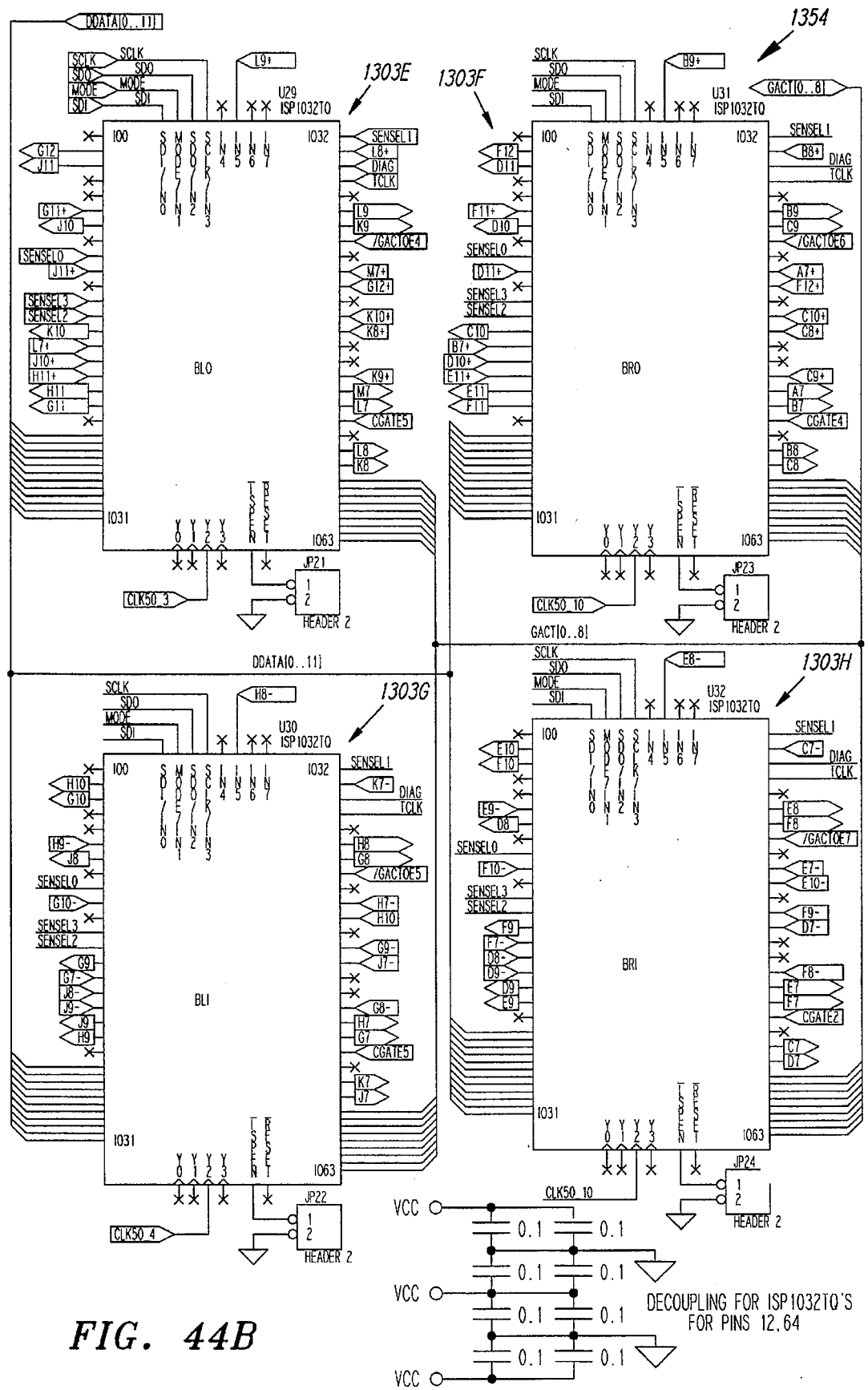

FIGS. 44A–B are diagrams of the preferred octant counters 1354. Eight such octant counters 1354 are used in the real-time eye. Each octant counter 1354 preferably comprises an ISP1032TQ lattice IC chip. Octant counter 1303A processes the inputs from the photocathode elements 1339 which is associated with the TLO octant. Similarly, octant counter 1303B processes the inputs for the TRO octant, octant counter 1303C for the TLI octant, octant counter 1303D for the TRI octant, octant counter 1303E for the BLO octant, octant counter 1303F for the BRO octant, octant counter 1303G for the BLI octant, and octant counter 1303M for the BRI octant. The preferred software modules for octant counters 1354 are included in Appendix A.

Each octant counter 1354 contains data input connections for each of the 12 PMT photo-cathode elements 1339 that is preferably associated with each octant. Upon detection of light photons by a PMT photo-cathode element 1339, an electrical signal is sent to its corresponding octant counter 1354. For the x-ray pencil beam which passes through a single collimator aperture, each of the eight octant counters 1354 produces a 9-bit value which contains the intensity data from all 12 of each octant's associated PMT photo-cathode elements 1339.

Figure 45:
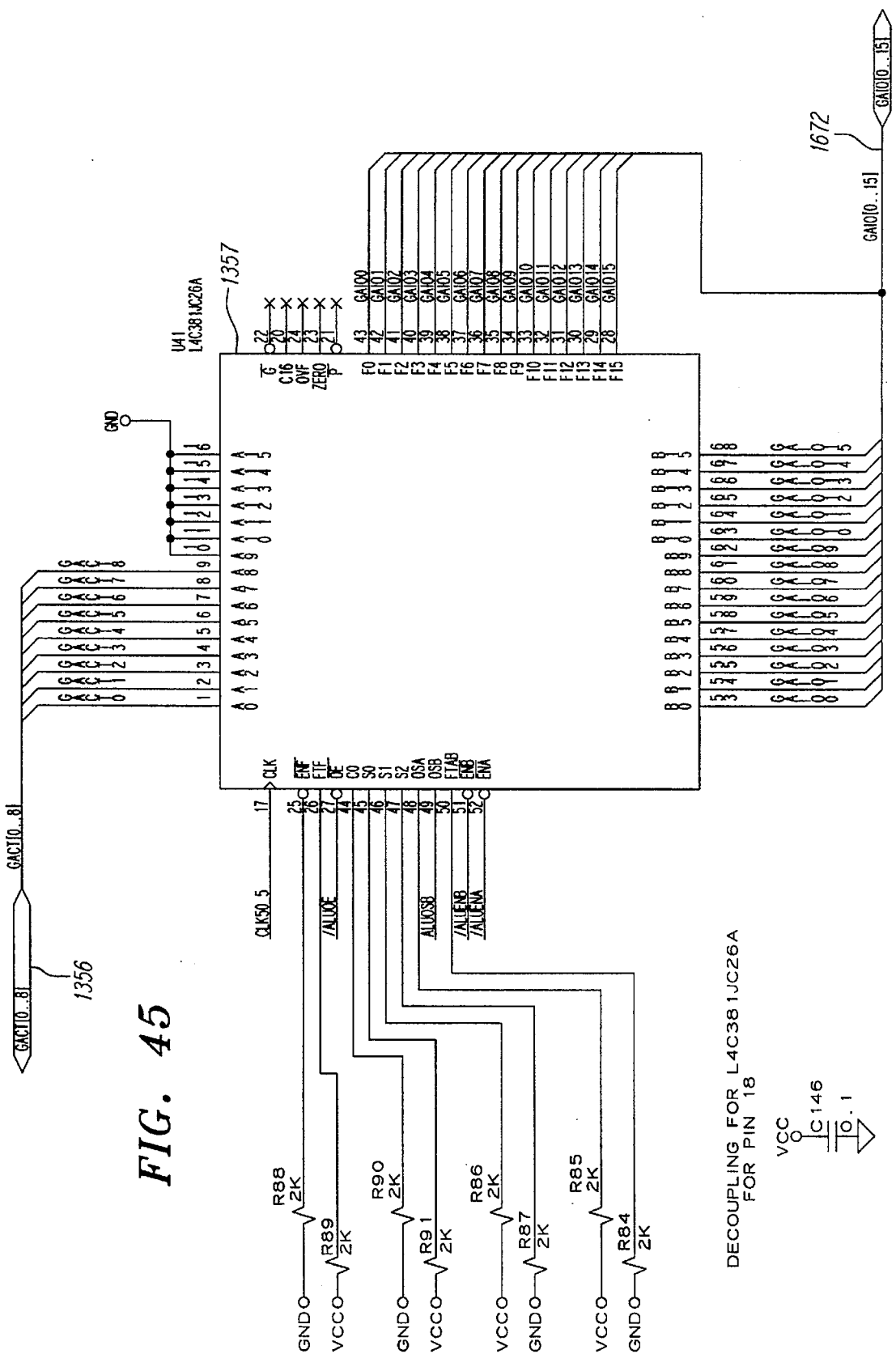
FIG. 45 is a schematic of a preferred gain & alignment ALU.

FIG. 45 diagrams the frame-summation chip 1357, which is an arithmetic logic unit ("ALU") and is preferably a L4C381JC26A IC chip available from Logic Devices, Inc. The 9 bit output from each octant counter 1354 is input to the frame-summation chip 1357 through connection 1356. The frame-summation chip 1357 processes eight numbers for each collimator aperture. For each succeeding frame, the frame-summation chip 1357 sums the corresponding values for the same octant for the same aperture from the previous frames. In the preferred embodiment, the octant values for 100–120 frames are added together to construct the data used for x-ray beam alignment.

Figure 46:
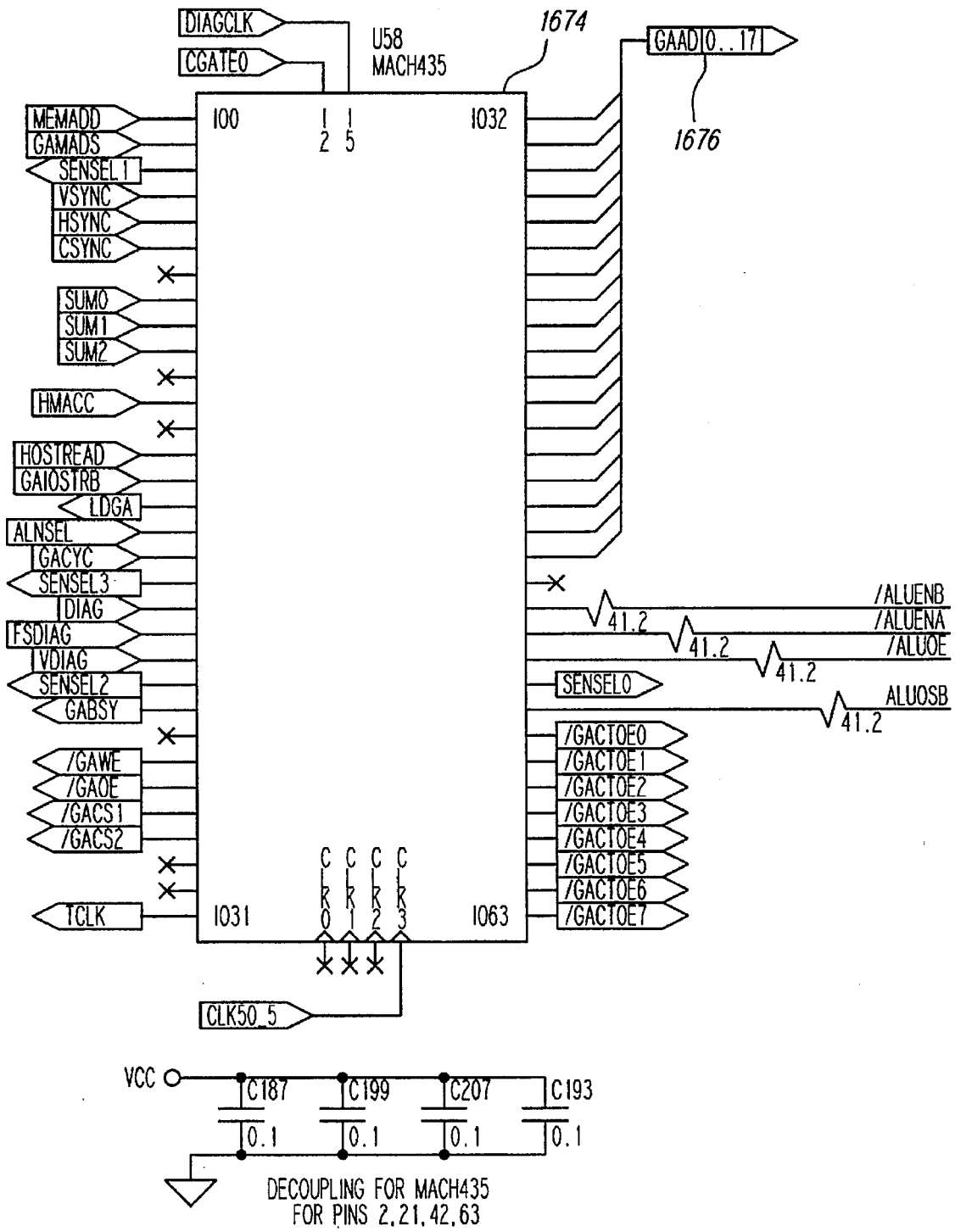
FIG. 46 is a schematic of a preferred gain a alignment engine.

FIG. 46 diagrams the gain & alignment engine 1674, which is preferably a MACH435 IC chip available from AMD Corp. The gain & alignment engine 1674 determines the items of beam alignment data which is to be processed and manner of processing intended for that item of data. Additionally, the gain & alignment engine 1674 controls the timing of the components within the beam alignment extractor 816. The preferred software modules for the gain & alignment engine 1674 are included in Appendix A.

Figure 47:
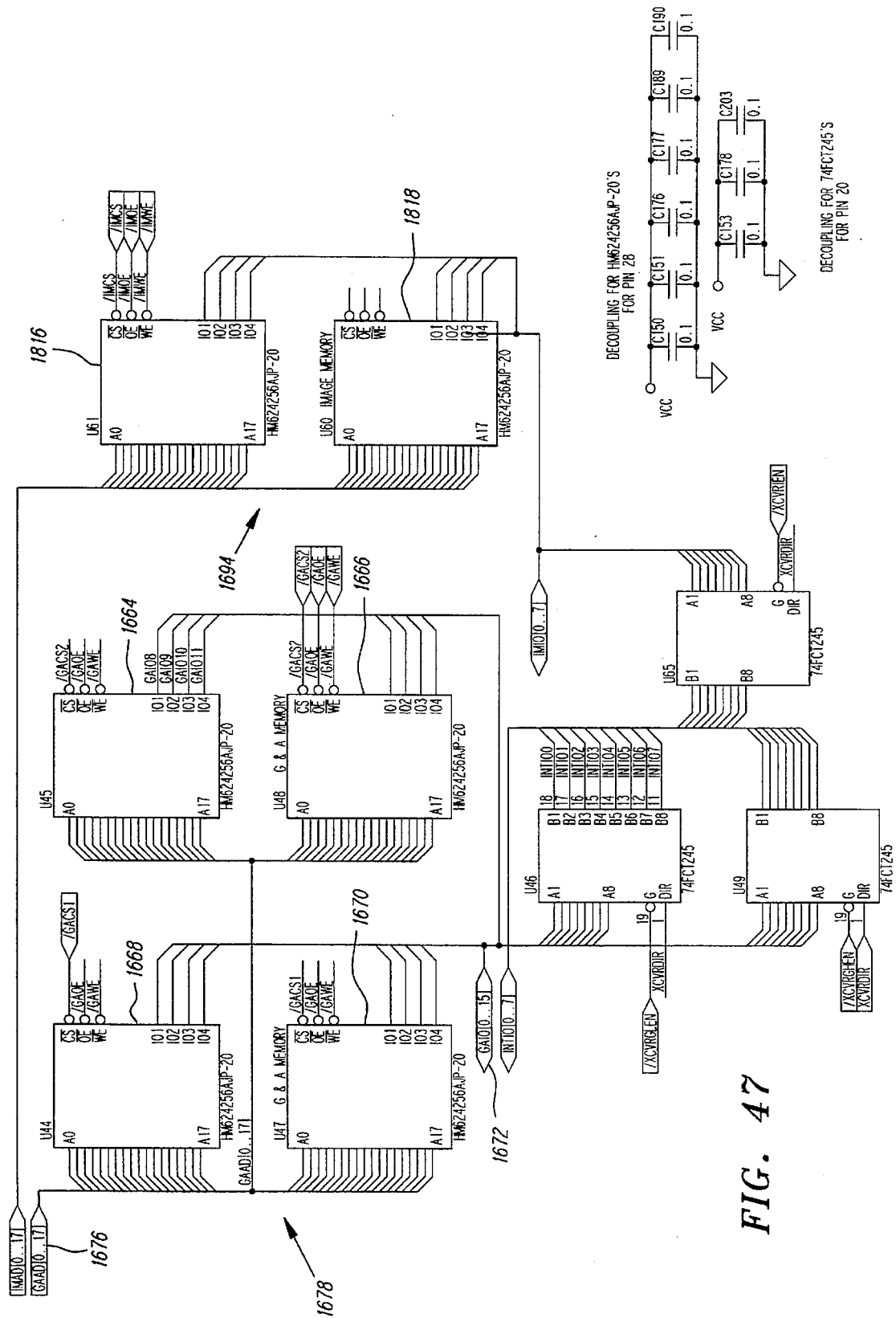
FIG. 47 is a schematic of the preferred memory for the preferred image reconstruction engine and gain & alignment circuitry.

FIG. 47 is a diagram showing the gain & alignment memory chips 1678 which is comprised of four 1-Mbyte SRAM memory chips 1664, 1666, 1668, and 1670, each available under the model number MM624256AJP-20 from Hitachi Corporation. For each frame, eight values are collected for each collimator aperture. These values are stored in the gain a alignment memory 1678 after being processed through the frame-summation chip 1357. After 100–120 frames, the control computer will preferably access and process the data which is stored in the gain & alignment memory 1678 to correct the alignment of the x-ray beam.

FIGS. 48A–I are diagrams of string counters 1372 for strings one through nine. Nine such string counters are used in the image reconstruction circuitry, each of which is preferably comprised of two gate arrays 1680 and 1682, preferably IC part numbers ISP1032TQ available from Lattice Corp. Each string counter 1372 contains a total of 16 subcounters, with each gate array 1680 and 1682 containing 8 individual subcounters. Since there are a total of nine string counters 1372 and each string counter 1372 contains 8 individual subcounters, the total number of individual subcounters is 144. Since all nine string counters 1372 function similarly, only the string one string counter 47A will be discussed in detail. The preferred software modules for string counters 1372 are included in Appendix A.

Figure 48A:
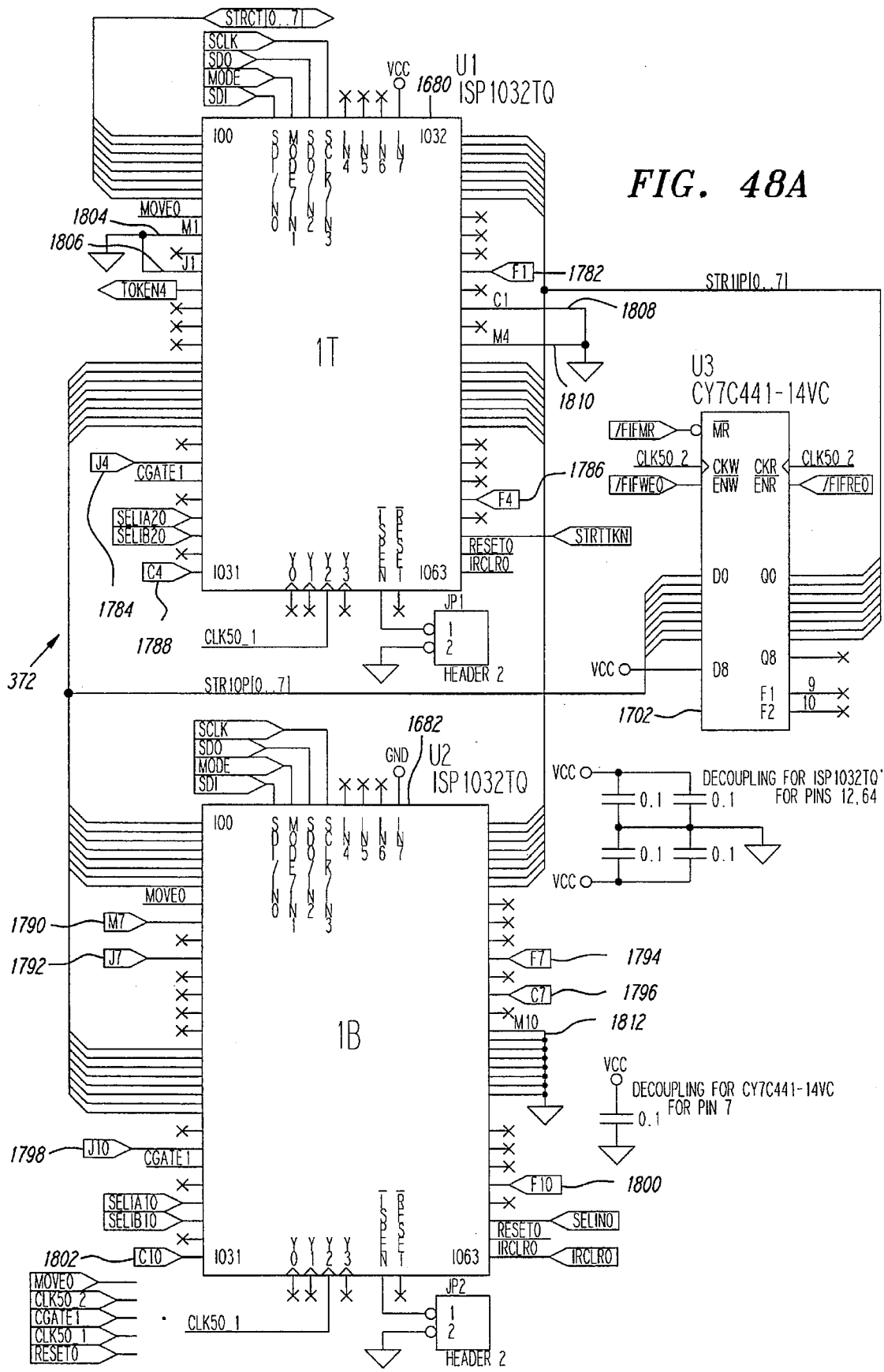
FIG. 48A–I are schematics of string counters for strings one through nine for a preferred image reconstruction engine.
Figure 48B:
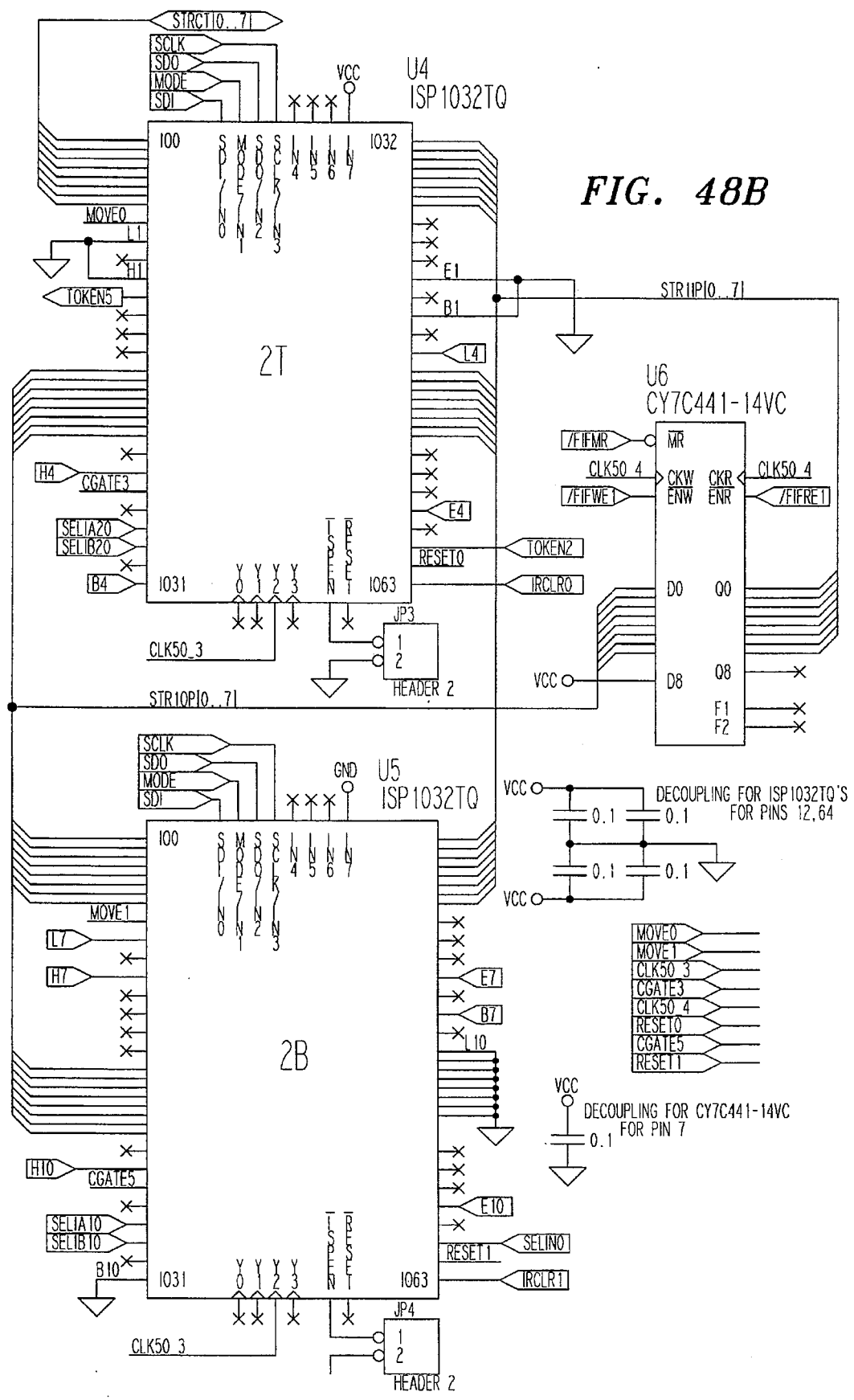
Figure 48C:
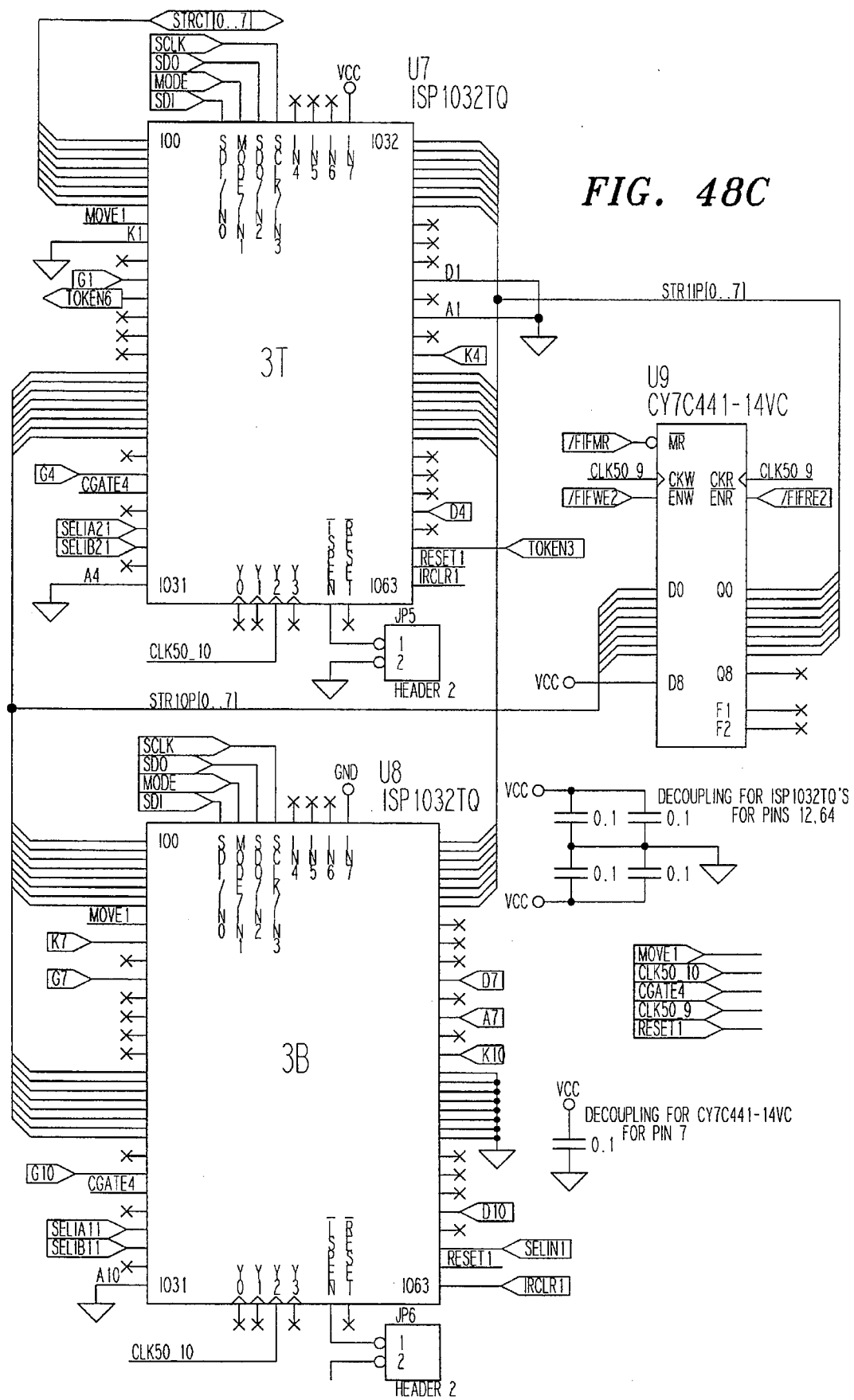
Figure 48D:
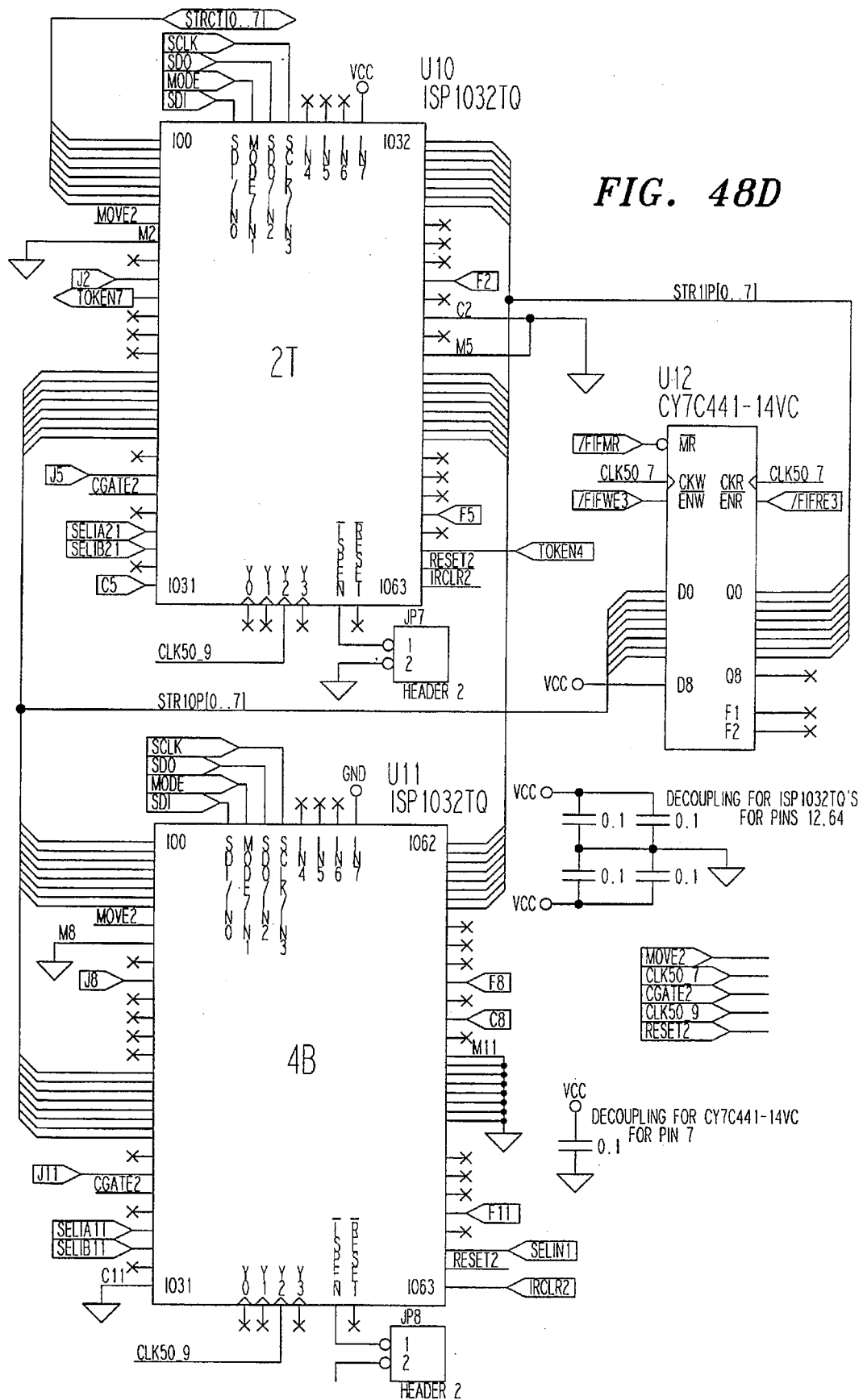
Figure 48E:
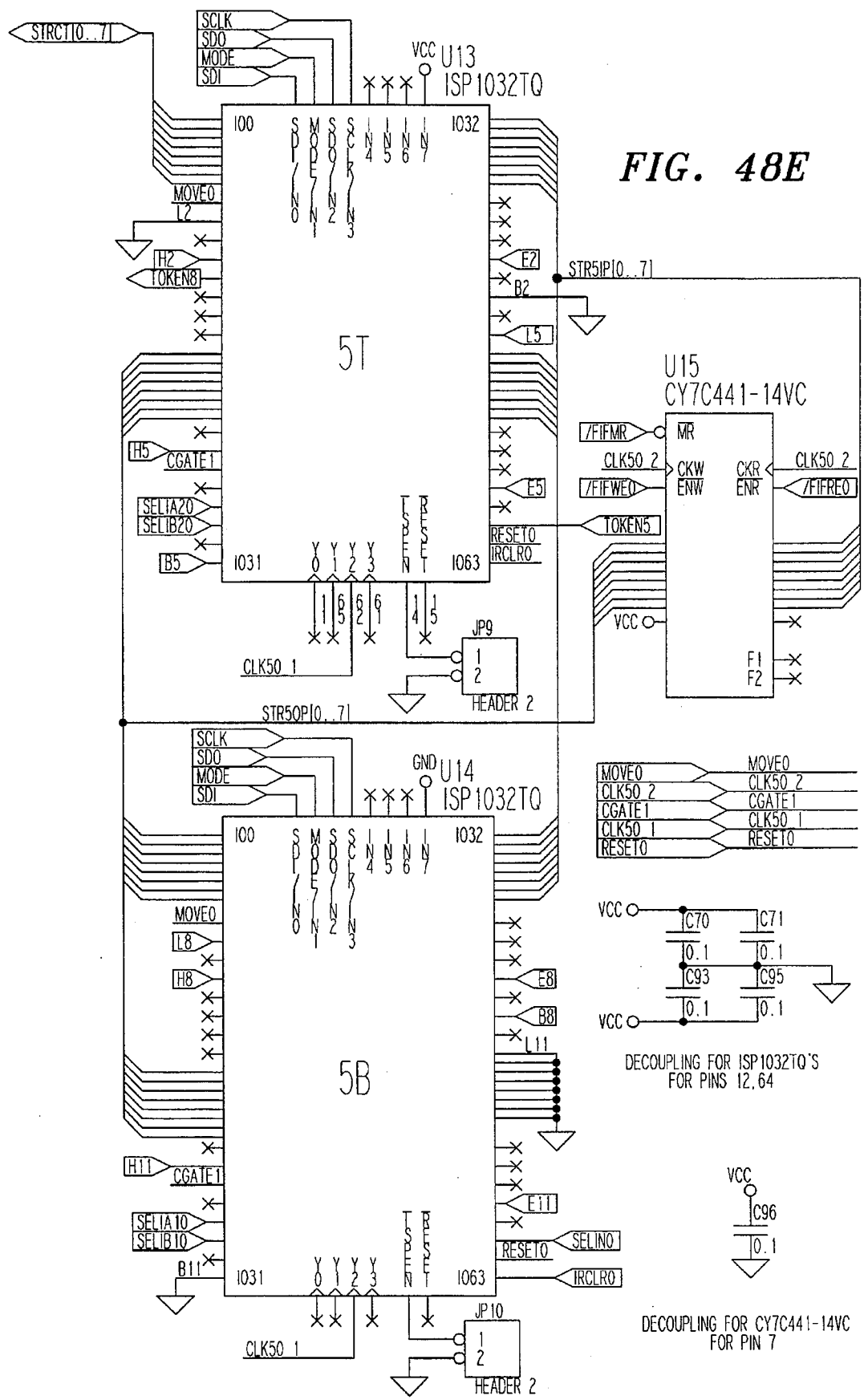
Figure 48F:
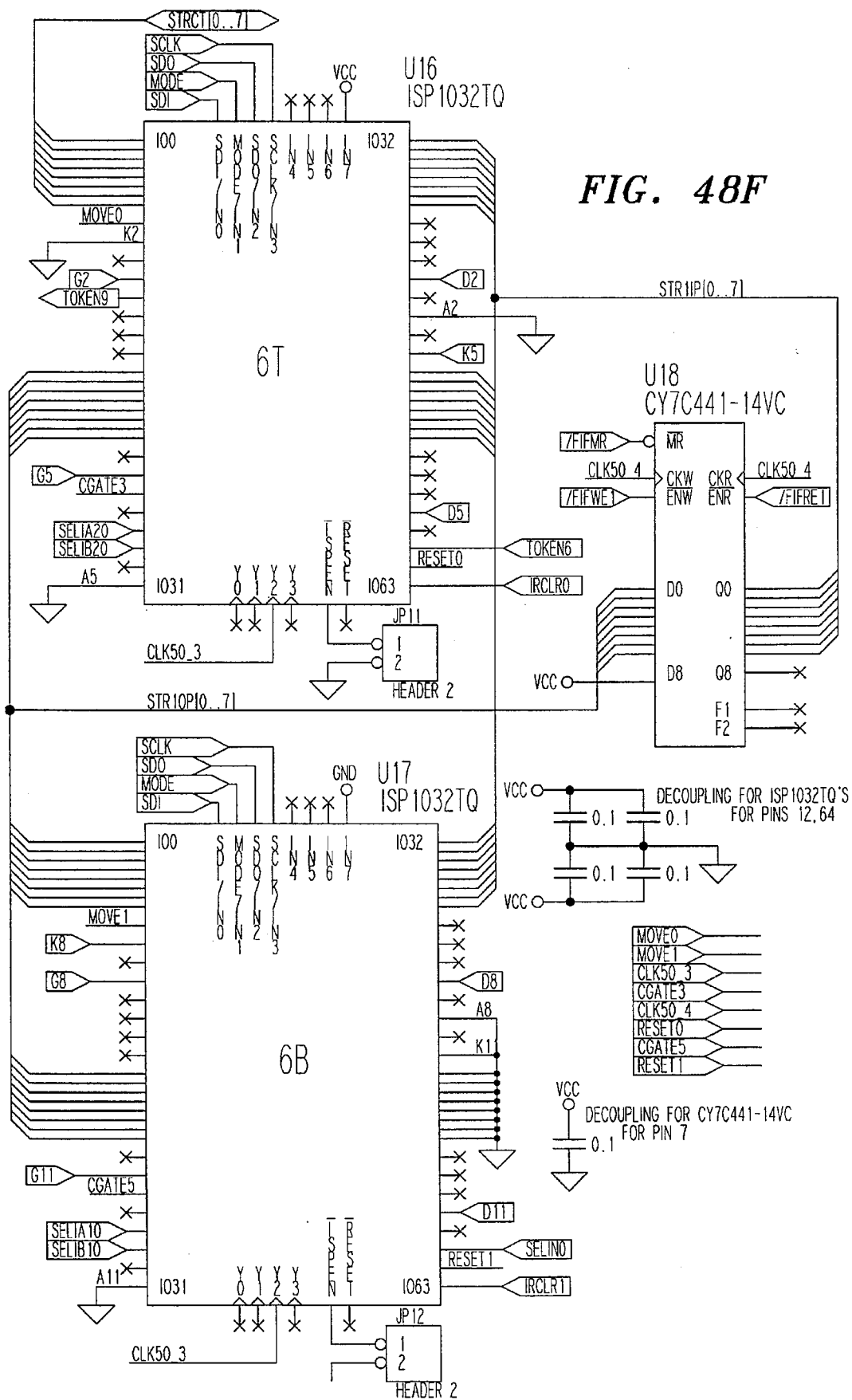
Figure 48G:
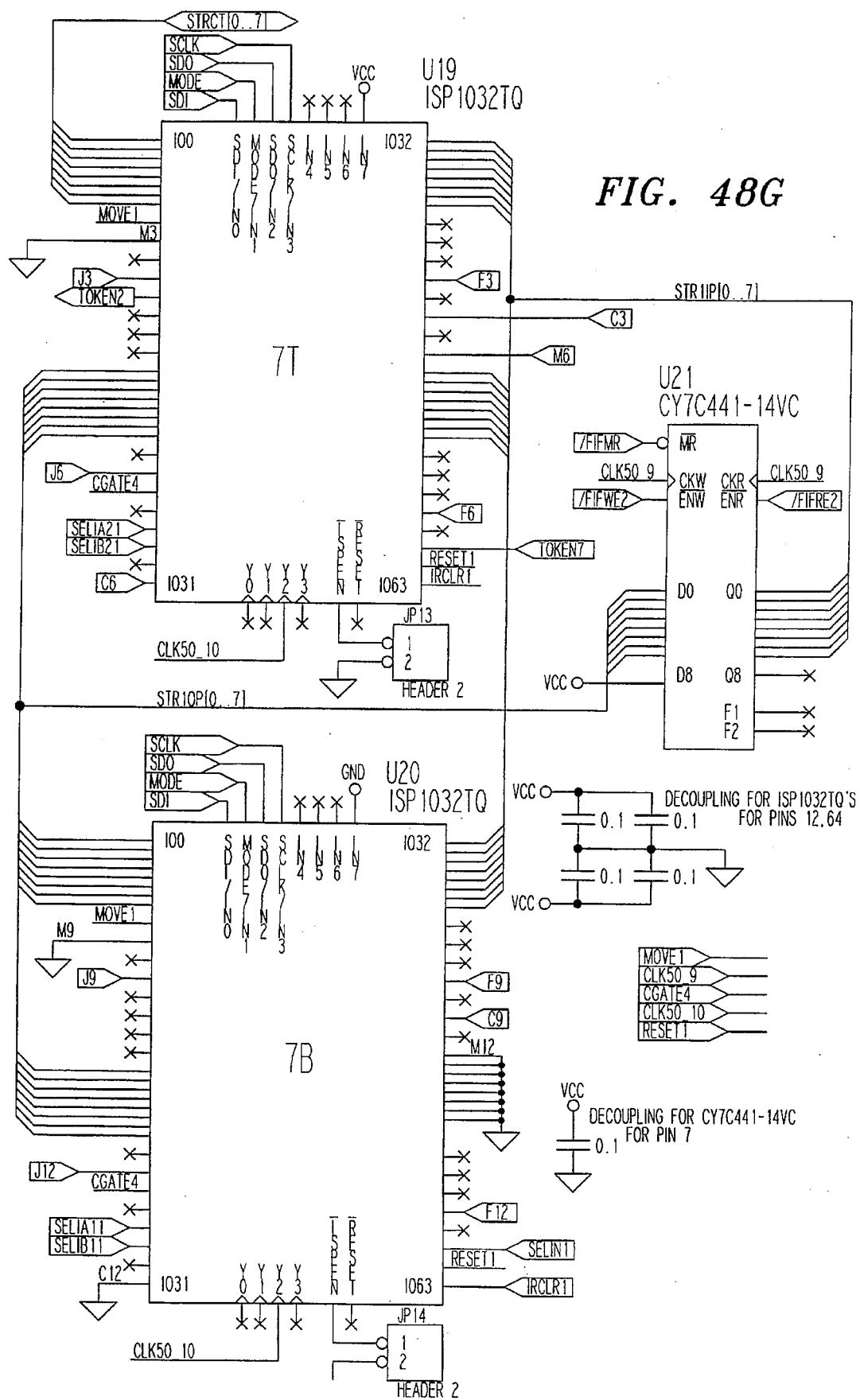
Figure 48H:
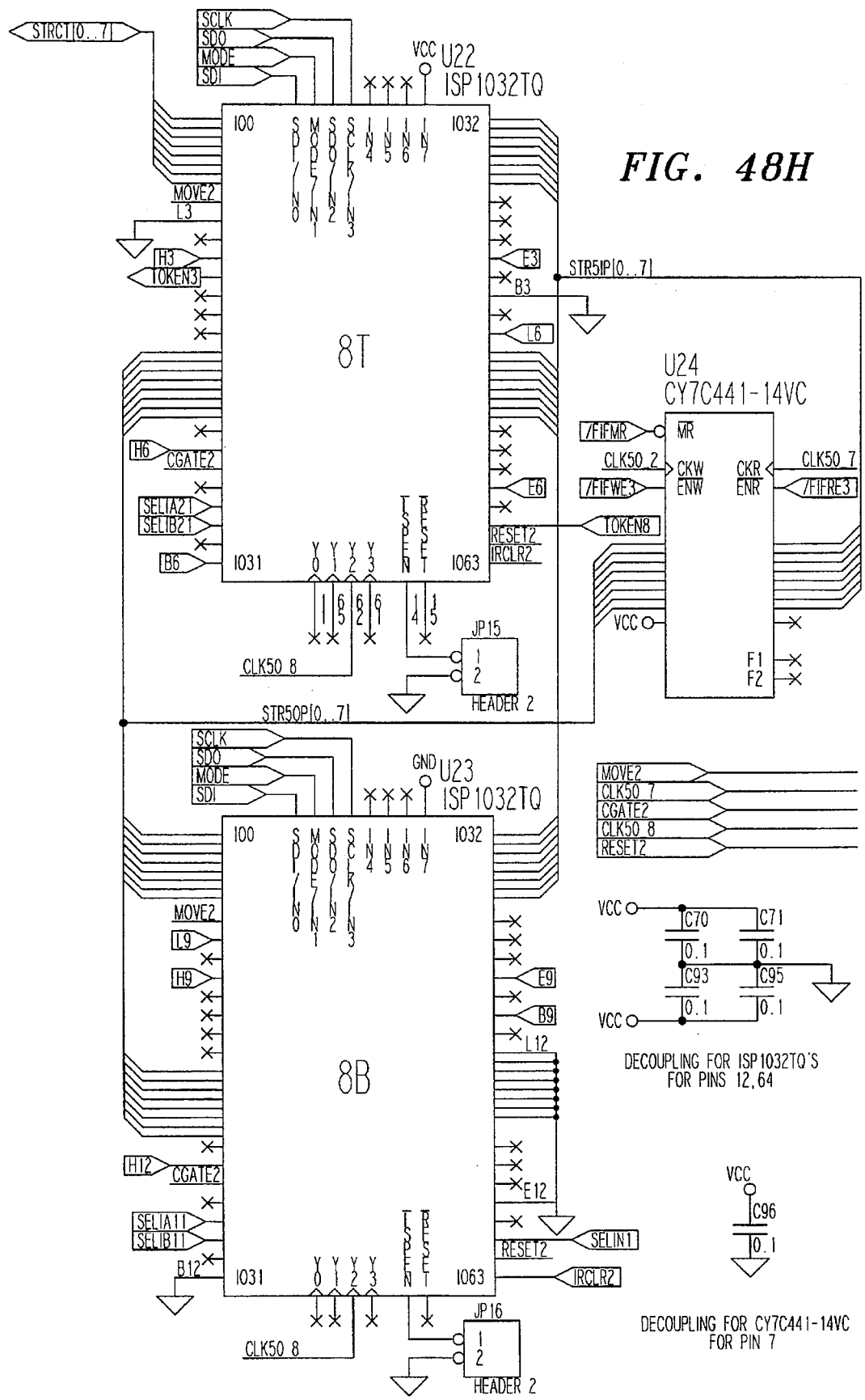
Figure 48I:
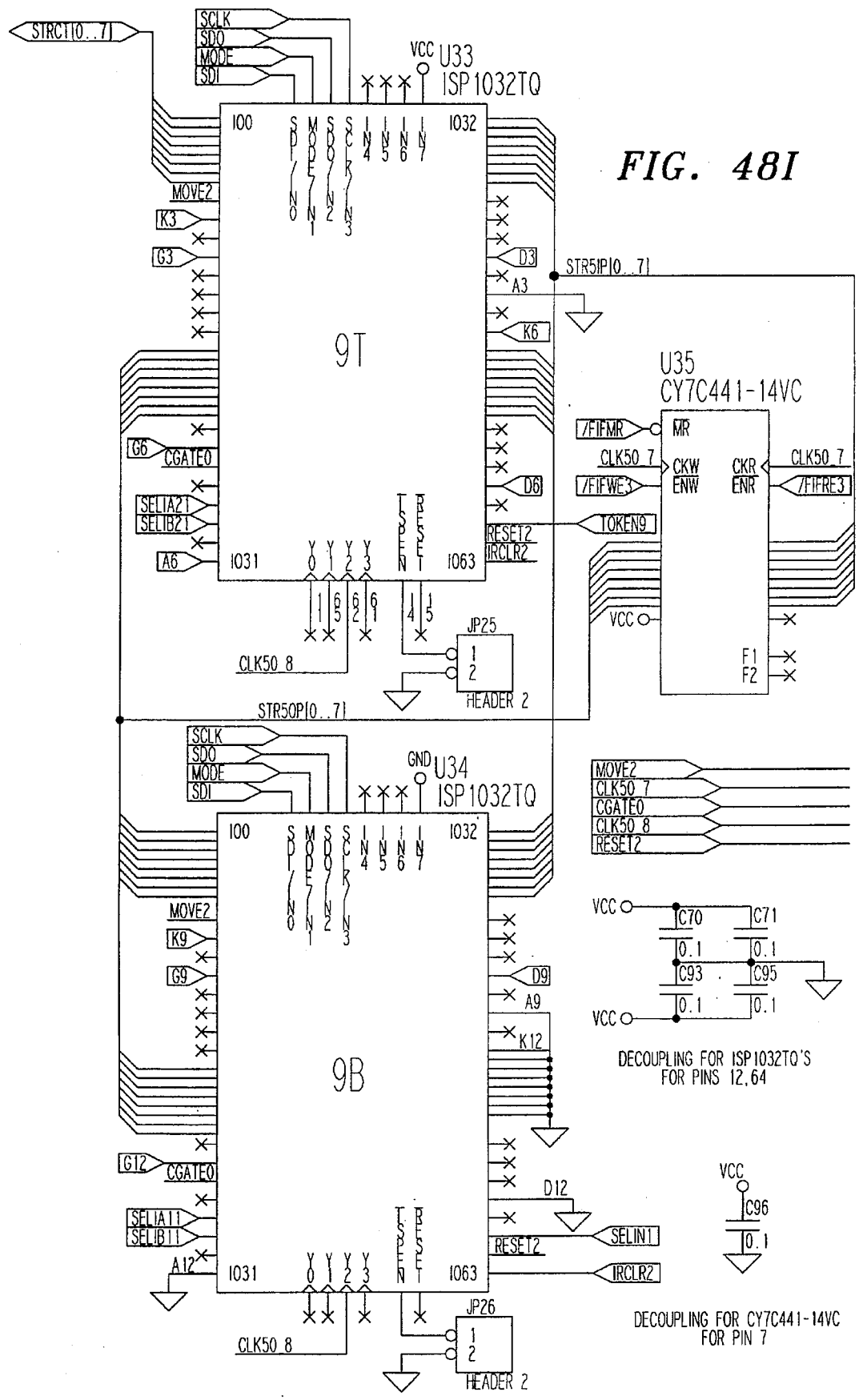

Referring back to FIG. 36, the detector element inputs for string one are marked with "1." Since only the 96 elements within the center pseudo circle 1780 correspond to active detector elements, the inputs mapped from active detector elements for string one are element F1, J4, F4, C4, M7, J7, F7, C7, J10, F10, and C10. Referring to FIG. 48A, data connection 1782 on string counter 1372 is mapped to the input from active detector element F1. Data connections 1784, 1786, 1788, 1790, 1792, 1794, 1796, 1798, 1800, and 1802 are mapped to active detector elements J4, F4, C4, M7, J7, F7, C7, J10, F10, C10 respectively. The inputs from elements M1, J1, C1, M4, and M10 correspond to the inactive detector elements for string counter one. Therefore, data connections 1804, 1806, 1808, 1810, and 1812 which correspond to inactive detector elements M1, J1, C1, M4, and M10 respectively, are all tied to ground.

Each of the other string counters are similarly mapped to their respective active and inactive detector elements. FIG. 36 diagrams the 144 logical detector elements and the string counter number that they are mapped.

FIG. 48A also diagrams a line FIFO ("first in first out") chip 1702, preferably part no. CY7C441-14VC available from Cypress Semiconductor. The RTE image reconstruction circuitry consists of nine line FIFOs, with each line FIFO 1702 paired with a corresponding string counter 1372. Partial image pixel values from string counter 1372 are input into line FIFO 1702 as the string counter acquires data from the multi-detector array. After the 166th string counter data value is input into the line FIFO 1702, every succeeding data value will cause the line FIFO 1702 to return a data value that was stored 166 counts before to the its corresponding string counter 1372. The data values are returned to the string counter 1372 to be summed with new data values acquired for the same image pixel.

Figure 49:
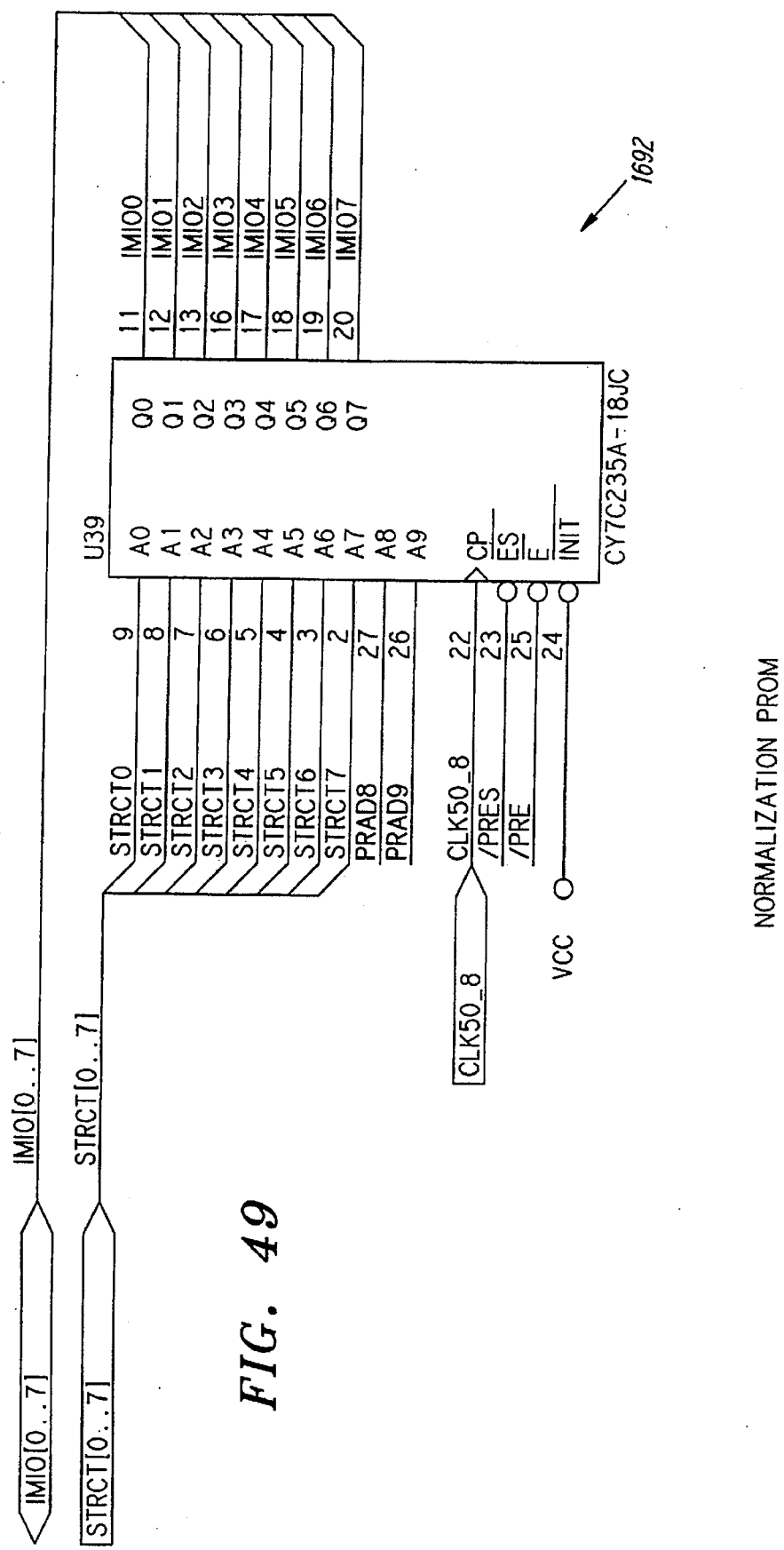
FIG. 49 is a a schematic of a preferred normalization PROM for a preferred image reconstruction engine.

FIG. 49 diagrams the normalization PROM 1692, which is a CY7C235A-18JC Cypress Semiconductor unit. As explained previously, each string counter 1372 is mapped to 16 logical detector elements on a 12-by-12 array of logical detector elements. However, each string counter 1372 may receive meaningful input data from only among the 96 active detector elements which comprise the center pseudo-circular array. As shown in FIG. 36, the number of active detector elements providing input data may be 10, 11 or 12 depending on the particular string counter. The normalization PROM 1692 normalizes the outputs from the nine string counters 1372 by calculating the proper output levels based upon the number of active input detector elements for each string.

Figure 50:
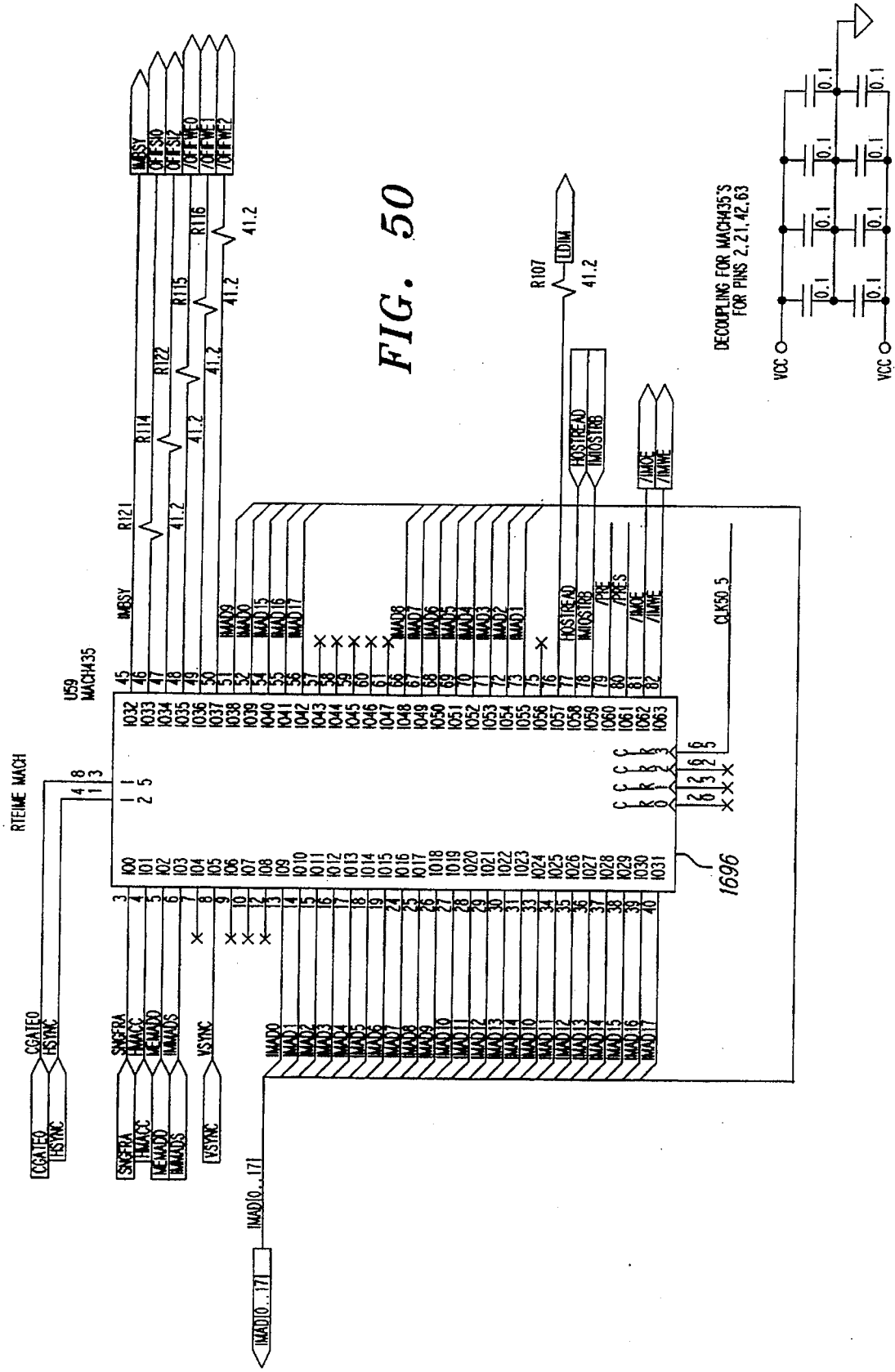
FIG. 50 is a schematic of the controller for the preferred image reconstruction engine.

FIG. 50 diagrams the image reconstruction controller 1696. Image reconstruction controller 1696 functions as the "engine" within the image reconstruction engine 814. Image reconstruction controller 1696 controls the timing and operation of the string counters 1372. The image reconstruction controller 1696 is the component which keeps track of both the strings and the individual image pixels which are reconstructed. Image reconstruction controller 1696 also controls the operation of the image memory unit 1694. The preferred software modules for the image reconstruction controller 1696 are included in Appendix A.

FIG. 47 diagrams the image memory unit 1694, which is preferably comprised of two conventional 1-Mbyte MM624256AJP-20 SRAM chips 1816 and 1818. The normalized pixel data output from the normalization PROM is input to the image memory unit 1694 through electrical connection 1718. The image memory unit 1694 combines and correctly orders the pixel data for the entire image.

Figure 51:
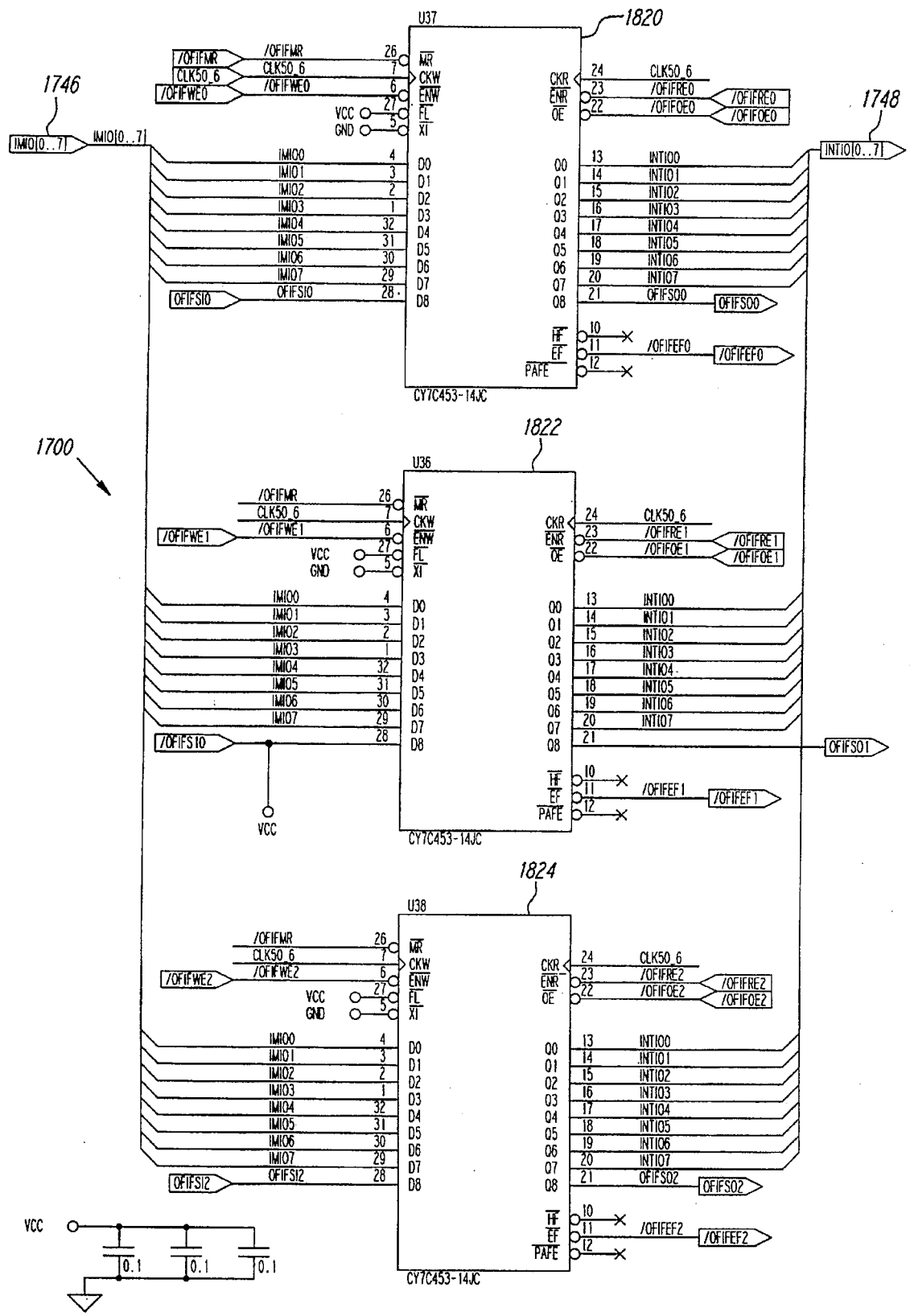
FIG. 51 is a schematic diagram of the preferred output FIFOs for the preferred image reconstruction engine.

FIG. 51 is a diagram of the output FIFOs 1700. The output FIFOs 1700 preferably comprises three CY7C453-14JC devices 1820, 1822, and 1824. The output FIFOs 1700 store three lines of pixel data before outputting this data in frame order through RTE output circuit 818. The output FIFOs 1700 function in this manner because a completed scan of one collimator aperture row will result in the completion of three lines of image pixels. The pixel data is continually input from the normalization PROM 1692 until the three lines of pixel data are stored.

Figure 52:
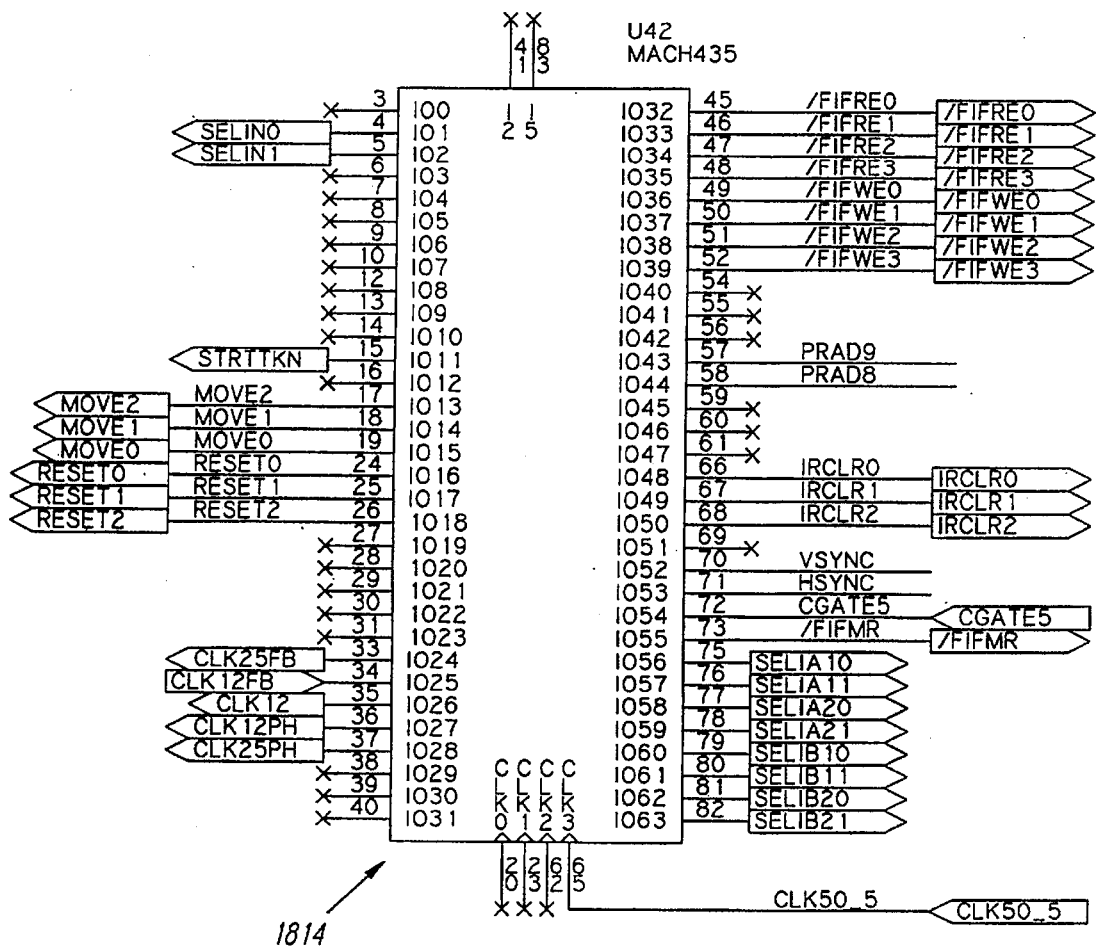
FIG. 52 is a schematic of the preferred output FIFO controller for the preferred image reconstruction image.

FIG. 52 diagrams the output FIFO controller 1814. Output FIFO controller 1814 consists of a lattice chip available under the model number MACH435 IC chip from AMD Corp. Output FIFO controller 1814 controls the operation of the three output FIFOs 1700. The preferred software modules for the output FIFO controller 1814 are included in Appendix A.

Detector Controller

The detector controller 805 (FIG. 21) for the detectors 822 and 1522 receives image pixel data and beam alignment data from the detectors and transmits control information to the detectors. Right receiver 880 optically receives image pixel data and beam alignment data from the right detector 822 through high-speed fiber-optic cable 826. Consequently, right receiver 880 includes the light signal to electrical signal conversion circuitry described more fully in conjunction with FIG. 40. The left receiver 846 operates in a similar fashion to receive image pixel data and beam alignment data from the left detector 1522.

Right transmitter 886 optically transmits threshold and gain control data to the right data receiver 812 though fiber-optic cable 824. Consequently, beam controller interface 794 includes the electrical to light conversion circuitry described more fully in conjunction with FIG. 41. Right transmitter 886 also receives synchronization signals from beam deflection lookup table 918 (FIG. 25). The left transmitter 848 operates in a similar manner to communicate control signals to the left detector 1522.

Figure 53:
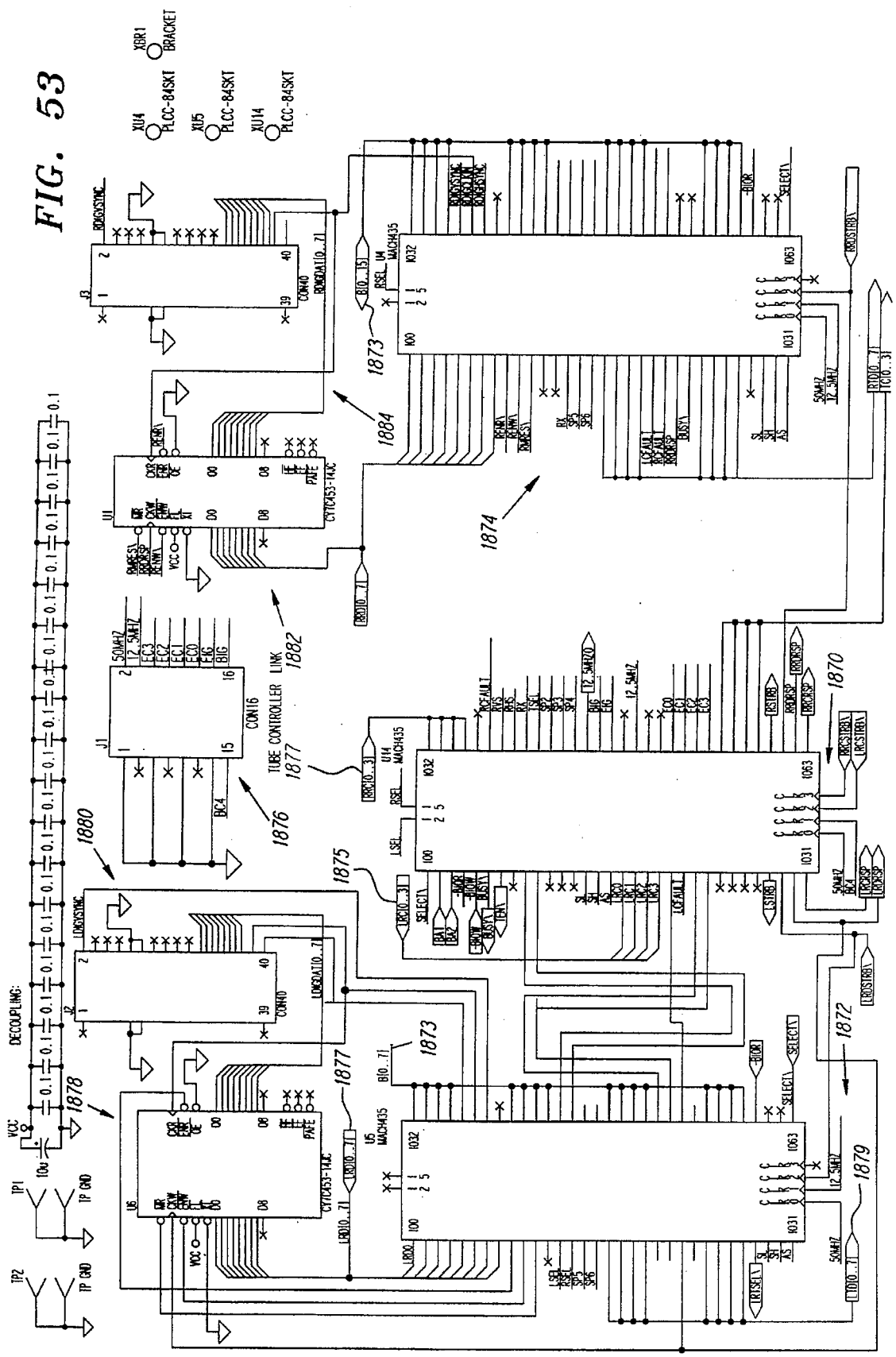
FIG. 53 is a circuit diagram of the preferred control logic for detector controller.

FIG. 53 is a circuit diagram of the preferred control logic for the detector controller 805. Control PAL 1870, preferably a conventional MACH435 programmable IC chip, provides the control signals to coordinate the activity of the detector controller 805 and the left and right multiplexer PALs 1872 and 1874. Control PAL 1870 receives left data control signals LRC from the left receiver 846 via leads 1875. Similarly, control PAL 1870 receives right data control signals from the right receiver via leads 1877. Control PAL 1870 receives timing input control signals through a tube controller link 1876. The software modules for the control PAL 1870 are included in Appendix A.

Left multiplexer PAL 1872 preferably functions as data multiplexers for the items of data which are received and transmitted by the left receiver 846 and the left transmitter 848. Left multiplexer PAL 1872 preferably loads gain and threshold control data from a bidirectional data bus via leads 1873. Left multiplexer PAL 1872 also preferably loads image pixel data and alignment data from the left receiver 846 via leads 1877.

Left multiplexer preferably transmits gain and threshold control signals, via leads 1879, to the left transmitter 848, which then optically transmits this data to the left detector 1522. The alignment data received by the left multiplexer PAL 1872 is redirected to the control computer via the bidirectional data bus via leads 1873. The image pixel data received by the left multiplexer PAL 1872 is sequentially redirected to a data FIFO 1878. Data FIFO 1878 and connector 1880 function as a data interface between the left multiplexer PAL 1872 and the left frame buffer 850. Right multiplexer PAL 1874 functions similarly to control and select the items of data which are received and transmitted by the right receiver 880 and right transmitter 886. Similarly, data FIFO 1882 and connector 1884 function as the data interface between the right multiplexer PAL 1874 and the right frame buffer 872. The preferred software modules for the left and right multiplexer PALs 1872 and 1874 are included in Appendix A.

In the preferred embodiment, detector controller 805 is fabricated as a PC module that plugs into the bus of the control computer 890. The preferred interface circuitry between detector controller 805 and the control computer 890 is described more fully in connection with the detailed description of FIG. 54B.

Tube Controller

Tube controller 807 generates scan control data which directs the operation of the beam controller 796, thereby controlling the scanning pattern of the x-ray source 798. Tube controller 807 functionally comprises a beam deflection lookup table 918 which stores beam deflection data for each point on the target anode, programmable scan controller 920, beam transmitter 916, I/O transceiver 964, and I/O latch 958.

Figure 54A:
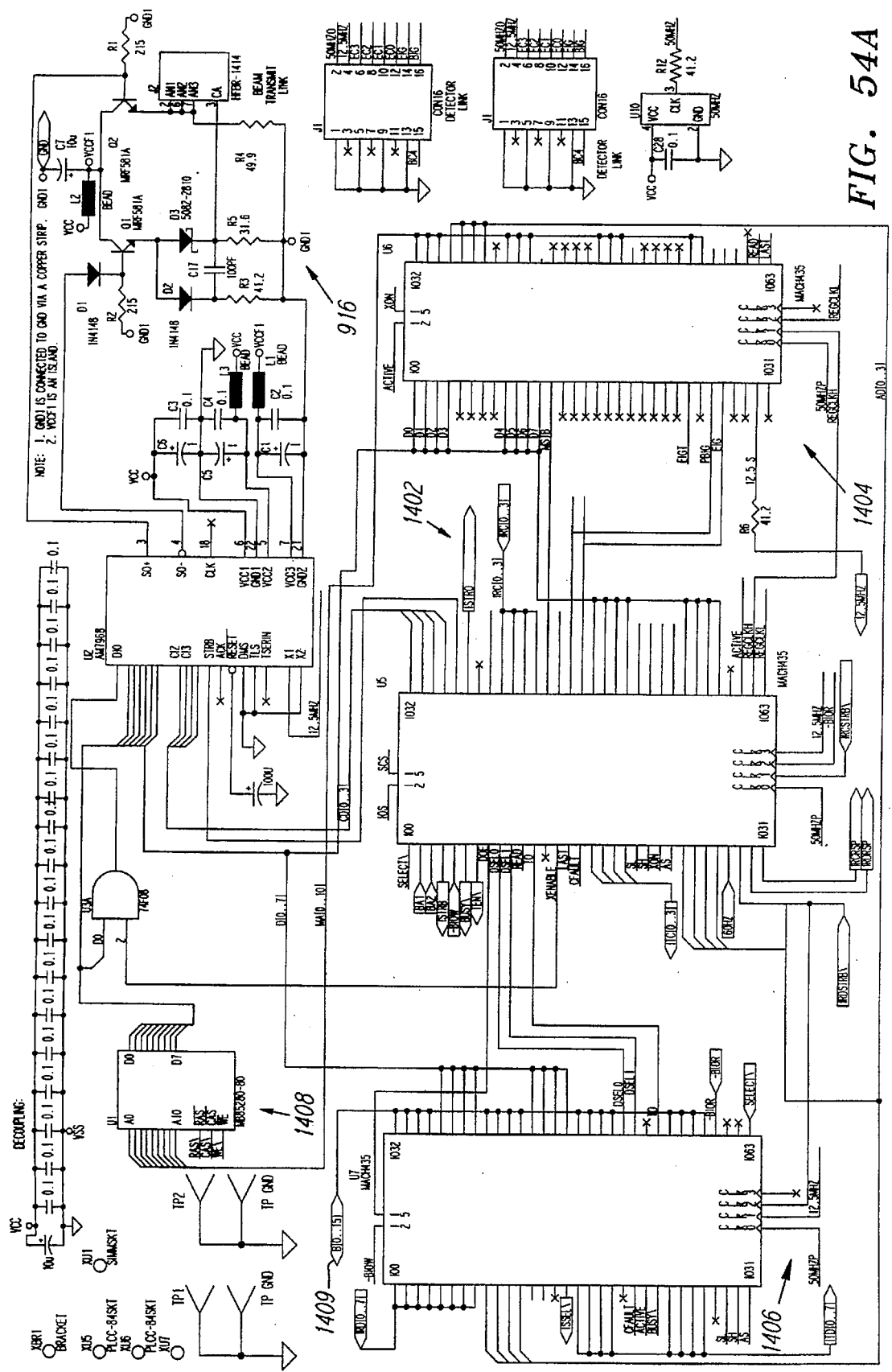
FIG. 54I is a circuit diagram of the control logic for the preferred tube controller.
FIG. 54B is a diagram of the preferred interface circuitry connecting the tube controller circuits with the PC bus within the control computer.

FIG. 54A is a circuit diagram of the control logic for the tube controller 807. Control PAL 1402 generally performs the functions of the programmable scan controller 920, by processing control instructions received from control computer 890, and distributing signals for loading, running or stopping the scan patterns to the memory control PAL 1404 and data PAL 1406. Control PAL 1402 provides control signals to direct the operation of the components within the tube controller 807. For example, control PAL 1402 is programmed to set the "measure and move" times for each collimator hole scanned. The preferred programming module for the control PAL 1402 is included in Appendix A.

Beam deflection lookup table 918 is preferably comprised of a memory control PAL 1404 and lookup table memory 1408. Memory control PAL 1404 generates control signals to direct the storage and retrieval of information in the lookup table memory 1408. At appropriate times, memory control PAL 1404 directs the retrieval of the beam deflection data from the lookup table memory 1408. The retrieved beam deflection data is sent to the beam transmitter 916 for transmission to the beam controller 796. Beam transmitter 916 is preferably a conventional optical transmission circuit, which is discussed more fully in connection with the detailed description of FIG. 41. The preferred programming module for memory control PAL 1404 is included in Appendix A.

Data PAL 1406 is programmed to function as the data multiplexer for the data which is received or transmitted by the tube controller 807. The preferred programming module for data PAL 1406 is included in Appendix A.

Figure 54B:
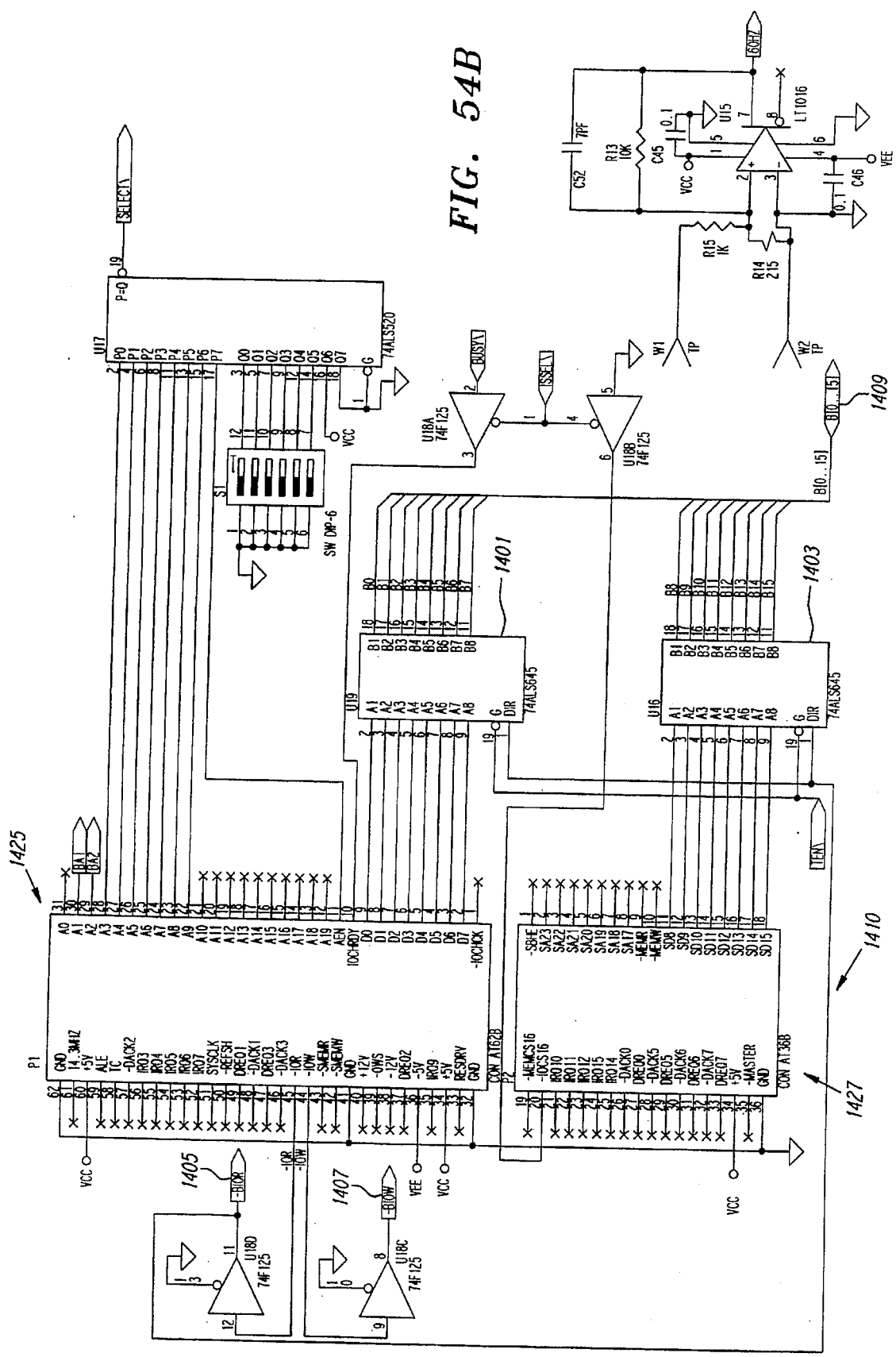

In the preferred embodiment, tube controller 807 is fabricated as a PC module that plugs into the bus of the control computer 890. FIG. 54B is a diagram of the preferred interface circuitry for connecting the tube controller 807 and the control computer 890. Connectors 1425 and 1427 interface the tube controller 807 with the bus of the control computer 890. Data transceivers 1401 and 1403 transfer binary information between the tube controller 807 and the control computer 890 on a three state bidirectional 16 bit data bus B[0 ... 15] via leads 1409. I/O read control signals are applied via lead 1405 and I/O write control signals are applied via lead 1407.

The tube controller also controls the I/O transceiver 964 and the I/O latch 958. The tube controller 807 directs the various sets of control signals received from the control computer to the I/O transceiver 964 and the I/O latch 958 for further transmission of these control signals over an optical link to the I/O controller. I/O transceiver 964 preferably includes optical communications circuitry which is more fully discussed in connection with the detailed description of FIGS. 40 and 41.

Beam Controller

FIGS. 55A–E diagram the control logic within the beam controller interface 794, which processes and distributes analog coil current control signals to the various coil drivers. The digital scan control data generated by the tube controller 807 is optically coupled to the beam controller input circuit 1408, which preferably includes the optical communications circuit described more fully in connection with the detailed description of FIG. 40. Beam controller input circuit 1408 outputs eight parallel bits of digital scan control data to an eight-bit data bus D[0 ... 7] and four parallel bits of control data CD to a control PAL 1410, which distributes and/or reformats the digital scan control data within the beam controller interface 794. The preferred software modules for control PAL 1410 are included in Appendix A.

Figure 55A:
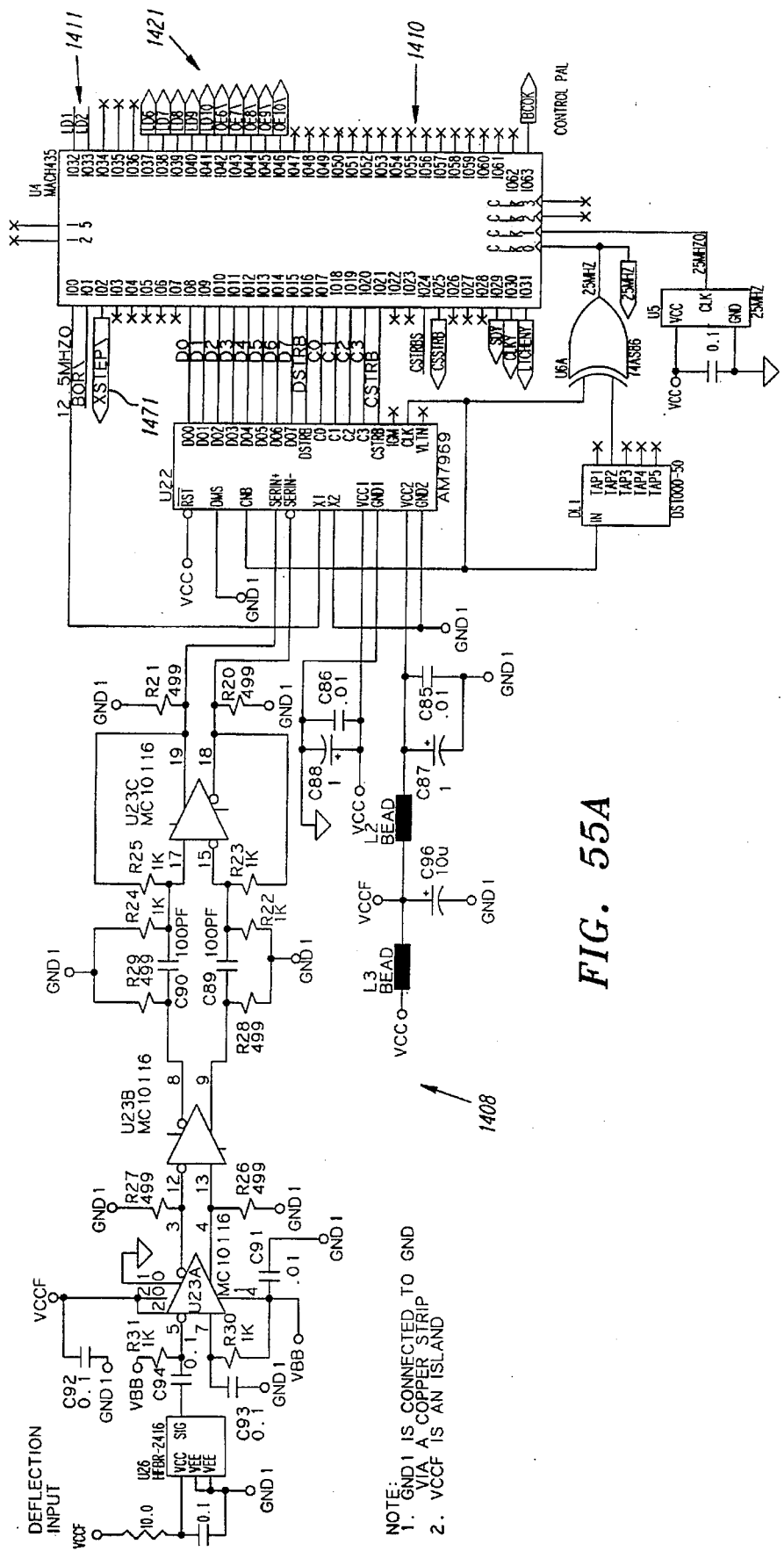
Figure 55C:
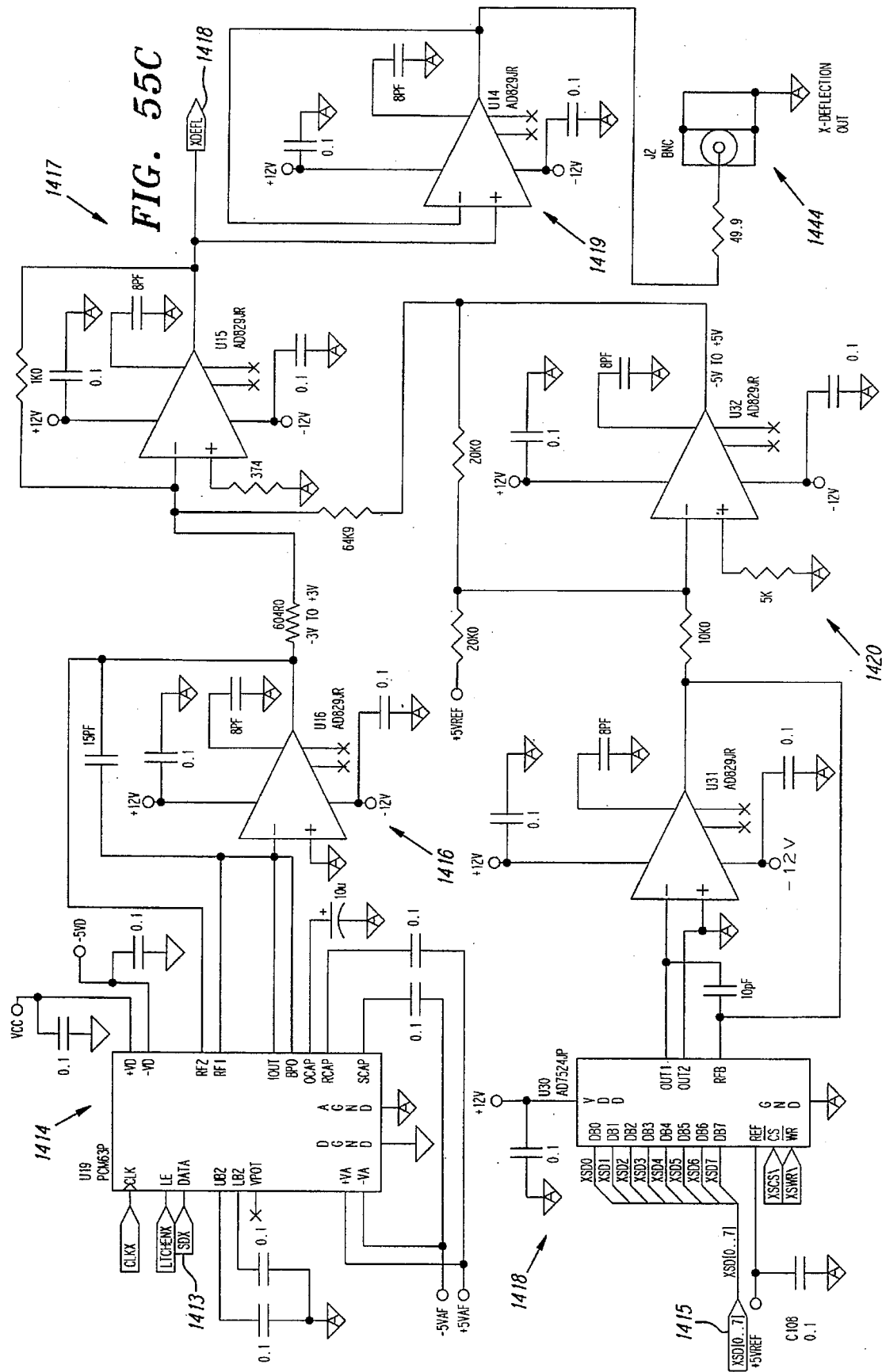
Figure 55D:
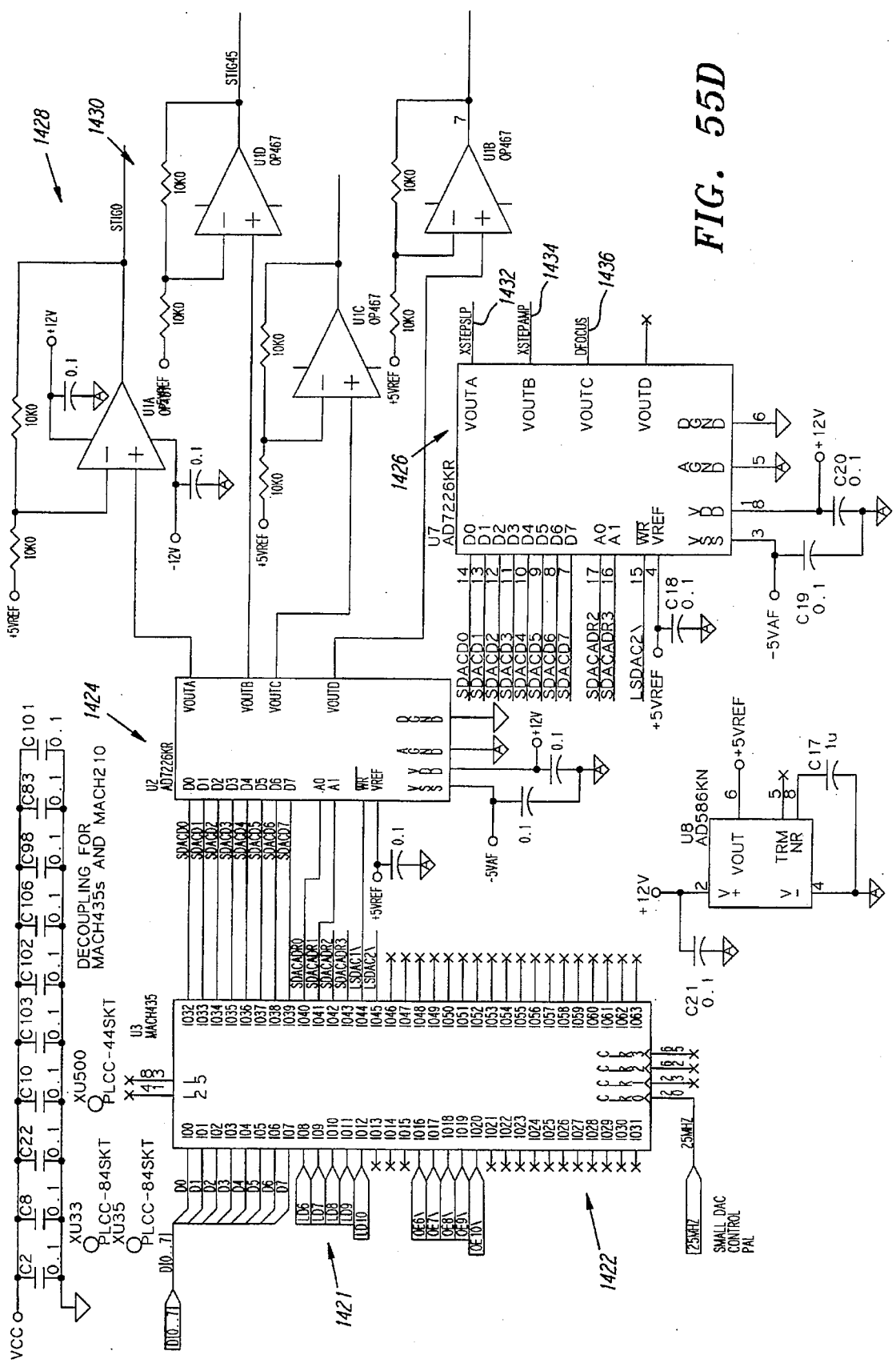
Figure 55E:
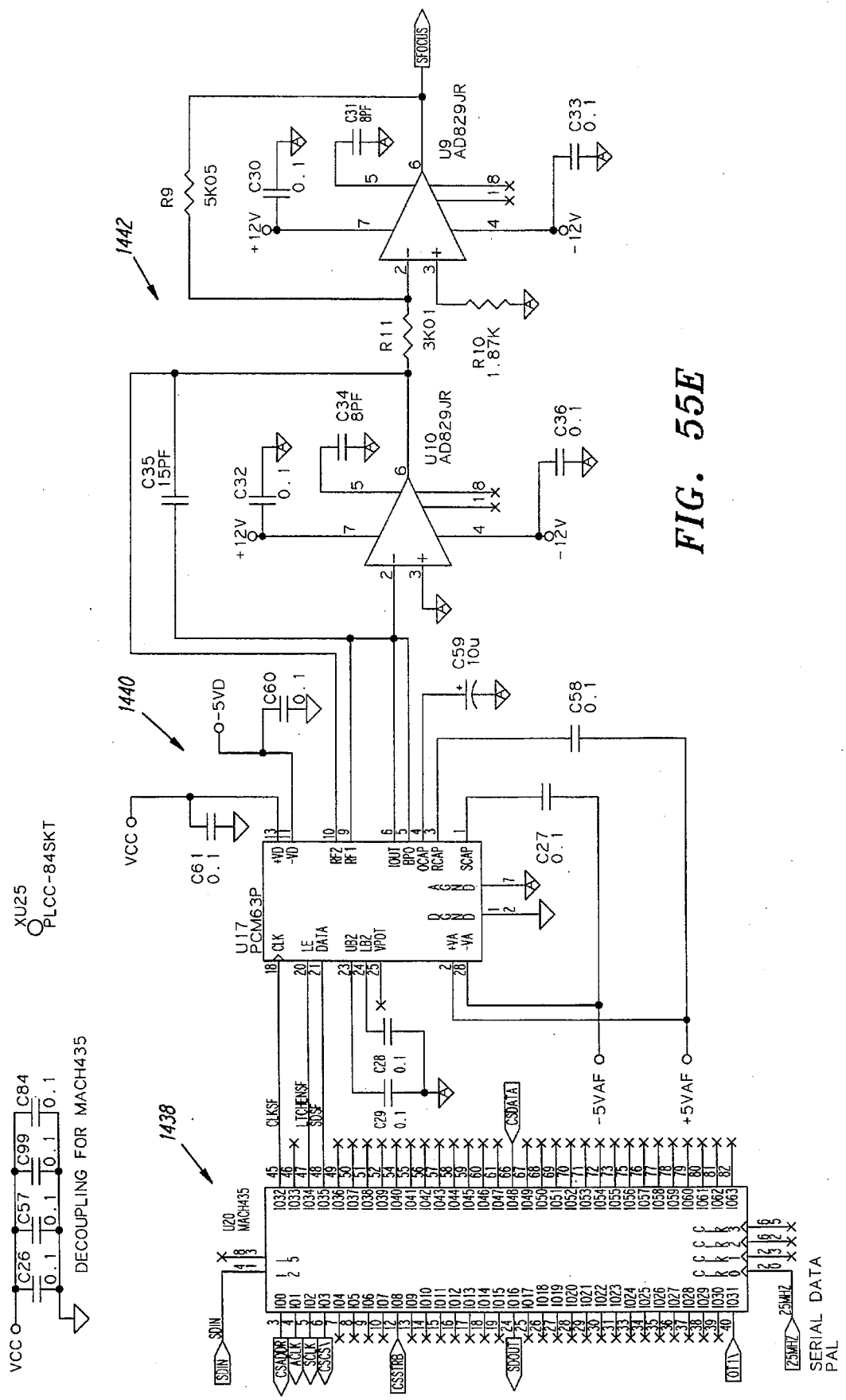

Referring to FIGS. 55B–C, control PAL 1410 preferably outputs control signals, via leads 1411 (LD1 and LD2), to instruct the x-deflection PAL 1412 to sequentially load parallel bits of digital x-deflection coil control data DXDEF from the eight-bit data bus D[0 ... 7]. The x-deflection PAL 1412 essentially manipulates the digital x-deflection coil control data DXDEF to generate a smoothly ramping triangular waveform at the x-deflection driver 778. Approximately every 1.28 usec, the x-deflection PAL 1412 preferably converts the parallel bits of digital x-deflection coil control data DXDEF to serial bits of digital x-deflection coil control data SDX. The serial x-deflection coil control data SDX is coupled, via output line 1413, to a twenty-bit serial DAC 1414 which converts the information to an analog signal that is preferably applied to an intermediate x-deflection amplifier 1416. The preferred software modules for x-deflection PAL 1412 are included in Appendix A.

Approximately every 80 nsec, the x-deflection PAL 1412 mathematically manipulates the sequentially acquired items of digital x-deflection coil control data DXDEF to calculate an eight-bit x-slope value, which is referred to as the x-slope control data XSD. The x-slope control data XSD is transmitted to DAC 1418 for conversion to an analog signal, and its analog output signal is preferably coupled to a series of intermediate x-slope amplifiers 1420. The amplified analog x-slope control signals XSD is preferably summed with the amplified analog x-deflection coil control data SDX to generate a smoothly ramping output waveform, which is amplified by intermediate amplifier 1417 to produce the x-deflection coil control signal XDEFL. The x-deflection coil control signal XDEFL is preferably output, via output line 1418, to a preferred x-deflection driver 778, which is described more fully in connection with the detailed description of FIG. 56. Alternatively, the x-deflection coil control signal XDEFL can be coupled, through an amplifier 1419 and a BNC connector 1444, to a commercially available amplifier, for example a Centronics amplifier, which then drives the current in the x-deflection coil.

Analog y-deflection coil control signals are generated in the same fashion and output to a y-deflection driver 782. However, if a raster scan pattern is employed, then the serial y-deflection coil control data SDY is directly generated by the control PAL 1410, therefore a y-deflection PAL, y-slope control data YSD, and related circuitry are not required.

Control PAL 1410 also outputs control signals, via leads 1421 (LD6, LD7, LD8, LD9, and LD10), to instruct the small DAC control PAL 1422 to sequentially load x-step control data (XCD), dynamic focus coil control data (DFCD), and stigmator control data (SCD) from the data bus D[0 ... 7]. Small DAC control PAL 1422 redistributes the XCD and DFCD control signals to multi-channel DAC 1426 and redistributes SCD control signals to multi-channel DAC 1424. DAC 1424 preferably outputs analog 0° stigmator coil control signals to the 0° stigmator driver 786 through an intermediate 0° amplifier 1428. Analog 45° stigmator coil control signals are similarly output to the 45° stigmator driver through an intermediate 0° amplifier 1430. DAC 1426 preferably outputs analog x-step slope control signals XSTEPSLP to the x-step driver 780 via output line 1432. Similarly, analog x-step amplitude control signals XSTEPAMP are preferably output to the x-step driver 780 via output line 1434 and analog dynamic focus coil control signals DFOCUS are preferably output to the dynamic focus driver 776 via output line 1436. The preferred software modules for small DAC control PAL 1422 are included in Appendix A.

Serial data PAL 1438 preferably receives static focus coil control data SDIN from the I/O controller 762. Serial data PAL 1438 couples control data SDIN to a DAC 1440, which converts this information to analog static focus coil control signals which are sent to the static focus driver 774 through intermediate focus amplifiers 1442. The preferred software modules for serial data PAL 1438 are included in Appendix A.

Figure 56:
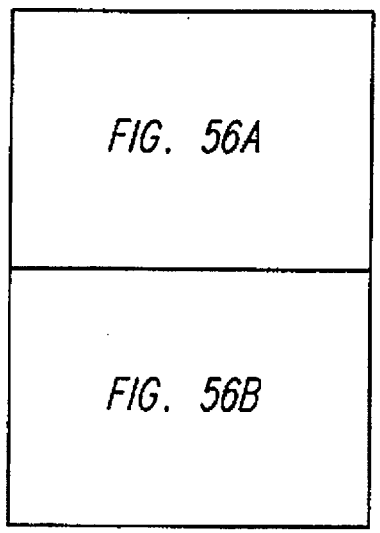
FIGS. 56A–B comprise schematics of the preferred x-deflection driver.
Figure 56A:
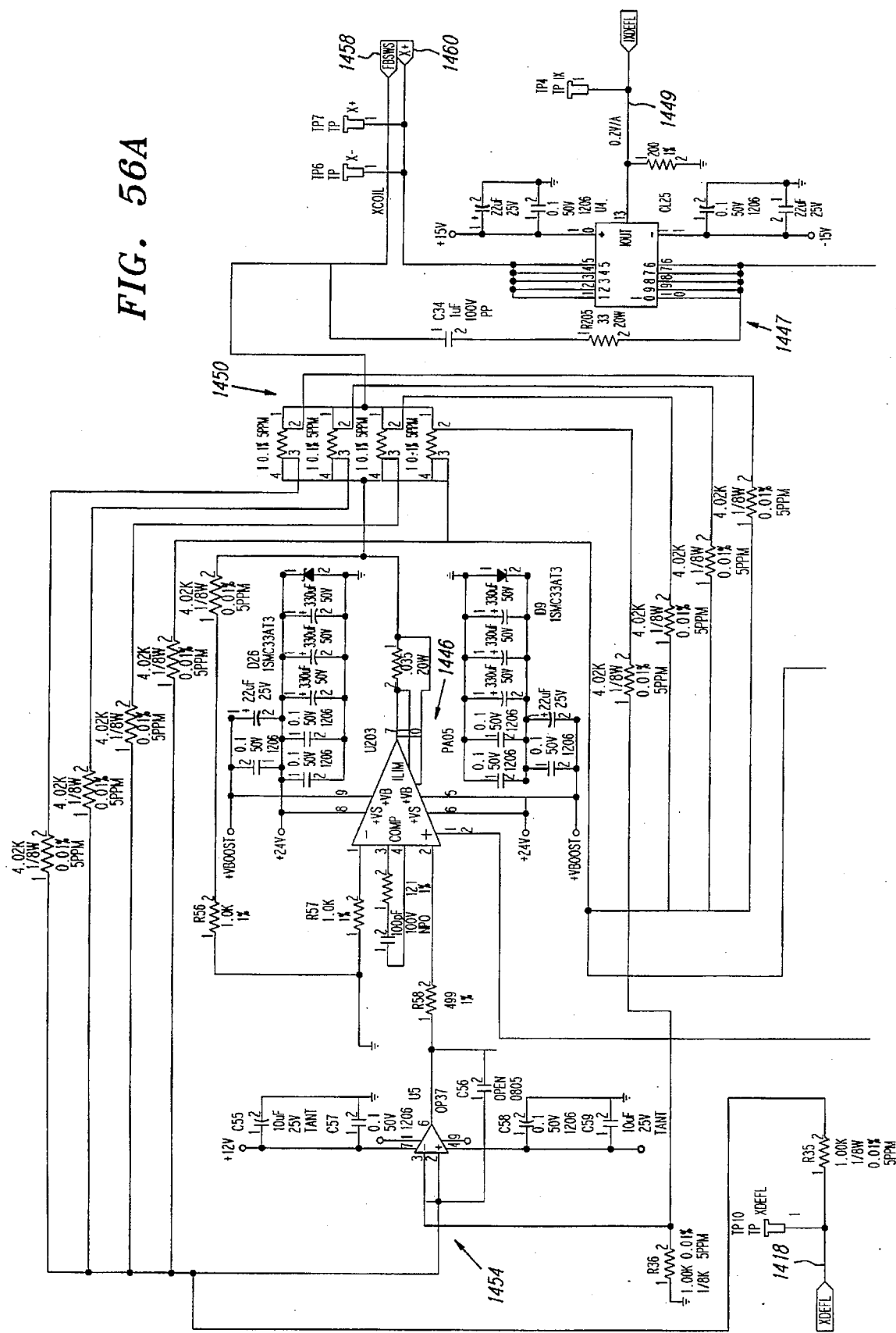
Figure 56B:
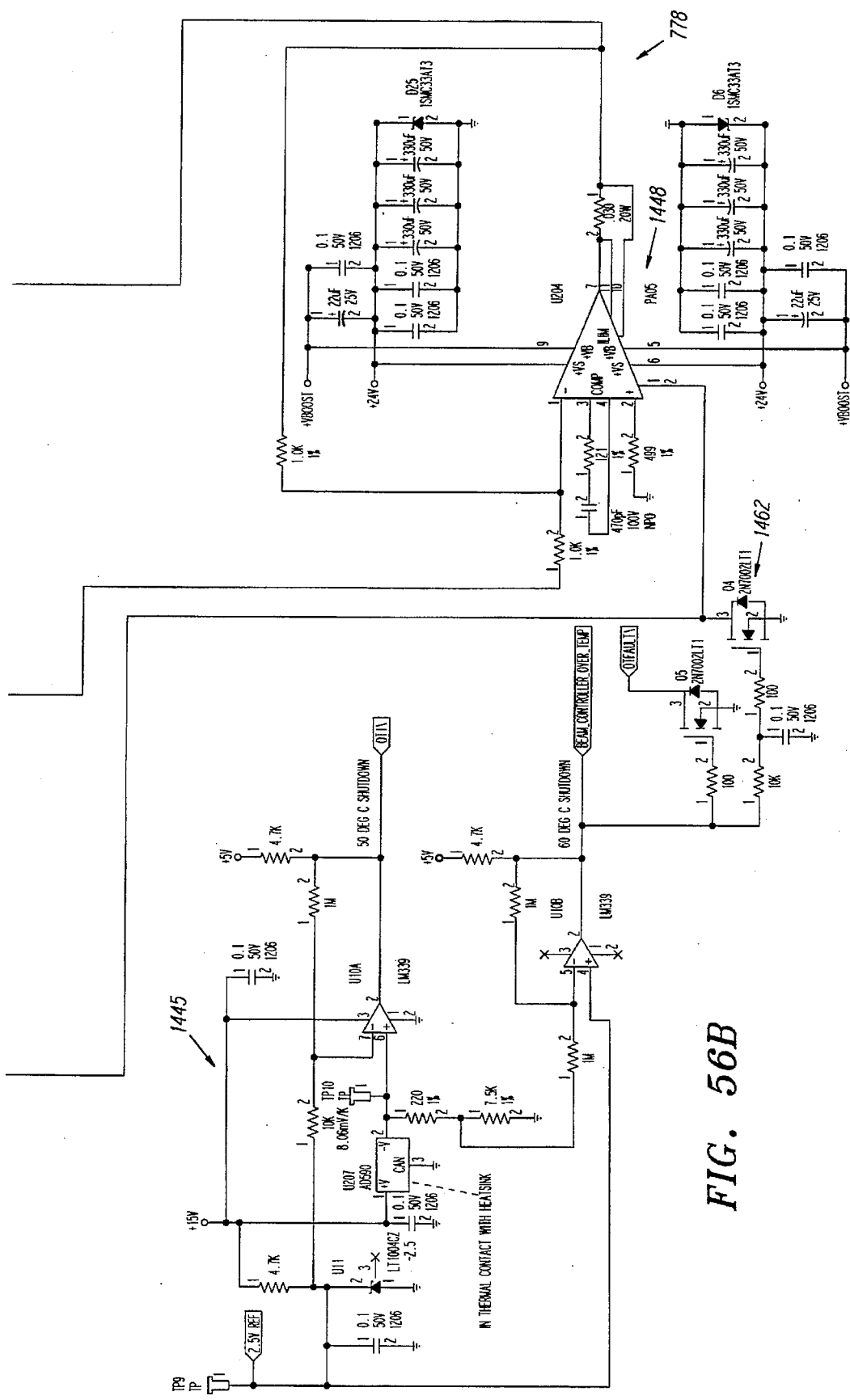

The analog coil control signals from the beam controller interface 794 are preferably transmitted to suitable power amplifier circuits within the coil drivers to drive the current patterns in their corresponding focus or deflection coils. For example, the analog x-deflection coil control signals XDEFL from the beam controller interface 794 are preferably coupled, via input line 1418, to a preferred x-deflection driver 778 (FIG. 56). The XDEFL control signals are applied to a control amplifier 1454, which regulates the activity of power amplifiers 1446 and 1448. The x-deflection driver 778 is preferably a circle bridge circuit in which power amplifiers 1446 and 1448 differentially drive both ends of the x-deflection coil. The output voltages of the power amplifiers 1446 and 1448 are coupled, through current sense resistors 1450 and current sensor 1447, to the x-deflection coil via output lines 1458 and 1460. Resistors 1450 sense the current in the x-deflection coil and preferably feeds the current information back to regulate the control amplifier 1454. The current in the x-deflection coil is also monitored by a current sensor 1447, which transmits the measured Current, via output line 1449, to the current sense monitor 788. Temperature sensor 1445, which measures the temperature at the x-deflection driver 778, employs a temperature switch 1462 to disable the x-deflection driver 778 if a temperature fault condition occurs. The y-deflection driver 782 preferably includes a similar circuit to drive the current in the y-deflection coil.

Figure 57A:
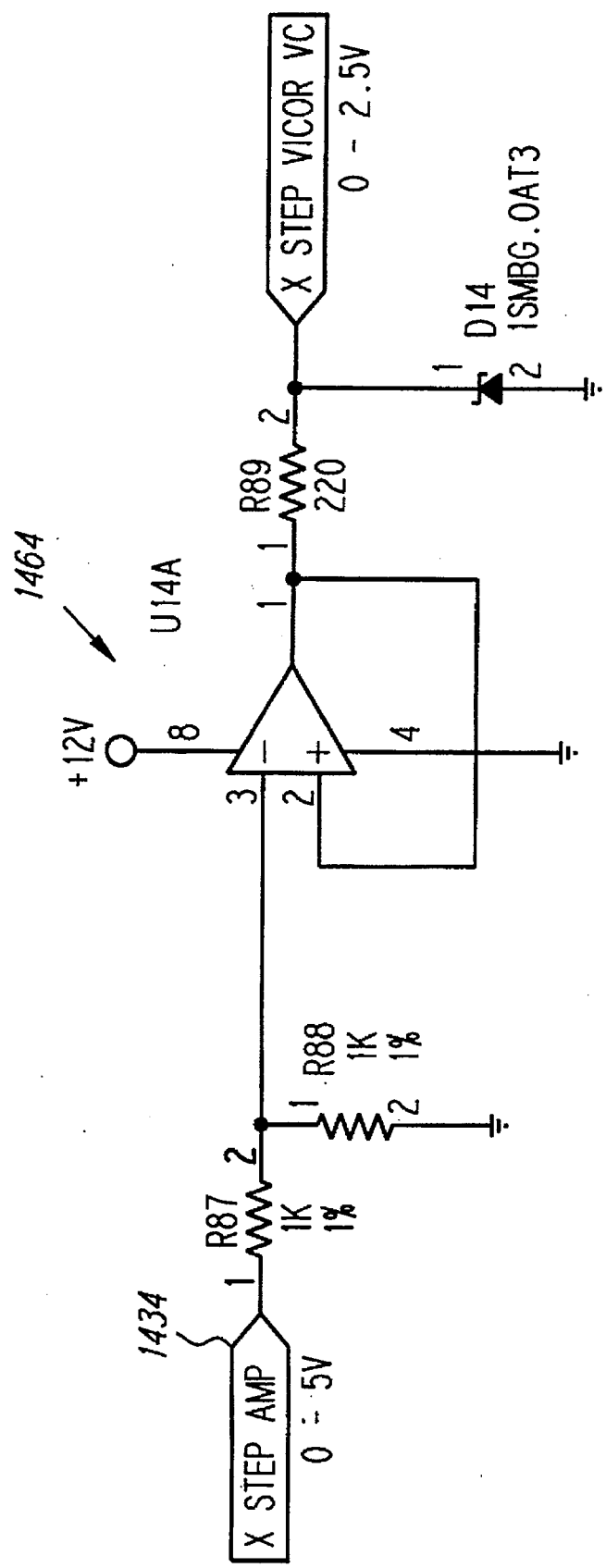
FIGS. 57A–B comprise schematics of the preferred x-step driver.
Figure 57B:
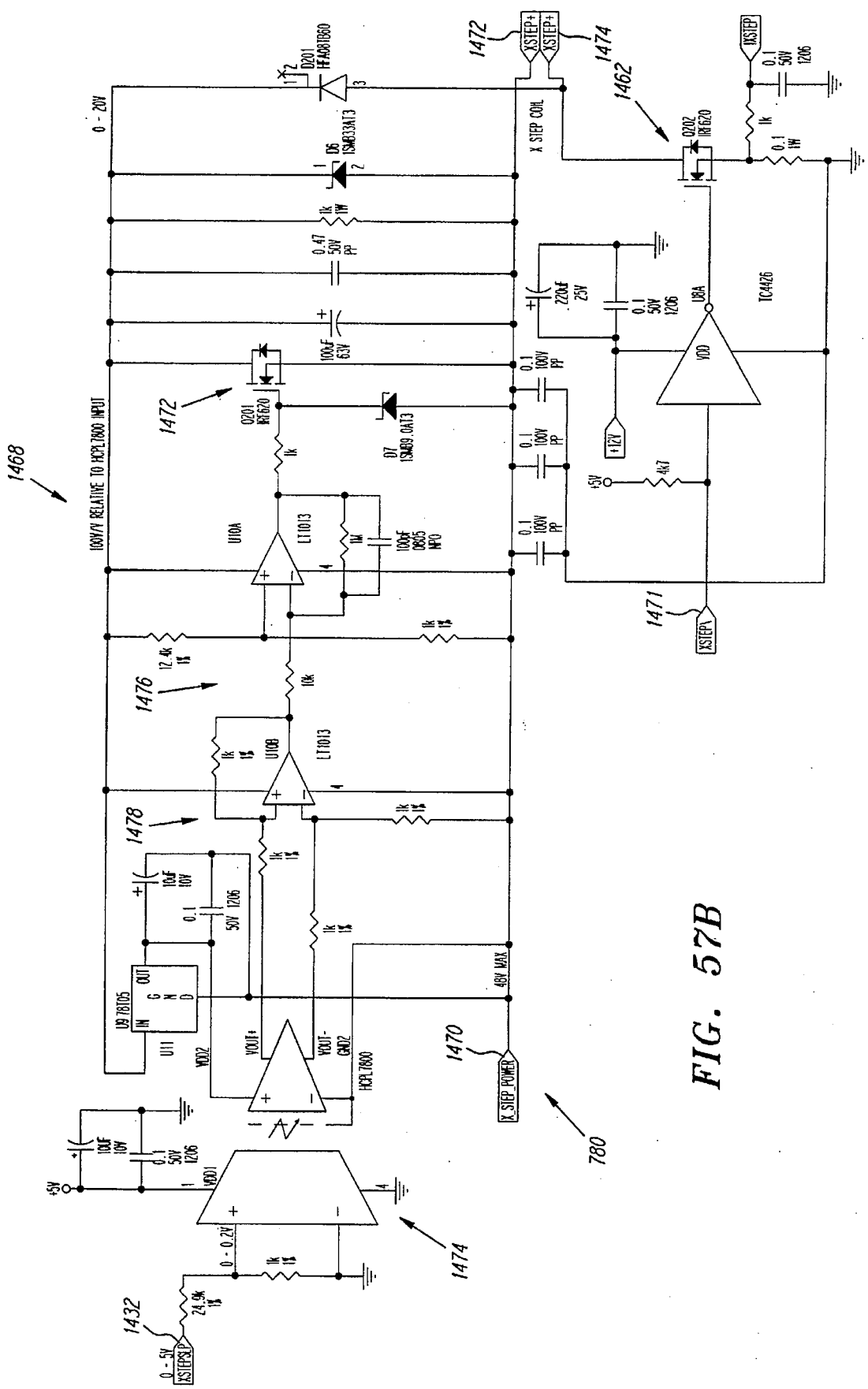

X-step driver 780, which preferably comprises x-step ramp control switch 1462, x-step voltage control circuit 1464, and decay control circuit 1468 (FIGS. 57A–B), is preferably employed to generate a sawtooth current wave form in the x-step coil. The x-step driver 780 is connected across the x-step coil via output leads 1472 and 1474. Referring to FIG. 57A, x-step amplitude control signals XSTEPAMP from the beam controller interface 794 are preferably applied to x-step voltage control circuit 1464 to control the voltage level of a VICOR multi-output switching power supply (not shown), which supplies an input voltage to the x-step driver 780 via input line 1470.

Ramp switch control signals XSTEP\ are preferably applied from the control PAL 1410, via input line 1471, to control the operation of the x-step ramp control switch 1462. When the x-step ramp control switch 1462 is switched on, voltage from the VICOR multi-output power supply is applied to the x-step coil, allowing the current in the x-step coil to ramp up for a specified time period, preferably 1 to 200 nsec. The amplitude of the current pattern is determined by the voltage level of the VICOR multi-output power supply, which is preferably set by the x-step voltage control circuit 1464.

When the x-step ramp control switch 1462 is switched off, decay control circuit 1468 applies a voltage to the x-step coil to control and shape the slope of the current decay in the x-step coil. X-step slope control signals XSTEPSLP are preferably applied to the decay control circuit 1468 via input line 1432. An isolation amplifier 1474 is preferably employed to optically couple the x-step slope control signals XSTEPSLP to the decay control circuit 1468, to avoid potential problems relating to high voltages applied to the circuit by the VICOR power supply. The output of the isolation amplifier 1474 is preferably coupled to an intermediate x-step amplifier 1478. Intermediate x-step amplifier 1478 preferably converts the differential output from isolation amplifier 1474 into a single ended signal, which is coupled to the inverting input of a control amplifier 1476. Control amplifier 1476 manages the voltage across transistor 1472, which functions as a variable load, such that the voltage applied to the x-step coil during the current decay period produces an optimal current decay rate in the x-step coil. If a particular x-ray imaging application requires the use of a y-step coil, then a y-step driver similar to the x-step driver of FIGS. 67A–B is preferably employed.

Catheter Including X-Ray Sensitive Optical-Sensor Location Device

Figure 58:
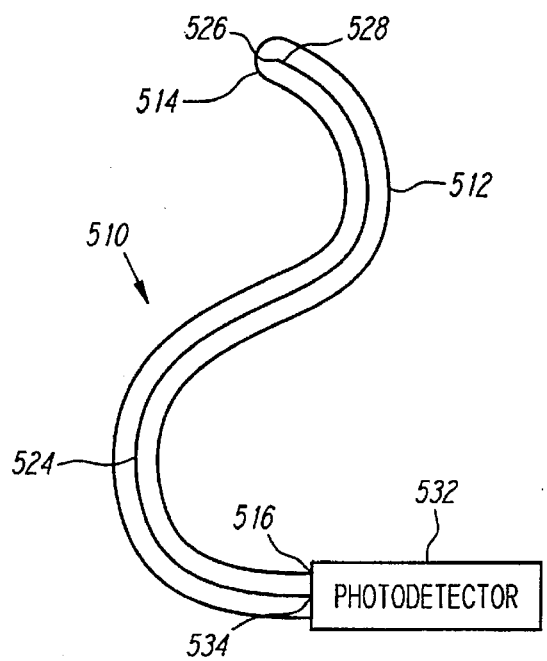
FIG. 58 is a diagram showing a presently preferred embodiment of a catheter including an x-ray sensor locating device.
Figure 59:
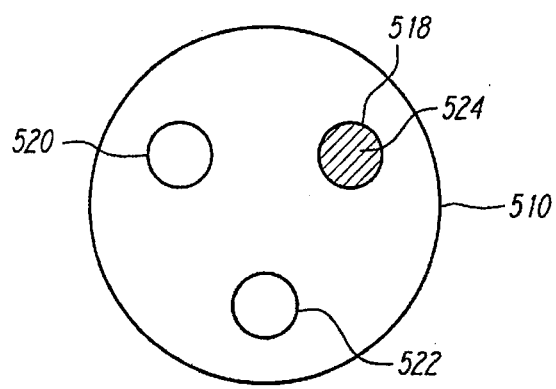
FIG. 59 is a cross-sectional view of the catheter of FIG. 58.
Figure 60:
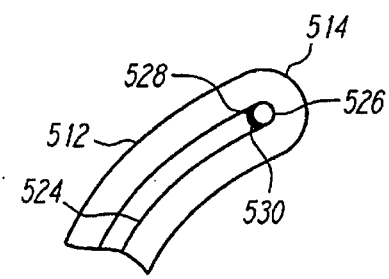
FIG. 60 is a detailed view of the distal end of a preferred embodiment of the catheter of FIG. 58.

Referring to FIGS. 58–60, diagrams are presented of a catheter 510 that is a presently preferred embodiment of this aspect of the invention. As shown in FIG. 58, catheter 510 may be formed from a variety of materials, such as plastic and steel. Catheter 510 comprises an elongated body 512 having a distal end 514 adapted to be inserted into a body cavity, vessel, tract, or the like and a proximal end 516 which remains outside of the patient or object into which the catheter 510 is inserted.

FIG. 59 depicts the cross-sectional view of catheter 510. In FIG. 59, catheter 510 is shown to include a plurality of lumens 518, 520, and 522. While the catheter 510 is shown including three lumens 518, 520, and 522, this embodiment is merely illustrative and the number of lumens provided in any actual catheter fabricated according to the teachings of the present invention and the uses therefore will depend solely on the end use to which catheter 510 will be put. Such a catheter may be steerable to be positioned by manipulation as is known in the art.

Referring again to FIG. 58, an optical fiber 524 is disposed in lumen 518 of catheter 510. For small diameter catheters, such as ones used in cardiac applications, optical fiber 524 preferably has a diameter of approximately 0.010–0.020 inches. Those of ordinary skill in the art will of course recognize that optical fiber 524 may have other diameters without departing from the scope of this aspect of the present invention.

An x-ray marker 526 (also referred to herein as an x-ray mini sensor), is optically coupled to a distal end 528 of the optical fiber 524. Presently preferred is an x-ray marker 526, shaped into a cube with sides of length 0.030 in. (0.076 cm), that is glued with optical cement to a 0.018 in. diameter optical fiber 524. X-ray marker 526 preferably comprises an x-ray sensitive scintillating phosphor or crystal material, such as for example, terbium-doped gadolinium oxysulfate ($Gd_2O_2S_2$:Tb), available from USR Optronix, Inc. of Hackettstown, N.J. The presently preferred material for the x-ray marker 526 is a scintillator crystal material such as: (1) YSO (cerium doped yttrium oxy-orthosilicate, available from Airtron (Litton) of Charlotte, N.C.); (2) LSO (cerium doped lutetium oxy-orthosilicate, available from Schlumberger, Inc.); and (3) BGO (bismuth germanate, available from Rexon Components, Inc. of Beachwood, Ohio). YSO and LSO are advantageous in that they have short decay times and therefore may be used to measure x-ray intensity by pulse counting the incident x-ray photons. Those of ordinary skill in the art will recognize that other materials or devices which are responsive in the x-ray spectrum may also be used in the present invention and are to be considered as x-ray marker materials within the meaning of that phrase as used herein.

FIG. 60 diagrams the distal end of an embodiment of catheter 510 according to this invention. In this embodiment, terbium doped gadolinium oxysulfate phosphor material in a finely ground powder form is preferably both physically mounted and optically coupled to the distal 528 end of optical fiber 524 using an epoxy 530, such as QUICKSTIK, available from GC Electronics of Rockford, Ill. The epoxy 530 is preferably used to adhere the x-ray marker 526 to the optical fiber 524 by placing a small amount of the epoxy 530 at the distal end of optical fiber 524 and then dipping the distal end 528 of optical fiber 524 into a finely divided phosphor powder. Those of ordinary skill in the art will recognize that the epoxy 530 is preferably compatible with the phosphor material and is preferably optically clear at the phosphor emission wavelength. Similar techniques may be employed to affix a scintillating crystal to the distal end 528 of optical fiber 524. In addition, other methods for optically coupling a marker material to an optical fiber, such as employment of a lens, are equivalent and fall within the scope of the present invention.

A photodetector 532 is optically coupled to the proximal end 534 of optical fiber 524. Photodetector 532 may be a photodiode, a photomultiplier tube, a phototransistor, a charge-coupled device, or other device which transduces the light signal generated at x-ray marker 526 due to exposure to an x-ray flux into an electrical signal when the light signal is transmitted down optical fiber 524 to photodetector 532. The magnitude of the electric signal generated by photodetector 532 is related to the magnitude of the intensity of the x-ray flux sensed by x-ray mini sensor 526. In one preferred embodiment of this invention, the proximal end 534 of optical fiber 524 is coupled to the light-sensitive window of an RCA XT2020 photomultiplier tube using a high viscosity clear silicone oil, such as available from Dow Corning Corporation of Midland, Mich.

The electrical signal from photodetector 532 is converted to a digital signal by conventional means such as an A/D converter and then broken down into a series of values representing the instantaneous x-ray flux intensity at x-ray mini sensor 526 corresponding to the various apertures 140 of collimation grid 90—thus as the apertures 140 of collimation grid 90 sequentially emit x-ray pencil beams 50, a value corresponding to the measured x-ray flux intensity at sensor 526 is stored for each aperture in a memory array for use as discussed below.

As will be discussed in further detail below, an electrical signal will be generated by photodetector 532 when the catheter 510 is exposed to x-ray radiation. Catheter 510 of the present invention is therefore highly useful when employed in applications with reverse-geometry scanning-beam x-ray systems, enabling location of the catheter's position with a high degree of accuracy.

Although the catheter 510 of FIGS. 58–60 is shown employing a single optically-coupled x-ray marker 526, catheters having a plurality of such optically coupled x-ray markers may be fabricated according to the principles of the present invention. The number of such markers employed in any actual embodiment of the catheter of the present invention will depend solely on the application for which the particular catheter is designed. Specific illustrative examples are disclosed herein.

This aspect of the present invention may be employed in a wide variety of both steerable and non-steerable catheters for various applications. Without limitation, such catheters and applications will include multi-electrode catheters employed in electrophysiology, and catheters for ablation of cardiac arrhythmia, coronary atherectomy catheters, etc. This aspect of the present invention will also be usefully employed, for example, in angioplasty balloon catheters, and in laparoscopy equipment. Such catheters now employ bands of radio-opaque material such as metal, so that they may be located by x-ray techniques during performance of angioplasty procedures. Those of ordinary skill in the art will doubtless be able to envision other applications for the present invention.

Figure 61A:
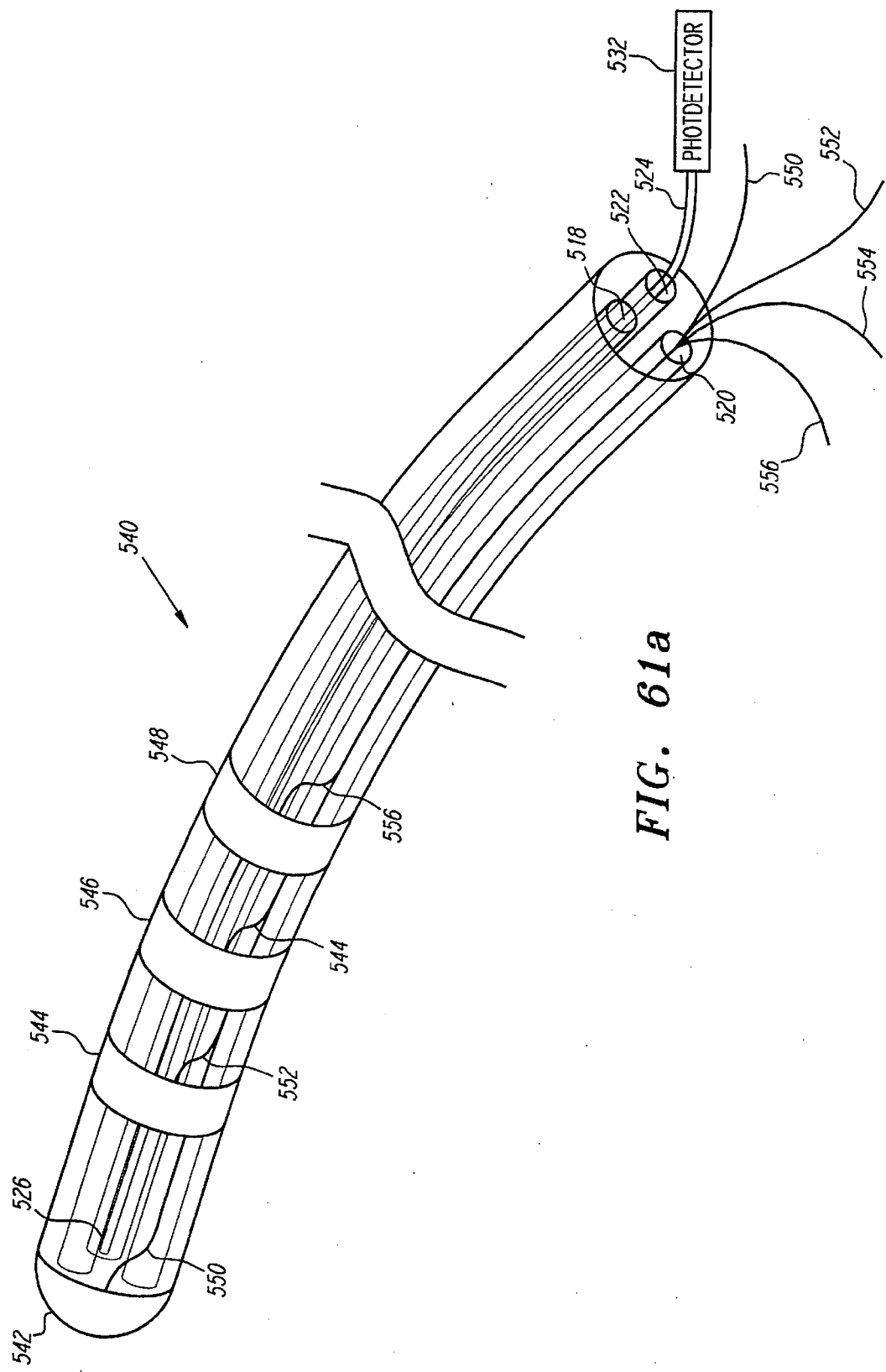
FIG. 61a depicts an electrophysiology catheter that incorporates an embodiment of an x-ray sensor locating device.
Figure 61B:
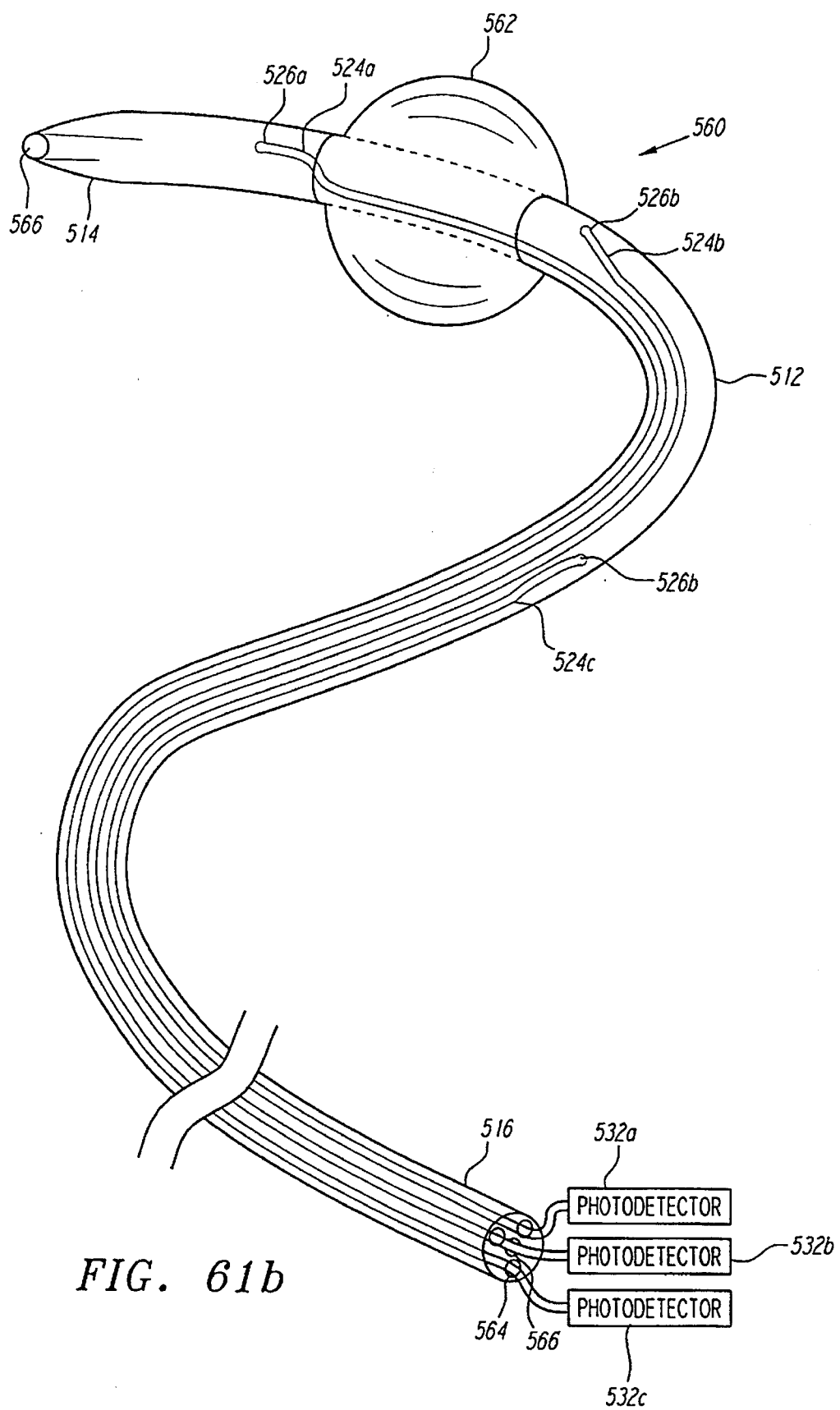
FIG. 61b depicts a balloon angioplasty catheter that incorporates an embodiment of an x-ray sensor locating device.

Referring now to FIGS. 61a–61c, certain exemplary catheters employing the present invention are described. Referring first to FIG. 61a, a multi-electrode electrophysiology catheter 540 for use in measuring intracardiac action potentials incorporates an embodiment of the present invention and is shown diagrammatically. An example of such a commercial electrophysiology catheter of this type is Steerocath Model No. 2037 available from EP Technologies, Inc. of Mountain View, Calif. For convenience, features of the catheter 540 which are the same as features of catheter 510 of FIGS. 58–60 are identified by the same reference numerals. Thus, catheter 540 is shown to include a plurality of lumens 518, 520, and 522. An optical fiber 524 is disposed in lumen 518 of catheter 540. An x-ray marker material 526 is affixed to a distal end 528 of the optical fiber 524.

A plurality of conductive electrodes 542, 544, 546, and 548 are disposed in spaced-apart relationship near the distal end 514 of catheter 540. Electrodes 542, 544, 546, and 548 are individually electrically coupled to conductors 550, 552, 554, and 556, respectively. Conductors 550, 552, 554, and 556 are disposed in lumen 520 and emerge from its orifice at the proximal end 516 of catheter 540 and may be suitably connected to an electrophysiology recording and analysis system as is known in the art. As shown in FIG. 61a, a photodetector 532 is coupled to the proximal end 534 of optical fiber 524.

Referring now to FIG. 61b, a diagram of a balloon angioplasty catheter 560 employing an embodiment of the present invention is presented. For Convenience, features of the angioplasty catheter 560 which are the same as features of catheter 510 of FIGS. 58–60 are identified by the same reference numerals. Thus, angioplasty catheter 560 comprises an elongated body 512 having a distal end 514 adapted to be inserted into a bodily cavity, vessel, tract, or the like and a proximal end 516 available to a person performing a medical procedure.

Angioplasty catheter 560 includes an inflatable balloon 562 disposed near its distal end 514 which is used as is known in the art. Balloon 562 may be inflated from a lumen 564 with which it communicates. Angioplasty catheter 560 preferably includes a central guidewire lumen 566 through which a guidewire is threaded as is known in the art.

Angioplasty catheter 560 according to the present invention has advantages over prior art angioplasty catheters because it incorporates a plurality of x-ray markers as taught by the present invention. The embodiment illustrated in FIG. 61b shows three such x-ray markers 526a, 526b, and 526c, but those of ordinary skill in the art will recognize that an arbitrary number of markers could be employed if needed.

In the particular example of FIG. 61b, x-ray marker 526a is disposed near the distal side of the balloon and x-ray marker 526b is disposed near the proximal side of the balloon. In addition, x-ray marker 526c is disposed further down the body 512 of the catheter towards its proximal end 516. X-ray markers 526a, 526b, and 526c are optically coupled to first ends of optical fibers 524a, 524b, and 524c, respectively. Optical fibers 524a, 524b, and 524c are shown disposed in individual lumens 518a, 518b, and 518c, although those of ordinary skill in the art will recognize that they might all be disposed in a single lumen if design considerations warranted such placement.

Optical fibers 524a, 524b, and 524c are connected at their second ends to photodetectors 532a, 532b, and 532c. The present invention represents a significant advantage over prior art catheters in which x-ray opaque bands are physically attached to selected positions of the catheter. The catheter of the present invention provides the advantage that the positions of the individual x-ray markers (and thus the position of balloon 562) may be uniquely and accurately determined due to their individual coupling to photodetectors 532a, 532b, and 532c. The present invention is easily interfaced to the widely used digital computer video equipment employed with modern x-ray systems so that, when used in conjunction with a scanning x-ray system, the positions of the x-ray markers may be indicated, for example, by blinking cursors, etc., avoiding the ambiguity which is characteristic of interpretation of x-ray displays to locate prior-art catheters.

Referring now to FIG. 61c, a diagram of an atherectomy catheter employing an embodiment of the present invention is presented. For convenience, features of the catheter 580 which are the same as features of catheter 510 of FIGS. 58–60 are identified by the same reference numerals. Thus, atherectomy catheter 580 preferably comprises an elongated body 512 having a distal end 514 adapted to be inserted into a body cavity, vessel, tract, or the like and a proximal end 516 available to a person performing a medical procedure.

A central guidewire lumen 582 runs through the body of atherectomy catheter 580 from distal end 514 to proximal end 516 as is known in the art. A tapered coil spring 584 is typically internally disposed at the distal end 514 of atherectomy catheter 580. A rotating cutting section 586 comprises a cylindrical member axially disposed in the catheter body behind the tapered distal end 514. A cutting blade 588 is slidably mounted in rotating cutting section 586. Rotating cutting section 586 is coupled to a shaft 590 which runs through a lumen 582 and may be coupled to a motor for rotation. These elements and their relationship to one another are well known.

Atherectomy catheter 580 has advantages over known atherectomy catheters because it incorporates a plurality of x-ray markers as taught by the present invention. The embodiment illustrated in FIG. 61c shows three such x-ray markers 526a, 526b, and 526c, but those of ordinary skill in the art will recognize that an arbitrary number of markers could be employed if needed.

In the particular example of the atherectomy catheter of FIG. 61c, x-ray marker 526a is disposed near the distal side of the rotating cutting section 586 and x-ray marker 526b is disposed near the proximal side of the rotating cutting section 586. In addition, x-ray marker 526c is disposed further down the body 512 of the catheter towards its proximal end 516. X-ray markers 526a, 526b, and 526c are optically coupled to first ends of optical fibers 524a, 524b, and 524c, respectively. Optical fibers 524a, 524b, and 524c are shown disposed in individual lumens 518a, 518b, and 518c, although they might all be disposed in a single lumen if design considerations warranted such placement.

Optical fibers 524a, 524b, and 524c are connected at their second ends to photodetectors 532a, 532b, and 532c. The present invention represents a significant advantage over prior art catheters in which x-ray opaque bands are physically attached to selected positions of the catheter. The catheter of the present invention provides the advantage that the positions of the individual x-ray markers (and thus of rotating cutting section 586) may be uniquely and accurately determined due to their individual coupling to photodetectors 532a, 532b, and 532c. As in the embodiment of FIG. 61b, the positions of the x-ray markers in atherectomy catheter 580 of FIG. 61c may be indicated, for example, by blinking cursors, etc., avoiding the ambiguity which is characteristic of interpretation of x-ray displays to locate prior-art catheters.

In the case of the atherectomy catheter, it is important to know which way the opening for the cutting blade is facing. This can be readily determined according to the present invention by partially shielding the x-ray marker material 526, for example, on three sides, leaving only approximately 90° of rotation open to radiation. If more than one marker is shielded and the openings are oriented in different directions, an accurate assessment of catheter rotational orientation may be made.

This aspect of the present invention is illustrated in FIG. 61d, which is a view down the catheter of a plurality of x-ray markers according to the present invention. Although four x-ray markers are depicted in FIG. 61d, other numbers may be employed to affect the resolution with which the rotational position of the catheter may be determined.

Referring now to FIG. 61d, x-ray markers 526a, 526b, 526c, and 526d are disposed in a shielding member 590, which is illustrated in cross section as generally cross shaped. Shielding member 590 is fabricated from a material which will attenuate x-ray radiation. In the typical medical x-ray environment, shield member 590 may comprise, for example, tungsten having a thickness of about 0.010 in. It will be possible to utilize other materials and thicknesses because of the ability to compare the outputs of different photodetectors.

Each of x-ray markers 526a, 526b, 526c, and 526d is separately connected to an optical fiber and a photodetector (not shown). In the configuration shown the rotational position of the catheter can be determined by comparing the outputs of the photodetectors.

Those of ordinary skill in the art will recognize that the FIG. 61d does not indicate whether x-ray markers 526a, 526b, 526c, and 526d are disposed at the same point along the length of the catheter in which they are placed. This does not matter and will be a matter of design choice, subject of course to the inaccuracy which would result from twisting of the catheter if they are disposed at different positions along the length of the catheter.

The particular applications and examples disclosed herein are merely illustrative and those of ordinary skill in the art will be readily able to envision other applications for which the present invention is suited. It is intended that all such applications fall within the scope of the present invention.

Determination of the X and Y Coordinate Location of a Maneuverable Positioner

Figure 62:
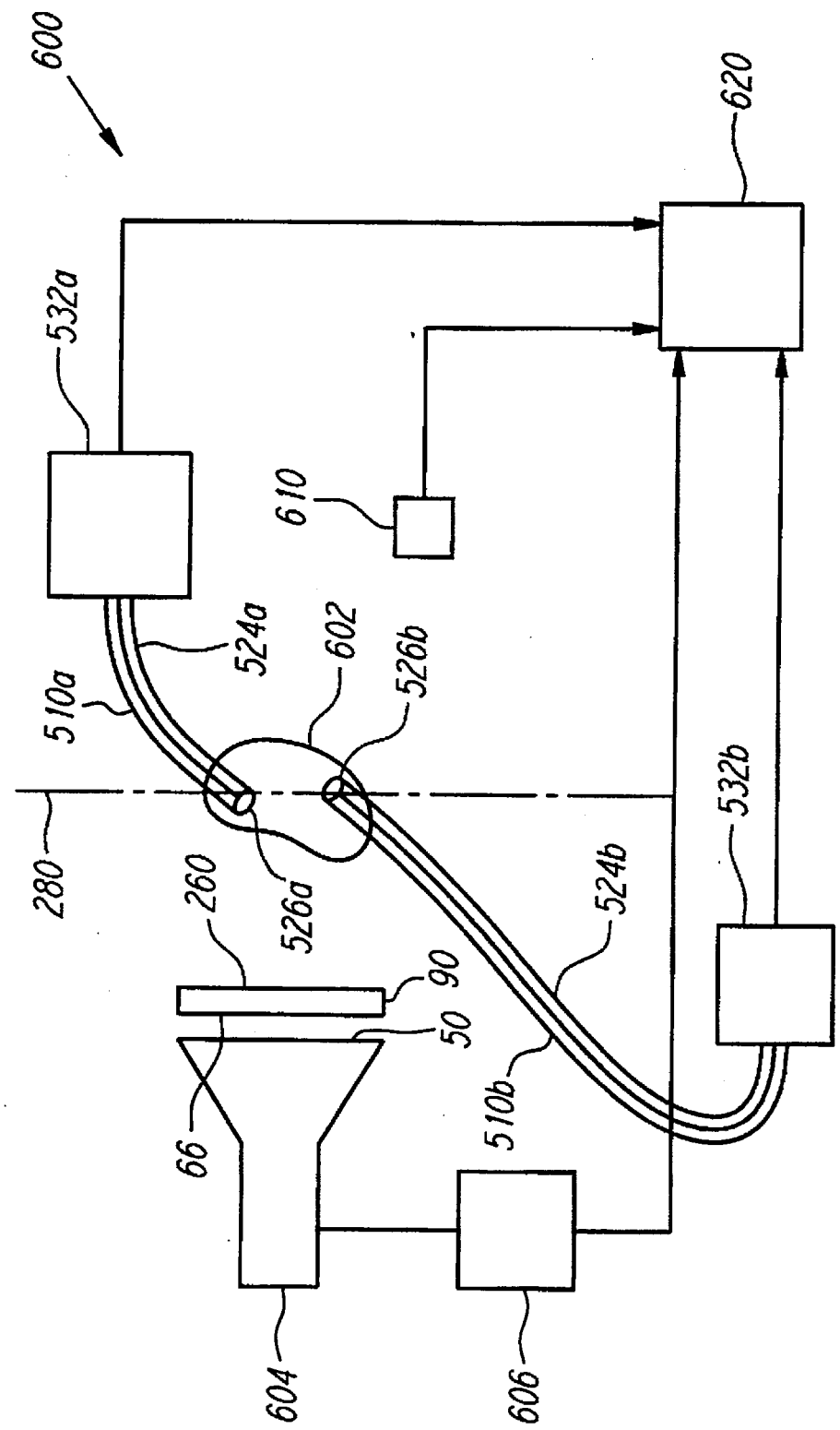
FIG. 62 is a block diagram illustrating an embodiment of a scanning-beam x-ray system interacting with embodiments of the catheter of FIG. 58.

Referring to FIG. 62, this diagram illustrates one technique to locate the precise x and y coordinates of a maneuverable positioner incorporating an x-ray marker or x-ray mini sensor. The x and y coordinates specify the location where the x-ray marker 526 of a maneuverable positioner is located, on a plane 280 which is parallel to the output face 260 of collimation grid 90. In FIG. 62, a preferred reverse-geometry scanning-beam x-ray imaging system 600 is shown employed with catheters 510a and 510b disposed in an object 602. Object 602 could be, for example, a patient into which catheters 510a and 510b have been inserted. Photodetectors 532a and 532b are coupled to the proximal ends of the optical fibers inside of catheters 510a and 510b respectively. Two catheters 510a and 510b, and their associated photodetectors 532a and 532b are shown for purposes of illustration, but those of ordinary skill in the art will recognize that any number of catheters and photodetectors may be employed according to the principles of the present invention.

Collimation grid 90 is preferably positioned between the x-ray tube 604, and an x-ray detector 610 to ensure that x-ray beams from selected positions of the scanned x-ray tube 604 are directed to the x-ray detector 610. As the x-ray beams travel their various paths from the collimation grid 90 to the x-ray detector 610, some of the emissions are intercepted by and irradiate the x-ray sensors 526a and 526b disposed on the distal ends of optical fibers 524a and 524b in catheters 510a and 510b, respectively. The x-ray markers respond by emitting light, which is directed down the optical fibers 524a and 524b to photodetectors 532a and 532b, which convert the light to electrical signals, which are further conditioned and amplified before being transmitted to a control unit 620.

Control unit 620 is supplied with the x and y addresses from the scan controller 606 and with the output signals from photodetectors 532a and 532b. Control unit 620 correlates the output signals from photodetectors 532a and 532b with the scan address information from scan controller 606. This information is processed to determine the positions of the x-ray sensor in catheters 510a and 510b, and hence is an accurate indicator of the positions of the ends of the catheters themselves.

Figure 63:
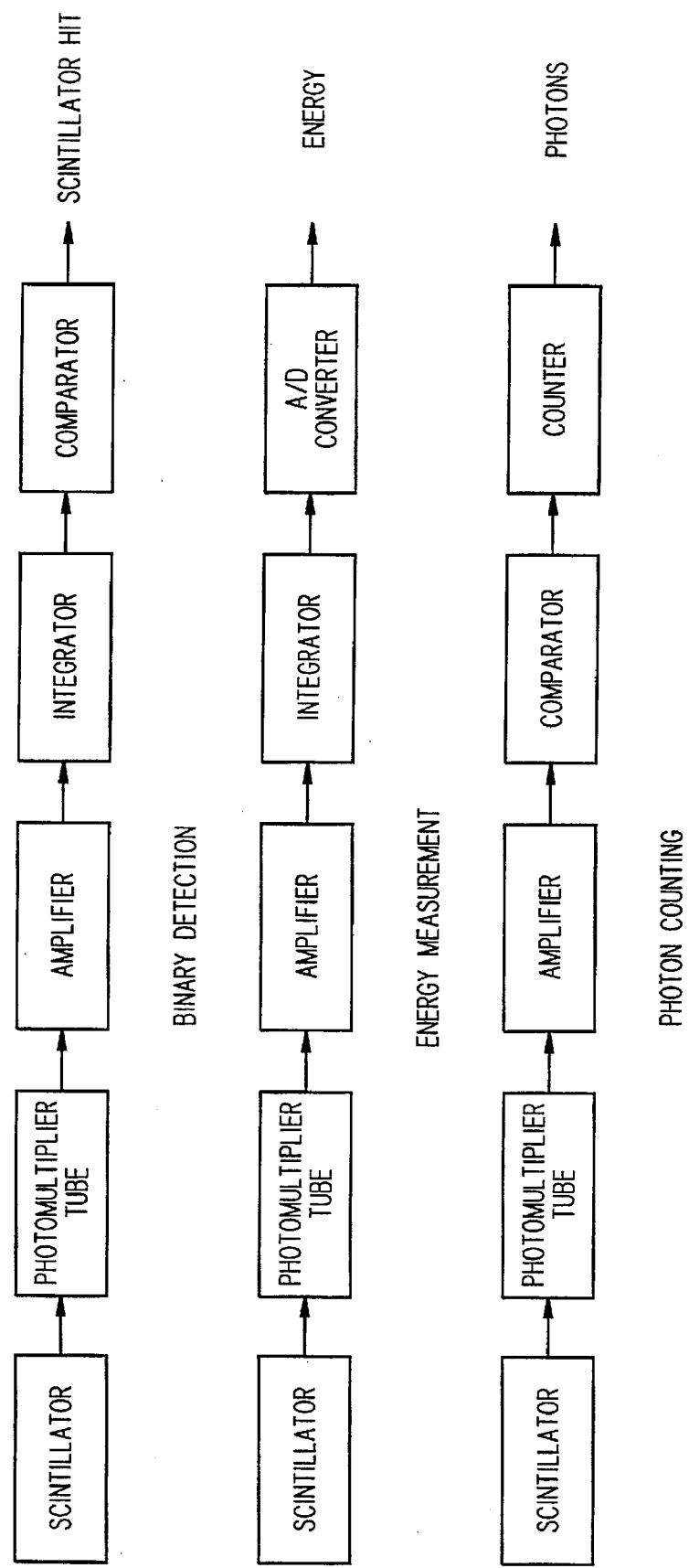
FIG. 63 is a block diagram of the preferred x-ray detection methods for catheter location.

FIG. 63 diagrams three preferred x-ray detection methods for catheter location. For the binary detection method, the control unit 620 employs an integrator and a comparator to process the amplified output signals from the photodetectors 532a and 532b, to determine if the x-ray sensors 526a and 526b were illuminated by x-rays for each x and y scan address.

Figure 64:
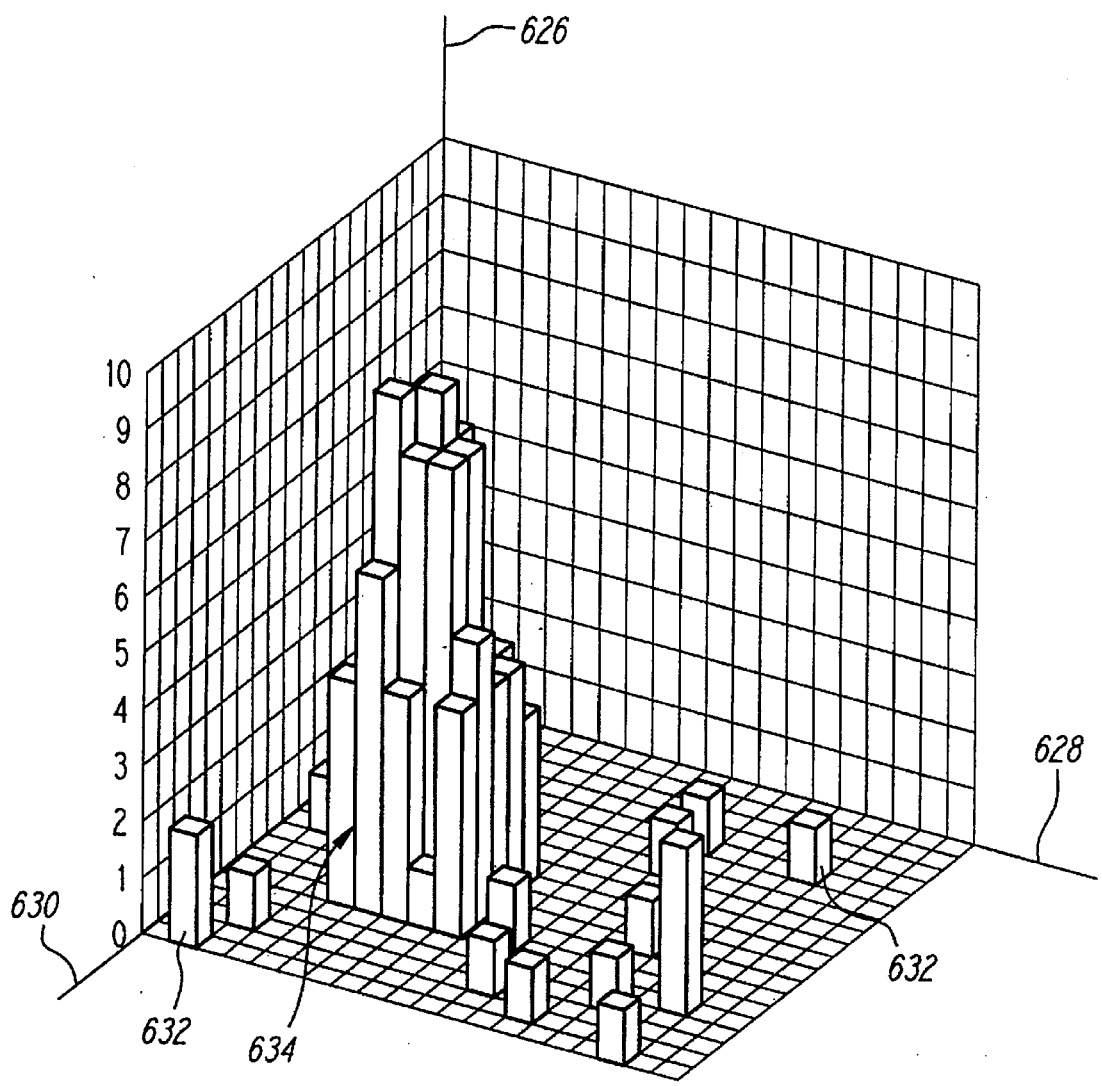
FIG. 64 graphically depicts a theoretical data set from the x-ray sensor in the maneuverable positioner according to a preferred embodiment of the present invention.

The energy measurement method employs a integrator and an analog-to-digital converter to measure the x-ray energy levels received at the x-ray sensors 526a and 526b for each x and y scan address. In this method, the x-ray intensity values at x-ray sensors 526a and 526b of catheters 510a and 510b respectively, are measured for each x-ray beam that is emitted at the target. Since each aperture of collimation grid 90 may be scanned once per x-ray tube scan cycle (this need not be the case and any predetermined group of apertures could be used as long as they reasonably cover the field), the measured x-ray intensity values from the x-ray detector 610 may be stored in a memory array associated with a computer processor. FIG. 64 shows the sample data which may be accumulated within such a memory array during one scan cycle of the x-ray tube for a single x-ray marker. The vertical axis 626 of FIG. 64 represents x-ray flux intensity as measured by x-ray marker 526 and the horizontal axes 628 and 630 represent the X, Y coordinates of the position respectively, of collimator aperture 140 which was being illuminated when the intensity data was captured.

As is shown, there may be spurious intensity readings scattered throughout the array. These are marked with the numeral 632. The spurious readings 632 are most likely the result of scattered x-rays striking the x-ray mini sensor 526 and not of primary x-rays emanating directly from collimation grid 90. The spurious readings 632 are preferably filtered out by well-known techniques leaving the main body of the data which is depicted here as a large tall structure 634. This structure 634 represents mostly x-rays directly from apertures of collimation grid 90 which were measured by x-ray marker 526. The shape and width of this structure will vary depending upon the distance Z of x-ray mini sensor 526 from target 50. It is also possible to determine Z from this information alone, as detailed below. The X and Y coordinates of the position of structure 634 will vary within the data array depending upon the X and Y coordinates of the position of x-ray marker 526 in space. The actual X and Y coordinates of the position of x-ray marker 526 can be determined by analyzing this data in a conventional manner to identify the collimation grid aperture which lies at its geometric center or centroid. Then, given the distance Z determined below, the x-ray marker 526 lies on a plane a distance Z from target 50 and on a line from target 50 to x-ray detector 610 which passes through the identified aperture. This defines a precise position in space which can be easily calculated.

The final method is the photon counting method, which employs a comparator and counter to determine the number of photons detected at the x-ray sensors 526a and 526b for each x and y scan address. For this method, the x-ray sensors 526a and 526b are preferably formed of a scintillator material with a fast response time, e.g., YSO and LSO, to provide a signal train which can be used to count x-ray photons impinging upon the x-ray sensor. The amplified output signals from the photodetectors 532a and 532b are fed to a comparator, which outputs a signal pulse when the input signal rises above a threshold corresponding to individual x-rays striking the x-ray mini sensor 526. Data from the photon counting method is preferably processed in the same way as for the energy measurement method above.

Determination of the Z Coordinate of a Maneuverable Positioner

The presently preferred method to determine the Z-axis coordinate (or height) of a maneuverable positioner which incorporates an x-ray marker is to count the number of x-ray pencil beams that strike the x-ray marker per image frame. The Z coordinate or height value of a given position is normally a distance from target 50 to a plane 280 parallel to output face—260 of collimator grid 90 in which sensor 526a is located, although it can obviously be linearly translated to be a distance from any reference point to x-ray marker 526a. To illustrate the presently preferred method, references will be made to the catheter 510a and scanning-beam x-ray system 600 as diagrammed in FIG. 62.

Figure 65:
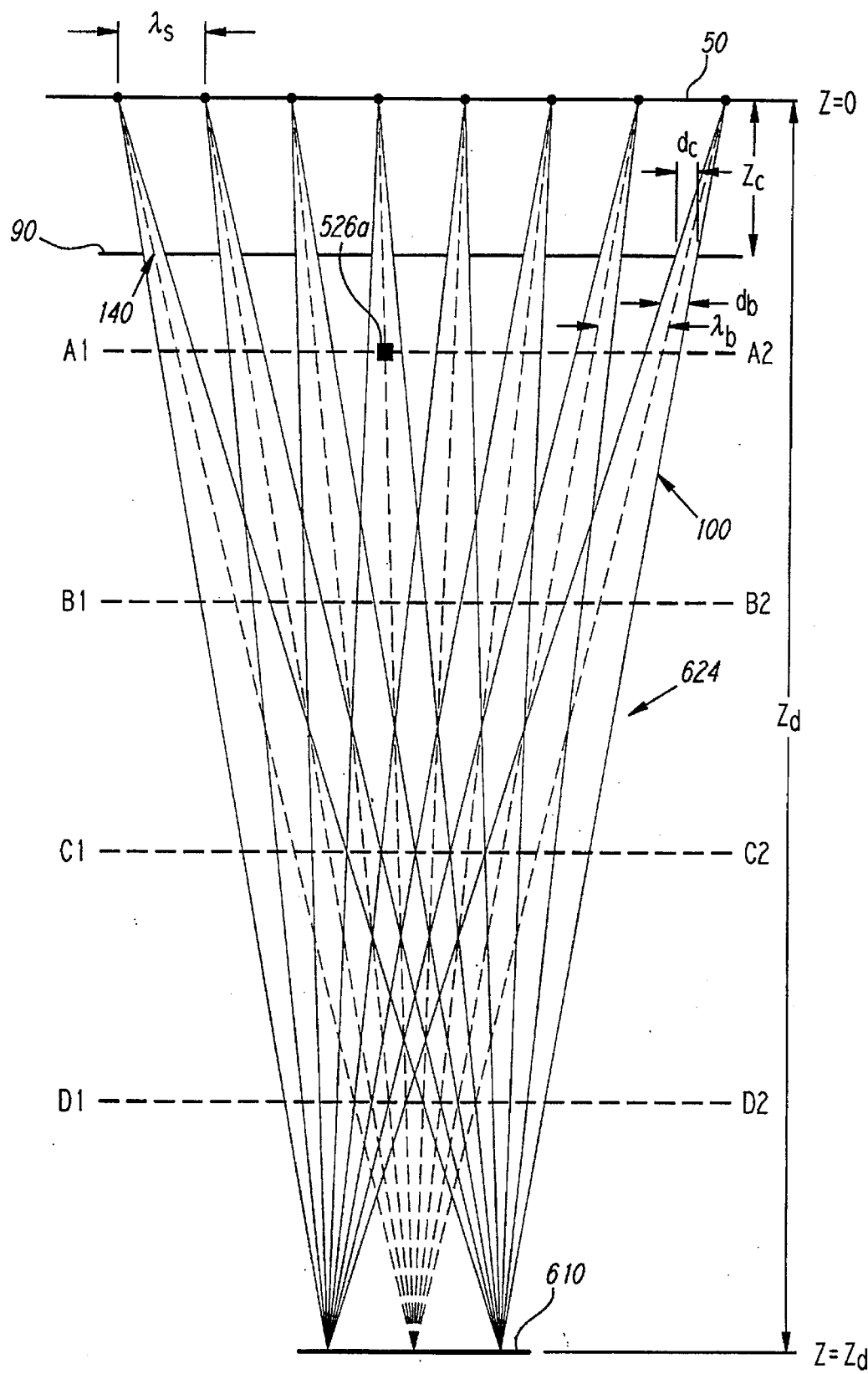
FIG. 65 depicts x-ray beams emanating from an x-ray tube target through a collimation grid to a detector and a maneuverable positioner with an x-ray sensor in a scanning-beam x-ray imaging system.

As target 50 is scanned by an electron beam 40, x-rays are emitted in virtually all directions at the surface of target 50. Referring to FIG. 65, collimation grid 90 is preferably fabricated as discussed above of a relatively x-ray opaque material and has a plurality of apertures 140 disposed therein which provide paths for the x-rays from collimation grid input face 66 to collimation grid output face 260 along which some of these x-rays may travel. X-rays which emanate through apertures 140 of collimation grid 90 preferably form into x-ray pencil beams 100.

Figure 65A:
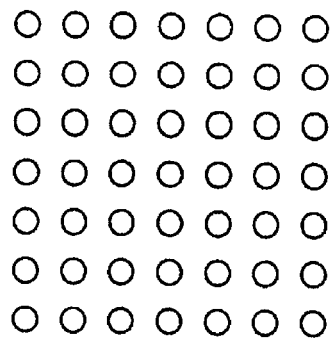
FIGS. 65A, 65B, 65C and 65D are representative of the overlap of x-rays detected by individual detectors of a multi-detector array at locations A1-A2, B1-B2, C1-C2 and D1-D2 of FIG. 65, respectively.
Figure 65B:
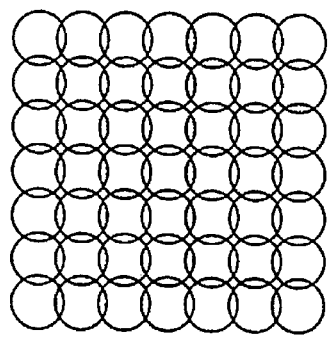
Figure 65C:
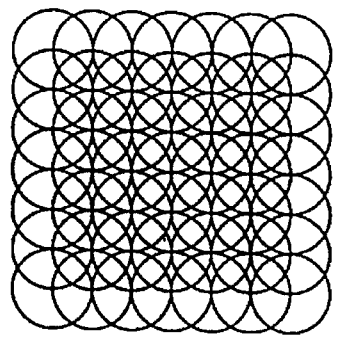
Figure 65D:
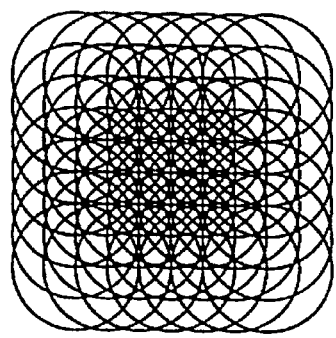

As shown in FIG. 65, these individual x-ray pencil beams 100 diverge slightly into a cone shape 624 as they proceed toward x-ray detector 610. It should be remembered that only one x-ray pencil beam 100 will be generated at any one time. FIG. 65, for purposes of illustration, only depicts 8 x-ray pencil beams 100. At plane A1–A2, which cuts through the x-ray pencil beams 100 parallel to collimation grid output face 260, the x-ray beams have not diverged enough to create beam overlaps. Thus a small x-ray marker 526a located within plane A1–A2 will "see" only a single beam at a time. FIG. 65A depicts the x-ray pencil beam 100 cross-sectional pattern at plane A1–A2 for a 7-by-7 array of beams. Moving away from collimation grid 90 is plane B1–B2 which is parallel to plane A1–A2. FIG. 65B similarly shows the x-ray pencil beam 100 cross-sectional pattern at plane B1–B2. In plane B1–B2, the x-ray pencil beams 100 have diverged enough to create some overlap among the x-ray pencil beams 100. Thus a small x-ray marker 526a located at plane B1–B2 may "see" more than a single beam. The diagrams of FIGS. 65C and 65D of planes C1–C2 and D1–D2 respectively show what happens as a small x-ray sensor 526 approaches x-ray detector 610—it "sees" more and more overlapping x-ray pencil beams 100 the closer it gets to the x-ray detector 610. At the surface of x-ray detector 610 it will see all of the x-ray pencil beams 100 emanating from collimation grid output face 260.

As discussed above, the pencil beams of x-rays 100 are not all generated simultaneously. Because the x-ray tube is a scanning x-ray tube—much like the cathode ray tube used in television sets and computer monitors—at most one aperture is "illuminated" at any given instant by electron beam 40 and, as a result, generates x-rays which emanate from the aperture 140 corresponding to that location on target 50 at that instant. Thus, to an x-ray marker 526 within the cone 624 of x-rays formed between collimation grid output face 260 and x-ray detector 610, a series of x-ray pulses will be seen during each cycle of the x-ray tube (a "cycle" of the x-ray tube corresponds to a complete scan and typically occurs, in a preferred embodiment of the present invention, 15–30 times per second depending on how the system is adjusted by the user). This series of pulses corresponds to the x-ray pencil beams 100 which are seen by the x-ray sensor 526. Accordingly, an x-ray marker 526 located close to the output face 260 of collimation grid 90 will measure a relatively low number of pulses per x-ray tube cycle while the same x-ray marker, if located close to x-ray detector 610 will measure a much higher number of pulses per x-ray cycle. It is this property that permits the measurement of the Z coordinate.

A method for determining the Z coordinate based upon the number of pulses per x-ray tube cycle is derived mathematically as follows:

It is assumed that the beam diameter $d_b$ is 0 at target 50 and $d_c$ at the collimation grid output face 260. For any distance Z from target 50:

$$d_b = d_c \left[ \frac{Z}{Z_c} \right] \quad \text{EQ. 9}$$

The spacing between the x-ray pencil beams 100 $\lambda_b$ varies linearly with $\lambda_s$ at target 50 to 0 at the x-ray detector 610. For any distance Z from target 50:

$$\lambda_b = \lambda_s \left[ 1 - \frac{Z}{Z_d} \right] \quad \text{EQ. 10}$$

A square unit of area within the cone-shaped x-ray field 624 generated by the x-ray system has a number of beam centers passing through it of:

$$\left[ \frac{1}{\lambda_b} \right]^2 \quad \text{EQ. 11}$$

The total area of these beams is:

$$\left[ \frac{1}{\lambda_b} \right]^2 \frac{\pi}{4} d_b^2 \quad \text{EQ. 4}$$

if there is no overlap. Since the beams fit into a square of unit area, the overlap is:

$$\left[ \frac{1}{\lambda_b} \right]^2 \frac{\pi}{4} d_b^2 = \frac{\pi}{4} \left[ \frac{d_b}{\lambda_b} \right]^2 \quad \text{EQ. 12}$$

-continued $$= \frac{\pi}{4} \left[ \frac{d_c \frac{Z}{Z_c}}{\lambda_s \left[ 1 - \frac{Z}{Z_d} \right]} \right]^2 \quad \text{EQ. 14}$$

$$= \frac{\pi}{4} \frac{d_c^2}{\lambda_s^2} \frac{1}{\left[ \frac{Z_c}{Z} - \frac{Z_c}{Z_d} \right]^2} \quad \text{EQ. 15}$$

Assuming that $\lambda_s$=0.0203 in (0.052 cm), $d_c$=0.015 in (0.0380 cm), $Z_c$=1.0 in (2.54 cm) and $Z_d$=37.2 in (94.5 cm), then the overlap at a given distance Z is set forth in the following TABLE III:

TABLE III

| DISTANCE (in) | (CM) | OVERLAP |
|---|---|---|
| 1 | 2.54 | 0 |
| 2 | 5.08 | 2 |
| 3 | 7.62 | 5 |
| 4 | 10.16 | 9 |
| 5 | 12.70 | 15 |
| 6 | 15.24 | 23 |
| 7 | 17.78 | 33 |
| 8 | 20.32 | 46 |
| 9 | 22.86 | 62 |
| 10 | 25.40 | 83 |
| 11 | 27.94 | 108 |
| 12 | 30.48 | 139 |
| 13 | 33.02 | 176 |
| 14 | 35.56 | 223 |
| 15 | 38.10 | 279 |
| 16 | 40.64 | 348 |
| 17 | 43.18 | 433 |
| 18 | 45.72 | 537 |
| 19 | 48.26 | 666 |
| 20 | 50.80 | 827 |
| 21 | 53.34 | 1027 |
| 22 | 55.88 | 1281 |
| 23 | 42 | 1604 |
| 24 | 60.96 | 2021 |
| 25 | 63.50 | 2567 |
| 26 | 66.04 | 3295 |
| 27 | 8.58 | 4284 |
| 28 | 71.12 | 5663 |
| 29 | 73.66 | 7647 |
| 30 | 76.20 | 10614 |

Thus, for example an x-ray sensor 526a in catheter 510a will measure 62 pulses per x-ray tube scan cycle at a distance of 9 in (22.86 cm) from target 50.

Another preferred method for determining the information in Table III is to measure the actual number of pulses detected by the marker 526a at predetermined locations. One can construct a look-up table which can be consulted to display the Z coordinate as a function of the number of pulses detected by the marker 526a. Where possible, this method can also be used within a living patient or other object where it is possible to determine a first absolute Z coordinate and a second absolute Z coordinate within the x-ray cone 624 by another means, such as by direct measurement, then Z coordinates within the object or patient can be determined by interpolation.

Another technique to measure the Z-axis or distance of the marker 526a in a catheter 510 is based upon the measurement of the x-ray intensity at the marker 526a. This technique is related to the intensity measurement technique to determine the x and y coordinates discussed above. As mentioned above, when the collimator grid apertures 140 are illuminated by the x-ray beam, the x-ray mini sensor 638 from catheter 510 will receive the greatest x-ray intensity from the aperture whose axis it is closest to. This not only gives X and Y location, but also gives Z location in the following way. Referring to FIG. 64, the girth of structure 634 is directly related to the Z location of the marker 526. If the marker 526 is far from the source, the girth will be large; if close, it will be small. The preferred place to measure the girth is akin to the full width at half maximum, i.e., measure the girth at one half the height of the structure 634. It can also be measured at other points and will give like results. Most reliable is believed to be the range from approximately ¼ the height to ¾ the height.

Figure 66:
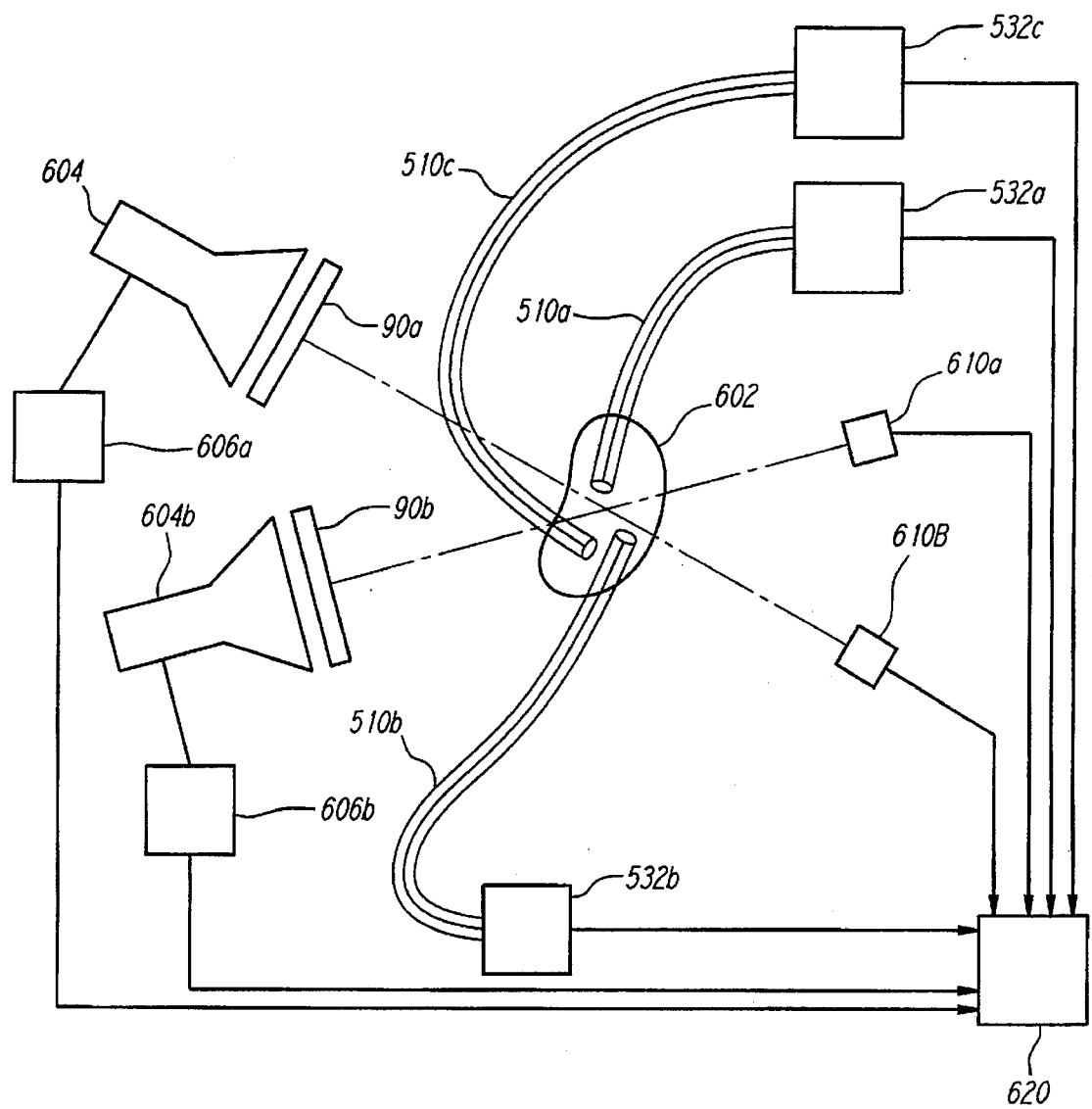
FIG. 66 is a block diagram illustrating an application of catheters incorporating x-ray sensors with two scanning-beam x-ray systems.

Referring now to FIG. 66, this diagram depicts an alternate method to determine the location of a catheter in three dimensions. Two x-ray tubes 604a and 604b, employing independent scan controllers 106a and 106b and collimation grids 90a and 90b, may be used in combination with catheters 510a, 510b, and 510c, photodetectors 532a, 532b, and 532c, and control unit 620 to accurately locate the positions of the catheters 510a, 510b, and 510c in two dimensions with respect to each of the two sources. Triangulation can be used to Combine the two 2-dimensional measurements into a single 3-dimensional position.

An alternate method to determine the Z coordinate of a catheter is based upon photon counting, i.e., by using an x-ray mini sensor 526 having a fast response time, e.g., YSO and LSO, to provide a signal train which can be used to count x-ray photons impinging upon the x-ray sensor. Since photon counting is just another x-ray intensity measurement method, it can be employed with any of the foregoing methods to determine the Z coordinate of a catheter.

Display of X, Y and Z Coordinates for Maneuverable Positioner

Given the X, Y and Z coordinates of the position of x-ray sensor 526 as calculated above, a number of useful things can be done with that data. One preferred use is to draw a cursor on the monitor screen which is displaying the x-ray image of the object or patient. This can enhance and emphasize the display of the location of x-ray sensor 526 (often located at the tip of a maneuverable positioner being positioned within the body or object). Similarly, "waypoints" which are defined by the X, Y and Z coordinates of positions where the sensor has been or where it is going may be displayed as computer-generated icons on the monitor screen to guide the user in positioning the x-ray sensor and its associated maneuverable positioner. Waypoints may be captured and stored for display or study and they can be captured about the surface of an object of interest within a body or object such as an aneurysm, a stent, a tumor, features on a heart, and the like. The locus of these waypoints may then be displayed on a computer screen to give a 2 or a 3 dimensional image of the object, to study any changes in its location, condition or shape, and the like.

Apart from visual display of the data in terms of a visual image on a monitor screen, the actual X, Y and Z data numbers corresponding to a location of interest within the patient or object may be displayed or printed out or otherwise made available to a user so that the user may return the maneuverable positioner to an exact same location. For example, certain procedures on the heart require that electrical measurements be made of the heart. The electrical values so measured may be stored in concert with the exact locations at which the respective measurements were made. Then, once it is decided how to proceed given the measured data, corrective action can be taken at specified sites which can be precisely located by means of the recorded X, Y and Z information corresponding to the site(s) of interest.

While embodiments, applications and advantages of the invention have been shown and described with sufficient clarity to enable one skilled in the art to make and use the invention, it would be equally apparent to those skilled in the art that many more embodiments, applications and advantages are possible without deviating from the inventive concepts disclosed and described herein. The invention therefore should only be restricted in accordance with the spirit of the claims appended hereto and is not to be restricted by the preferred embodiments, specification or drawings.

What is claimed is:

1. An x-ray sensor for determining the position of an associated object in a field of view covered by an x-ray source external to the object comprising
   an x-ray marker, said x-ray marker comprising an x-ray to optical scintillator,
   said scintillator optically coupled to a single optical fiber at a first end of said single optical fiber,
   said x-ray marker and said single optical fiber disposed within a lumen of a catheter,
   said single optical fiber comprising a display device coupler attached to a second end of said single optical fiber for attaching said optical fiber to a display device, including circuitry for displaying the position of said x-ray marker in relation to another object.

2. The x-ray sensor of claim 1 wherein said display device coupler comprises a photodetector, said photodetector capable of converting said optical signals to corresponding electrical signals, said photodetector comprising an output end, said output end is electrically coupleable to said display device.

3. An x-ray sensor for determining the position of an associated object in a field of view covered by a scanning x-ray beam comprising:
   an x-ray marker optically coupled to an optical fiber;
   an x-ray shield, said x-ray shield partially shielding said x-ray marker and allowing x-ray radiation to reach said x-ray marker only from selected directions,
   said x-ray marker, said optical fiber, and said x-ray shield disposed within a catheter.

4. The x-ray sensor of claim 3 wherein said x-ray shield is in the shape of a cross.

5. The x-ray sensor of claim 3 wherein said x-ray shield selectively shields said x-ray marker from said x-ray radiation on three sides.

6. A catheter comprising:
   an elongated body formed from a pliant material, said elongated body having a distal end, a proximate end and at least one lumen axially disposed therein;
   an optical fiber disposed in said at least one lumen, said optical fiber having a distal end disposed at a selected location with respect to said distal end of said elongated body and having a proximate end associated with said proximate end of said elongated body;
   an x-ray marker affixed to said distal end of said optical fiber;
   an x-ray shield, said x-ray marker located in close proximity to said x-ray shield such that said x-ray shield selectively prevents x-ray radiation from exciting said x-ray marker from selected directions.

7. The catheter of claim 6 wherein said selected directions are defined by a conic section having an apex at said x-ray marker and having an axis perpendicular to said elongated body.

8. A catheter comprising:
   an elongated body formed from a pliant material having a distal end, a proximate end and a plurality of lumens axially disposed therein;
   a plurality of x-ray markers, each of said x-ray markers disposed in one of said lumens at selected positions along said elongated body;
   a plurality of optical fibers, each of said optical fibers disposed in one of said lumens and having a distal end optically coupled to a different one of said x-ray markers and a proximate end associated with said proximate end of said elongated body;
   an x-ray shield having planar portions associated with each of said x-ray markers, each of said planar portions arranged in close proximity to said x-ray marker with which it is associated such that said planar portions selectively allow x-ray radiation to reach each of said x-ray markers only from selected directions.

9. The catheter of claim 8 wherein
   two adjacent planar portions define an x-ray shielded corner, each of said x-ray markers disposed in one of said x-ray shielded corners.

10. The catheter of claim 8 wherein said x-ray shield has the general shape of an elongated cross, said elongated cross having an axis, said axis parallel to said elongated body, each of said planar portions extending from said axis at a right angle to its adjacent planar section, each of said x-ray markers disposed between adjacent planar portions.

11. A catheter comprising:
    an elongated body formed from a pliant material, said elongated body having a distal end, a proximate end and a plurality of lumens axially disposed therein;
    a plurality of x-ray markers, each of said x-ray markers disposed in one of said lumens at selected positions along said elongated body;
    a plurality of optical fibers, each of said plurality of optical fiber disposed in one of said lumens and having a distal end optically coupled to a different one of said x-ray markers and a proximate end associated with said proximate end of said elongated body;
    at least one conductive electrode disposed on an outer surface of said elongated body near said distal end thereof; and
    a conductor electrically connected to said at least one electrode, said conductor running through said at least one lumen of said elongated body and accessible at said proximate end of said elongated body for electrical connection thereto.

12. An x-ray sensing catheter comprising:
    an elongated body formed from a pliant material, said elongated body having a distal end, a proximate end and at least one lumen axially disposed therein;
    a single optical fiber disposed in said at least one lumen, said optical fiber having a distal end disposed at a selected location with respect to said distal end of said elongated body and having a proximate end associated with said proximate end of said elongated body;
    an x-ray marker affixed to said distal end of said optical fiber; and
    x-ray shielding partially arranged around said x-ray marker, said x-ray shielding selectively allowing projected x-ray radiation to reach said x-ray marker only from selected directions.

13. The x-ray sensing catheter according to claim 12 further comprising:
    at least one conductive electrode disposed on an outer surface of said elongated body near said distal end thereof; and
    a conductor electrically connected to said at least one electrode, said conductor running through said at least one lumen of said elongated body and accessible at said proximate end of said elongated body for electrical connection thereto.

14. An x-ray sensor comprising:

an x-ray marker, said x-ray marker comprising an x-ray to optical signal scintillator, said x-ray marker generating optical signals in response to x-ray radiation;

a single optical fiber having a distal end and a proximate end, said distal end of said optical fiber affixed to said x-ray marker;

a catheter comprising an elongated body formed from a pliant material, said x-ray marker and said optical fiber residing in a lumen of said catheter, said lumen extending axially through said elongated body, said elongated body having a distal end and a proximate end;

said distal end of said optical fiber disposed at a selected location with respect to said distal end of said elongated body;

said proximate end of said optical fiber associated with said proximate end of said elongated body;

at least one conductive electrode disposed on an outer surface of said elongated body near said distal end thereof; and a conductor electrically connected to said at least one electrode, said conductor running through said at least one lumen of said elongated body and accessible at said proximate end of said elongated body for electrical connection thereto.

15. The x-ray sensor of claim 14 further comprising:

a photodetector comprising an input end and an output end, said input end is optically coupled to said proximate end of said optical fiber, said output end is electrically coupleable to a display device, wherein said display device comprises circuitry for displaying the position of said x-ray marker in relation to another object.

16. The x-ray sensor of claim 14 wherein said x-ray to optical signal scintillator comprises a crystalline material.

17. The x-ray sensor of claim 16 wherein said x-ray to optical signal scintillator has a fast response and minimum afterglow time.

18. The x-ray sensor of claim 14 wherein said x-ray to optical signal scintillator comprises a phosphor material.

19. The x-ray sensor of claim 14 further comprising at least a second x-ray marker and at least a second optical fiber, said second x-ray marker associated with said second optical fiber.

* * * * *